US009719121B2

(12) United States Patent
Fake et al.

(10) Patent No.: US 9,719,121 B2

(45) **Date of Patent: *Aug. 1, 2017**

(54) PRODUCTION OF GLUCAN POLYMERS FROM ALTERNATE SUCROSE SOURCES

(71) Applicant: E I DU PONT DE NEMOURS AND COMPANY, Wilmington, DE (US)

(72) Inventors: Dean M Fake, Wilmington, DE (US); Susan Marie Hennessey, Avondale, PA (US); Brian D Mather, Newark, DE (US); Jennifer S Ovental, Raleigh, NC (US); Wayne Atkinson, New Castle, DE (US); Tyler D Pritchett, Bear, DE (US); Negash Adugna, Wilmington, DE (US)

(73) Assignee: EI DU PONT DE NEMOURS AND COMPANY, Wilmington, DE (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/666,443

(22) Filed: Mar. 24, 2015

(65) Prior Publication Data

US 2015/0275256 A1 Oct. 1, 2015

Related U.S. Application Data

(60) Provisional application No. 61/969,958, filed on Mar. 25, 2014.

(51) Int. Cl.

| | |
|---|---|
| ***C12P 19/18*** | (2006.01) |
| ***C12N 9/10*** | (2006.01) |
| ***C12P 19/04*** | (2006.01) |

(52) U.S. Cl.

CPC ............ *C12P 19/18* (2013.01); *C12N 9/1051* (2013.01); *C12P 19/04* (2013.01)

(58) Field of Classification Search

CPC .................................................... C12N 9/1051

See application file for complete search history.

(56) References Cited

U.S. PATENT DOCUMENTS

| | | | | |
|---|---|---|---|---|
| 5,952,205 | A | 9/1999 | Catani et al. | |
| 6,207,149 | B1 | 3/2001 | Fuglsang et al. | |
| 6,242,225 | B1 | 6/2001 | Catani et al. | |
| 6,660,502 | B2 | 12/2003 | Catani et al. | |
| 7,000,000 | B1 | 2/2006 | O'Brien et al. | |
| 8,269,064 | B2 | 9/2012 | Kok-Jacon et al. | |
| 8,871,474 | B2 * | 10/2014 | Payne | C08B 37/0009 435/193 |
| 9,228,176 | B2 * | 1/2016 | Payne | C08B 37/0009 |
| 9,228,177 | B2 * | 1/2016 | Payne | C08B 37/0009 |
| 9,260,701 | B2 * | 2/2016 | Payne | C08B 37/0009 |
| 9,260,702 | B2 * | 2/2016 | Payne | C08B 37/0009 |
| 9,284,539 | B2 * | 3/2016 | Payne | C08B 37/0009 |
| 9,284,540 | B2 * | 3/2016 | Payne | C08B 37/0009 |
| 9,296,996 | B2 * | 3/2016 | Payne | C08B 37/0009 |
| 9,296,997 | B2 * | 3/2016 | Payne | C08B 37/0009 |
| 2013/0196384 | A1 | 8/2013 | Caimi et al. | |
| 2013/0244287 | A1 | 9/2013 | O'Brien et al. | |
| 2013/0244288 | A1 | 9/2013 | O'Brien et al. | |
| 2014/0087431 | A1 | 3/2014 | Payne et al. | |
| 2015/0232319 | A1 | 8/2015 | Paullin et al. | |
| 2015/0232785 | A1 | 8/2015 | Paullin et al. | |

FOREIGN PATENT DOCUMENTS

| | | | |
|---|---|---|---|
| WO | 0043580 | A1 | 7/2000 |
| WO | 2013036918 | A2 | 3/2013 |
| WO | 2013036968 | A1 | 3/2013 |
| WO | 2013096502 | A1 | 6/2013 |
| WO | 2013096511 | A1 | 6/2013 |
| WO | 2014052386 | A2 | 4/2014 |

OTHER PUBLICATIONS

Enzyme information for glucosyltransferase enzyme classification in BRENDA < http://www.brenda-enzymes.org/enzyme.php?ecno=2.4.1.- > Retrieved Nov. 22, 2016.*

Corresponding PCT Application PCT/US2015/022135, filed Mar. 24, 2015.

International Search Report, PCT Application PCT/US2015/022135, mailed May 29, 2015.

Abo et al., Peptide Sequences for Sucrose Splitting and Glucan Binding Within *Streptococcus* Sobrinus Glucosyltransferase (Water-Insoluble Glucan Synthetase), Journal of Bacteriology, vol. 173, No. 3 (1991), pp. 989-996.

Cantarel et al., The Carbohydrate-Active Enzymes Database (CAZY): An Expert Resource for Glycogenomics, Nucleic Acids Research, vol. 37, Published on-line (2008), Database Issue: D233-238.

Cote et al., Some Structural Features of an Insoluble α-D-Glucan from a Mutant Strain of Leuconostoc Mesentreoides NRRL B-1355, Journal of Industrial Microbiology & Biotechnology, vol. 23, (1999), pp. 656-660.

Eifuku et al., Production and Partial Characterization of the Extra-Cellular Polysaccharides from Oral *Streptococcus* Salivarius, Carbohydrate Research, vol. 194 (1989), pp. 247-260.

Giffard et al., Molecular Characterization of a Cluster of at least two Glucosyltransferase Genes in *Streptocoocus* Salivarious ATCC 25975, Journal of General Microbiology, vol. 137 (1991), pp. 2577-2593.

Jeans et al., Characterization and Classification of Dextrans from Ninety-Six Strains of Bacteria, Contribution FRMO the Strach and Dextrose Section, Northern Utilization Research Branch, vol. 76 (1954), pp. 5041-5052.

(Continued)

*Primary Examiner* — Suzanne M Noakes

(57) ABSTRACT

Reaction solutions are disclosed herein comprising water, incompletely refined sucrose, and a glucosyltransferase enzyme that synthesizes insoluble poly alpha-1,3-glucan having at least 50% alpha-1,3 glycosidic linkages and a weight average degree of polymerization ($DP_w$) of at least 100. The yield of poly alpha-1,3-glucan by a reaction solution herein is at least 7% of the weight of sucrose that was converted in the reaction solution. Further disclosed are methods of producing poly alpha-1,3-glucan using incompletely refined sucrose, and poly alpha-1,3-glucan produced by these methods.

20 Claims, No Drawings

(56) References Cited

OTHER PUBLICATIONS

Kingston et al., Role of the C-Terminal YG Repeats of the Primer-Dependent Streptococcal Glycosyltransferase, FTGJ, In Binding to Dextran and Mutan, Microbiology, vol. 148, (2002), pp. 549-558.
Konishi et al., Structure and Enzymatic Properties of Genetically Trucated Forms of the Water-Insoluble Glucan-Synthesizing Glucosyltransferase from *Streptococcus* Sobrinus, J. Biochem, vol. 26, (1999), pp. 287-295.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.
Monchois et al., Isolation of an Active Catalytic Core of *Streptococcus* Downei MFE28 GTF-I Glucosyltransferase, vol. 181, No. 7 (1999), pp. 2290-2292.
Monchois et al., Glucansucrases: Mechanism of Action and Structure-Function Relationships, FEMS Microbiology Reviews, vol. 23 (1999), pp. 131-151.
Simpson et al., Four Glucosyltransferases GTFJ, GTFK, GTFL and GTFM, from Glucosyltransferaes, GTFJ, GTFK, GTFL and GTFM, from *Streptoccous*Salivarous ATCC 25975, Microbiology, vol. 141 (1995), pp. 1451-1460.
Singh et al., Pullulan: Microbial Sources, Production and Applications, Carbohydrate Polymers, vol. 73 (2008), pp. 515-531.
Yoshimi et al., Functional Analysis of the α-1.3-Glucan Synthase Genes AGSA and AGSB in Aspergillus Nidulans, AGS B is the Major α-1,3-Glucan Synthase in This Fungus, PLOS One, vol. 8, Issue 1 (2013), pp. 1-16.
McCowage et al., ICUMSA Method, GS1/3-7. Determination of the Solution Colour of Raw Sugars, Brown Sugars and Coloured Syrups at PH 7.0—Official, International Commission For Uniform Methods of Sugar Analysis (2011), pp. 1-5.
Colorimetry: Cielab Color Space, Scwiegerling et al., Excerpt From Field Guide to Visual and Opthalmic Optics, SPIE Press, Bellingham WA (2004), SPIE/International Society for Optics and Photonics, Spiedigitallibrary.org, Copyright 2015.
Rogers, Molecular Oral Microbiology,Horizon Scientific Press (2008), Chapter 5: The Molecular Biology of Cariogenic Bacterial, Roy RB Russell, pp. 120-122.
Tsumuraya et al., Structure of the Water-Insoluble α-D-Glucan of *Streptococcus* Salivarius HHT, Carbohydrate Research, vol. 74 (1979), pp. 217-225.

* cited by examiner

PRODUCTION OF GLUCAN POLYMERS FROM ALTERNATE SUCROSE SOURCES

This application claims the benefit of U.S. Provisional Application No. 61/969,958 (filed Mar. 25, 2014), which is incorporated herein by reference in its entirety.

FIELD OF INVENTION

The invention is in the field of polysaccharide synthesis. For example, this invention pertains to producing insoluble poly alpha-1,3-glucan using sucrose that is not completely refined.

REFERENCE TO SEQUENCE LISTING SUBMITTED ELECTRONICALLY

The official copy of the sequence listing is submitted electronically via EFS-Web as an ASCII formatted sequence listing with a file named 20150324_CL6221USNP_SequenceListing created on Mar. 16, 2015, and having a size of 569 kilobytes and is filed concurrently with the specification. The sequence listing contained in this ASCII-formatted document is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages.

Poly alpha-1,3-glucan has been isolated by contacting an aqueous solution of sucrose with a glucosyltransferase (gtf) enzyme isolated from *Streptococcus salivarius* (Simpson et al., *Microbiology* 141:1451-1460, 1995). U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Enzymatic synthesis of poly alpha-1,3-glucan has previously been performed using white, refined sucrose. Since this form of sucrose is relatively expensive, it is desirable to develop new enzymatic processes for poly alpha-1,3-glucan synthesis using sucrose that is unrefined or otherwise incompletely refined.

SUMMARY OF INVENTION

In one embodiment, the disclosure concerns a reaction solution comprising water, sucrose, and a glucosyltransferase enzyme that synthesizes insoluble poly alpha-1,3-glucan having at least 50% alpha-1,3 glycosidic linkages and a weight average degree of polymerization ($DP_w$) of at least 100, wherein the sucrose is unrefined or partially refined. The yield of poly alpha-1,3-glucan by the reaction solution is at least 7% of the weight of sucrose that was converted to products in the reaction solution.

In another embodiment of the reaction solution, the sucrose is from sugar beet and has not been crystallized.

In another embodiment of the reaction solution, the sucrose is from sugar cane and (i) has not been crystallized, or (ii) has been crystallized using no more than three crystallization steps.

In another embodiment of the reaction solution, the sucrose has an ICUMSA value greater than 150.

In another embodiment of the reaction solution, the relative reaction rate of the reaction solution is at least 0.8 with respect to the reaction rate of a reaction solution comprising water, white refined sucrose and the glucosyltransferase enzyme.

In another embodiment of the reaction solution, the poly alpha-1,3-glucan produced by the reaction solution has an L* value less than 93.

In another embodiment, the glucosyltransferase enzyme comprises an amino acid sequence that is at least 90% identical to SEQ ID NO:4, SEQ ID NO:8, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.

In another embodiment, the disclosure concerns a method for producing poly alpha-1,3-glucan comprising the step of contacting water, sucrose, and a glucosyltransferase enzyme, wherein the sucrose is unrefined or partially refined. The poly alpha-1,3-glucan produced in the contacting step has at least 50% alpha-1,3 glycosidic linkages and a weight average degree of polymerization ($DP_w$) of at least 100. The yield of poly alpha-1,3-glucan produced in the method is at least 7% of the weight of the sucrose that was converted to products in the contacting step. The method optionally comprises isolating the poly alpha-1,3-glucan produced in the contacting step.

In another embodiment, the sucrose used in the method is from sugar beet and has not been crystallized.

In another embodiment, the sucrose used in the method is from sugar cane and (i) has not been crystallized, or (ii) has been crystallized using no more than three crystallization steps.

In another embodiment, the sucrose used in the method has an ICUMSA value greater than 150.

In another embodiment, the relative reaction rate of producing poly alpha-1,3-glucan in the contacting step of the method is at least 0.8 with respect to the reaction rate of the contacting step if white refined sucrose is used instead of unrefined or partially refined sucrose.

In another embodiment, the poly alpha-1,3-glucan optionally isolated in the method has an L* value less than 93.

In another embodiment, the glucosyltransferase enzyme used in the method comprises an amino acid sequence that is at least 90% identical to SEQ ID NO:4, SEQ ID NO:8, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.

In another embodiment, the disclosure concerns isolated poly alpha-1,3-glucan produced by the above method, wherein the poly alpha-1,3-glucan has an L* value less than 93.

BRIEF DESCRIPTION OF THE SEQUENCES

TABLE 1

Summary of Nucleic Acid and Protein Sequence Identification Numbers

| Description | Nucleic acid SEQ ID NO. | Protein SEQ ID NO. |
|---|---|---|
| "0874 gtf", *Streptococcus sobrinus*. DNA codon-optimized for expression in *E. coli*. The first 156 amino acids of the protein are deleted compared to GENBANK Identification No. 450874; a start methionine is included. | 1 | 2 (1435 aa) |
| "6855 gtf", *Streptococcus salivarius* SK126. DNA codon-optimized for expression in *E. coli*. The first 178 amino acids of the protein are deleted compared to GENBANK Identification No. 228476855; a start methionine is included. | 3 | 4 (1341 aa) |
| "2379 gtf", *Streptococcus salivarius*. DNA codon-optimized for expression in *E. coli*. The first 203 amino acids of the protein are deleted compared to GENBANK Identification No. 662379; a start methionine is included. | 5 | 6 (1247 aa) |
| "7527" or "gtfJ", *Streptococcus salivarius*. DNA codon-optimized for expression in *E. coli*. The first 42 amino acids of the protein are deleted compared to GENBANK Identification No. 47527; a start methionine is included. | 7 | 8 (1477 aa) |
| "1724 gtf", *Streptococcus downei*. DNA codon-optimized for expression in *E. coli*. The first 162 amino acids of the protein are deleted compared to GENBANK Identification No. 121724; a start methionine is included. | 9 | 10 (1436 aa) |
| "0544 gtf", *Streptococcus mutans*. DNA codon-optimized for expression in *E. coli*. The first 164 amino acids of the protein are deleted compared to GENBANK Identification No. 290580544; a start methionine is included. | 11 | 12 (1313 aa) |
| "5926 gtf", *Streptococcus dentirousetti*. DNA codon-optimized for expression in *E. coli*. The first 144 amino acids of the protein are deleted compared to GENBANK Identification No. 167735926; a start methionine is included. | 13 | 14 (1323 aa) |
| "4297 gtf", *Streptococcus oralis*. DNA codon-optimized for expression in *E. coli*. The first 228 amino acids of the protein are deleted compared to GENBANK Identification No. 7684297; a start methionine is included. | 15 | 16 (1348 aa) |
| "5618 gtf", *Streptococcus sanguinis*. DNA codon-optimized for expression in *E. coli*. The first 223 amino acids of the protein are deleted compared to GENBANK Identification No. 328945618; a start methionine is included. | 17 | 18 (1348 aa) |
| "2765 gtf", unknown *Streptococcus* sp. C150. DNA codon-optimized for expression in *E. coli*. The first 193 amino acids of the protein are deleted compared to GENBANK Identification No. 322372765; a start methionine is included. | 19 | 20 (1340 aa) |
| "4700 gtf", *Leuconostoc mesenteroides*. DNA codon-optimized for expression in *E. coli*. The first 36 amino acids of the protein are deleted compared to GENBANK Identification No. 21654700; a start methionine is included. | 21 | 22 (1492 aa) |
| "1366 gtf", *Streptococcus criceti*. DNA codon-optimized for expression in *E. coli*. The first 139 amino acids of the protein are deleted compared to GENBANK Identification No. 146741366; a start methionine is included. | 23 | 24 (1323 aa) |
| "0427 gtf", *Streptococcus sobrinus*. DNA codon-optimized for expression in *E. coli*. The first 156 amino acids of the protein are deleted compared to GENBANK Identification No. 940427; a start methionine is included. | 25 | 26 (1435 aa) |
| "2919 gtf", *Streptococcus salivarius* PS4. DNA codon-optimized for expression in *E. coli*. The first 92 amino acids of the protein are deleted compared to GENBANK Identification No. 383282919; a start methionine is included. | 27 | 28 (1340 aa) |

TABLE 1-continued

Summary of Nucleic Acid and Protein Sequence Identification Numbers

| Description | Nucleic acid SEQ ID NO. | Protein SEQ ID NO. |
|---|---|---|
| "2678 gtf", *Streptococcus salivarius* K12. DNA codon-optimized for expression in *E. coli*. The first 188 amino acids of the protein are deleted compared to GENBANK Identification No. 400182678; a start methionine is included. | 29 | 30 (1341 aa) |
| "2381 gtf", *Streptococcus salivarius*. DNA codon-optimized for expression in *E. coli*. The first 273 amino acids of the protein are deleted compared to GENBANK Identification No. 662381; a start methionine is included. | 31 | 32 (1305 aa) |
| "3929 gtf", *Streptococcus salivarius* JIM8777. DNA codon-optimized for expression in *E. coli*. The first 178 amino acids of the protein are deleted compared to GENBANK Identification No. 387783929; a start methionine is included. | 33 | 34 (1341 aa) |
| "6907 gtf", *Streptococcus salivarius* SK126. DNA codon-optimized for expression in *E. coli*. The first 161 amino acids of the protein are deleted compared to GENBANK Identification No. 228476907; a start methionine is included. | 35 | 36 (1331 aa) |
| "6661 gtf", *Streptococcus salivarius* SK126. DNA codon-optimized for expression in *E. coli*. The first 265 amino acids of the protein are deleted compared to GENBANK Identification No. 228476661; a start methionine is included. | 37 | 38 (1305 aa) |
| "0339 gtf", *Streptococcus gallolyticus* ATCC 43143. DNA codon-optimized for expression in *E. coli*. The first 213 amino acids of the protein are deleted compared to GENBANK Identification No. 334280339; a start methionine is included. | 39 | 40 (1310 aa) |
| "0088 gtf", *Streptococcus mutans*. DNA codon-optimized for expression in *E. coli*. The first 189 amino acids of the protein are deleted compared to GENBANK Identification No. 3130088; a start methionine is included. | 41 | 42 (1267 aa) |
| "9358 gtf", *Streptococcus mutans* UA159. DNA codon-optimized for expression in *E. coli*. The first 176 amino acids of the protein are deleted compared to GENBANK Identification No. 24379358; a start methionine is included. | 43 | 44 (1287 aa) |
| "8242 gtf", *Streptococcus gallolyticus* ATCC BAA-2069. DNA codon-optimized for expression in *E. coli*. The first 191 amino acids of the protein are deleted compared to GENBANK Identification No. 325978242; a start methionine is included. | 45 | 46 (1355 aa) |
| "3442 gtf", *Streptococcus sanguinis* SK405. DNA codon-optimized for expression in *E. coli*. The first 228 amino acids of the protein are deleted compared to GENBANK Identification No. 324993442; a start methionine is included. | 47 | 48 (1348 aa) |
| "7528 gtf", *Streptococcus salivarius*. DNA codon-optimized for expression in *E. coli*. The first 173 amino acids of the protein are deleted compared to GENBANK Identification No. 47528; a start methionine is included. | 49 | 50 (1427 aa) |
| "3279 gtf", *Streptococcus* sp. C150. DNA codon-optimized for expression in *E. coli*. The first 178 amino acids of the protein are deleted compared to GENBANK Identification No. 322373279; a start methionine is included. | 51 | 52 (1393 aa) |
| "6491 gtf", *Leuconostoc citreum* KM20. DNA codon-optimized for expression in *E. coli*. The first 244 amino acids of the protein are deleted compared to GENBANK Identification No. 170016491; a start methionine is included. | 53 | 54 (1262 aa) |
| "6889 gtf", *Streptococcus salivarius* SK126. DNA codon-optimized for expression in *E. coli*. The first 173 amino acids of the protein are deleted compared to GENBANK Identification No. 228476889; a start methionine is included. | 55 | 56 (1427 aa) |
| "4154 gtf", *Lactobacillus reuteri*. DNA codon-optimized for expression in *E. coli*. The first 38 amino acids of the protein are deleted compared to GENBANK Identification No. 51574154; a start methionine is included. | 57 | 58 (1735 aa) |

TABLE 1-continued

Summary of Nucleic Acid and Protein Sequence Identification Numbers

| Description | Nucleic acid SEQ ID NO. | Protein SEQ ID NO. |
|---|---|---|
| "3298 gtf", *Streptococcus* sp. C150. The first 209 amino acids of the protein are deleted compared to GENBANK Identification No. 322373298; a start methionine is included. | | 59 (1242 aa) |
| "Wild type gtfJ", *Streptococcus salivarius*. GENBANK Identification No. 47527. | | 60 (1518 aa) |
| Wild type gtf corresponding to 2678 gtf, *Streptococcus salivarius* K12. GENBANK Identification No. 400182678. | | 61 (1528 aa) |
| Wild type gtf corresponding to 6855 gtf, *Streptococcus salivarius* SK126. GENBANK Identification No. 228476855. | | 62 (1518 aa) |
| Wild type gtf corresponding to 2919 gtf, *Streptococcus salivarius* PS4. GENBANK Identification No. 383282919. | | 63 (1431 aa) |
| Wild type gtf corresponding to 2765 gtf, *Streptococcus* sp. C150. GENBANK Identification No. 322372765. | | 64 (1532 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and the like are used interchangeably herein. Poly alpha-1,3-glucan is a polymer comprising glucose monomeric units linked together by glycosidic linkages (i.e., glucosidic linkages), wherein at least about 50% of the glycosidic linkages are alpha-1,3-glycosidic linkages. Poly alpha-1,3-glucan is a type of polysaccharide. The term "alpha-1,3-glycosidic linkage" as used herein refers to the type of covalent bond that joins alpha-D-glucose molecules to each other through carbons 1 and 3 on adjacent alpha-D-glucose rings.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings.

"Alpha-D-glucose" herein can also be referred to as "glucose".

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

"White refined" sucrose herein refers to sucrose comprising at least 99.0 wt % sucrose. Additionally, or alternatively, white refined sucrose can refer to sucrose having an ICUMSA value of 150 or less (e.g., 45 or less), a minimum polarization of 99.70%, and/or an L* value of at least 87.0.

An "ICUMSA" (International Commission for Uniform Methods of Sugar Analysis) value, or "standard ICUMSA" value, is an international unit for expressing the purity of a sucrose sample in solution, and is directly related to the color of the sucrose. The greater the ICUMSA value of a sucrose sample, the darker the sucrose sample is. Methods of determining ICUMSA values for sucrose samples are well known in the art and are disclosed by the International Commission for Uniform Methods of Sugar Analysis in *ICUMSA Methods of Sugar Analysis: Official and Tentative Methods Recommended by the International Commission for Uniform Methods of Sugar Analysis* (*ICUMSA*) (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH* 7.0—*Official*, Verlag Dr Albert Bartens, 2011 revision), which is incorporated herein by reference. ICUMSA values can be expressed in "reference base units" (RBU).

ICUMSA values herein can be measured by a method very similar to ICUMSA Method GS1/3-7, but differing by using a cellulose acetate filter instead of a cellulose nitrate filter. Thus, ICUMSA values disclosed herein can alternatively be referred to as "modified ICUMSA" values. Given how ICUMSA is measured, it would be understood that ICUMSA values provided herein for a solid sugar samples (e.g., raw cane sugar) were obtained using an aqueous solution of the sugar sample (about 200 g/L).

The "polarization" ("pol") of a sucrose sample herein refers to the apparent sucrose content in the sample expressed as a mass percent measured by the optical rotation of polarized light passing through a solution comprising the sucrose sample at 20° C. The greater the polarization of a sucrose sample, the more pure the sucrose in the sample is.

Sucrose that is "not completely refined" ("incompletely refined" sucrose) herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA of incompletely refined sucrose herein is greater than 150.

The terms sucrose "crystallization" "crystallization step", "fractional crystallization" and the like are used interchangeably herein and refer to a process of crystallizing sucrose from a solution comprising incompletely refined sucrose and separating the sucrose crystals from the supernatant (mother liquor). The crystals resulting from this process typically represents sucrose that is more pure compared to the sucrose as it existed before the crystallization step. It is important to note, however, that incompletely refined sucrose having gone through one, two, three, or more crystallization steps may still constitute incompletely refined sucrose (i.e., the crystallized sucrose may not have the purity of white refined sucrose). Cane sugar typically requires three or more crystallization steps to prepare white refined sugar, whereas beet juice in certain embodiments may only need one crystallization step to reach such purity. Various means are known in the art for crystallizing sucrose, such as evaporation, boiling, and/or vacuum-drying processes.

The term "L* value" as used herein refers to the lightness component of the CIE 1976 (L*, a*, b*) ("CIELAB") three-dimensional color space specified by the International Commission on Illumination (CIE, Vienna, Austria). The three coordinates of the L*a*b* color space represent, respectively, lightness of the color of a solid (L*=0 indicates black and L*=100 indicates diffuse white), the color of the object along a scale between red/magenta and green (a*, negative values indicate green while positive values indicate magenta), and the color of the object along a scale between yellow and blue (b*, negative values indicate blue and positive values indicate yellow). The asterisks (*) used in referring to a L*a*b* color space of an object are pronounced as "star" (e.g., L* is "L-star") and serve to distinguish this color space from Hunter's L, a, b color system. The L*, a*, and b* components of a CIELAB color space of an object can be calculated using the formulae disclosed by J. Schwiegerling (*Field Guide to Visual and Ophthalmic Optics*, SPIE Press, Bellingham, Wash., 2004), which is incorporated herein by reference. L*, a*, b* values herein are with respect to solid material such as dry sucrose or dry poly alpha-1,3-glucan.

"Dry" sucrose as used herein can characterize sucrose that comprises no more than 2.0, 1.5, 1.0, 0.5, 0.25, 0.10, 0.05, or 0.01 wt % water.

The "molecular weight" of poly alpha-1,3-glucan herein can be represented as number-average molecular weight ($M_n$) or as weight-average molecular weight ($M_w$). Alternatively, molecular weight can be represented as Daltons, grams/mole, $DP_w$ (weight average degree of polymerization), or $DR_n$ (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", "glucansucrase" and the like are used interchangeably herein. The activity of a gtf enzyme herein catalyzes the reaction of the substrate sucrose to make the products poly alpha-1,3-glucan and fructose. Other products (byproducts) of a gtf reaction can include glucose (results from when glucose is hydrolyzed from the glucosyl-gtf enzyme intermediate complex), various soluble oligosaccharides (e.g., DP2-DP7), and leucrose (results from when glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

A "reaction solution" as used herein generally refers to a solution comprising sucrose, water, at least one active glucosyltransferase enzyme, and optionally other components. A reaction solution can alternatively be referred to herein as a "glucan synthesis reaction", "glucan reaction", or "gtf reaction", for example. Other components that can be in a glucan synthesis reaction include fructose, glucose, leucrose, and soluble oligosaccharides (e.g., DP2-DP7). It would be understood that certain glucan products, such as poly alpha-1,3-glucan with a degree of polymerization (DP) of at least 8 or 9, are water-insoluble and thus are not dissolved in a glucan synthesis reaction, but rather may be present out of solution. It is in the reaction solution where the step of contacting water, sucrose and a glucosyltransferase enzyme is performed. The term "under suitable reaction conditions" as used herein, refers to reaction conditions that support conversion of sucrose to poly alpha-1,3-glucan via glucosyltransferase enzyme activity.

A "control" reaction solution as used herein can refer to a reaction solution comprising white refined sucrose instead of incompletely refined sucrose. All the other features (e.g., sucrose concentration, temperature, pH, type of gtf) of a control reaction solution can be the same as the reaction solution to which it is being compared.

The "percent dry solids" of a glucan synthesis reaction refers to the wt % of all the sugars in the glucan synthesis reaction. The percent dry solids of a gtf reaction can be calculated, for example, based on the amount of sucrose used to prepare the reaction.

The "yield" of poly alpha-1,3-glucan by a reaction solution herein represents the weight of poly alpha-1,3-glucan product expressed as a percentage of the weight of sucrose substrate that is converted in the reaction. For example, if 100 g of sucrose in a reaction solution is converted to products, and 10 g of the products is poly alpha-1,3-glucan, the yield of the poly alpha-1,3-glucan would be 10%. This yield calculation can be considered as a measure of selectivity of the reaction toward poly alpha-1,3-glucan.

The term "relative reaction rate" as used herein refers to the rate of a particular glucan synthesis reaction as compared to another glucan synthesis reaction. For example, if reaction A has a rate of x, and reaction B has a rate of y, then the relative reaction rate of reaction A with respect to the reaction rate of reaction B can be expressed as x/y (x divided by y). The terms "reaction rate" and "rate of reaction" are used interchangeably herein to refer to the change in concentration/amount of reactant(s) or the change in concentration/amount of product(s) per unit time per unit of enzyme. Preferred reactant and product herein of a glucan synthesis reaction are, respectively, sucrose and poly alpha-1,3-glucan.

A "fraction" of a glucan synthesis reaction herein refers to a liquid solution portion of a glucan synthesis reaction. A fraction can be a portion of, or all of, the liquid solution from a glucan synthesis reaction, and has been separated from a solid glucan product synthesized in the reaction. A fraction can alternatively be referred to as a "mother liquor." An example of a fraction is a filtrate of a glucan synthesis reaction. Since a fraction can contain dissolved sugars such as sucrose, fructose, glucose, leucrose, soluble oligosaccharides (e.g., DP2-DP7), a fraction can also be referred to as a "mixed sugar solution" derived from a glucan synthesis reaction.

The terms "filtrate", "glucan reaction filtrate", "glucan filtrate" and the like are used interchangeably herein and refer to a fraction that has been filtered away from a solid glucan product synthesized in a glucan synthesis reaction.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polynucleotide and polypeptide sequences are disclosed herein as features of certain embodiments. Variants of these sequences that are at least about 70-85%, 85-90%, or 90%-95% identical to the sequences disclosed herein can be used. Alternatively, a variant amino acid sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. A variant nucleotide or amino acid sequence has the same function/activity of the disclosed sequence, or at least about 85%, 86%, 87%, 88%, 89%, 90%, 91%, 92%, 93%, 94%, 95%, 96%, 97%, 98%, or 99% of the function/activity of a disclosed sequence.

The term "isolated" as used in certain embodiments refers to any cellular component that is completely separated from its native source (e.g., an isolated polynucleotide or polypeptide molecule). In some instances, an isolated polynucleotide or polypeptide molecule is part of a greater composition, buffer system or reagent mix. For example, an isolated polynucleotide or polypeptide molecule can be comprised within a cell or organism in a heterologous manner. Other examples are isolated glucosyltransferase and isolated poly alpha-1,3-glucan. It is believed that the glucosyltransferase reaction processes disclosed herein are synthetic, non-naturally occurring processes.

Enzymatic synthesis of poly alpha-1,3-glucan has previously been performed using white, refined sucrose. Since this form of sucrose is relatively expensive, it is desirable to develop new enzymatic processes for poly alpha-1,3-glucan synthesis using sucrose that is unrefined or otherwise incompletely refined.

Embodiments of the present disclosure concern a reaction solution comprising at least water, sucrose, and a glucosyltransferase enzyme that synthesizes insoluble poly alpha-1,3-glucan having at least 50% alpha-1,3 glycosidic linkages and a weight average degree of polymerization ($DP_w$) of at least 100, wherein the sucrose is unrefined or partially refined (i.e., not completely refined). The reaction solution produces insoluble poly alpha-1,3-glucan having at least 50% alpha-1,3 glycosidic linkages and a $DP_w$ of at least 100. The yield of poly alpha-1,3-glucan by the reaction solution is at least 7% of the weight of sucrose that was converted to products in the reaction solution.

Significantly, embodiments of this reaction solution produce poly alpha-1,3-glucan with yields and molecular weights comparable to the glucan yields and molecular weights produced by reaction solutions using white refined sucrose instead of incompletely refined sucrose. These results indicate that the contaminants present in incompletely refined sucrose generally do not impede its use by glucosyltransferase in polymerizing poly alpha-1,3-glucan.

Sucrose that is not completely refined can be used in a reaction solution as presently disclosed. Such sucrose has not been processed to white refined sucrose. Examples include unrefined sucrose compositions comprising raw sucrose (raw sugar). Other forms of incompletely refined sucrose useful herein include forms of sucrose derived from sugarcane (*Saccharum* spp. such as *S. officenarum*), sugar beet (*Beta* spp. such as *B. vulgaris*) (can alternatively be referred to herein as "beet"), date palm (*Phoenix dactylifera*), *sorghum* (*Sorghum* spp. such as *S. vulgare* and *S. bicolor*), sugar maple (*Acer saccharum*), cassava (*Manihot esculenta*), or corn, for example. Incompletely refined forms of sugarcane and/or sugar beet sucrose can be used in preferred embodiments herein. Sugarcane contains about 20% sucrose in its juice, whereas sugar beet contains about 10 to 15% sucrose in its juice.

Incompletely refined sucrose in certain embodiments may be from a plant that produces sucrose and, optionally, is grown for sucrose production. Such a plant, such as those listed above, can be from any region of the world where the plant is typically grown. For example, sucrose herein may be from a plant grown in South America (e.g., Brazil, Colombia, Argentina, Guyana), North America (e.g., U.S.A., Mexico, West Indies, Central America [e.g., Belize]), Australia, Asia (e.g., India, China, Russia, Turkey, Thailand, Pakistan, Philippines, Indonesia), Africa (e.g., Egypt, Mozambique, Zimbabwe) and Europe (e.g., France, Germany, Ukraine, Russia, Turkey).

Incompletely refined sucrose may be provided as a composition obtained at any stage of a process of sucrose purification from a juice of a plant (e.g., sugarcane or sugar beet) containing sucrose. Such processes are disclosed in *Handbook of Sugar Refining: A Manual for the Design and Operation of Sugar Refining Facilities* (Ed. C. C. Chou, John Wiley & Sons, Inc., 2000), Chen and Chou (*Cane Sugar Handbook: A Manual for Cane Sugar Manufacturers and Their Chemists,* 12th Edition, John Wiley & Sons, Inc., 1993), and Asadi (*Beet-Sugar Handbook,* 1st Edition, Wiley-Interscience, 2006), for example, which are all incorporated herein by reference. Some preferred compositions and processes from these references are discussed as follows.

Incompletely refined sucrose herein may be provided as a composition resulting from any step of a sucrose-purification process, such as (i) initial extraction (e.g., hot water extraction) of "raw juice" from plant material; (ii) juice purification by carbonatation (i.e., using lime and carbon dioxide to form a calcium carbonate precipitate that co-precipitates impurities), yielding "thin juice"; (iii) evaporation of water from thin juice, yielding "thick juice", and/or (iv) boiling or vacuum-concentrating thick juice to crystallize sucrose (such once-crystallized sucrose typically is not white refined sugar) (the crystals can be removed from the supernatant by centrifugation, for example). The products of steps (i) and (ii) can be filtered in certain embodiments before further processing, for example. The supernatant of crystallization (iv) can be recycled and mixed with other supernatant and/or thick juice, which is then subject to a crystallization (yielding crystals as in step [iv] that can also be used herein). Recycling of supernatant eventually results in "molasses". Thus, incompletely refined sucrose can be provided as raw juice, thin juice, thick juice, molasses, and/or sucrose crystals that have gone through no more than one crystallization, for example. These forms of incompletely refined sucrose, and respective process steps used to obtain them, preferably characterize examples of incompletely refined sucrose obtained from sugar beet, but may also characterize sucrose obtained from other sources such as sugarcane.

Examples of incompletely refined sucrose from sugar beets useful herein include beet raw juice, beet thin juice (comprises about 10-20 wt % sucrose), beet thick juice (comprises about 60-90 wt % sucrose) and sugar beet molasses (about 50-60 wt % sucrose). Beet thin and/or thick juice are used in certain embodiments. ICUMSA values herein can be at least 1000 (e.g., ~1000-1300) for beet thin juice, at least 1300 (e.g., ~1300-1800) for beet thick juice, and/or at least 50000 for beet molasses (e.g., ~50000-60000), for example.

Alternatively, incompletely refined sucrose herein may be "raw sucrose" ("raw sugar"), which is provided by removing all the water from raw juice (i.e., raw sucrose is solid). Alternatively still, incompletely refined sucrose herein may be "VHP sucrose" ("VHP", "VHP sugar", "very high polarization" sucrose), which is provided by first carbonatating and filtering raw juice, followed by evaporating raw juice to crystallize a portion of the sucrose therein; the crystallized sucrose removed from the supernatant is VHP sucrose. VHP sucrose has thus gone through one crystallization. Alternatively still, incompletely refined sucrose herein may be "VVHP sucrose" ("VVHP", "VVHP sugar", "very very high polarization" sucrose), which is provided by dissolving VHP sucrose in water and re-crystallizing the sucrose. VVHP sucrose has thus been through two crystallizations. These forms of incompletely refined sucrose (raw sucrose, VHP, VVHP), and respective process steps used to obtain them, preferably characterize examples of incompletely refined sucrose obtained from sugarcane, but may also characterize sucrose obtained from other sources such as sugar beets.

Raw sucrose (e.g., "raw cane sugar") herein can have a polarization value of 94% to 97%, an ICUMSA value of about 600 to 1200, and/or an L* value below 87.0 (e.g., less than 85, 80, 75, 70, 65, 60, 55, or 50). It should be understood that raw sucrose is not "brown sugar", which is a product of mixing a molasses syrup with white refined sugar followed by drying. VHP sucrose herein can have a polarization value of at least 99.30%, and/or an ICUMSA value of about 300 to 1000, for example. VHP sucrose can optionally have any of the following characteristics: 0.15% maximum moisture content, 0.15% maximum ash content, 97% solubility in water, and/or golden brown color. VVHP sucrose herein can have a polarization value of at least 99.50%, and/or an ICUMSA value of over 150 to about 400, for example.

Incompletely refined sucrose herein is not white refined sucrose. White refined sucrose herein refers to sucrose comprising at least 99.0 wt % sucrose (e.g., at least 99.5 wt % or 99.9 wt %). Additionally, or alternatively, white refined sucrose can refer to sucrose having an ICUMSA value of 150 or less (e.g., 45 or less), a minimum polarization of 99.70% (e.g., at least 99.80%), and/or an L* value of at least 87.0 (e.g., at least 87.5, 88.0, or 88.5). White refined sucrose in certain embodiments can also have any of the following characteristics: 0.04% maximum moisture content, 0.04% maximum ash content, 100% solubility in water, sparkling white color, and/or fine granulation.

In certain embodiments, incompletely refined sucrose has not been crystallized. There can be mentioned incompletely refined sucrose obtained sugar beet, including, for example, beet raw juice, beet thin juice and beet thick juice. Alternatively, incompletely refined sucrose herein has had no more than one, two, three, or more crystallization steps. Incompletely refined sucrose from sugar cane that has had no more than two or three crystallizations can be used, for example. Alternatively still, incompletely refined sucrose can be used if it has been through one, two, three, or more crystallizations, but has an ICUMSA greater than 150. A crystallization step can comprise, for example, boiling and/or vacuum-drying an aqueous solution comprising sucrose at least to the point that dissolved sucrose begins to fall out of the solution as crystals.

The ICUMSA value of incompletely refined sucrose herein can be greater than 150, for example. Alternatively, incompletely refined sucrose can have an ICUMSA value of at least about 200, 300, 400, 500, 600, 700, 800, 900, 1000, 1100, 1200, 1300, 1400, 1500, 2000, 2500, 3000, 4000, 5000, 6000, 7000, 8000, 9000, 10000, 20000, 30000, 40000, 50000, or 60000 (or any integer value between 151 and 60000), for example. The ICUMSA in certain embodiments can range from about 1000-1300, such as when the incompletely refined sucrose is beet thin juice. The ICUMSA in other embodiments herein can range from about 1300-1800, such as when the incompletely refined sucrose is beet thick juice, or about 50000 to 60000, such as when the incompletely refined sucrose is beet molasses. Still in other embodiments, the ICUMSA can range from about 600-1200, such as when the incompletely refined sucrose is raw sucrose; about 300-1000, such as when the incompletely refined sucrose is VHP sucrose; or over 150 to about 400, such as when the incompletely refined sucrose is VVHP sucrose.

It is believed that ICUMSA values of sucrose compositions herein ("modified ICUMSA") are the same as, or very similar to, the ICUMSA values that would be measured for the compositions using other ICUMSA methods.

A reaction solution herein refers to a solution comprising at least incompletely refined sucrose, water and an active glucosyltransferase enzyme, and optionally other components. Other components that can be in a glucan synthesis reaction include fructose, glucose, leucrose, soluble oligosaccharides (e.g., DP2-DP7), for example. It would be understood that certain glucan products, such as poly alpha-1,3-glucan with a DP of at least 8 or 9, may be water-insoluble and thus are not dissolved in a glucan synthesis reaction, but rather may be present out of solution. A reaction solution herein may be one that, in addition to producing insoluble glucan product, produces byproducts such as leucrose and/or soluble oligosaccharides.

A reaction solution as disclosed herein comprises a glucosyltransferase enzyme that produces poly alpha-1,3-glucan having at least 50% alpha-1,3 glycosidic linkages and a $DP_w$ of at least 100. Examples of such glucosyltransferase enzymes useful herein are disclosed in U.S. Pat. No. 7,000,000, and U.S. Pat. Appl. Publ. Nos. 2013/0244288 and 2013/0244287 (all of which are incorporated herein by reference). Still other examples of glucosyltransferases that can be used in a reaction solution herein for producing poly alpha-1,3-glucan are disclosed in U.S. Pat. Appl. Publ. No. 2014/0087431 (U.S. patent application Ser. No. 14/036,049), which is incorporated herein by reference. For example, a glucosyltransferase enzyme herein can (i) comprise, or consist of, an amino acid sequence that is 100% identical to, or at least 90%, 91%, 92%, 93%, 94%, 95%, 96%, 97%, 98%, or 99% identical to, SEQ ID NO:4, 8, 10, 12, 14, 20, 26, 28, 30, or 34, and (ii) have glucosyltransferase activity.

A reaction solution in certain other embodiments comprises a glucosyltransferase enzyme that (i) comprises, or consists of, an amino acid sequence that is 100% identical to, or at least 90%, 91%, 92%, 93%, 94%, 95%, 96%, 97%, 98%, or 99% identical to, SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 59, 60, 61, 62, 63, or 64, and (ii) has glucosyltransferase activity.

A glucosyltransferase enzyme herein may be derived from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme in some aspects herein produces poly alpha-1,3-glucan having at least 50% alpha-1,3 glycosidic linkages in a glucan synthesis reaction in which incompletely refined sucrose is used. It is believed that a glucosyltransferase enzyme in certain embodiments synthesizes poly alpha-1,3-glucan in which at least about 60%, 70%, 80%, 90%, 95%, 96%, 97%, 98%, 99%, or 100% (or any integer between 60% and 100%) of the constituent glycosidic linkages are alpha-1,3 linkages. Accordingly, the glucosyltransferase enzyme in the foregoing embodiments synthesizes poly alpha-1,3-glucan in which there is less than about 50%, 40%, 30%, 20%, 10%, 5%, 4%, 3%, 2%, 1%, or 0% (or any integer value between 0% and 50%) of glycosidic linkages that are not alpha-1,3.

In other aspects herein, a glucosyltransferase enzyme can synthesize poly alpha-1,3-glucan with no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

A glucosyltransferase enzyme in some aspects herein can synthesize poly alpha-1,3-glucan having a molecular weight in $DP_n$ or $DP_w$ of at least about 100. Alternatively, the glucosyltransferase enzyme can synthesize poly alpha-1,3-glucan having a molecular weight in $DP_n$ or $DP_w$ of at least about 400. Alternatively still, the glucosyltransferase enzyme can synthesize poly alpha-1,3-glucan having a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000).

One or more different glucosyltransferase enzymes may be used in certain aspects. The glucosyltransferase enzyme in certain embodiments does not have, or has very little (less than 1%), dextransucrase, reuteransucrase, or alternansucrase activity. A reaction solution herein may contain one, two, or more glucosyltransferase enzymes, for example.

A glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Primers that can be used in certain embodiments include dextran and other carbohydrate-based primers, such as hydrolyzed glucan, for example. Dextran for use as a primer can be dextran T10 (i.e., dextran having a molecular weight of 10 kD), for example.

Examples of glucosyltransferase enzymes herein can be any of the amino acid sequences disclosed herein and that further include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example.

A glucosyltransferase enzyme herein typically lacks an N-terminal signal peptide. An expression system for producing a glucosyltransferase enzyme herein may employ an enzyme-encoding polynucleotide that further comprises sequence encoding an N-terminal signal peptide to direct extra-cellular secretion, if desired. The signal peptide in such embodiments is cleaved from the enzyme during the secretion process. The signal peptide may either be native or heterologous to the glucosyltransferase. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

Several glucosyltransferase enzyme sequences disclosed herein lack an N-terminal signal peptide (as well as a variable domain) (refer to Table 1). An N-terminal start-methionine (amino acid position 1) has been added to each sequence for intracellular expression purposes (expressed enzyme can be obtained in a cell lysate, for example). One of skill in the art would understand that an intervening heterologous amino acid sequence such as an epitope and/or signal peptide could optionally be added between the start methionine and glucosyltransferase sequence. Thus, for example, a glucosyltransferase enzyme herein may comprise, or consist of, an amino acid sequence that (i) is 100% identical to, or at least 90%, 91%, 92%, 93%, 94%, 95%, 96%, 97%, 98%, or 99% identical to, the amino acid sequence beginning at position 2 of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 59, 60, 61, 62, 63, or 64, and (ii) has glucosyltransferase activity.

A glucosyltransferase enzyme for a glucan synthesis reaction herein may be produced by any means known in the art. For example, a glucosyltransferase enzyme may be produced recombinantly in a heterologous expression system, such as a microbial heterologous expression system. Examples of heterologous expression systems include bacterial (e.g., *E. coli* such as TOP10 or MG1655; *Bacillus* sp.) and eukaryotic (e.g., yeasts such as *Pichia* sp. and *Saccharomyces* sp.) expression systems.

In certain embodiments, a heterologous gene expression system may be one that is designed for protein secretion. The glucosyltransferase enzyme comprises a signal peptide (signal sequence) in such embodiments. The signal peptide may be either its native signal peptide or a heterologous signal peptide.

A glucosyltransferase enzyme described herein may be used in any purification state (e.g., pure or non-pure). For example, the glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v) in a reaction solution for producing poly alpha-1,3-glucan from sucrose.

The activity of a glucosyltransferase enzyme herein can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480nm}$ for five minutes.

The temperature of a reaction solution herein can be controlled, if desired. In certain embodiments, the temperature of the reaction is between about 5° C. to about 50° C. The temperature in certain other embodiments is between about 20° C. to about 40° C., or about 20° C. to about 30° C. (e.g., about 25° C.).

The initial concentration of sucrose in a reaction solution herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer value between 40 and 160 g/L), for example. "Initial concentration of sucrose" refers to the sucrose concentration in a gtf reaction solution just after all the reaction solution components have been added (at least water, incompletely refined sucrose, gtf enzyme). All of, or a portion of, the sucrose in a reaction solution can be from incompletely refined sucrose added to the solution. Though it is preferable that all the sucrose be incompletely refined, white refined sucrose may additionally be used in a reaction solution.

It would be understood that, with certain incompletely refined sucrose compositions that are in liquid form (e.g., beet thin juice, beet thick juice, molasses), such compositions would be added accordingly to a reaction solution to achieve a particular initial concentration of sucrose in a particular reaction volume. For example, an incompletely refined sucrose composition from sugar beets (e.g., beet thin juice, beet thick juice, molasses) could be diluted into a reaction solution such that the initial sucrose concentration of the reaction is about 70-90 g/L or 80-85 g/L.

The pH of a glucan synthesis reaction in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a glucan synthesis reaction can be from 0 mM to about 100 mM, or about 10, 20, or 50 mM, for example. A suitable amount of DTT (dithiothreitol, e.g., about 1.0 mM) can optionally be added to a reaction solution.

A reaction solution herein may be contained within any vessel suitable for applying one or more of the reaction conditions disclosed herein. For example, a reaction solution herein may be in a stainless steel, plastic, or glass vessel or container of a size suitable to contain a particular reaction. Such a vessel can optionally be equipped with a stirring device.

Examples of other conditions and components suitable for carrying out a reaction solution herein are disclosed in U.S. Pat. No. 7,000,000, and U.S. Pat. Appl. Publ. Nos. 2013/0244288, 2013/0244287, 2013/0196384, 2013/0157316, and 2014/0087431, all of which are incorporated herein by reference.

The yield of poly alpha-1,3-glucan by a reaction solution of the present disclosure is at least 7% of the weight of sucrose that was converted to products in the reaction solution. Alternatively, the yield of poly alpha-1,3-glucan can be at least about 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, or 47%. In certain embodiments, the yield of poly alpha-1,3-glucan in a reaction solution herein is about the same as the yield of poly alpha-1,3-glucan by a control reaction solution in which white refined sucrose is used instead of incompletely refined sucrose. All the foregoing yields can be obtained using a reaction solution maintained at a temperature of about 20-30° C. (e.g., 25° C.) and/or using a gtf comprising SEQ ID NO:8, for example. Certain of these embodiments may use thick beet juice or thin beet juice as incompletely refined sucrose.

In certain embodiments, the relative reaction rate of a reaction solution is at least about 0.8 with respect to the reaction rate of a reaction solution comprising water, white refined sucrose and a glucosyltransferase enzyme. For example, the relative reaction rate of a reaction solution is at least about 0.8 with respect to a control reaction (i.e., the reaction rate of a reaction solution herein is at least 80% of the rate of a control reaction). The relative reaction rate herein can alternatively be at least about 0.82, 0.84, 0.86, 0.88, 0.90, 0.92, 0.94, 0.96, 0.98, 1.00, 1.02, or 1.04, for example. The reaction rate of a reaction solution can be expressed in terms the change in concentration/amount of reactant(s) (e.g., sucrose) and/or the change in concentration/amount of product(s) (e.g., poly alpha-1,3-glucan) per unit time per unit concentration of active glucosyltransferase enzyme.

A reaction solution herein can produce poly alpha-1,3-glucan having an L* value less than 93, for example. Alternatively, the L* value of poly alpha-1,3-glucan produced by a reaction solution herein can be less than 92, 90, 88, 86, 84, 82, 80, 78, 76, 74, 72, 70, 68, 66, 64, 62, or 60. Examples of ranges of L* values of poly alpha-1,3-glucan products herein can be about 82-87 (e.g., when beet thin juice or beet thick juice is used in a reaction solution) or 80-82 (e.g., when VHP sucrose is used in a reaction solution). L* values can be determined, for example, for poly alpha-1,3-glucan that has been removed from a reaction solution, washed with at least one half reaction volume of water in two displacement washes (e.g., wash with at least one 1-L of water if the reaction volume was 2 L), and then dried, ground and sieved through 60-mesh sieve. Drying should be performed at a temperature that does not discolor the poly alpha-1,3-glucan. Thus, any color in the poly alpha-1,3-glucan should be derived from the incompletely refined sucrose.

A reaction solution herein produces poly alpha-1,3-glucan having at least 50% alpha-1,3 glycosidic linkages. It is believed that in certain embodiments poly alpha-1,3-glucan is produced in which at least about 60%, 70%, 80%, 90%, 95%, 96%, 97%, 98%, 99%, or 100% (or any integer between 60% and 100%) of the constituent glycosidic linkages are alpha-1,3 linkages. Accordingly, the poly alpha-1,3-glucan produced in the foregoing embodiments has less than about 50%, 40%, 30%, 20%, 10%, 5%, 4%, 3%, 2%, 1%, or 0% (or any integer value between 0% and 50%) glycosidic linkages that are not alpha-1,3.

The glycosidic linkage profile of a poly alpha-1,3-glucan product herein can be determined using any method known in the art. For example, linkage profile can be determined using methods that use nuclear magnetic resonance (NMR) spectroscopy (e.g., $^{13}$C NMR or $^{1}$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

A reaction solution herein produces poly alpha-1,3-glucan having a molecular weight in $DP_n$ or $DP_w$ of at least about 100. Alternatively, poly alpha-1,3-glucan produced in a reaction solution herein can have a molecular weight in $DP_n$ or $DP_w$ of at least about 400. Alternatively still, the poly alpha-1,3-glucan can have a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000).

The molecular weight of poly alpha-1,3-glucan herein can be measured using any of several means known in the art. For example, glucan polymer molecular weight can be measured using high-pressure liquid chromatography (HPLC), size exclusion chromatography (SEC), or gel permeation chromatography (GPC).

The present disclosure also concerns a method for producing poly alpha-1,3-glucan comprising the step of contacting at least water, sucrose, and a glucosyltransferase enzyme, wherein the sucrose is unrefined or partially refined (i.e., not completely refined). The poly alpha-1,3-glucan produced in this method, which can optionally be isolated, has at least 50% alpha-1,3 glycosidic linkages and a weight average degree of polymerization ($DP_w$) of at least 100. Further, the yield of poly alpha-1,3-glucan produced in the method is at least 7% of the weight of the sucrose that was converted to products by being contacted with the water and glucosyltransferase enzyme. Any of the features of a reaction solution herein as disclosed above and in the Examples can characterize this method. The following features of the method are examples.

Incompletely refined sucrose in certain embodiments of the method can be from sugar beet (e.g., beet thin juice or beet thick juice) and has not been crystallized. In another example, incompletely refined sucrose is from sugar cane (e.g., raw sucrose, VHP, or VVHP sucrose) and has had no more than two or three crystallization steps.

Incompletely refined sucrose used in the disclosed method can have an ICUMSA value greater than 150, for example.

Poly alpha-1,3-glucan produced in certain embodiments of the method has an L* value less than 93. L* values herein can be determined, for example, with respect to poly alpha-1,3-glucan that has been removed from a reaction solution; optionally washed one, two, or more times with water; and dried.

The relative reaction rate of producing poly alpha-1,3-glucan in the contacting step of the method is at least 0.8 with respect to the reaction rate if white refined sucrose is used instead of incompletely refined sucrose.

The disclosed method comprises contacting at least water, incompletely refined sucrose, and a glucosyltransferase enzyme. This contacting step can comprise providing a reaction solution comprising water, incompletely refined sucrose and a glucosyltransferase enzyme. It will be understood that, as the glucosyltransferase enzyme synthesizes poly alpha-1,3-glucan, the reaction solution becomes a reaction mixture given that insoluble poly alpha-1,3-glucan falls out of solution as indicated by clouding of the reaction. The contacting step of the disclosed method can be performed in any number of ways. For example, the desired amount of incompletely refined sucrose can first be dissolved or mixed in water (optionally, other components may also be added at this stage of preparation, such as buffer components), followed by addition of a glucosyltransferase enzyme. The solution may be kept still, or agitated via stirring or orbital shaking, for example. The reaction can be, and typically is, cell-free.

Completion of a reaction in certain embodiments can be determined visually (no more accumulation of insoluble poly alpha-1,3-glucan) and/or by measuring the amount of sucrose left in the solution (residual sucrose), where a percent sucrose consumption of over about 90% can indicate reaction completion. Typically, a reaction of the disclosed process will take about 12, 24, 36, 48, 60, 72, 84, or 96 hours to complete, depending on certain parameters such as the amount of sucrose and glucosyltransferase enzyme used in the reaction.

The percent sucrose consumption of a reaction in certain embodiments of the disclosed method is at least 90%, 91%, 92%, 93%, 94%, 95%, 96%, 97%, 98%, 99%, or 100% of the sucrose initially contacted with water and a glucosyltransferase enzyme. Alternatively, the percent sucrose consumption may be >90% or >95%.

The yield of poly alpha-1,3-glucan produced in some aspects of a glucan synthesis method herein can be at least about 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, or 47% based on the weight of sucrose converted in the reaction.

Poly alpha-1,3-glucan produced in the disclosed method may optionally be isolated. For example, insoluble poly alpha-1,3-glucan may be separated by centrifugation or filtration. In doing so, poly alpha-1,3-glucan is separated from most of the reaction solution, which may comprise water, fructose and certain byproducts (e.g., leucrose, soluble oligosaccharides DP2-DP7). This solution may also comprise residual sucrose and glucose monomer. Isolation can optionally further comprise washing the poly alpha-1,3-glucan one, two, or more times with water, and/or drying the poly alpha-1,3-glucan.

The present disclosure also concerns poly alpha-1,3-glucan produced by a reaction solution or method disclosed herein. This poly alpha-1,3-glucan has an L* value that is less than 93. Any of the features of poly alpha-1,3-glucan as disclosed above and in the Examples can characterize poly alpha-1,3-glucan of this embodiment. The following features are examples.

A poly alpha-1,3-glucan product herein may be isolated, and can additionally be provided in a dry form, for example. In certain embodiments, a poly alpha-1,3-glucan product is provided in an isolated, dry amount of at least 1 gram (e.g., at least 100 g or 500 g). "Dry" poly alpha-1,3-glucan comprises no more than 2.0, 1.5, 1.0, 0.5, 0.25, 0.10, 0.05, or 0.01 wt % water, for example.

It is believed that a poly alpha-1,3-glucan product in certain embodiments may contain one or more of the following compounds: caramels, melanoidins, hexose alkaline degradation products (HADPs) (polymeric C6 sugar condensation products formed under alkaline conditions), polyphenol-iron complexes (e.g., iron catechol complexes), melanins. One or more of these compounds are further believed to provide darker coloration to the poly alpha-1,3-glucan product, compared to the coloration, if any, of a poly alpha-1,3-glucan product rendered by a reaction solution in which only white refined sucrose is used. Such coloration differences can be determined using L* values, for example.

Non-limiting examples of compositions and methods disclosed herein include:

1. A reaction solution comprising water, sucrose, and a glucosyltransferase enzyme that synthesizes insoluble poly alpha-1,3-glucan having at least 50% alpha-1,3 glycosidic linkages and a weight average degree of polymerization ($DP_w$) of at least 100, wherein the sucrose is unrefined or partially refined;
   wherein the yield of poly alpha-1,3-glucan by the reaction solution is at least 7% of the weight of sucrose that was converted to products in the reaction solution.
2. The reaction solution of embodiment 1, wherein the sucrose is from sugar beet and has not been crystallized.
3. The reaction solution of embodiment 1, wherein the sucrose is from sugar cane and (i) has not been crystallized, or (ii) has been crystallized using no more than three crystallization steps.
4. The reaction solution of embodiment 1, 3, or 3, wherein the sucrose has an ICUMSA value greater than 150.
5. The reaction solution of embodiment 1, 2, 3, or 4, wherein the relative reaction rate of the reaction solution is at least 0.8 with respect to the reaction rate of a reaction solution comprising water, white refined sucrose and the glucosyltransferase enzyme.
6. The reaction solution of embodiment 1, 2, 3, 4, or 5, wherein the poly alpha-1,3-glucan produced by the reaction solution has an L* value less than 93.
7. The reaction solution of embodiment 1, 2, 3, 4, 5, or 6, wherein the glucosyltransferase enzyme comprises an amino acid sequence that is at least 90% identical to SEQ ID NO:4, SEQ ID NO:8, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.
8. A method for producing insoluble poly alpha-1,3-glucan comprising:
   (a) contacting at least water, sucrose, and a glucosyltransferase enzyme, wherein the sucrose is unrefined or partially refined, whereby poly alpha-1,3-glucan is produced having at least 50% alpha-1,3 glycosidic linkages and a weight average degree of polymerization ($DP_w$) of at least 100; and
   b) optionally, isolating the poly alpha-1,3-glucan produced in step (a);
   wherein the yield of poly alpha-1,3-glucan is at least 7% of the weight of sucrose converted to products in step (a).
9. The method of embodiment 8, wherein the sucrose is from sugar beet and has not been crystallized.
10. The method of embodiment 8, wherein the sucrose is from sugar cane and (i) has not been crystallized, or (ii) has been crystallized using no more than three crystallization steps.
11. The method of embodiment 8, 9, or 10, wherein the sucrose has an ICUMSA value greater than 150.
12. The method of embodiment 8, 9, 10, or 11, wherein the relative reaction rate of producing poly alpha-1,3-glucan in step (a) is at least 0.8 with respect to the reaction rate of step (a) if white refined sucrose is used instead of the unrefined or partially refined sucrose.
13. The method of embodiment 8, 9, 10, 11, or 12, wherein the poly alpha-1,3-glucan isolated in step (b) has an L* value less than 93.
14. The method of embodiment 8, 9, 10, 11, 12, or 13, wherein the glucosyltransferase enzyme comprises an amino acid sequence that is at least 90% identical to SEQ ID NO:4, SEQ ID NO:8, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.
15. Isolated poly alpha-1,3-glucan produced by the method of claim 8, 9, 10, 11, 12, 13, or 14, wherein the poly alpha-1,3-glucan has an L* value less than 93.

EXAMPLES

The present disclosure is further exemplified in Examples 2-12 provided below. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

General Methods

Sucrose ICUMSA Measurement

ICUMSA measurements were made closely following ICUMSA Method GS1/3-7 (R. J. McCowage, R. M. Urquhart and M. L. Burge, *Determination of the Solution Colour of Raw Sugars, Brown Sugars and Coloured Syrups at pH* 7.0—*Official*, Verlag Dr Albert Bartens, 2011 revision), which is incorporated herein by reference. The essential steps of ICUMSA color measurement of a sucrose sample was as follows. Sucrose was added to deionized water (dissolved if in solid form such as cane sugar, diluted if in liquid form such as beet juice) to a specified concentration based on expected ICUMSA range, as specified in ICUMSA Method GS1/3-7. The sucrose solution was filtered to remove any undissolved impurities and the absorbance of the filtered sucrose solution was measured. The ICUMSA color of the solution was then calculated according to Equation 1:

$$ColorICUMSA(UI) = \frac{Abs}{b \times c} \times 1000$$

where Abs=sample solution absorbance reading; b=Optical cell path (cm); c=sucrose concentration in g/mL.

The above ICUMSA method follows ICUMSA Method GS1/3-7, but with the following modifications:

1. Cellulose acetate 0.45-micron filters (square 50 mm) were used instead of cellulose nitrate 0.45-micron filters.
2. Instead of calculating RDS ("refractometric dry substance") and density, sucrose concentration of a sample was determined by the following steps: Effective ppt salinity was measured using a refractometer and converted to % Brix using a linear relationship obtained from published data (% Brix=0.1258 ppt salinity+0.0152). The refractive index measurements were performed on additionally diluted samples and the Brix values converted back to standard concentrations used in the UV measurement.

Deionized water was used for sucrose dissolution. Sucrose solution samples were not de-aerated as no foam or bubbles were observed in the solutions. Cellulose acetate filters were pre-housed in a plastic funnel for sterifilter applications.

L*a*b* Color Measurement of Poly Alpha-1,3-Glucan

Poly alpha-1,3-glucan color was measured using the CIE L*a*b* measurement system. Two sample preparation methods were used depending on the amount of poly alpha-1,3-glucan available. The two methods gave equivalent L*a*b* measurements.

In the first method, dried poly alpha-1,3-glucan was ground in a coffee grinder to a fine powder. 0.77 g of powder was transferred to an evacuable 13-mm KBr Pellet Die and the poly alpha-1,3-glucan was formed into a pellet at 7000 pounds. The color of the pellet was measured using a Konica Minolta 2600D spectrophotometer.

In the second method, dried poly alpha-1,3-glucan was ground in a coffee grinder to a fine powder. Ground poly alpha-1,3-glucan was sieved through a 60-mesh screen and filled into a 1-cm cuvette. The color of the ground poly alpha-1,3-glucan was measured using a HUNTERLAB COLORQUEST XE spectrophotometer.

Preparation of Crude Extracts of Glucosyltransferase (Gtf) Enzyme

Gtf enzymes (e.g., SEQ ID NO:8)) were prepared as follows. *E. coli* TOP10® cells (Invitrogen, Carlsbad Calif.) were transformed with a pJexpress404®-based construct containing a particular gtf-encoding DNA sequence. Each sequence was codon-optimized to express the gtf enzyme in *E. coli*. Individual *E. coli* strains expressing a particular gtf enzyme were grown in LB (Luria broth) medium (Becton, Dickinson and Company, Franklin Lakes, N.J.) with ampicillin (100 μg/mL) at 37° C. with shaking to $OD_{600}$=0.4-0.5, at which time IPTG (isopropyl beta-D-1-thiogalactopyranoside, Cat. No. 16758, Sigma-Aldrich, St. Louis, Mo.) was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with dithiothreitol (DTT, 1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA (bicinchoninic acid) protein assay (Sigma-Aldrich) and SDS-PAGE to confirm expression of the gtf enzyme, and the supernatant was stored at −20° C.

Relative Reaction Rate of Gtf

The enzymatic reaction of sucrose to poly alpha-1,3-glucan by glucosyltransferase follows Michaelis-Menten kinetics. At high sucrose concentrations the reaction rate is zeroth order in sucrose. The concentration of sucrose was measured by HPLC periodically throughout the reaction. The reaction rate was calculated as the rate of sucrose consumption during the zeroth order reaction. That is, the reaction rate was calculated as the negative of the slope of the linear region of a sucrose concentration vs. time graph. The reaction rate was then divided by the enzyme activity loaded to the reactor to give a normalized reaction rate, which eliminated reaction rate differences due to variations in enzyme concentration. Finally the normalized reaction rate was divided by the normalized reaction rate for white refined sugar to give Relative Reaction Rate.

Determination of Gtf Enzymatic Activity

Gtf enzyme (e.g., SEQ ID NO:8) activity was confirmed following a protocol such as the following, which measures the production of reducing sugars (fructose and glucose) in a gtf reaction solution. A reaction solution is prepared by adding a crude gtf extract to a mixture containing sucrose (50 or 150 g/L), potassium phosphate buffer (pH 6.5, 50 mM), and optionally dextran (1 mg/mL, dextran T10, Cat. No. D9260, Sigma-Aldrich); the gtf extract is added to 2.5%-5% by volume. The reaction solution is then incubated at 22-25° C. for 24-30 hours, after which it is centrifuged. Supernatant (0.01 mL) is added to a mixture containing 1 N NaOH and 0.1% triphenyltetrazolium chloride (Sigma-Aldrich). The mixture is incubated for five minutes after which its $OD_{480nm}$ is determined using an ULTROSPEC spectrophotometer (Pharmacia LKB, New York, N.Y.) to gauge the presence of the reducing sugars fructose and glucose.

Determination of Weight Average Degree of Polymerization $DP_W$)

The $DP_W$ of a glucan product synthesized by a gtf enzyme (e.g., SEQ ID NO:8) was determined by size-exclusion chromatography (SEC). An example SEC protocol is as follows. Dry poly alpha-1,3-glucan polymer is dissolved at 5 mg/mL in N,N-dimethyl-acetamide (DMAc) and 5% LiCl with overnight shaking at 100° C. The SEC system is an Alliance™ 2695 separation module from Waters Corporation (Milford, Mass.) coupled with three on-line detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC are four styrene-divinyl benzene columns from Shodex (Japan) and two linear KD-806M, KD-802 and KD-801 columns to improve resolution at the low molecular weight region of a polymer distribution. The mobile phase is DMAc with 0.11% LiCl. The chromatographic conditions used are 50° C. in the column and detector compartments, 40° C. in the sample and injector compartment, a flow rate of 0.5 mL/min, and an injection volume of 100 μL. The software packages used for data reduction are Empower™ version 3 from Waters (calibration with broad glucan polymer standard) and Astra® version 6 from Wyatt (triple detection method with column calibration).

Determination of Glycosidic Linkages

Glycosidic linkages in a glucan product synthesized by a gtf enzyme (e.g., SEQ ID NO:8) can be determined by following a $^{13}C$ NMR (nuclear magnetic resonance) such as the following. Dry glucan polymer (25-30 mg) is dissolved in 1 mL of deuterated dimethyl sulfoxide (DMSO) containing 3% by weight of LiCl with stirring at 50° C. Using a glass pipet, 0.8 mL of the solution is transferred into a 5-mm NMR tube. A quantitative $^{13}C$ NMR spectrum is acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse gated decoupling pulse sequence using waltz decoupling is used with an acquisition time of 0.629 second, an inter-pulse delay of 5 seconds, and 6000 pulses. The time domain data is transformed using an exponential multiplication of 2.0 Hz.

Example 1 (Comparative)

Preparation of Poly Alpha-1,3-Glucan Using White Refined Sucrose

This Example describes producing alpha-1,3-glucan in a gtf-catalyzed reaction using white refined sucrose.

An 80 g/L sucrose solution was prepared as follows. 1500 g of deionized water was charged to a jacketed, agitated 2-L glass reactor controlled at 23° C. 2.7 g of $KH_2PO_4$ buffer was added to the reactor. Next, 160 g of white refined sucrose (ICUMSA 47; United Sugars Corporation, Bloomington, Minn.) was added to the reactor, after which the volume in the reactor was adjusted to 2 L with more deionized water. FermaSure® (DuPont) was then added (1 mL/L reaction), and the pH was adjusted to 5.5 using 5 wt % aqueous sodium hydroxide or 5 wt % aqueous sulfuric acid. The glucan polymerization reaction was initiated by adding 0.3 vol % of crude gtf enzyme (SEQ ID NO:8) extract (General Methods), and maintained at 23° C.

After the reaction was determined to be complete by either complete consumption of sucrose or no change in sucrose concentration between measurements, 200 mL of the reaction slurry was filtered using a FILTRATEST (Bokela GmbH Karlsruhe, Germany). This filtration separated mother liquor (filtrate) from poly alpha-1,3-glucan wet cake. Residual sugars in the wet cake were washed out with two displacement washes (200-L each) of deionized water. The wet cake was then dried in a convection oven at 80° C. for approximately 24 hours. The polymerization yield was calculated using the final weight of dried polymer divided by the amount of sucrose reacted.

The molecular weight of the poly alpha-1,3-glucan product was measured by SEC (General Methods) and is presented as $DP_W$ (Table 2), which can be calculated as the average polymer molecular weight divided by the monomer molecular weight. The color of the dried glucan polymer product was measured according to the General Methods and is presented as L* in Table 2.

Example 2

Preparation of Poly Alpha-1,3-Glucan Using VHP Sucrose

This Example describes producing alpha-1,3-glucan in a gtf-catalyzed reaction using VHP, which is a type of incompletely refined sucrose.

The polymerization procedure of Example 1 was followed except that VHP sucrose (ICUMSA 501, Iracema Mill, Brazil) was used instead of white refined sucrose.

After the reaction was determined to be complete by either complete consumption of sucrose or no change in sucrose concentration between measurements, the reaction slurry was filtered using a Buchner funnel and vacuum flask. This filtration separated mother liquor (filtrate) from poly alpha-1,3-glucan wet cake. Residual sugars in the wet cake were washed out with two displacement washes (1-L each) of deionized water. The wet cake was then dried in a vacuum oven at 40° C. and 360 mm Hg for approximately 48 hours. The polymerization yield was calculated using the final weight of dried polymer divided by the amount of sucrose reacted. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 3

Preparation of Poly Alpha-1,3-Glucan Using VVHP Sucrose

This Example describes producing alpha-1,3-glucan in a gtf-catalyzed reaction using VVHP, which is a type of incompletely refined sucrose.

The polymerization and polymer isolation procedures of Example 2 were followed except that VVHP sucrose (ICUMSA 421, Ferrari Mill, Brazil) was used instead of VHP sucrose. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 4

Preparation of Poly Alpha-1,3-Glucan Using Beet Thick Juice

This Example describes producing alpha-1,3-glucan in a gtf-catalyzed reaction using beet thick juice, which is a type of incompletely refined sucrose.

The polymerization and polymer isolation procedures of Example 2 were generally followed except that beet thick juice sucrose (ICUMSA 1414, Southern Minnesota Beet Sugar Cooperative) was used instead of VHP sucrose. The polymerization procedure was conducted as follows. 235 g of beet thick juice was added to the reactor and diluted with deionized water until the sucrose concentration was 80 g/L (approximately 1765 mL of water was added). 2.72 g of $KH_2PO_4$ buffer was added and the pH was adjusted to 5.5 with 5 wt % sodium hydroxide. The glucan polymerization reaction was initiated by adding 0.3 vol % of crude gtf enzyme (SEQ ID NO:8) extract (General Methods), and maintained at 23° C. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 5

Preparation of Poly Alpha-1,3-Glucan Using Beet Thin Juice

This Example describes producing alpha-1,3-glucan in a gtf-catalyzed reaction using beet thin juice, which is a type of incompletely refined sucrose.

The polymerization and polymer isolation procedures of Example 2 were generally followed except that beet thin juice sucrose (ICUMSA 1158, Southern Minnesota Beet Sugar Cooperative) was used instead of VHP sucrose and a one 1-L wash followed by a 500-mL water wash was used instead of two 1-L washes. 1229 mL of beet thin juice was added to 771 mL of deionized water to prepare a starting sucrose concentration of 80 g/L. 2.72 g of $KH_2PO_4$ buffer was added and the pH was adjusted to 5.5 using 5 wt % sulfuric acid. The glucan polymerization reaction was initiated by adding 0.3 vol % of crude gtf enzyme (SEQ ID NO:8) extract (General Methods), and maintained at 23° C. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 6

Preparation of Poly Alpha-1,3-Glucan Using Beet Molasses

This Example describes producing alpha-1,3-glucan in a gtf-catalyzed reaction using beet molasses, which is a type of incompletely refined sucrose.

The polymerization and polymer isolation procedures of Example 2 were generally followed except that beet molasses (ICUMSA 57781, Southern Minnesota Beet Sugar Cooperative) was used instead of VHP sucrose and three 1-L water washes were used instead of two 1-L washes. 291 mL of beet molasses was added to 1709 mL of deionized water to prepare a starting sucrose concentration of 83.4 g/L. 2.72 g of $KH_2PO_4$ buffer was added and the pH was adjusted to 5.5 using 5 wt % sodium hydroxide. The glucan polymerization reaction was initiated by adding 0.3 vol % of crude gtf enzyme (SEQ ID NO:8) extract (General Methods), and maintained at 23° C. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 7

Preparation of Poly Alpha-1,3-Glucan Using Brazil Raw Cane Sugar

This Example describes producing alpha-1,3-glucan in a gtf-catalyzed reaction using Brazil raw cane sugar, which is a type of incompletely refined sucrose.

In a 1-liter Erlenmeyer flask, 75 g of Brazil raw cane sugar (ICUMSA 2655) was dissolved in approximately 500 mL of deionized water. 1.02 g $KH_2PO_4$ and 0.15 mL of Ferma-Sure® were added, afterwhich water was added to a volume of 750 mL. The pH was adjusted to 5.5 using 5 wt % sodium hydroxide. The flask was placed in an incubation stirrer oven at 25° C. The glucan polymerization reaction was initiated by adding 0.3 vol % of crude gtf enzyme (SEQ ID NO:8) extract (General Methods), and maintained at 25° C. The reaction was completed in 30 hours. After reaction completion, the reaction was filtered with a Buchner funnel and vacuum flask. The resulting cake was displacement-washed with two 800-mL water washes and one 200-mL water wash. The poly alpha-1,3-glucan was dried in a vacuum oven at 40° C. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 8

Preparation of Poly Alpha-1,3-Glucan Using New Orleans Raw Cane Sugar

This Example describes producing alpha-1,3-glucan in a gtf-catalyzed reaction using New Orleans raw cane sugar, which is a type of incompletely refined sucrose.

The polymerization and polymer isolation procedures of Example 7 were followed except that New Orleans raw cane sugar (ICUMSA 2850) was used as the sucrose component. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 9

Preparation of Poly Alpha-1,3-Glucan Using Mozambique Raw Cane Sugar

This Example describes producing alpha-1,3-glucan in a gtf-catalyzed reaction using Mozambique raw cane sugar, which is a type of incompletely refined sucrose.

The polymerization and polymer isolation procedures of Example 7 were followed except that Mozambique raw cane sugar (ICUMSA 3022) was used as the sucrose component. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 10

Preparation of Poly Alpha-1,3-Glucan Using Zimbabwe Raw Cane Sugar

This Example describes producing alpha-1,3-glucan in a gtf-catalyzed reaction using Zimbabwe raw cane sugar, which is a type of incompletely refined sucrose.

The polymerization and polymer isolation procedures of Example 7 were followed except that Zimbabwe raw cane sugar (ICUMSA 4183) was used as the sucrose component. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 11

Preparation of Poly Alpha-1,3-Glucan Using Belize Raw Cane Sugar

This Example describes producing alpha-1,3-glucan in a gtf-catalyzed reaction using Belize raw cane sugar, which is a type of incompletely refined sucrose.

The polymerization and polymer isolation procedures of Example 7 were followed except that Belize raw cane sugar (ICUMSA 5150) was used as the sucrose component. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

Example 12

Preparation of Poly Alpha-1,3-Glucan Using Guyana Raw Cane Sugar

This Example describes producing alpha-1,3-glucan in a gtf-catalyzed reaction using Guyana raw cane sugar, which is a type of incompletely refined sucrose.

The polymerization and polymer isolation procedures of Example 7 were followed except that Guyana raw cane sugar (ICUMSA 8153) was used as the sucrose component. The molecular weight, yield and color of poly alpha-1,3-glucan prepared in this procedure are presented in Table 2.

Thus, poly alpha-1,3-glucan can be synthesized in a gtf reaction solution comprising incompletely refined sucrose.

TABLE 2

Poly Alpha-1,3-Glucan Produced Using Various Types of Incompletely Refined Sucrose

| | Sucrose Used In Reaction | | | Relative Reaction | Poly Alpha-1,3-Glucan Product | | |
|---|---|---|---|---|---|---|---|
| Example | Source | Type | ICUMSA | Rate[a] | $DP_W$ | L* | Yield |
| 1 | United Sugars Corporation | White Refined | 47 | 1.00 | 708 | 93.9[b] | 18% |
| 2 | Iracema Mill, Brazil | VHP | 501 | 0.88 | 765 | 78 | 21% |
| 3 | Ferrari Mill, Brazil | VVHP | 421 | 0.88 | 876 | 88 | 17% |
| 4 | Southern Minnesota Beet Sugar Cooperative | Beet Thick Juice | 1414 | 0.97 | 760 | 86 | 21% |
| 5 | Southern Minnesota Beet Sugar Cooperative | Beet Thin Juice | 1158 | 1.01 | 781 | 83 | 13% |
| 6 | Southern Minnesota Beet Sugar Cooperative | Beet Molasses | 57781 | 0.92 | 756 | 65 | 8% |
| 7 | Brazil | Raw Cane Sugar | 2655 | 1.00 | 565 | 78 | 16% |
| 8 | New Orleans | Raw Cane Sugar | 2850 | 0.92 | 573 | 86 | 17% |
| 9 | Mozambique | Raw Cane Sugar | 3022 | 1.01 | 532 | 82 | 16% |
| 10 | Zimbabwe | Raw Cane Sugar | 4183 | 0.88 | 553 | 71 | 16% |
| 11 | Belize | Raw Cane Sugar | 5150 | 0.74 | 721 | 62 | 11% |
| 12 | Guyana | Raw Cane Sugar | 8153 | 0.95 | 577 | 62 | 16% |

[a]Relative rates of the reactions in Examples 2-12 were calculated with respect to the rate of the reaction in Example 1.

[b]This L* was determined for polymer produced following the Example 1 procedure, except that a 500-mL reaction was used instead of 2-L and the product was dried in an oven at 40° C. and 360 mm Hg for approximately 48 hours.

The data in Table 2 generally indicate that gtf reaction solutions comprising incompletely refined sucrose (Examples 2-12) can perform at the same level of, or even better than, gtf reaction solutions comprising white refined sucrose (Example 1). For the most part, reactions containing incompletely refined sucrose had reaction rates that were nearly or completely equivalent with the rate of a reaction containing white refined sucrose. Also, several reactions containing incompletely refine sucrose produced glucan with $DP_W$ and/or yield greater than what was observed using white refined sucrose (e.g., Examples 2-6).

Thus, multiple different types of incompletely refined sucrose can be used to enzymatically produce poly alpha-1,3-glucan.

What is claimed is:

1. An isolated reaction solution comprising water, sucrose, and a glucosyltransferase enzyme that synthesizes insoluble poly alpha-1,3-glucan having at least 95% alpha-1,3 glycosidic linkages and a weight average degree of polymerization ($DP_w$) of at least 100, wherein the sucrose is unrefined or partially refined and the glucosyltransferase enzyme comprises an amino acid sequence that is: at least 90% identical to SEQ ID NO:4; at least 92% identical to SEQ ID NO:30 or 34; at least 93% identical to SEQ ID NO:10, 14, or 26; or at least 94% identical to SEQ ID NO:20 or 28;

wherein the yield of said poly alpha-1,3-glucan by the reaction solution is at least 7% of the weight of sucrose that was converted to products in the reaction solution.

2. The reaction solution of claim 1, wherein the sucrose is from sugar beet and has not been crystallized.

3. The reaction solution of claim 1, wherein the sucrose is from sugar cane and (i) has not been crystallized, or (ii) has been crystallized using no more than three crystallization steps.

4. The reaction solution of claim 1, wherein the sucrose has an ICUMSA (International Commission for Uniform Methods of Sugar Analysis) value greater than 150.

5. The reaction solution of claim 1, wherein the relative reaction rate of said reaction solution is at least 0.8 with respect to the reaction rate of a reaction solution comprising water, white refined sucrose and said glucosyltransferase enzyme.

6. The reaction solution of claim 1, wherein the poly alpha-1,3-glucan produced by the reaction solution has an L* value less than 93.

7. The reaction solution of claim 1, wherein the glucosyltransferase enzyme comprises an amino acid sequence that is at least 95% identical to SEQ ID NO:4, SEQ ID NO:10, SEQ ID NO:14, SEQ ID NO:20, SEQ ID NO:26, SEQ ID NO:28, SEQ ID NO:30, or SEQ ID NO:34.

8. A method for producing insoluble poly alpha-1,3-glucan comprising:

(a) contacting at least water, sucrose, and a glucosyltransferase enzyme in an isolated reaction solution, wherein the sucrose is unrefined or partially refined and the glucosyltransferase enzyme comprises an amino acid sequence that is: at least 90% identical to SEQ ID NO:4; at least 92% identical to SEQ ID NO:30 or 34; at least 93% identical to SEQ ID NO:10, 14, or 26; or at least 94% identical to SEQ ID NO:20 or 28;

whereby poly alpha-1,3-glucan is produced having at least 95% alpha-1,3 glycosidic linkages and a weight average degree of polymerization ($DP_w$) of at least 100; and b) optionally, isolating the poly alpha-1,3-glucan produced in step (a);

wherein the yield of poly alpha-1,3-glucan is at least 7% of the weight of sucrose converted to products in step (a).

9. The reaction solution of claim 1, wherein a heterologous amino acid sequence of 1-300 residues is at the N-terminus and/or C-terminus of said glucosyltransferase enzyme.

10. The reaction solution of claim 1, wherein the glucosyltransferase enzyme consists of an amino acid sequence that is: at least 90% identical to SEQ ID NO:4; at least 92% identical to SEQ ID NQ:30 or 34; at least 93% identical to SEQ ID NO:10, 14, or 26; or at least 94% identical to SEQ ID NO:20 or 28.

11. The reaction solution of claim 10, wherein the glucosyltransferase enzyme consists of an amino acid sequence that is at least 95% identical to SEQ ID NO:4, SEQ ID NO:10, SEQ ID NO:14, SEQ ID NO:20, SEQ ID NO:26, SEQ ID NO:28, SEQ ID NO:30, or SEQ ID NO:34.

12. The reaction solution of claim 11, wherein the glucosyltransferase enzyme consists of an amino acid sequence that is at least 97% identical to SEQ ID NO:4, SEQ ID NO:10, SEQ ID NO:14, SEQ ID NO:20, SEQ ID NO:26, SEQ ID NO:28, SEQ ID NO:30, or SEQ ID NO:34.

13. The reaction solution of claim 1, wherein the reaction solution comprises only one or two glucosyltransferase enzymes.

14. The reaction solution of claim 13, wherein the reaction solution comprises only one glucosyltransferase enzyme.

15. The reaction solution of claim 1, wherein the reaction solution is comprised within an inert vessel.

16. The reaction solution of claim 15, wherein the reaction solution is comprised within a stainless steel vessel, plastic vessel, or glass vessel.

17. The reaction solution of claim 1, wherein the reaction solution is cell-free.

18. The reaction solution of claim 1, wherein said poly alpha-1,3-glucan has at least about 99% alpha-1,3 glycosidic linkages.

19. The reaction solution of claim 1, wherein said poly alpha-1,3-glucan has about 100% alpha-1,3 glycosidic linkages.

20. The reaction solution of claim 1, wherein said yield of poly alpha-1,3-glucan is at least 20%.

* * * * *

SEQUENCE LISTING

```
<160> NUMBER OF SEQ ID NOS: 64

<210> SEQ ID NO 1
<211> LENGTH: 4308
<212> TYPE: DNA
<213> ORGANISM: Streptococcus sobrinus

<400> SEQUENCE: 1

atggttgacg gcaaatacta ctattatgat caggacggta acgtaaagaa gaatttcgcg      60

gtgagcgttg gtgacaaaat ctactacttc gatgaaactg gtgcatataa ggataccagc     120

aaagtggacg ccgacaagag cagcagcgcg gttagccaaa acgcgaccat ctttgcggcg     180

aataaccgtg cgtacagcac ctctgcaaag aattttgaag cggtggataa ctacctgacc     240

gcagacagct ggtatcgtcc gaaatccatc ctgaaggacg gcaaaacctg gaccgagagc     300

ggtaaggatg atttccgtcc actgctgatg gcatggtggc ctgacaccga aactaagcgc     360

aactacgtga actatatgaa taaagtggtc ggtattgaca agacgtacac tgcggaaacg     420

tcgcaagcgg atttgaccgc agcggcggag ctggttcaag cgcgtatcga gcagaagatt     480

accagcgaaa acaacaccaa atggctgcgc gaagcaatct ccgcgttcgt taagacgcag     540

cctcagtgga acggcgagtc cgaaaagccg tatgacgatc acttgcagaa cggtgcgctg     600

ctgtttgata accaaaccga cctgacgcca gacacccaaa gcaattaccg tttgctgaac     660

cgtaccccga ccaatcagac tggtagcctg gatagccgtt ttacgtataa tccgaatgac     720

ccgttgggcg gctacgattt cttgctggcg aacgacgttg acaatagcaa tccggtcgtc     780

caggctgaac agttgaactg gctgcattat ctgctgaact ttggctctat ttacgctaac     840

gatgccgacg ccaattttga cagcattcgc gttgatgccg tcgataatgt cgatgctgat     900

ctgctgcaaa tcagcagcga ttacctgaaa gcagcgtatg gcatcgacaa gaataacaag     960

aatgcgaaca accatgttag catcgtcgaa gcgtggagcg acaatgatac cccgtatttg    1020

cacgacgatg gcgataatct gatgaacatg gacaacaaat ttcgcctgtc catgctgtgg    1080

agcctggcaa agccgctgga caaacgtagc ggtttgaacc cgctgattca caatagcctg    1140

gtggaccgcg aggtggacga tcgtgaagtg gaaaccgtgc cgtcctacag ctttgctcgt    1200

gcacatgata gcgaggtgca ggacatcatc cgtgacatta tcaaggctga gattaaccca    1260

aatagctttg gttatagctt cactcaagaa gagatcgagc aagcctttaa gatttacaac    1320

gaggatttga agaaaacgga caagaaatac acccactaca atgtgccgct gagctacacc    1380

ctgctgctga ccaacaaggg cagcatcccg cgtgtgtact atggtgatat gttcaccgat    1440

gatggccaat acatggcaaa caagaccgtc aactacgacg caatcgagag cctgctgaaa    1500

gcccgtatga aatatgtcag cggtggccaa gcaatgcaga actatcaaat tggtaatggc    1560

gagattttga ccagcgtgcg ctatggtaaa ggtgccctga agcagagcga taagggtgac    1620

gcgacgacgc gcactagcgg tgttggcgtg gttatgggta atcagccgaa cttctccctg    1680

gacggtaaag ttgtggccct gaatatgggt gcggcccatg cgaatcaaga ataccgtgca    1740

ctgatggtca gcactaaaga cggtgtggca acttacgcaa ccgatgctga cgcatccaaa    1800
```

-continued

```
gcgggcctgg tcaagcgtac cgacgagaac ggctacctgt acttcctgaa tgatgatctg   1860
aagggcgtcg cgaaccctca ggtttccggc ttcttgcaag tgtgggttcc agttggtgcc   1920
gccgatgacc aggacattcg cgtcgccgcc agcgacacgg cgagcacgga tggtaaaagc   1980
ctgcatcaag atgcggcgat ggacagccgc gtcatgtttg agggtttcag caattttcaa   2040
tccttcgcga ccaaagaaga agaatacacg aatgttgtta tcgcgaacaa tgtcgataag   2100
ttcgttagct ggggtatcac cgattttgaa atggctccgc agtatgttag cagcaccgac   2160
ggtcagttct tggacagcgt catccagaat ggctatgcgt ttactgatcg ctatgatctg   2220
ggtatgtcca aggcgaacaa gtatggcacg gcagaccaac tggttaaggc aatcaaagcc   2280
ctgcacgcta aaggcctgaa agttatggcg gactgggtcc cggatcaaat gtacaccttt   2340
ccaaaacagg aagttgtgac cgttacccgc accgacaaat tcggtaaacc gatcgccggc   2400
tctcaaatca atcacagctt gtatgtgacc gacaccaaat ccagcggcga cgactaccaa   2460
gcgaagtacg gcggtgcctt cctggatgaa ctgaaagaaa agtacccgga actgttcacg   2520
aaaaagcaaa ttagcacggg ccaagcgatt gatccgagcg tgaaaatcaa gcagtggagc   2580
gcaaaatact tcaatggttc gaatatcctg ggtcgcggtg cggactatgt gctgagcgac   2640
caggtcagca ataagtattt caacgtggcg agcgacacct tgttcctgcc gtccagcctg   2700
ctgggcaagg tcgtggagag cggcattcgt tacgacggca agggttacat ctacaacagc   2760
tccgcgaccg gcgatcaggt caaagcgtct ttcattacgg aagccggtaa cctgtattac   2820
ttcggcaaag acggttacat ggttactggt gcccagacga ttaatggcgc caactacttc   2880
ttcctggaaa acggtacggc actgcgtaat acgatttaca ccgatgctca aggtaatagc   2940
cactattacg cgaatgatgg caaacgctat gaaaatggct atcaacagtt cggtaacgat   3000
tggcgctact ttaaagatgg taacatggca gtcggcctga ccacggttga tggcaacgtg   3060
caatactttg acaaagacgg cgtccaggca aaggataaga ttatcgtcac ccgtgatggc   3120
aaggtccgtt acttcgatca gcacaacggt aacgcggcga ccaacacgtt cattgctgat   3180
aaaactggcc attggtatta cctgggtaaa gatggcgtcg cggtgactgg cgcccagacc   3240
gtcggcaaac aaaaactgta cttcgaggcc aacggtcaac aagttaaagg tgactttgtt   3300
acgtccgatg agggcaaact gtatttctat gacgttgatt ctggtgacat gtggacggac   3360
accttcatcg aggataaggc gggcaactgg ttctatttgg gcaaggatgg tgcggcagtt   3420
acgggtgccc aaacgattcg cggtcagaag ctgtacttca aggccaatgg tcaacaggtc   3480
aagggtgaca ttgttaaggg caccgacggt aaaatccgct actatgatgc aaaatccggt   3540
gaacaggtgt tcaacaaaac ggtgaaagct gcggatggca aaacgtatgt tatcggtaat   3600
gatggtgtcg cggtggaccc tagcgtggtt aaaggtcaaa cctttaagga cgcttcgggc   3660
gctctgcgtt tctacaactt gaagggtcaa ctggtcactg gcagcggctg gtatgaaacc   3720
gcgaaccatg actgggttta cattcagtcc ggcaaggcac tgaccggcga acagaccatt   3780
aacggtcaac acctgtattt caaagaagat ggtcaccaag tcaagggtca gttggtcacg   3840
ggcaccgatg gtaaagtgcg ttactatgac gccaacagcg gtgaccaagc attcaacaag   3900
agcgtcactg tgaatggtaa aacctattac tttggcaacg atggtacggc gcagactgct   3960
ggcaacccga agggtcagac gttcaaggat ggctccgaca tccgtttttta ctctatggaa   4020
ggccaactgg tgaccggctc gggttggtac gagaacgcgc aaggccagtg gctgtatgtg   4080
aaaaacggta aggtgctgac tggtctgcaa accgttggca gccagcgtgt ttacttcgac   4140
```

```
gagaatggta ttcaggccaa gggcaaagca gtgcgtacca gcgatggcaa aattcgttat   4200

ttcgacgaaa acagcggcag catgatcacg aatcaatgga agttcgtcta tggtcagtat   4260

tactactttg gtaacgacgg tgcacgtatt taccgtggtt ggaactaa                4308


<210> SEQ ID NO 2
<211> LENGTH: 1435
<212> TYPE: PRT
<213> ORGANISM: Streptococcus sobrinus

<400> SEQUENCE: 2

Met Val Asp Gly Lys Tyr Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350
```

```
Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Glu Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765
```

```
Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
        915                 920                 925

Ala Ser Phe Ile Thr Glu Ala Gly Asn Leu Tyr Tyr Phe Gly Lys Asp
    930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp  Trp Arg Tyr Phe Lys  Asp Gly Asn
        995                 1000                1005

Met Ala  Val Gly Leu Thr Thr  Val Asp Gly Asn Val  Gln Tyr Phe
    1010                1015                1020

Asp Lys  Asp Gly Val Gln Ala  Lys Asp Lys Ile Ile  Val Thr Arg
    1025                1030                1035

Asp Gly  Lys Val Arg Tyr Phe  Asp Gln His Asn Gly  Asn Ala Ala
    1040                1045                1050

Thr Asn  Thr Phe Ile Ala Asp  Lys Thr Gly His Trp  Tyr Tyr Leu
    1055                1060                1065

Gly Lys  Asp Gly Val Ala Val  Thr Gly Ala Gln Thr  Val Gly Lys
    1070                1075                1080

Gln Lys  Leu Tyr Phe Glu Ala  Asn Gly Gln Gln Val  Lys Gly Asp
    1085                1090                1095

Phe Val  Thr Ser Asp Glu Gly  Lys Leu Tyr Phe Tyr  Asp Val Asp
    1100                1105                1110

Ser Gly  Asp Met Trp Thr Asp  Thr Phe Ile Glu Asp  Lys Ala Gly
    1115                1120                1125

Asn Trp  Phe Tyr Leu Gly Lys  Asp Gly Ala Ala Val  Thr Gly Ala
    1130                1135                1140

Gln Thr  Ile Arg Gly Gln Lys  Leu Tyr Phe Lys Ala  Asn Gly Gln
    1145                1150                1155

Gln Val  Lys Gly Asp Ile Val  Lys Gly Thr Asp Gly  Lys Ile Arg
    1160                1165                1170

Tyr Tyr  Asp Ala Lys Ser Gly  Glu Gln Val Phe Asn  Lys Thr Val
```

```
    1175                1180                1185

Lys Ala  Ala Asp Gly Lys Thr  Tyr Val Ile Gly Asn  Asp Gly Val
    1190                1195                1200

Ala Val  Asp Pro Ser Val Val  Lys Gly Gln Thr Phe  Lys Asp Ala
    1205                1210                1215

Ser Gly  Ala Leu Arg Phe Tyr  Asn Leu Lys Gly Gln  Leu Val Thr
    1220                1225                1230

Gly Ser  Gly Trp Tyr Glu Thr  Ala Asn His Asp Trp  Val Tyr Ile
    1235                1240                1245

Gln Ser  Gly Lys Ala Leu Thr  Gly Glu Gln Thr Ile  Asn Gly Gln
    1250                1255                1260

His Leu  Tyr Phe Lys Glu Asp  Gly His Gln Val Lys  Gly Gln Leu
    1265                1270                1275

Val Thr  Gly Thr Asp Gly Lys  Val Arg Tyr Tyr Asp  Ala Asn Ser
    1280                1285                1290

Gly Asp  Gln Ala Phe Asn Lys  Ser Val Thr Val Asn  Gly Lys Thr
    1295                1300                1305

Tyr Tyr  Phe Gly Asn Asp Gly  Thr Ala Gln Thr Ala  Gly Asn Pro
    1310                1315                1320

Lys Gly  Gln Thr Phe Lys Asp  Gly Ser Asp Ile Arg  Phe Tyr Ser
    1325                1330                1335

Met Glu  Gly Gln Leu Val Thr  Gly Ser Gly Trp Tyr  Glu Asn Ala
    1340                1345                1350

Gln Gly  Gln Trp Leu Tyr Val  Lys Asn Gly Lys Val  Leu Thr Gly
    1355                1360                1365

Leu Gln  Thr Val Gly Ser Gln  Arg Val Tyr Phe Asp  Glu Asn Gly
    1370                1375                1380

Ile Gln  Ala Lys Gly Lys Ala  Val Arg Thr Ser Asp  Gly Lys Ile
    1385                1390                1395

Arg Tyr  Phe Asp Glu Asn Ser  Gly Ser Met Ile Thr  Asn Gln Trp
    1400                1405                1410

Lys Phe  Val Tyr Gly Gln Tyr  Tyr Tyr Phe Gly Asn  Asp Gly Ala
    1415                1420                1425

Arg Ile  Tyr Arg Gly Trp Asn
    1430                1435


<210> SEQ ID NO 3
<211> LENGTH: 4026
<212> TYPE: DNA
<213> ORGANISM: Streptococcus salivarius

<400> SEQUENCE: 3

atgatcgacg gcaaatacta ttatgttaat gaggacggta gccacaaaga aaactttgcg      60

attacggtta atggtcaact gctgtatttc ggtaaggacg gcgcactgac ctctagcagc     120

acttacagct ttaccccagg tacgacgaac atcgtggatg gcttttctat caacaaccgc     180

gcgtatgact ccagcgaagc gtcctttgaa ctgattgatg gctacttgac tgccgactcc     240

tggtatcgtc cggcttccat catcaaggac ggtgtcacgt ggcaggccag caccgcagag     300

gactttcgcc cgctgctgat ggcgtggtgg ccaaacgtgg atacccaggt gaactatctg     360

aactacatgt ctaaagtgtt taacctggac gcaaagtata gcagcaccga taaacaagag     420

actctgaagg ttgcagctaa ggatattcag attaagatcg agcagaaaat tcaggcggag     480

aaaagcaccc aatggctgcg cgaaacgatc agcgcttttg tgaaaaccca accacagtgg     540
```

-continued

```
aacaaagaga ctgagaatta ctcgaaaggt ggtggtgagg atcatctgca aggcggtgca    600
ctgctgtacg tgaatgatag ccgtaccccg tgggcaaata gcgattatcg ccgcctgaac    660
cgcaccgcta ccaatcaaac gggtacgatt gacaagtcca ttctggacga gcagagcgac    720
ccaaatcaca tgggcggttt cgacttcctg ctggcgaatg atgttgacct gtccaacccg    780
gttgtgcagg cagagcagct gaaccagatt cactacttga tgaattgggg ctctatcgtg    840
atgggtgaca aagacgcaaa ctttgatggt atccgtgtcg atgcagttga caacgtcgat    900
gccgacatgc tgcaactgta taccaactac ttccgtgaat actacggtgt taacaaaagc    960
gaagcgaacg cactggcgca cattagcgtt ttggaagcgt ggagcttgaa tgataatcac   1020
tacaacgaca aaaccgatgg tgcagcattg gcgatggaga ataagcagcg tctggcgctg   1080
ctgtttagcc tggctaaacc gattaaagag cgcaccccgg cagtgagccc gctgtataac   1140
aacaccttca atacgaccca acgcgatgag aaaaccgact ggatcaataa agacggttct   1200
aaggcctata acgaggatgg tactgtgaag cagagcacca ttggtaagta caatgaaaaa   1260
tatggtgatg catcgggcaa ttatgtgttc atccgtgccc atgataacaa tgtccaagac   1320
atcattgcgg agatcattaa gaaagaaatc aacccgaaaa gcgatggttt caccatcact   1380
gacgccgaaa tgaaacaagc gttcgagatt tacaataagg acatgctgag cagcgacaag   1440
aagtacaccc tgaataacat cccggcagct tatgccgtga tgttgcagaa catggaaacg   1500
attacccgtg tctattatgg tgacctgtac accgacgacg gccactacat ggaaaccaag   1560
tccccgtatt acgacaccat cgttaacctg atgaaaagcc gtatcaagta cgtcagcggt   1620
ggccaggccc aacgtagcta ctggctgccg accgacggca agatggacaa tagcgacgtt   1680
gagctgtatc gcaccaacga agtgtatacc agcgtccgtt acggtaaaga cattatgacc   1740
gcgaacgata ccgagggtag caagtacagc cgcaccagcg gccaggtcac cctggttgca   1800
aacaacccga agctgaccct ggaccagagc gcgaagctga atgtggaaat gggtaagatt   1860
cacgcgaatc agaaataccg tgccctgatt gtgggcacgg ctgacggtat caagaatttc   1920
accagcgacg cagatgctat cgcggcaggc tacgtgaaag aaaccgactc caatggcgtt   1980
ctgacttttg gcgctaatga catcaaaggt tatgaaacct tcgacatgtc cggctttgtt   2040
gctgtttggg tgccggtcgg cgcgagcgat gatcaggaca ttcgtgtcgc tcctagcact   2100
gaggccaaga aagagggtga attgaccctg aaagcgaccg aagcatacga ttcccagctg   2160
atctatgaag gttttagcaa ttttcaaacc atcccggatg gtagcgaccc gagcgtgtac   2220
accaatcgca agatcgcaga gaacgtggac ctgttcaagt cctggggtgt tacctcgttt   2280
gaaatggcac cgcagttcgt ttccgcagat gatggcactt ttctggactc tgtgatccaa   2340
aacggctatg cgtttgccga tcgttacgat ttggcgatga gcaagaacaa caaatacggc   2400
agcaaagagg acttgcgtga cgcgctgaaa gccctgcata aagcaggcat ccaggcgatt   2460
gcagactggg tcccggacca gatttatcag ttgccgggca aagaagtggt cacggcgact   2520
cgcaccgacg gcgcaggccg taaaatcgcg gacgcgatca ttgatcatag cctgtacgtt   2580
gcgaacacta agagcagcgg caaagattac caggcgaagt acggtggtga gttcttggcg   2640
gagctgaagg ccaagtaccc ggagatgttc aaagtgaaca tgatttctac cggcaaaccg   2700
attgatgaca gcgtcaaact gaaacagtgg aaagcagaat actttaacgg caccaacgtc   2760
ttggagcgcg gtgtgggtta tgtcctgagc gatgaagcca cgggtaaata ctttaccgtc   2820
acgaaggatg gcaacttcat tccgttgcag ctgacgggta atgagaaagt cgtgaccggc   2880
tttagcaatg atggcaaagg tatcacctac ttcggtacga gcggcactca agcgaaatct   2940
```

```
gcgttcgtta cgttcaatgg taatacttac tattttgacg ctcgtggtca catggttacg   3000

aacggcgagt attcgccgaa cggtaaggat gtttaccgtt tcctgccgaa tggtattatg   3060

ctgtctaacg ctttttacgt tgatgcaaat ggtaacacgt acctgtacaa cagcaagggc   3120

caaatgtaca aaggcggtta caccaaattt gacgttaccg aaacggacaa agatggtaag   3180

gaaagcaagg tggtgaagtt tcgttacttt acgaacgaag gtgtcatggc aaaaggcgtt   3240

accgtgattg acggcttcac gcaatacttt ggtgaagatg gtttccaagc gaaagacaag   3300

ctggtcacgt tcaagggcaa gacgtactac ttcgatgcac acaccggcaa tgcgatcaag   3360

gacacctggc gtaatatcaa tggcaagtgg tatcatttcg acgcgaacgg cgttgcagcg   3420

accggcgctc aggtcatcaa tggccaaaaa ctgtatttca acgaggacgg cagccaagtg   3480

aaaggcggtg ttgtcaaaaa cgcggacggt acgtattcta aatacaaaga gggttctggt   3540

gaactggtta ccaacgagtt cttcacgacg gatggcaatg tttggtacta cgcaggcgcg   3600

aatggcaaga ccgttacggg tgcccaggtg attaacggcc aacacctgta cttcaatgcg   3660

gacggttcgc aagtgaaggg cggtgtggtc aagaacgcgg atggcaccta tagcaaatat   3720

gatgcgtcta ccggcgaacg cctgaccaat gagtttttca ccacgggtga taacaactgg   3780

tactacattg gcgcaaacgg caagagcgtg acgggcgagg tcaagatcgg tgacgatacc   3840

tatttctttg ccaaagatgg caagcaagtt aagggtcaaa ctgtcagcgc gggtaacggt   3900

cgtattagct actactatgg tgatagcggt aagcgtgcgg tgagcacttg gatcgaaatc   3960

caaccgggtg tttatgtcta cttcgacaag aacggcattg cctatccgcc tcgtgtgctg   4020

aattaa                                                              4026
```

```
<210> SEQ ID NO 4
<211> LENGTH: 1341
<212> TYPE: PRT
<213> ORGANISM: Streptococcus salivarius

<400> SEQUENCE: 4

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175
```

```
Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590
```

```
Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
        995                 1000                 1005

Lys Asp  Val Tyr Arg Phe Leu  Pro Asn Gly Ile Met  Leu Ser Asn
```

```
    1010                1015                1020

Ala Phe  Tyr Val Asp Ala Asn  Gly Asn Thr Tyr Leu  Tyr Asn Ser
    1025                1030                1035

Lys Gly  Gln Met Tyr Lys Gly  Gly Tyr Thr Lys Phe  Asp Val Thr
    1040                1045                1050

Glu Thr  Asp Lys Asp Gly Lys  Glu Ser Lys Val Val  Lys Phe Arg
    1055                1060                1065

Tyr Phe  Thr Asn Glu Gly Val  Met Ala Lys Gly Val  Thr Val Ile
    1070                1075                1080

Asp Gly  Phe Thr Gln Tyr Phe  Gly Glu Asp Gly Phe  Gln Ala Lys
    1085                1090                1095

Asp Lys  Leu Val Thr Phe Lys  Gly Lys Thr Tyr Tyr  Phe Asp Ala
    1100                1105                1110

His Thr  Gly Asn Ala Ile Lys  Asp Thr Trp Arg Asn  Ile Asn Gly
    1115                1120                1125

Lys Trp  Tyr His Phe Asp Ala  Asn Gly Val Ala Ala  Thr Gly Ala
    1130                1135                1140

Gln Val  Ile Asn Gly Gln Lys  Leu Tyr Phe Asn Glu  Asp Gly Ser
    1145                1150                1155

Gln Val  Lys Gly Gly Val Val  Lys Asn Ala Asp Gly  Thr Tyr Ser
    1160                1165                1170

Lys Tyr  Lys Glu Gly Ser Gly  Glu Leu Val Thr Asn  Glu Phe Phe
    1175                1180                1185

Thr Thr  Asp Gly Asn Val Trp  Tyr Tyr Ala Gly Ala  Asn Gly Lys
    1190                1195                1200

Thr Val  Thr Gly Ala Gln Val  Ile Asn Gly Gln His  Leu Tyr Phe
    1205                1210                1215

Asn Ala  Asp Gly Ser Gln Val  Lys Gly Gly Val Val  Lys Asn Ala
    1220                1225                1230

Asp Gly  Thr Tyr Ser Lys Tyr  Asp Ala Ser Thr Gly  Glu Arg Leu
    1235                1240                1245

Thr Asn  Glu Phe Phe Thr Thr  Gly Asp Asn Asn Trp  Tyr Tyr Ile
    1250                1255                1260

Gly Ala  Asn Gly Lys Ser Val  Thr Gly Glu Val Lys  Ile Gly Asp
    1265                1270                1275

Asp Thr  Tyr Phe Phe Ala Lys  Asp Gly Lys Gln Val  Lys Gly Gln
    1280                1285                1290

Thr Val  Ser Ala Gly Asn Gly  Arg Ile Ser Tyr Tyr  Tyr Gly Asp
    1295                1300                1305

Ser Gly  Lys Arg Ala Val Ser  Thr Trp Ile Glu Ile  Gln Pro Gly
    1310                1315                1320

Val Tyr  Val Tyr Phe Asp Lys  Asn Gly Ile Ala Tyr  Pro Pro Arg
    1325                1330                1335

Val Leu  Asn
    1340
```

```
<210> SEQ ID NO 5
<211> LENGTH: 3744
<212> TYPE: DNA
<213> ORGANISM: Streptococcus salivarius

<400> SEQUENCE: 5

atgccaagcc acattaagac catcaacggc aaacaatact acgtggagga tgacggtacg     60

attcgcaaga attacgtcct ggagcgtatc ggtggcagcc aatactttaa tgcagaaacc    120
```

```
ggtgaactgt ctaatcagaa agagtatcgt ttcgacaaaa atggtggtac tggtagcagc    180
gcggacagca cgaacaccaa cgtgactgtg aacggtgaca aaaacgcatt ttacggtacc    240
acggacaaag acattgagct ggtcgacggc tatttcaccg cgaacacctg gtatcgcccg    300
aaagaaatcc tgaaagacgg caaagaatgg accgccagca cggagaacga taaacgcccg    360
ctgctgaccg tctggtggcc tagcaaagca atccaggcgt cttatctgaa ctacatgaaa    420
gagcaaggcc tgggtaccaa ccaaacgtac acgagcttct ccagccaaac ccaaatggat    480
caagcagccc tggaagtgca aaagcgtatt gaagagcgca tcgcacgcga gggcaatacc    540
gactggctgc gcacgaccat caagaacttc gtgaaaaccc aaccgggttg gaacagcacc    600
tctgaaaatc tggacaataa tgatcatctg caaggtggcg ccctgctgta caataacgac    660
tcccgcacga gccacgcgaa cagcgactat cgcctgctga atcgtacgcc gaccagccag    720
accggcaaac acaatccgaa atacaccaaa gataccagca atggtggttt cgaatttctg    780
ctggcgaacg acatcgataa ctctaatccg gcggttcaag cagagcaact gaactggctg    840
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa aatacggtgc tgatcaaagc caagatcagg cgatcaaaca cttgagcatc   1020
ctggaagcgt ggtcccataa cgacgcctac tataacgaag ataccaaagg cgcgcagttg   1080
ccgatggatg atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatggcgaa ctacgcgttc gtacgcgcgc atgatagcga ggtgcaatcg   1260
attattggcc agatcatcaa aaacgagatc aatccgcaaa gcaccggtaa tacgttcacc   1320
ctggatgaga tgaagaaagc gtttgagatt tacaacaagg atatgcgtag cgcgaataag   1380
cagtatacgc agtacaacat cccgagcgcg tatgcgttga tgctgaccca caaggatacc   1440
gttccgcgtg tgtattacgg tgatatgtat acggacgacg gtcagtacat ggcgcaaaag   1500
agcccatact atgatgcgat cgaaacgctg ctgaaaggtc gcatccgcta tgccgcaggt   1560
ggtcaggaca tgaaggtcaa ctatattggt tacggtaaca ctaacggctg ggatgctgcg   1620
ggcgtgctga ccagcgtacg ttatggcacg ggcgcaaata gcgccagcga tacgggtacc   1680
gccgaaacgc gtaatcaagg tatggcagtg attgttagca accaaccggc gctgcgtctg   1740
actagcaatt tgaccattaa catgggtgcc gcacaccgta atcaggctta ccgtccgctg   1800
ctgctgacga ccaacgatgg cgtcgcgacc tatttgaacg atagcgatgc gaatggtatc   1860
gttaagtaca ccgacggtaa tggtaatctg accttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca agttatctac gaaggcttca gcaacttcca ggacttcgtt   2100
cagaatccga gccagtatac caacaaaaag attgcagaga atgcaaattt gttcaaatcc   2160
tggggtatta ccagctttga atttgcgccg cagtacgtga gctcggatga tggtagcttc   2220
ctggacagcg ttattcagaa cggttatgcg tttacggacc gctacgacat tggtatgagc   2280
aaagacaaca aatatggttc gctggcggat ttgaaggcag cactgaagag cttgcatgcc   2340
gttggtatta gcgcaatcgc ggattgggtt cctgatcaga tctacaatct gccaggcgac   2400
gaggtcgtca ccgcaacccg cgttaacaac tacggcgaaa ccaaagatgg tgcaatcatt   2460
```

```
gatcactctt tgtacgcggc caaaacccgt acttttggta acgactacca gggtaagtat   2520

ggtggtgcgt tcctggacga gctgaaacgt ctgtatccgc agatctttga ccgcgttcag   2580

atttctaccg gtaagcgcat gaccacggac gagaagatca cccaatggtc tgcaaagtat   2640

atgaacggta cgaacatctt ggaccgtggc tctgaatacg ttttgaagaa tggtctgaat   2700

ggttactatg gcaccaatgg tggcaaagtt tcgctgccga aagttgtggg tagcaatcaa   2760

agcacgaatg gcgacaatca aaacggcgac ggtagcggca agtttgaaaa gcgtctgttc   2820

agcgtgcgtt accgttataa caatggccag tacgcgaaaa atgcctttat caaagataac   2880

gacggcaatg tttactattt cgacaatagc ggtcgtatgg ctgtcggtga gaaaacgatt   2940

gacggcaagc agtacttctt cctggctaat ggcgttcagc tgcgtgacgg ctaccgtcaa   3000

aatcgtcgcg gtcaggtgtt ttactacgac cagaatggtg tgctgaacgc aaacggtaaa   3060

caagacccga agcctgacaa caataacaat gcgagcggcc gtaatcaatt cgtccagatc   3120

ggtaacaacg tgtgggcgta ttatgatggc aatggtaaac gtgtcaccgg tcaccagaac   3180

atcaacggtc aggagttgtt tttcgataac aacggtgtcc aggttaaggg tcgtacggtg   3240

aatgagaacg gtgcaattcg ctactatgac gcgaatagcg gtgagatggc acgcaatcgt   3300

ttcgcggaga ttgaaccggg cgtctgggca tactttaaca atgacggcac cgcagtgaag   3360

ggttctcaga atatcaatgg tcaagacctg tacttcgacc agaacggtcg tcaggtcaag   3420

ggtgcgctgg ccaatgttga tggcaacctg cgctattacg acgttaacag cggtgagctg   3480

taccgtaatc gtttccacga aatcgacggc agctggtatt actttgatgg taacggtaat   3540

gcggtgaagg gtatggtcaa tatcaacggc caaaatctgt tgtttgacaa taacggcaaa   3600

cagattaagg gtcatctggt ccgcgtcaac ggcgtcgtgc gctattttga tccgaactct   3660

ggtgaaatgg cggttaatcg ttgggttgag gtgagcccag gttggtgggt ttactttgac   3720

ggtgaaggtc gtggtcagat ctaa                                          3744
```

```
<210> SEQ ID NO 6
<211> LENGTH: 1247
<212> TYPE: PRT
<213> ORGANISM: Streptococcus salivarius

<400> SEQUENCE: 6

Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
        35                  40                  45

Tyr Arg Phe Asp Lys Asn Gly Gly Thr Gly Ser Ser Ala Asp Ser Thr
    50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140
```

```
Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
    210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
        275                 280                 285

Ile Thr Gly Gly Ser Glu Asp Glu Asn Phe Asp Gly Val Arg Val Asp
    290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
    370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
        515                 520                 525

Ile Gly Tyr Gly Asn Thr Asn Gly Trp Asp Ala Ala Gly Val Leu Thr
    530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
```

```
                565                 570                 575

Ala Leu Arg Leu Thr Ser Asn Leu Thr Ile Asn Met Gly Ala Ala His
            580                 585                 590

Arg Asn Gln Ala Tyr Arg Pro Leu Leu Leu Thr Thr Asn Asp Gly Val
        595                 600                 605

Ala Thr Tyr Leu Asn Asp Ser Asp Ala Asn Gly Ile Val Lys Tyr Thr
    610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
    690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
        755                 760                 765

Ala Asp Leu Lys Ala Ala Leu Lys Ser Leu His Ala Val Gly Ile Ser
    770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
        835                 840                 845

Lys Arg Leu Tyr Pro Gln Ile Phe Asp Arg Val Gln Ile Ser Thr Gly
    850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                885                 890                 895

Asn Gly Leu Asn Gly Tyr Tyr Gly Thr Asn Gly Gly Lys Val Ser Leu
            900                 905                 910

Pro Lys Val Val Gly Ser Asn Gln Ser Thr Asn Gly Asp Asn Gln Asn
        915                 920                 925

Gly Asp Gly Ser Gly Lys Phe Glu Lys Arg Leu Phe Ser Val Arg Tyr
    930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990
```

```
Gln Leu Arg Asp Gly Tyr Arg Gln  Asn Arg Arg Gly Gln  Val Phe Tyr
        995                 1000                 1005

Tyr Asp  Gln Asn Gly Val Leu  Asn Ala Asn Gly Lys  Gln Asp Pro
    1010                 1015                 1020

Lys Pro  Asp Asn Asn Asn Asn  Ala Ser Gly Arg Asn  Gln Phe Val
    1025                 1030                 1035

Gln Ile  Gly Asn Asn Val Trp  Ala Tyr Tyr Asp Gly  Asn Gly Lys
    1040                 1045                 1050

Arg Val  Thr Gly His Gln Asn  Ile Asn Gly Gln Glu  Leu Phe Phe
    1055                 1060                 1065

Asp Asn  Asn Gly Val Gln Val  Lys Gly Arg Thr Val  Asn Glu Asn
    1070                 1075                 1080

Gly Ala  Ile Arg Tyr Tyr Asp  Ala Asn Ser Gly Glu  Met Ala Arg
    1085                 1090                 1095

Asn Arg  Phe Ala Glu Ile Glu  Pro Gly Val Trp Ala  Tyr Phe Asn
    1100                 1105                 1110

Asn Asp  Gly Thr Ala Val Lys  Gly Ser Gln Asn Ile  Asn Gly Gln
    1115                 1120                 1125

Asp Leu  Tyr Phe Asp Gln Asn  Gly Arg Gln Val Lys  Gly Ala Leu
    1130                 1135                 1140

Ala Asn  Val Asp Gly Asn Leu  Arg Tyr Tyr Asp Val  Asn Ser Gly
    1145                 1150                 1155

Glu Leu  Tyr Arg Asn Arg Phe  His Glu Ile Asp Gly  Ser Trp Tyr
    1160                 1165                 1170

Tyr Phe  Asp Gly Asn Gly Asn  Ala Val Lys Gly Met  Val Asn Ile
    1175                 1180                 1185

Asn Gly  Gln Asn Leu Leu Phe  Asp Asn Asn Gly Lys  Gln Ile Lys
    1190                 1195                 1200

Gly His  Leu Val Arg Val Asn  Gly Val Val Arg Tyr  Phe Asp Pro
    1205                 1210                 1215

Asn Ser  Gly Glu Met Ala Val  Asn Arg Trp Val Glu  Val Ser Pro
    1220                 1225                 1230

Gly Trp  Trp Val Tyr Phe Asp  Gly Glu Gly Arg Gly  Gln Ile
    1235                 1240                 1245
```

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg     60

gtcactagcc ctgaagccac gaaagaggcg gacaaacgca cgaacactaa agaggccgac    120

gttctgacgc ctgcaaaaga aacgaacgca gtcgagactg cgaccaccac taacacccag    180

gcgacggcgg aggccgccac gaccgcgacc accgcggacg tcgcggtggc tgcggtgccg    240

aacaaagaag cggtcgttac cacggatgct ccggcggtca cgaccgagaa agcggaagaa    300

cagccggcta ccgttaaagc agaagtcgtc aatacggaag tgaaagcgcc ggaagcggct    360

ctgaaagaca gcgaggttga ggcagcgctg agcctgaaga acatcaagaa cattgatggc    420

aagtattact atgttaatga ggatggcagc cacaaagaga atttcgctat taccgtgaat    480

ggccagctgc tgtactttgg taaagacggt gcgctgacgt cctctagcac gtattctttt    540

accccaggca ctaccaatat cgtggacggt tttagcatta acaaccgcgc ttacgacagc    600
```

```
agcgaggcga gctttgagct gatcgacggt tacttgaccg cagacagctg gtatcgtccg    660
gctagcatca tcaaagatgg tgttacgtgg caagcgtcca ccgccgagga ttttcgtccg    720
ctgctgatgg catggtggcc gaatgtggat acgcaggtga actatttgaa ttacatgtcc    780
aaagttttca acctggacgc gaaatactct agcaccgaca aacaggaaac cctgaaagtg    840
gcagcaaaag acattcaaat caagattgaa caaaagattc aagcggagaa gagcacgcag    900
tggctgcgtg aaactatcag cgcctttgtg aaaacccagc cgcagtggaa caaagaaacc    960
gagaattaca gcaagggtgg tggtgaggac cacctgcaag gtggcgcact gctgtatgtt   1020
aacgacagcc gtaccccttg ggcgaatagc gattaccgtc gtctgaatcg caccgcaacc   1080
aatcagacgg gcacgatcga taagtctatt ctggacgagc agtctgaccc aaaccacatg   1140
ggcggtttcg actttctgct ggcgaacgac gtcgacctga gcaatccggt cgtgcaggct   1200
gagcagctga atcaaatcca ctatctgatg aattggggtt ccattgtgat gggtgacaag   1260
gatgcgaact ttgacggcat tcgtgtcgat gcagttgaca acgtggacgc ggacatgttg   1320
caactgtata ccaattactt ccgtgagtac tacggtgtga acaagagcga agctaacgca   1380
ctggctcaca tcagcgttct ggaggcgtgg agcctgaatg ataatcatta caatgacaag   1440
accgatggtg cggcactggc aatggagaat aagcaacgtc tggcgctgtt gttttcgttg   1500
gcgaaaccga tcaaagagcg taccccggca gtgagcccgc tgtataacaa caccttcaat   1560
accacccagc gtgatgaaaa gaccgattgg attaacaaag acggtagcaa ggcttacaac   1620
gaagatggca cggtcaaaca atcgaccatc ggtaagtaca acgagaaata cggtgacgca   1680
tccggtaact acgttttcat ccgtgcccac gataacaacg tccaggacat catcgccgag   1740
atcatcaaga aagagatcaa cccgaaaagc gacggcttca ccatcaccga cgccgaaatg   1800
aagcaagcct ttgaaatcta taacaaagat atgctgtcga gcgacaaaaa gtataccctg   1860
aataacattc cggcagcgta tgccgtgatg ttgcagaata tggaaacgat tacccgcgtc   1920
tattacggtg atctgtatac ggacgacggt cactacatgg aaaccaaatc tccgtattac   1980
gataccatcg tgaatttgat gaagagccgt atcaagtatg tttcgggtgg ccaggcgcaa   2040
cgtagctatt ggctgccgac cgacggtaag atggacaata gcgacgttga gctgtaccgc   2100
acgaatgagg tttacacgag cgtgcgctat ggtaaggata tcatgaccgc taatgatacc   2160
gaaggctcta agtattcccg caccagcggc caagtcacct tggtcgcgaa caatccgaag   2220
ctgaatctgg accaaagcgc caagttgaat gtggagatgg gcaaaatcca tgcgaatcag   2280
aagtatcgcg cactgattgt cggcactgcg gacggcatta agaactttac ttccgacgcg   2340
gacgccattg cagcgggtta tgtgaaagaa accgatagca acggcgtgct gaccttcggt   2400
gctaacgaca ttaagggcta cgaaacgttt gatatgagcg gtttcgtggc ggtgtgggtt   2460
ccggtgggtg catctgacaa tcaggacatt cgtgttgcgc cgagcaccga ggcaaagaaa   2520
gaaggtgagc tgaccttgaa ggcgacggaa gcgtatgata gccagctgat ttacgaaggc   2580
tttagcaatt tccagacgat cccagatggc agcgatccgt ccgtgtatac gaaccgcaag   2640
attgcggaga acgtggatct gttcaaaagc tggggtgtca ccagctttga gatggcaccg   2700
caatttgtct cggcggatga tggcaccttt ctggatagcg ttattcagaa tggctacgcc   2760
ttcgccgacc gttatgacct ggccatgtcc aagaacaaca agtatggtag caaagaggac   2820
ctgcgtgatg cactgaaagc actgcataag gcgggtattc aagctatcgc agactgggtt   2880
ccagaccaga tctaccagct gccgggcaaa gaagttgtca ccgccacccg tacggatggt   2940
```

```
gctggccgta agatcgcaga cgcgattatc gaccattctc tgtatgttgc aaacagcaaa   3000

agcagcggca aagattatca agcaaagtac ggtggcgagt tcctggccga gctgaaagcc   3060

aaatacccgg aaatgttcaa agttaacatg attagcacgg gtaagccgat tgatgactcc   3120

gtgaaattga agcaatggaa agccgagtac ttcaatggca ccaacgtttt ggaacgtggt   3180

gtcggctatg ttctgagcga cgaggcgacc ggtaagtatt tcacggtgac caaagaaggc   3240

aatttcattc cgctgcaact gacgggtaaa gagaaagtta tcacgggttt ctccagcgat   3300

ggtaagggta tcacctattt cggtacgagc ggtacgcagg cgaagtctgc gtttgttacc   3360

ttcaatggta acacctacta tttcgacgcg cgtggccaca tggttaccaa tagcgaatac   3420

agcccgaatg gcaaggacgt ctaccgtttt ctgccgaacg gtatcatgct gagcaatgcg   3480

ttttacattg atgcgaacgg taatacctac ctgtacaact ctaagggtca aatgtacaaa   3540

ggcggttaca cgaaattcga tgtttctgaa acggataagg acggtaaaga gtccaaggtc   3600

gtcaagttcc gctactttac gaacgaaggc gtcatggcca agggtgttac cgtcattgat   3660

ggttttaccc aatacttcgg tgaggacggc tttcaagcga aggataagct ggtcaccttc   3720

aagggcaaga cgtattactt cgacgcacac actggtaatg gtatcaaaga tacctggcgc   3780

aatatcaatg gtaaatggta ctatttcgac gcgaatggcg ttgctgcgac cggtgcgcag   3840

gtgattaacg gccagaaact gtacttcaac gaggatggct cccaagtcaa aggcggcgtg   3900

gttaagaacg cagacggcac ctatagcaaa tacaaagaag gttttggtga gctggttact   3960

aacgagtttt tcacgactga tggcaatgtt tggtactacg ccggtgcaaa tggtaaaacc   4020

gttaccggtg cacaagtgat caacggccaa catttgtact tcaatgcgga cggttcccag   4080

gtgaagggtg gcgttgtcaa gaacgcggat ggcacctaca gcaagtacaa tgctagcact   4140

ggtgaacgtc tgacgaacga gttctttacg accggtgata acaattggta ttacattggc   4200

gcaaacggta agagcgtgac gggtgaggtc aagattggtg atgatactta ctttttcgcg   4260

aaggatggca aacaagttaa aggtcaaacc gtcagcgccg gtaatggtcg cattagctac   4320

tactacggtg acagcggcaa gcgtgcggtt agcacctgga ttgagattca gccgggtgtt   4380

tatgtgtatt tcgacaaaaa cggtttggcg taccctccgc gtgttctgaa ttaa         4434
```

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Thr Asn Thr Gln Ala Thr Ala Glu
    50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110
```

```
Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
        275                 280                 285

Ile Glu Gln Lys Ile Gln Ala Glu Lys Ser Thr Gln Trp Leu Arg Glu
    290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Gly Glu Asp His Leu Gln Gly Gly Ala
                325                 330                 335

Leu Leu Tyr Val Asn Asp Ser Arg Thr Pro Trp Ala Asn Ser Asp Tyr
            340                 345                 350

Arg Arg Leu Asn Arg Thr Ala Thr Asn Gln Thr Gly Thr Ile Asp Lys
        355                 360                 365

Ser Ile Leu Asp Glu Gln Ser Asp Pro Asn His Met Gly Gly Phe Asp
    370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
            420                 425                 430

Asp Asn Val Asp Ala Asp Met Leu Gln Leu Tyr Thr Asn Tyr Phe Arg
        435                 440                 445

Glu Tyr Tyr Gly Val Asn Lys Ser Glu Ala Asn Ala Leu Ala His Ile
    450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
            500                 505                 510

Pro Leu Tyr Asn Asn Thr Phe Asn Thr Thr Gln Arg Asp Glu Lys Thr
        515                 520                 525

Asp Trp Ile Asn Lys Asp Gly Ser Lys Ala Tyr Asn Glu Asp Gly Thr
```

```
    530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
            580                 585                 590

Phe Thr Ile Thr Asp Ala Glu Met Lys Gln Ala Phe Glu Ile Tyr Asn
        595                 600                 605

Lys Asp Met Leu Ser Ser Asp Lys Lys Tyr Thr Leu Asn Asn Ile Pro
    610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
                645                 650                 655

Ser Pro Tyr Tyr Asp Thr Ile Val Asn Leu Met Lys Ser Arg Ile Lys
            660                 665                 670

Tyr Val Ser Gly Gly Gln Ala Gln Arg Ser Tyr Trp Leu Pro Thr Asp
        675                 680                 685

Gly Lys Met Asp Asn Ser Asp Val Glu Leu Tyr Arg Thr Asn Glu Val
    690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
                725                 730                 735

Asn Asn Pro Lys Leu Asn Leu Asp Gln Ser Ala Lys Leu Asn Val Glu
            740                 745                 750

Met Gly Lys Ile His Ala Asn Gln Lys Tyr Arg Ala Leu Ile Val Gly
        755                 760                 765

Thr Ala Asp Gly Ile Lys Asn Phe Thr Ser Asp Ala Asp Ala Ile Ala
    770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
                805                 810                 815

Ala Val Trp Val Pro Val Gly Ala Ser Asp Asn Gln Asp Ile Arg Val
            820                 825                 830

Ala Pro Ser Thr Glu Ala Lys Lys Glu Gly Glu Leu Thr Leu Lys Ala
        835                 840                 845

Thr Glu Ala Tyr Asp Ser Gln Leu Ile Tyr Glu Gly Phe Ser Asn Phe
    850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
            900                 905                 910

Ser Val Ile Gln Asn Gly Tyr Ala Phe Ala Asp Arg Tyr Asp Leu Ala
        915                 920                 925

Met Ser Lys Asn Asn Lys Tyr Gly Ser Lys Glu Asp Leu Arg Asp Ala
    930                 935                 940

Leu Lys Ala Leu His Lys Ala Gly Ile Gln Ala Ile Ala Asp Trp Val
945                 950                 955                 960
```

-continued

```
Pro Asp Gln Ile Tyr Gln Leu Pro Gly Lys Glu Val Val Thr Ala Thr
                965                 970                 975

Arg Thr Asp Gly Ala Gly Arg Lys Ile Ala Asp Ala Ile Ile Asp His
            980                 985                 990

Ser Leu Tyr Val Ala Asn Ser Lys  Ser Ser Gly Lys Asp  Tyr Gln Ala
        995                 1000                 1005

Lys Tyr  Gly Gly Glu Phe Leu  Ala Glu Leu Lys Ala  Lys Tyr Pro
    1010                 1015                 1020

Glu Met  Phe Lys Val Asn Met  Ile Ser Thr Gly Lys  Pro Ile Asp
    1025                 1030                 1035

Asp Ser  Val Lys Leu Lys Gln  Trp Lys Ala Glu Tyr  Phe Asn Gly
    1040                 1045                 1050

Thr Asn  Val Leu Glu Arg Gly  Val Gly Tyr Val Leu  Ser Asp Glu
    1055                 1060                 1065

Ala Thr  Gly Lys Tyr Phe Thr  Val Thr Lys Glu Gly  Asn Phe Ile
    1070                 1075                 1080

Pro Leu  Gln Leu Thr Gly Lys  Glu Lys Val Ile Thr  Gly Phe Ser
    1085                 1090                 1095

Ser Asp  Gly Lys Gly Ile Thr  Tyr Phe Gly Thr Ser  Gly Thr Gln
    1100                 1105                 1110

Ala Lys  Ser Ala Phe Val Thr  Phe Asn Gly Asn Thr  Tyr Tyr Phe
    1115                 1120                 1125

Asp Ala  Arg Gly His Met Val  Thr Asn Ser Glu Tyr  Ser Pro Asn
    1130                 1135                 1140

Gly Lys  Asp Val Tyr Arg Phe  Leu Pro Asn Gly Ile  Met Leu Ser
    1145                 1150                 1155

Asn Ala  Phe Tyr Ile Asp Ala  Asn Gly Asn Thr Tyr  Leu Tyr Asn
    1160                 1165                 1170

Ser Lys  Gly Gln Met Tyr Lys  Gly Gly Tyr Thr Lys  Phe Asp Val
    1175                 1180                 1185

Ser Glu  Thr Asp Lys Asp Gly  Lys Glu Ser Lys Val  Val Lys Phe
    1190                 1195                 1200

Arg Tyr  Phe Thr Asn Glu Gly  Val Met Ala Lys Gly  Val Thr Val
    1205                 1210                 1215

Ile Asp  Gly Phe Thr Gln Tyr  Phe Gly Glu Asp Gly  Phe Gln Ala
    1220                 1225                 1230

Lys Asp  Lys Leu Val Thr Phe  Lys Gly Lys Thr Tyr  Tyr Phe Asp
    1235                 1240                 1245

Ala His  Thr Gly Asn Gly Ile  Lys Asp Thr Trp Arg  Asn Ile Asn
    1250                 1255                 1260

Gly Lys  Trp Tyr Tyr Phe Asp  Ala Asn Gly Val Ala  Ala Thr Gly
    1265                 1270                 1275

Ala Gln  Val Ile Asn Gly Gln  Lys Leu Tyr Phe Asn  Glu Asp Gly
    1280                 1285                 1290

Ser Gln  Val Lys Gly Gly Val  Val Lys Asn Ala Asp  Gly Thr Tyr
    1295                 1300                 1305

Ser Lys  Tyr Lys Glu Gly Phe  Gly Glu Leu Val Thr  Asn Glu Phe
    1310                 1315                 1320

Phe Thr  Thr Asp Gly Asn Val  Trp Tyr Tyr Ala Gly  Ala Asn Gly
    1325                 1330                 1335

Lys Thr  Val Thr Gly Ala Gln  Val Ile Asn Gly Gln  His Leu Tyr
    1340                 1345                 1350
```

```
Phe Asn  Ala Asp Gly Ser Gln  Val Lys Gly Gly Val  Val Lys Asn
    1355                 1360                 1365

Ala Asp  Gly Thr Tyr Ser Lys  Tyr Asn Ala Ser Thr  Gly Glu Arg
    1370                 1375                 1380

Leu Thr  Asn Glu Phe Phe Thr  Thr Gly Asp Asn Asn  Trp Tyr Tyr
    1385                 1390                 1395

Ile Gly  Ala Asn Gly Lys Ser  Val Thr Gly Glu Val  Lys Ile Gly
    1400                 1405                 1410

Asp Asp  Thr Tyr Phe Phe Ala  Lys Asp Gly Lys Gln  Val Lys Gly
    1415                 1420                 1425

Gln Thr  Val Ser Ala Gly Asn  Gly Arg Ile Ser Tyr  Tyr Tyr Gly
    1430                 1435                 1440

Asp Ser  Gly Lys Arg Ala Val  Ser Thr Trp Ile Glu  Ile Gln Pro
    1445                 1450                 1455

Gly Val  Tyr Val Tyr Phe Asp  Lys Asn Gly Leu Ala  Tyr Pro Pro
    1460                 1465                 1470

Arg Val  Leu Asn
    1475
```

```
<210> SEQ ID NO 9
<211> LENGTH: 4311
<212> TYPE: DNA
<213> ORGANISM: Streptococcus downei

<400> SEQUENCE: 9

atggttgacg gcaaatacta ctactacgat caggacggca acgtaaagaa aaacttcgcg     60

gttagcgtgg gcgagaaaat ctattacttt gacgaaactg gcgcctacaa agacaccagc    120

aaagttgagg cggacaaaag cggcagcgac attagcaagg aagagactac cttcgcggca    180

aacaaccgcg cctacagcac cagcgcggag aattttgagg cgatcgacaa ttatctgacc    240

gcggactcct ggtatcgtcc taaatccatc ctgaaggatg gcaaaacgtg gacggaaagc    300

agcaaagatg actttcgtcc gctgctgatg gcgtggtggc cggataccga aacgaagcgc    360

aattacgtga actacatgaa caaagttgtt ggcatcgaca agacctatac cgcggaaacc    420

agccaggccg acttgaccgc tgcggcggaa ctggtgcaag cacgcattga gcagaagatc    480

acgaccgaac agaacacgaa atggctgcgt gaggcaatct cggcatttgt taaaacgcaa    540

ccgcagtgga acggtgaaag cgagaagccg tacgacgatc acctgcaaaa cggtgctctg    600

aaatttgata atcagagcga cctgaccccg gatacgcaaa gcaactaccg tctgttgaac    660

cgtaccccga ctaatcagac gggtagcctg gacagccgct tcacttataa cgcgaacgac    720

cctttgggcg gttatgagct gctgctggca aatgacgtcg ataacagcaa tccgatcgtg    780

caggcggagc agctgaactg gctgcattac ctgctgaatt ttggtacgat ctacgccaaa    840

gatgccgacg ctaacttcga tagcattcgt gtggacgcgg ttgataacgt cgatgcggat    900

ctgctgcaaa ttagcagcga ttacctgaaa gcagcctacg gcattgataa gaataacaaa    960

aacgcgaaca accacgtgag cattgtcgaa gcctggagcg ataatgatac cccgtacctg   1020

catgacgatg gtgacaacct gatgaatatg gataacaaat ttcgcctgtc catgctgtgg   1080

tcgctggcca aaccgctgga caagcgtagc ggtctgaacc cgctgattca taacagcttg   1140

gtggatcgtg aagttgatga ccgcgaggtt gaaacggttc cgagctattc ttttgcacgt   1200

gcgcatgata gcgaggtcca ggacttgatc cgtgacatca tcaaggcaga gatcaatccg   1260

aacgcattcg gttatagctt tacccaagac gagattgacc aggcctttaa gatttacaat   1320
```

```
gaggatctga agaaaacgga taagaaatac acccactata atgtgccgtt gagctacacc   1380
ctgctgctga cgaataaggg tagcatccca cgtgtctact atggtgatat gtttaccgac   1440
gatggtcagt atatggcgaa caaaaccgtc aactatgacg ccattgaatc tctgctgaaa   1500
gcgcgtatga agtatgtcgc tggcggtcaa gcaatgcaga actaccaaat cggtaatggt   1560
gagatcctga ccagcgttcg ttatggtaag ggtgccctga aacagagcga caaaggtgat   1620
gcgaccacgc gcaccagcgg tgtcggtgtc gttatgggca atcagccaaa ctttagcttg   1680
gacggcaaag tggtggctct gaacatgggc gcagctcatg cgaatcagga gtatcgtgcg   1740
ctgatggtta gcacgaaaga cggtgttgcc acgtatgcga ccgatgcaga tgcgagcaaa   1800
gccggtctgg tcaaacgtac cgacgaaaac ggctacctgt atttcctgaa tgacgacctg   1860
aagggtgtgg ccaatcctca ggtgagcggt ttcttgcagg tgtgggttcc ggtgggtgcc   1920
gcggatgatc aagatatccg tgttgcagct agcgataccg catccaccga tggcaagagc   1980
ctgcaccaag acgccgcgat ggatagccgt gttatgtttg aaggcttctc taactttcag   2040
tcctttgcca cgaaagaaga ggaatatacc aacgtcgtta tcgccaacaa tgtggataag   2100
ttcgttagct ggggtatcac ggatttcgag atggccccac aatatgtttc cagcaccgac   2160
ggtcaattcc tggactctgt cattcagaac ggttatgctt ttacggaccg ttatgacttg   2220
ggcatgtcta aggcaaacaa atacggcacg gccgatcaac tggttaaggc cattaaggcc   2280
ctgcacgcga agggcctgaa ggttatggca gattgggtgc cggatcagat gtataccttc   2340
ccgaaacagg aagtcgtgac cgttacccgt accgacaaat ttggcaaacc gatcgcaggt   2400
tcccaaatca atcatagcct gtatgttacc gataccaagt ccagcggcga tgactatcag   2460
gccaaatatg gtggtgcgtt tctggacgag ctgaaggaga aatatccgga gctgttcacg   2520
aagaaacaaa tcagcacggg tcaagctatt gacccgagcg tgaaaatcaa acagtggtct   2580
gctaagtatt tcaatggctc caacatcctg ggtcgcggtg cggactacgt actgtcggat   2640
caggcgagca acaaatacct gaacgtgtct gacgataaac tgttcctgcc gaaaaccttg   2700
ctgggccaag ttgtcgagag cggtatccgc tttgacggca ctggttatgt gtacaactct   2760
agcactacgg gtgaaaaagt taccgattcc ttcattacgg aggcaggtaa tctgtactac   2820
ttcggtcaag acggctatat ggtgaccggc gcacagaaca ttaagggcag caactattac   2880
ttcctggcca atggtgcggc cctgcgtaac accgtttaca ccgatgcgca aggtcagaat   2940
cactattacg gcaacgacgg caagcgttat gagaatggtt accaacagtt cggcaacgat   3000
tcttggcgtt acttcaaaaa tggcgtgatg gcgctgggtc tgactacggt ggatggtcac   3060
gtgcagtatt tcgataaaga tggtgtccag gccaaggata agatcattgt cacccgcgat   3120
ggcaaagtcc gctatttcga ccagcacaac ggtaatgcgg ttactaacac gttcgttgcg   3180
gacaagacgg gtcactggta ctatctgggc aaagacggcg tcgcggttac cggtgcgcag   3240
actgtgggta aacagcattt gtactttgaa gcgaacggtc aacaagtcaa gggtgacttc   3300
gtgacggcta aagacggtaa actgtacttc tatgatgtgg acagcggcga catgtggacc   3360
aataccttta tcgaggataa agcgggtaat tggttctacc tgggtaagga cggtgcggcc   3420
gtcaccggtg cacagacgat caaaggccag aaattgtatt tcaaagccaa cggtcagcaa   3480
gttaaaggtg acattgtcaa ggacgcggac ggtaagatcc gttattacga cgctcagacc   3540
ggtgaacagg tctttaacaa gtccgttagc gtcaacggta agacctacta tttcggtagc   3600
gacggcaccg cgcaaaccca ggcgaatccg aaaggccaaa cctttaagga tggtagcggc   3660
gttctgcgtt tctacaattt ggagggccag tatgtctcgg gcagcggctg gtacgaaacg   3720
```

```
gccgagcacg agtgggtata tgtgaaatcc ggtaaagttc tgaccggtgc ccagacgatt   3780

ggtaatcaac gtgtttactt caaggacaat ggtcaccagg tgaaaggcca gctggtcacg   3840

ggtaatgacg gtaaattgcg ttactacgac gcgaacagcg gtgatcaagc attcaacaaa   3900

tccgtcacgg ttaacggtaa aacctactac tttggcagcg atggtacggc gcagacgcag   3960

gctaatccta agggtcagac cttcaaagat ggtagcggcg tgctgcgttt ttacaacttg   4020

gaaggccaat acgtgtctgg cagcggttgg tacaagaatg cgcagggcca gtggctgtac   4080

gtgaaagatg gcaaggtcct gaccggtctg caaacggtcg gcaatcagaa ggtctacttc   4140

gacaaaaatg gcatccaagc aaagggtaag gccgttcgca cgtccgatgg taaagtgcgc   4200

tactttgatg agaatagcgg tagcatgatt acgaaccaat ggaagttcgt ttacggtcaa   4260

tactattact tcggttctga cggcgcagcg gtttaccgtg gttggaacta a            4311
```

<210> SEQ ID NO 10
<211> LENGTH: 1436
<212> TYPE: PRT
<213> ORGANISM: Streptococcus downei

<400> SEQUENCE: 10

```
Met Val Asp Gly Lys Tyr Tyr Tyr Tyr Asp Gln Asp Gly Asn Val Lys
1               5                   10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
    50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Leu Ala Asn Asp Val Asp Asn Ser
                245                 250                 255

Asn Pro Ile Val Gln Ala Glu Gln Leu Asn Trp Leu His Tyr Leu Leu
            260                 265                 270
```

```
Asn Phe Gly Thr Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
            420                 425                 430

Asp Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ala Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685
```

```
Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Asp Lys Leu Phe Leu
                885                 890                 895

Pro Lys Thr Leu Leu Gly Gln Val Val Glu Ser Gly Ile Arg Phe Asp
            900                 905                 910

Gly Thr Gly Tyr Val Tyr Asn Ser Ser Thr Thr Gly Glu Lys Val Thr
        915                 920                 925

Asp Ser Phe Ile Thr Glu Ala Gly Asn Leu Tyr Tyr Phe Gly Gln Asp
    930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
                965                 970                 975

Gln Gly Gln Asn His Tyr Tyr Gly Asn Asp Gly Lys Arg Tyr Glu Asn
            980                 985                 990

Gly Tyr Gln Gln Phe Gly Asn Asp  Ser Trp Arg Tyr Phe  Lys Asn Gly
        995                 1000                1005

Val Met  Ala Leu Gly Leu Thr  Thr Val Asp Gly His  Val Gln Tyr
    1010                1015                1020

Phe Asp  Lys Asp Gly Val Gln  Ala Lys Asp Lys Ile  Ile Val Thr
    1025                1030                1035

Arg Asp  Gly Lys Val Arg Tyr  Phe Asp Gln His Asn  Gly Asn Ala
    1040                1045                1050

Val Thr  Asn Thr Phe Val Ala  Asp Lys Thr Gly His  Trp Tyr Tyr
    1055                1060                1065

Leu Gly  Lys Asp Gly Val Ala  Val Thr Gly Ala Gln  Thr Val Gly
    1070                1075                1080

Lys Gln  His Leu Tyr Phe Glu  Ala Asn Gly Gln Gln  Val Lys Gly
    1085                1090                1095

Asp Phe  Val Thr Ala Lys Asp  Gly Lys Leu Tyr Phe  Tyr Asp Val
```

```
    1100                1105                1110

Asp Ser  Gly Asp Met Trp Thr  Asn Thr Phe Ile Glu  Asp Lys Ala
    1115                1120                1125

Gly Asn  Trp Phe Tyr Leu Gly  Lys Asp Gly Ala Ala  Val Thr Gly
    1130                1135                1140

Ala Gln  Thr Ile Lys Gly Gln  Lys Leu Tyr Phe Lys  Ala Asn Gly
    1145                1150                1155

Gln Gln  Val Lys Gly Asp Ile  Val Lys Asp Ala Asp  Gly Lys Ile
    1160                1165                1170

Arg Tyr  Tyr Asp Ala Gln Thr  Gly Glu Gln Val Phe  Asn Lys Ser
    1175                1180                1185

Val Ser  Val Asn Gly Lys Thr  Tyr Tyr Phe Gly Ser  Asp Gly Thr
    1190                1195                1200

Ala Gln  Thr Gln Ala Asn Pro  Lys Gly Gln Thr Phe  Lys Asp Gly
    1205                1210                1215

Ser Gly  Val Leu Arg Phe Tyr  Asn Leu Glu Gly Gln  Tyr Val Ser
    1220                1225                1230

Gly Ser  Gly Trp Tyr Glu Thr  Ala Glu His Glu Trp  Val Tyr Val
    1235                1240                1245

Lys Ser  Gly Lys Val Leu Thr  Gly Ala Gln Thr Ile  Gly Asn Gln
    1250                1255                1260

Arg Val  Tyr Phe Lys Asp Asn  Gly His Gln Val Lys  Gly Gln Leu
    1265                1270                1275

Val Thr  Gly Asn Asp Gly Lys  Leu Arg Tyr Tyr Asp  Ala Asn Ser
    1280                1285                1290

Gly Asp  Gln Ala Phe Asn Lys  Ser Val Thr Val Asn  Gly Lys Thr
    1295                1300                1305

Tyr Tyr  Phe Gly Ser Asp Gly  Thr Ala Gln Thr Gln  Ala Asn Pro
    1310                1315                1320

Lys Gly  Gln Thr Phe Lys Asp  Gly Ser Gly Val Leu  Arg Phe Tyr
    1325                1330                1335

Asn Leu  Glu Gly Gln Tyr Val  Ser Gly Ser Gly Trp  Tyr Lys Asn
    1340                1345                1350

Ala Gln  Gly Gln Trp Leu Tyr  Val Lys Asp Gly Lys  Val Leu Thr
    1355                1360                1365

Gly Leu  Gln Thr Val Gly Asn  Gln Lys Val Tyr Phe  Asp Lys Asn
    1370                1375                1380

Gly Ile  Gln Ala Lys Gly Lys  Ala Val Arg Thr Ser  Asp Gly Lys
    1385                1390                1395

Val Arg  Tyr Phe Asp Glu Asn  Ser Gly Ser Met Ile  Thr Asn Gln
    1400                1405                1410

Trp Lys  Phe Val Tyr Gly Gln  Tyr Tyr Tyr Phe Gly  Ser Asp Gly
    1415                1420                1425

Ala Ala  Val Tyr Arg Gly Trp  Asn
    1430                1435
```

<210> SEQ ID NO 11
<211> LENGTH: 3942
<212> TYPE: DNA
<213> ORGANISM: Streptococcus mutans

<400> SEQUENCE: 11

```
atgattgacg gcaaatacta ctactatgac aacaacggca aagtacgcac caatttcacg     60

ttgatcgcgg acggtaaaat cctgcatttt gatgaaactg gcgcgtacac cgacactagc    120
```

```
attgataccg tgaacaagga tattgtcacg acgcgtagca acctgtataa gaaatacaat    180
caagtgtatg atcgcagcgc gcagagcttc gagcatgttg atcactacct gacggcggaa    240
tcttggtacc gtccgaaata cattctgaaa gatggcaaga cctggaccca gagcaccgag    300
aaggacttcc gtcctctgct gatgacctgg tggccgagcc aggaaacgca gcgccagtat    360
gtcaacttca tgaacgccca gttgggtatc aacaaaacgt acgacgacac cagcaatcag    420
ctgcaattga acatcgctgc tgcaacgatc caagcaaaga tcgaagccaa aatcacgacg    480
ctgaagaaca ccgattggct gcgtcaaacg atcagcgcgt tcgtcaaaac ccaaagcgct    540
tggaatagcg acagcgaaaa gccgtttgat gaccatctgc aaaacggtgc ggttctgtat    600
gataacgaag gtaaattgac gccgtatgcc aatagcaact atcgtattct gaaccgcacg    660
ccgaccaacc agaccggtaa gaaggacccg cgttataccg ccgacaacac gatcggcggc    720
tacgagtttc tgctggccaa cgacgtggat aatagcaacc cggtggttca ggccgagcag    780
ctgaactggc tgcacttcct gatgaacttt ggtaatatct acgcaaacga ccctgacgct    840
aacttcgact ccatccgcgt tgacgctgtc gataatgtgg acgccgatct gttacagatc    900
gcgggtgact atctgaaagc ggcaaagggc atccataaga atgacaaagc ggcgaacgac    960
cacctgtcca ttctggaagc gtggagcgac aatgacactc cgtatctgca tgatgatggc   1020
gacaacatga ttaacatgga taacaaactg cgcctgagcc tgctgttctc cctggcgaaa   1080
ccgctgaatc agcgtagcgg tatgaacccg ttgattacga acagcctggt caaccgtact   1140
gatgataatg ccgaaacggc ggcagtgcca agctactctt ttatccgtgc ccacgatagc   1200
gaggtccagg atttgattcg tgatatcatt aaggctgaga ttaacccgaa cgtcgtcggt   1260
tacagcttca cgatggaaga gattaagaag gcatttgaga tctacaataa ggacctgttg   1320
gccacggaga agaagtatac ccactataac accgcattga gctacgcgtt gctgctgacg   1380
aacaagagca gcgtgccgcg tgtctactat ggtgatatgt ttacggacga tggtcaatac   1440
atggcccaca agaccattaa ctacgaggca atcgaaaccc tgctgaaagc acgtatcaag   1500
tacgtgtccg gtggtcaggc tatgcgcaac cagcaagtgg gtaattcgga gatcatcacc   1560
agcgtgcgtt acggtaaagg tgcgctgaag gcgatggata cgggtgaccg cactacccgt   1620
acctctggtg tggcggtcat tgagggcaac aacccgagct tgcgcctgaa ggcttctgat   1680
cgtgtggttg tgaatatggg tgcggcccac aaaaatcaag cctatcgccc gctgctgttg   1740
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact tccaggcatt tgctaccaag   2040
aaagaagagt ataccaatgt ggtcatcgct aagaatgtgg ataagttcgc ggagtggggt   2100
gtcaccgatt tcgagatggc tccgcaatac gtttctagca ccgacggtag ctttttggat   2160
agcgtgattc aaaacggtta tgcttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaaagaggtt   2340
gtgacggcaa cccgtgttga caaatacggt acgccggtag ctggcagcca gatcaaaaac   2400
acgctgtacg tggtcgatgg taaatctagc ggtaaggacc agcaggcgaa gtacggtggt   2460
```

```
gccttcctgg aagagctgca agcgaagtat ccggaactgt tcgcgcgcaa acagattagc   2520

accggtgttc cgatggaccc gagcgtcaag attaagcaat ggagcgcaaa atacttcaac   2580

ggcacgaata tcctgggtcg tggtgctggt tacgtgctga aagatcaggc aaccaacacc   2640

tactttaaca tcagcgacaa taaagagatc aatttcctgc caaagacgtt gctgaaccag   2700

gattctcaag ttggctttag ctacgacggt aagggctatg tgtactacag cacctcgggc   2760

taccaggcta aaaacacgtt catcagcgag ggtgacaagt ggtattactt cgacaataac   2820

ggttatatgg ttaccggcgc acagagcatt aatggtgtga actattactt cctgccgaat   2880

ggtttacagc tgcgtgatgc gattctgaaa aatgaggacg gtacgtacgc gtattatggc   2940

aatgatggtc gccgctacga gaatggctat tatcagttta tgagcggtgt ttggcgccat   3000

ttcaataatg gcgagatgtc cgttggtctg accgtcattg acggtcaagt tcaatacttt   3060

gacgagatgg gttaccaggc gaaaggcaaa ttcgttacca ccgcggatgg taagatccgt   3120

tacttcgata agcagagcgg caatatgtat cgtaatcgtt tcattgagaa cgaagagggc   3180

aaatggctgt acctgggtga ggacggcgcg gcagtcaccg gtagccagac gatcaatggt   3240

cagcacctgt attttcgtgc taacggcgtt caggttaagg gtgagttcgt gaccgatcgt   3300

catggccgca tctcttatta cgacggcaac agcggtgatc agatccgcaa ccgtttcgtc   3360

cgcaatgcgc aaggccagtg gttttacttt gacaacaatg gctatgcagt aactggtgct   3420

cgtacgatca acggccagca cctgtatttc cgcgcgaacg gtgttcaggt aaaaggtgag   3480

tttgttacgg accgccacgg ccgcattagc tattatgatg gtaatagcgg tgaccaaatt   3540

cgcaatcgtt tcgtgcgtaa tgcacagggt cagtggttct acttcgacaa taatggttat   3600

gcagtcacgg gtgcacgtac cattaacggc caacacctgt actttcgcgc caatggtgtg   3660

caagtgaaag gcgaatttgt tactgatcgt tatggtcgta tcagctacta tgatggcaat   3720

tctggcgacc aaattcgcaa tcgctttgtt cgtaacgccc aaggtcaatg gttctatttc   3780

gacaacaacg gttacgcggt gaccggtgcc cgcacgatta atggtcaaca cttgtacttc   3840

cgtgccaacg gtgtccaggt gaagggtgaa tttgtgaccg accgctatgg tcgcatttct   3900

tactacgacg caaattccgg tgaacgcgtc cgtatcaatt aa                      3942
```

<210> SEQ ID NO 12
<211> LENGTH: 1313
<212> TYPE: PRT
<213> ORGANISM: Streptococcus mutans

<400> SEQUENCE: 12

```
Met Ile Asp Gly Lys Tyr Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110
```

```
Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
    210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
        275                 280                 285

Ala Val Asp Asn Val Asp Ala Asp Leu Leu Gln Ile Ala Gly Asp Tyr
    290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
        355                 360                 365

Asn Pro Leu Ile Thr Asn Ser Leu Val Asn Arg Thr Asp Asp Asn Ala
    370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
            420                 425                 430

Glu Ile Tyr Asn Lys Asp Leu Leu Ala Thr Glu Lys Lys Tyr Thr His
        435                 440                 445

Tyr Asn Thr Ala Leu Ser Tyr Ala Leu Leu Leu Thr Asn Lys Ser Ser
    450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gly Gln Ala Met Arg Asn Gln Gln
            500                 505                 510

Val Gly Asn Ser Glu Ile Ile Thr Ser Val Arg Tyr Gly Lys Gly Ala
        515                 520                 525

Leu Lys Ala Met Asp Thr Gly Asp Arg Thr Thr Arg Thr Ser Gly Val
```

```
    530                 535                 540

Ala Val Ile Glu Gly Asn Asn Pro Ser Leu Arg Leu Lys Ala Ser Asp
545                 550                 555                 560

Arg Val Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
            580                 585                 590

Gln Glu Ala Ala Gly Leu Val Arg Tyr Thr Asn Asp Arg Gly Glu Leu
        595                 600                 605

Ile Phe Thr Ala Ala Asp Ile Lys Gly Tyr Ala Asn Pro Gln Val Ser
    610                 615                 620

Gly Tyr Leu Gly Val Trp Val Pro Val Gly Ala Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
            660                 665                 670

Asn Phe Gln Ala Phe Ala Thr Lys Lys Glu Glu Tyr Thr Asn Val Val
        675                 680                 685

Ile Ala Lys Asn Val Asp Lys Phe Ala Glu Trp Gly Val Thr Asp Phe
    690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
            740                 745                 750

Ile Lys Ala Leu His Ser Lys Gly Ile Lys Val Met Ala Asp Trp Val
        755                 760                 765

Pro Asp Gln Met Tyr Ala Leu Pro Glu Lys Glu Val Val Thr Ala Thr
    770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
            820                 825                 830

Leu Phe Ala Arg Lys Gln Ile Ser Thr Gly Val Pro Met Asp Pro Ser
        835                 840                 845

Val Lys Ile Lys Gln Trp Ser Ala Lys Tyr Phe Asn Gly Thr Asn Ile
    850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
            900                 905                 910

Tyr Val Tyr Tyr Ser Thr Ser Gly Tyr Gln Ala Lys Asn Thr Phe Ile
        915                 920                 925

Ser Glu Gly Asp Lys Trp Tyr Tyr Phe Asp Asn Asn Gly Tyr Met Val
    930                 935                 940

Thr Gly Ala Gln Ser Ile Asn Gly Val Asn Tyr Tyr Phe Leu Pro Asn
945                 950                 955                 960
```

```
Gly Leu Gln Leu Arg Asp Ala Ile Leu Lys Asn Glu Asp Gly Thr Tyr
                965                 970                 975

Ala Tyr Tyr Gly Asn Asp Gly Arg Arg Tyr Glu Asn Gly Tyr Tyr Gln
            980                 985                 990

Phe Met Ser Gly Val Trp Arg His  Phe Asn Asn Gly Glu  Met Ser Val
        995                 1000                1005

Gly Leu  Thr Val Ile Asp Gly  Gln Val Gln Tyr Phe  Asp Glu Met
    1010                 1015                1020

Gly Tyr  Gln Ala Lys Gly Lys  Phe Val Thr Thr Ala  Asp Gly Lys
    1025                 1030                1035

Ile Arg  Tyr Phe Asp Lys Gln  Ser Gly Asn Met Tyr  Arg Asn Arg
    1040                 1045                1050

Phe Ile  Glu Asn Glu Glu Gly  Lys Trp Leu Tyr Leu  Gly Glu Asp
    1055                 1060                1065

Gly Ala  Ala Val Thr Gly Ser  Gln Thr Ile Asn Gly  Gln His Leu
    1070                 1075                1080

Tyr Phe  Arg Ala Asn Gly Val  Gln Val Lys Gly Glu  Phe Val Thr
    1085                 1090                1095

Asp Arg  His Gly Arg Ile Ser  Tyr Tyr Asp Gly Asn  Ser Gly Asp
    1100                 1105                1110

Gln Ile  Arg Asn Arg Phe Val  Arg Asn Ala Gln Gly  Gln Trp Phe
    1115                 1120                1125

Tyr Phe  Asp Asn Asn Gly Tyr  Ala Val Thr Gly Ala  Arg Thr Ile
    1130                 1135                1140

Asn Gly  Gln His Leu Tyr Phe  Arg Ala Asn Gly Val  Gln Val Lys
    1145                 1150                1155

Gly Glu  Phe Val Thr Asp Arg  His Gly Arg Ile Ser  Tyr Tyr Asp
    1160                 1165                1170

Gly Asn  Ser Gly Asp Gln Ile  Arg Asn Arg Phe Val  Arg Asn Ala
    1175                 1180                1185

Gln Gly  Gln Trp Phe Tyr Phe  Asp Asn Asn Gly Tyr  Ala Val Thr
    1190                 1195                1200

Gly Ala  Arg Thr Ile Asn Gly  Gln His Leu Tyr Phe  Arg Ala Asn
    1205                 1210                1215

Gly Val  Gln Val Lys Gly Glu  Phe Val Thr Asp Arg  Tyr Gly Arg
    1220                 1225                1230

Ile Ser  Tyr Tyr Asp Gly Asn  Ser Gly Asp Gln Ile  Arg Asn Arg
    1235                 1240                1245

Phe Val  Arg Asn Ala Gln Gly  Gln Trp Phe Tyr Phe  Asp Asn Asn
    1250                 1255                1260

Gly Tyr  Ala Val Thr Gly Ala  Arg Thr Ile Asn Gly  Gln His Leu
    1265                 1270                1275

Tyr Phe  Arg Ala Asn Gly Val  Gln Val Lys Gly Glu  Phe Val Thr
    1280                 1285                1290

Asp Arg  Tyr Gly Arg Ile Ser  Tyr Tyr Asp Ala Asn  Ser Gly Glu
    1295                 1300                1305

Arg Val  Arg Ile Asn
    1310
```

<210> SEQ ID NO 13
<211> LENGTH: 3972
<212> TYPE: DNA
<213> ORGANISM: Streptococcus dentirousetti

<400> SEQUENCE: 13

```
atggttgacg gcaaatacta ctactacgat gcagacggca acgtaaagaa aaacttcgcg      60
gttagcgttg gcgatgccat tttctatttt gatgaaacgg gtgcctacaa agataccagc     120
aaagttgatg cggataagac cagctctagc gtcaatcaga ccacggaaac gttcgcagcg     180
aataaccgtg cgtatagcac cgcagccgag aactttgaag cgattgataa ctacctgact     240
gcggatagct ggtatcgtcc gaagtctatc ttgaaagatg gtacgacgtg gaccgaaagc     300
accaaggatg attttcgccc gctgctgatg gcgtggtggc cggataccga aaccaaacgt     360
aactacgtga actatatgaa caaggtggtc ggtatcgaca aaacgtacac cgcggaaacg     420
tcccaagctg acctgacggc ggcagccgaa ctggtgcagg cgcgtatcga gcagaaaatc     480
actagcgaaa agaatacgaa gtggctgcgt gaggcgattt ccgcgttcgt taagactcaa     540
ccgcagtgga atggcgagag cgagaaacct tatgatgacc acctgcaaaa tggtgcgctg     600
aagttcgaca atgaaaccag cctgaccccg gatacgcaga gcggctatcg catcctgaac     660
cgtaccccga cgaatcaaac cggtagcctg gacccgcgct tcacctttaa tcagaatgac     720
ccgctgggtg gttatgagta tttgctggct aatgatgtcg ataacagcaa cccggtcgtt     780
caggccgaga gcctgaactg gctgcattac ctgctgaatt ttggtagcat ttacgcgaat     840
gatccggagg ccaatttcga cagcatccgt gtggacgcgg tggacaatgt tgacgcagac     900
ctgctgcaaa ttagctcgga ttacctgaaa tcggcgtaca aaattgacaa gaacaacaaa     960
aatgcgaacg accacgttag catcgtcgag gcgtggagcg acaatgatac cccgtacctg    1020
aatgatgatg gcgacaatct gatgaacatg gataacaagt ttcgtctgag catgctgtgg    1080
agcctggcga agccaaccaa tgtccgtagc ggcttgaatc cgctgatcca caacagcgtg    1140
gttgaccgtg aggtggacga ccgtgaagtt gaggctaccc cgaattacag ctttgcacgc    1200
gcacacgaca gcgaagttca agatttgatt cgcgacatca tcaaagctga gatcaaccca    1260
aacagcttcg gttatagctt tacccaagag gaaatcgacc aggccttcaa gatctacaat    1320
gaggatttga agaaaaccaa taagaagtat acccactaca acgtcccgct gagctacacc    1380
ctgctgctga cgaacaaggg cagcattcca cgcatttact acggtgacat gtttacggat    1440
gacggtcagt atatggccaa caaaaccgtt aactatgacg ccattgagag cctgctgaaa    1500
gcacgtatga agtatgttag cggtggccaa gcgatgcaga attacaacat cggcaacggc    1560
gagattctga ccagcgtccg ttacggtaag ggtgccctga aacagagcga caaaggcgat    1620
aagactactc gtaccagcgg tattggcgtt gtgatgggta accagagcaa tttcagcctg    1680
gagggcaagg tggtggccct gaatatgggt gcaacgcata ccaaacagaa gtatcgtgca    1740
ttgatggtgt ctacggaaac cggcgtggcg atttacaata gcgatgaaga agcagaggca    1800
gcaggcctga tcaaaacgac cgatgagaat ggttatttgt actttctgaa tgacgatctg    1860
aagggcgtgg ctaacccgca ggtcagcggc ttcctgcaag tgtgggttcc ggttggtgca    1920
ccggctgacc aggacattcg tgtggcggcg accgatgcgg cttctaccga cggtaagagc    1980
ctgcatcagg acgcagctct ggattctcgc gtcatgtttg aaggtttcag caacttccag    2040
agcttcgcaa ccaaggaaga ggaatacacc aacgttgtta ttgcaaagaa cgtggataag    2100
ttcgtgagct ggggtatcac cgacttcgag atggcaccgc agtacgttag ctctaccgat    2160
ggcacctttc tggatagcgt gattcaaaat ggctatgcct ttacggaccg ttacgacctg    2220
ggtatgagca aagcaaacaa gtatggtact gctgaccaac tggtggccgc gattaaagcg    2280
ctgcatgcga agggtctgcg tgtgatggcg gattgggtcc cagatcaaat gtacactttc    2340
```

```
cctaagaagg aagtggttac cgttacccgt acggacaaat ttggcaatcc agtggcaggc   2400

agccaaatca accacacctt gtacgtcact gatactaagg gtagcggtga cgactaccag   2460

gcgaagtacg gtggcgcatt cctggatgaa ctgaaagaaa agtacccgga gctgtttacc   2520

aagaagcaaa tcagcaccgg tcaggcaatc gacccgagcg tgaaaatcaa gcagtggagc   2580

gcgaagtact tcaacggtag caatatcttg ggtcgcggtg cgaactacgt gctgtccgac   2640

caggcgtcta acaagtactt taacgtggcc gaaggtaaag tctttctgcc agcggcgatg   2700

ctgggtaagg tcgtcgagag cggtatccgt ttcgacggta aaggttatat ctataacagc   2760

agcaccactg gcgaacaagt gaaggacagc ttcattaccg aagcgggtaa cttgtactat   2820

tttggcaaag atggttatat ggtcatgggt gcacagaata tccagggtgc taactactac   2880

ttcttggcga atggtgcggc cctgcgcaat agcatcctga cggatcagga tggcaaaagc   2940

cactattatg caaatgacgg caagcgttat gagaacggct actatcaatt cggtaacgac   3000

tcctggcgct attttgaaaa cggcgttatg gccgttggtt tgacgcgcgt tgcgggccac   3060

gaccaatact ttgataagga tggtatccaa gcgaagaata agatcattgt tacgcgtgac   3120

ggtaaggtcc gctacttcga cgaacacaac ggcaatgctg ccacgaatac gtttatcagc   3180

gatcaagccg gccattggta ctacctgggt aaagatggtg tcgccgtgac gggtgcgcag   3240

accgttggca agcaacacct gtacttcgag gctaacggcc aacaagtaaa aggcgatttt   3300

gttaccgcca aggacggtaa gttgtatttt ctggacggtg actctggcga catgtggacc   3360

gataccttcg tccaggataa ggctggtcat tggttctatc tgggcaaaga cggtgcggcg   3420

gtaaccggtg cccagaccgt ccgtggtcag aagctgtact tcaaagcgaa tggccagcag   3480

gttaagggtg acattgtgaa aggcgcggat ggtaaaatcc gttactatga tgcaaattcc   3540

ggtgaccagg tttacaatcg cacggtgaaa ggctccgacg gcaagaccta tatcattggt   3600

aatgacggcg tcgcaatcac gcaaaccatc gccaaaggcc agaccatcaa ggatggcagc   3660

gttctgcgct tctatagcat ggagggtcag ctggtgaccg gcagcggctg gtattccaac   3720

gcgaaaggtc aatggttgta tgtcaagaac ggtcaagtcc tgacgggttt gcagacggtg   3780

ggcagccagc gtgtgtactt tgacgcaaat ggtattcaag cgaaaggtaa agcagtgcgt   3840

acctccgatg gcaaactgcg ttacttcgat gcgaacagcg gcagcatgat caccaatcag   3900

tggaaagaag ttaatggtca gtactactat ttcgacaaca acggtgttgc gatctatcgc   3960

ggttggaact aa                                                       3972
```

<210> SEQ ID NO 14
<211> LENGTH: 1323
<212> TYPE: PRT
<213> ORGANISM: Streptococcus dentirousetti

<400> SEQUENCE: 14

```
Met Val Asp Gly Lys Tyr Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
            20                  25                  30

Thr Gly Ala Tyr Lys Asp Thr Ser Lys Val Asp Ala Asp Lys Thr Ser
        35                  40                  45

Ser Ser Val Asn Gln Thr Thr Glu Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80
```

```
Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
        355                 360                 365

Arg Ser Gly Leu Asn Pro Leu Ile His Asn Ser Val Val Asp Arg Glu
    370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495
```

```
Ser Leu Leu Lys Ala Arg Met Lys Tyr Val Ser Gly Gly Gln Ala Met
            500                 505                 510

Gln Asn Tyr Asn Ile Gly Asn Gly Glu Ile Leu Thr Ser Val Arg Tyr
        515                 520                 525

Gly Lys Gly Ala Leu Lys Gln Ser Asp Lys Gly Asp Lys Thr Thr Arg
    530                 535                 540

Thr Ser Gly Ile Gly Val Val Met Gly Asn Gln Ser Asn Phe Ser Leu
545                 550                 555                 560

Glu Gly Lys Val Val Ala Leu Asn Met Gly Ala Thr His Thr Lys Gln
                565                 570                 575

Lys Tyr Arg Ala Leu Met Val Ser Thr Glu Thr Gly Val Ala Ile Tyr
            580                 585                 590

Asn Ser Asp Glu Glu Ala Glu Ala Ala Gly Leu Ile Lys Thr Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Pro Ala Asp Gln Asp Ile Arg Val Ala Ala Thr Asp Ala Ala Ser Thr
                645                 650                 655

Asp Gly Lys Ser Leu His Gln Asp Ala Ala Leu Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Lys Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Thr Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Ala Ala Ile Lys Ala Leu His Ala Lys Gly Leu Arg Val
        755                 760                 765

Met Ala Asp Trp Val Pro Asp Gln Met Tyr Thr Phe Pro Lys Lys Glu
    770                 775                 780

Val Val Thr Val Thr Arg Thr Asp Lys Phe Gly Asn Pro Val Ala Gly
785                 790                 795                 800

Ser Gln Ile Asn His Thr Leu Tyr Val Thr Asp Thr Lys Gly Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
                885                 890                 895

Pro Ala Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
```

```
        915                 920                 925

Asp Ser Phe Ile Thr Glu Ala Gly Asn Leu Tyr Tyr Phe Gly Lys Asp
    930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp  Ser Trp Arg Tyr Phe  Glu Asn Gly
        995                 1000                1005

Val Met  Ala Val Gly Leu Thr  Arg Val Ala Gly His  Asp Gln Tyr
    1010                1015                1020

Phe Asp  Lys Asp Gly Ile Gln  Ala Lys Asn Lys Ile  Ile Val Thr
    1025                1030                1035

Arg Asp  Gly Lys Val Arg Tyr  Phe Asp Glu His Asn  Gly Asn Ala
    1040                1045                1050

Ala Thr  Asn Thr Phe Ile Ser  Asp Gln Ala Gly His  Trp Tyr Tyr
    1055                1060                1065

Leu Gly  Lys Asp Gly Val Ala  Val Thr Gly Ala Gln  Thr Val Gly
    1070                1075                1080

Lys Gln  His Leu Tyr Phe Glu  Ala Asn Gly Gln Gln  Val Lys Gly
    1085                1090                1095

Asp Phe  Val Thr Ala Lys Asp  Gly Lys Leu Tyr Phe  Leu Asp Gly
    1100                1105                1110

Asp Ser  Gly Asp Met Trp Thr  Asp Thr Phe Val Gln  Asp Lys Ala
    1115                1120                1125

Gly His  Trp Phe Tyr Leu Gly  Lys Asp Gly Ala Ala  Val Thr Gly
    1130                1135                1140

Ala Gln  Thr Val Arg Gly Gln  Lys Leu Tyr Phe Lys  Ala Asn Gly
    1145                1150                1155

Gln Gln  Val Lys Gly Asp Ile  Val Lys Gly Ala Asp  Gly Lys Ile
    1160                1165                1170

Arg Tyr  Tyr Asp Ala Asn Ser  Gly Asp Gln Val Tyr  Asn Arg Thr
    1175                1180                1185

Val Lys  Gly Ser Asp Gly Lys  Thr Tyr Ile Ile Gly  Asn Asp Gly
    1190                1195                1200

Val Ala  Ile Thr Gln Thr Ile  Ala Lys Gly Gln Thr  Ile Lys Asp
    1205                1210                1215

Gly Ser  Val Leu Arg Phe Tyr  Ser Met Glu Gly Gln  Leu Val Thr
    1220                1225                1230

Gly Ser  Gly Trp Tyr Ser Asn  Ala Lys Gly Gln Trp  Leu Tyr Val
    1235                1240                1245

Lys Asn  Gly Gln Val Leu Thr  Gly Leu Gln Thr Val  Gly Ser Gln
    1250                1255                1260

Arg Val  Tyr Phe Asp Ala Asn  Gly Ile Gln Ala Lys  Gly Lys Ala
    1265                1270                1275

Val Arg  Thr Ser Asp Gly Lys  Leu Arg Tyr Phe Asp  Ala Asn Ser
    1280                1285                1290

Gly Ser  Met Ile Thr Asn Gln  Trp Lys Glu Val Asn  Gly Gln Tyr
    1295                1300                1305

Tyr Tyr  Phe Asp Asn Asn Gly  Val Ala Ile Tyr Arg  Gly Trp Asn
    1310                1315                1320
```

<210> SEQ ID NO 15
<211> LENGTH: 4047
<212> TYPE: DNA
<213> ORGANISM: Streptococcus oralis

<400> SEQUENCE: 15
atgatcgacg gcaaaaacta ctacgtacag gatgatggca cggtaaagaa gaatttcgcg 60
gtagaactga atggtcgtat cctgtatttt gatgcagaaa ccggcgctct ggttgatagc 120
aacgagtatc agttccaaca gggtacgagc agcctgaaca atgaattttc tcagaagaac 180
gcattctatg gtacgaccga taaggatatt gagactgtgg atggctacct gaccgcagat 240
agctggtatc gcccgaaatt catcctgaag gatggcaaga cgtggaccgc gagcacggaa 300
acggatctgc gtccgctgtt gatggcatgg tggccggaca agcgtaccca aatcaactat 360
ctgaactaca tgaaccagca gggtctgggt gcgggtgcgt ttgagaacaa agtggagcag 420
gccctgctga cgggtgcaag ccaacaggta caacgcaaga tcgaagagaa gattggtaaa 480
gagggtgata ccaagtggct gcgcaccctg atgggtgcgt tcgtgaaaac gcaaccaaac 540
tggaatatca aaaccgagtc tgaaacgacc ggcacgaaaa aggaccatct gcaaggcggt 600
gcactgctgt atacgaacaa cgagaaatcc ccgcacgcgg acagcaaatt tcgtctgctg 660
aatcgtaccc cgaccagcca aaccggcacg ccgaagtatt tcatcgacaa gtctaacggt 720
ggctacgaat ttctgctggc gaacgatttt gacaatagca atcctgcggt acaagctgag 780
cagctgaatt ggctgcacta catgatgaac tttggcagca ttgttgcgaa tgatccgacc 840
gcgaatttcg acggcgttcg tgtggatgct gttgataacg tcaatgcgga cttgttgcaa 900
attgcaagcg attactttaa gagccgttac aaagtcggtg agagcgaaga agaagcgatc 960
aagcacctgt ccatcctgga agcatggagc gataacgacc cggactacaa caaagatacc 1020
aagggtgcac agttggcgat tgataacaaa ctgcgcctga gcctgctgta ctctttcatg 1080
cgtaatctga gcatccgtag cggtgttgaa ccgacgatta ccaatagcct gaatgaccgt 1140
tccagcgaaa agaagaacgg cgagcgtatg gcaaattaca tcttcgtgcg tgcccacgat 1200
agcgaggtcc aaacggtgat cgccgacatc attcgcgaaa acatcaatcc gaacaccgac 1260
ggcctgacgt ttacgatgga cgagctgaag caggcattca agatttacaa cgaggacatg 1320
cgcaaggcgg acaaaaagta tacccagttt aacattccta ccgcacacgc gctgatgctg 1380
tctaataagg attctattac ccgcgtgtac tatggtgatc tgtatactga cgatggtcag 1440
tacatggaga agaaaagccc gtatcacgat gcgattgacg ctctgctgcg tgcacgtatt 1500
aaatacgtcg cgggtggcca ggatatgaaa gtgacctata tgggcgtgcc gcgtgaagcg 1560
gataagtgga gctataacgg cattctgacc agcgtgcgct atggcacggg cgctaacgaa 1620
gccacggatg agggcactgc ggaaacgcgc acgcaaggta tggcagtgat tgcgagcaat 1680
aatccaaatc tgaaactgaa tgaatgggac aagttgcaag tcaacatggg tgcggcgcat 1740
aagaatcaat attaccgtcc ggttctgctg accactaagg acggtatcag ccgttatctg 1800
accgatgaag aagtgcctca gagcctgtgg aaaaagacgg acgcaaacgg tattctgacc 1860
ttcgacatga atgatattgc tggctacagc aacgtgcaag ttagcggtta cctggccgtc 1920
tgggtcccgg tcggtgcgaa ggcggatcaa gatgcgcgca cgaccgcatc caagaagaaa 1980
aatgcgtcgg gtcaggtgta cgaaagcagc gcggctctgg atagccagct gatttacgaa 2040
ggtttcagca actttcaaga ctttgccact cgcgatgatc agtacacgaa caaggtcatt 2100

```
gcgaaaaacg tgaatctgtt caaagaatgg ggtgtgacca gcttcgagct gccgccgcag   2160
tacgtgagca gccaagatgg cacctttctg gacagcatta tccaaaacgg ctatgcattt   2220
gaagaccgtt acgatatggc gatgagcaag aataacaagt atggtagcct gaaagacctg   2280
ttgaacgcgc tgcgcgcact gcacagcgtc aacattcaag caatcgccga ttgggtgccg   2340
gaccaaattt acaacttgcc gggcaaagag gtggtgaccg caactcgtgt caacaactac   2400
ggcacctacc gtgagggtgc tgaaatcaaa gaaaagctgt atgtcgccaa tagcaagacc   2460
aacgaaaccg atttccaagg taaatacggt ggtgcgttcc tggatgagct gaaggcgaag   2520
tacccggaga ttttcgagcg tgtccaaatc agcaacggcc aaaagatgac taccgatgaa   2580
aagatcacca aatggagcgc gaaatacttt aatggcacca atattctggg tcgtggcgcg   2640
tactatgtcc tgaaagattg ggccagcaat gattacctga cgaaccgtaa cggcgagatt   2700
gttttgccga agcaactggt taacaagaat agctataccg gctttgtcag cgacgcgaac   2760
ggcacgaagt tctattctac ctctggctac caggcgaaga acagcttcat tcaagacgaa   2820
aacggtaatt ggtattactt tgacaaacgt ggttatctgg ttacgggcgc acacgagatt   2880
gatggcaagc atgtctactt cctgaaaaac ggtatccaac tgcgtgacag catccgtgag   2940
gatgagaacg gtaatcaata ctattacgac cagaccggcg cacaagtgct gaaccgttac   3000
tacacgacgg acggtcagaa ttggcgctat ttcgatgcga aaggtgttat ggcacgcggc   3060
ctggtaaaga ttggtgacgg ccaacagttt ttcgatgaaa acggttacca ggtcaagggc   3120
aagattgtta gcgcaaaaga cggcaagctg cgctactttg ataaagactc tggcaatgct   3180
gtcattaatc gtttcgcgca gggtgacaat ccgagcgact ggtactattt cggtgtggaa   3240
tttgctaaac tgacgggttt gcaaaagatc ggccagcaga cgctgtattt tgaccaagac   3300
ggtaagcaag tcaaaggtaa gatcgtaact ctgtcggaca aaagcattcg ttacttcgat   3360
gccaacagcg gtgaaatggc ggttggcaag ttcgcggaag gtgcaaagaa tgagtggtat   3420
tatttcgata aaaccggcaa agcggttact ggtttgcaga aaattggtaa gcagaccctg   3480
tactttgacc aggacggtaa acaggttaaa ggcaaggttg tcacgctggc tgataaaagc   3540
atccgctact tcgacgcaga ctccggcgag atggcggtcg gtaagtttgc agagggtgcg   3600
aagaacgagt ggtactattt tgatcagact ggcaaggccg tgactggttt gcaaaagatt   3660
gacaagcaaa ccttgtactt cgaccaggac ggtaaacaag tcaagggtaa gattgtgacg   3720
ttgagcgaca agtcgatccg ttactttgat gctaatagcg gtgagatggc tactaacaaa   3780
ttcgtcgagg gctcgcagaa tgaatggtac tacttcgatc aagcgggtaa ggctgttacg   3840
ggcttgcaac aggtcggtca gcaaactctg tacttcaccc aggatggtaa gcaagtgaag   3900
ggtaaggtcg tggacgtgaa cggtgtttct cgttatttcg acgcaaactc cggtgacatg   3960
gctcgttcta aatggattca actggaagat ggcagctgga tgtatttcga ccgtgacggt   4020
cgtggccaga attttggccg taactaa                                     4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala
            20                  25                  30
```

```
Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
        355                 360                 365

Val Glu Pro Thr Ile Thr Asn Ser Leu Asn Asp Arg Ser Ser Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445
```

```
Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
            740                 745                 750

Lys Tyr Gly Ser Leu Lys Asp Leu Leu Asn Ala Leu Arg Ala Leu His
        755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Lys Leu Tyr Val Ala
                805                 810                 815

Asn Ser Lys Thr Asn Glu Thr Asp Phe Gln Gly Lys Tyr Gly Gly Ala
            820                 825                 830

Phe Leu Asp Glu Leu Lys Ala Lys Tyr Pro Glu Ile Phe Glu Arg Val
        835                 840                 845

Gln Ile Ser Asn Gly Gln Lys Met Thr Thr Asp Glu Lys Ile Thr Lys
    850                 855                 860

Trp Ser Ala Lys Tyr Phe Asn Gly Thr Asn Ile Leu Gly Arg Gly Ala
```

```
865                 870                 875                 880

Tyr Tyr Val Leu Lys Asp Trp Ala Ser Asn Asp Tyr Leu Thr Asn Arg
                885                 890                 895

Asn Gly Glu Ile Val Leu Pro Lys Gln Leu Val Asn Lys Asn Ser Tyr
            900                 905                 910

Thr Gly Phe Val Ser Asp Ala Asn Gly Thr Lys Phe Tyr Ser Thr Ser
        915                 920                 925

Gly Tyr Gln Ala Lys Asn Ser Phe Ile Gln Asp Glu Asn Gly Asn Trp
    930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
                965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr  Tyr Thr Thr Asp Gly  Gln Asn Trp
        995                 1000                1005

Arg Tyr  Phe Asp Ala Lys Gly  Val Met Ala Arg Gly  Leu Val Lys
    1010                 1015                1020

Ile Gly  Asp Gly Gln Gln Phe  Phe Asp Glu Asn Gly  Tyr Gln Val
    1025                 1030                1035

Lys Gly  Lys Ile Val Ser Ala  Lys Asp Gly Lys Leu  Arg Tyr Phe
    1040                 1045                1050

Asp Lys  Asp Ser Gly Asn Ala  Val Ile Asn Arg Phe  Ala Gln Gly
    1055                 1060                1065

Asp Asn  Pro Ser Asp Trp Tyr  Tyr Phe Gly Val Glu  Phe Ala Lys
    1070                 1075                1080

Leu Thr  Gly Leu Gln Lys Ile  Gly Gln Gln Thr Leu  Tyr Phe Asp
    1085                 1090                1095

Gln Asp  Gly Lys Gln Val Lys  Gly Lys Ile Val Thr  Leu Ser Asp
    1100                 1105                1110

Lys Ser  Ile Arg Tyr Phe Asp  Ala Asn Ser Gly Glu  Met Ala Val
    1115                 1120                1125

Gly Lys  Phe Ala Glu Gly Ala  Lys Asn Glu Trp Tyr  Tyr Phe Asp
    1130                 1135                1140

Lys Thr  Gly Lys Ala Val Thr  Gly Leu Gln Lys Ile  Gly Lys Gln
    1145                 1150                1155

Thr Leu  Tyr Phe Asp Gln Asp  Gly Lys Gln Val Lys  Gly Lys Val
    1160                 1165                1170

Val Thr  Leu Ala Asp Lys Ser  Ile Arg Tyr Phe Asp  Ala Asp Ser
    1175                 1180                1185

Gly Glu  Met Ala Val Gly Lys  Phe Ala Glu Gly Ala  Lys Asn Glu
    1190                 1195                1200

Trp Tyr  Tyr Phe Asp Gln Thr  Gly Lys Ala Val Thr  Gly Leu Gln
    1205                 1210                1215

Lys Ile  Asp Lys Gln Thr Leu  Tyr Phe Asp Gln Asp  Gly Lys Gln
    1220                 1225                1230

Val Lys  Gly Lys Ile Val Thr  Leu Ser Asp Lys Ser  Ile Arg Tyr
    1235                 1240                1245

Phe Asp  Ala Asn Ser Gly Glu  Met Ala Thr Asn Lys  Phe Val Glu
    1250                 1255                1260

Gly Ser  Gln Asn Glu Trp Tyr  Tyr Phe Asp Gln Ala  Gly Lys Ala
    1265                 1270                1275
```

```
Val Thr  Gly Leu Gln Gln Val  Gly Gln Gln Thr Leu  Tyr Phe Thr
    1280                 1285                 1290

Gln Asp  Gly Lys Gln Val Lys  Gly Lys Val Val Asp  Val Asn Gly
    1295                 1300                 1305

Val Ser  Arg Tyr Phe Asp Ala  Asn Ser Gly Asp Met  Ala Arg Ser
    1310                 1315                 1320

Lys Trp  Ile Gln Leu Glu Asp  Gly Ser Trp Met Tyr  Phe Asp Arg
    1325                 1330                 1335

Asp Gly  Arg Gly Gln Asn Phe  Gly Arg Asn
    1340                 1345


<210> SEQ ID NO 17
<211> LENGTH: 4047
<212> TYPE: DNA
<213> ORGANISM: Streptococcus sanguinis

<400> SEQUENCE: 17

atgattgatg gtaaaaagta ttacgtacag gacgacggca cggttaagaa gaatttcgcg     60

gttgagctga atggcaagat cctgtacttc gatgcagaga ctggtgcgtt gattgacagc    120

gcggagtatc aattccaaca aggcaccagc agcctgaata atgagttcac tcaaaagaac    180

gccttttacg gtacgaccga taaggatgtg gaaaccattg atggttactt gaccgccgat    240

tcctggtatc gtccgaagtt cattctgaaa gatggcaaaa cctggacggc gagcacggaa    300

attgacttgc gtccgttgtt gatggcgtgg tggccggaca aacagaccca ggttagctac    360

ctgaattaca tgaaccagca aggcttgggt gcaggcgcct tcgaaaacaa agtagagcag    420

gcaattctga ccggtgcgtc ccaacaggta caacgtaaaa tcgaagaacg catcggtaaa    480

gagggtgata ccaagtggct gcgtaccctg atgggtgcat ttgtaaagac ccagccgaac    540

tggaacatta agaccgagtc cgaaaccact ggcacgaata aagatcatct gcaaggtggc    600

gcactgctgt atagcaattc cgacaagacg agccatgcca actctaagta ccgtatcctg    660

aaccgcaccc cgaccaacca aacgggcacg ccgaaatact ttattgacaa gagcaatggt    720

ggttatgaat ttctgctggc gaatgacttt gacaatagca atccggcagt gcaagcggaa    780

cagctgaact ggttgcactt tatgatgaat tttggctcca tcgttgcaaa tgatccgacg    840

gccaacttcg acggcgtccg cgttgacgct gtggataacg tgaatgcgga tctgttgcaa    900

attgcgagcg actatttcaa gagccgctat aaagtcggcg aaagcgaaga agaggccatt    960

aagcacctgt ccatcctgga agcgtggagc gacaacgacc cggactacaa caaggatact   1020

aaaggtgccc aactgccgat cgacaacaaa ctgcgtctga gcctgctgta ctccttcatg   1080

cgtaagctga gcatccgtag cggcgtcgag ccgaccatca ccaactctct gaatgatcgc   1140

agcacggaga agaagaatgg tgagcgtatg gcaaactata tcttcgttcg tgcacatgat   1200

agcgaggtgc aaacggtcat cgccgacatt atccgtgaga acatcaatcc gaataccgac   1260

ggcctgacgt tcacgatgga tgaactgaag caggccttta aaatttacaa tgaggatatg   1320

cgtaaagccg acaaaaagta cacgcagttc aatatcccga ccgcgcacgc gctgatgctg   1380

agcaacaaag attctatcac ccgcgtttac tacggtgacc tgtatacgga tgacggtcag   1440

tatatggaaa agaaaagccc gtatcacgac gccattgacg ctctgctgcg tgcgcgtatc   1500

aaatatgttg cgggtggtca ggacatgaag gtgacctata tgggcgtgcc gcgtgaggca   1560

gataaatgga gctataacgg catcctgacc agcgttcgtt atggtacggg tgccaacgag   1620

gcaaccgacg agggtacggc agaaacccgt acccagggca tggccgtcat tgccagcaac   1680
```

```
aatccgaacc tgaaactgaa cgagtgggac aagttgcagg tcaacatggg tgcagctcac   1740
aaaaaccaat actatcgtcc ggtgctgctg accaccaagg acggcatctc gcgctacctg   1800
accgacgaag aagtcccgca gagcctgtgg aaaaagaccg atgcgaacgg catcttgacg   1860
tttgacatga atgatattgc gggttacagc aacgtccaag tgagcggtta tctggccgtc   1920
tgggttcctg tgggtgcgaa ggcggaccag gacgctcgtg ttacggcatc taagaagaaa   1980
aatgcctctg gccaagttta cgaaagcagc gcagccctgg actcccagct gatctatgag   2040
ggcttcagca attttcagga ctttgccacc cgtgacgacc agtacactaa caaggttatc   2100
gcgaaaaacg tcaatctgtt taaagagtgg ggcgtcacca gcttcgaatt gccgccacag   2160
tatgtgagca gccaagacgg tacgttcctg gatagcatca tccagaatgg ttatgcattc   2220
gaagatcgct atgatatggc gatgagcaaa aacaataagt acggtagctt gaacgacctg   2280
ttgaacgcct tgcgtgcact gcatagcgtg aatatccaag cgattgcgga ttgggtgccg   2340
gaccagattt acaatctgcc gggtaaagaa gttgtcactg caacccgtgt taacaattat   2400
ggcacgtatc gtgagggtag cgagattaaa gagaacctgt acgttgctaa caccaaaacc   2460
aatggtacgg actaccaagg taagtatggt ggtgcgttct tggacgagct gaaagccaaa   2520
taccctgaga tttttgagcg cgtccaaatc agcaacggcc agaagatgac caccgacgag   2580
aagattacga aatggtccgc caaacacttt aacggcacga acattctggg tcgtggtgcg   2640
tattatgtgc tgaaagactg ggcgagcaac gagtacctga ataacaaaaa tggcgagatg   2700
gttctgccga agcagctggt taataaaaat gcatataccg gcttcgtcag cgacgcgagc   2760
ggcaccaaat actattctac cagcggctat caggctcgta atagctttat tcaagatgaa   2820
aatggtaatt ggtactactt caataaccgt ggttatttgg tgacgggtgc acaggaaatc   2880
gacggtaagc aactgtattt cctgaaaaac ggcattcagc tgcgtgattc tctgcgtgag   2940
gacgaaaacg gcaaccagta ttactatgat aagacgggtg cgcaagttct gaatcgttat   3000
tacactacgg acggccaaaa ttggcgctac ttcgacgtta aaggcgtcat ggcccgtggt   3060
ctggtcacga tgggtggtaa ccaacaattc tttgaccaaa acggttacca ggttaaaggc   3120
aaaattgcgc gtgcaaaaga cggtaaactg cgttacttcg ataaagacag cggtaatgcg   3180
gcagctaacc gtttcgccca aggcgataac cctagcgact ggtactattt cggtgcagat   3240
ggtgttgcgg ttacgggcct gcaaaaggtt ggtcagcaaa ctctgtactt tgatcaggac   3300
ggcaagcagg tgaaaggtaa agttgttacc ttggcggaca aaagcattcg ttatttcgat   3360
gcaaacagcg gcgagatggc ggtgaacaag tttgtggaag gtgctaagaa cgtgtggtac   3420
tacttcgatc aagcaggcaa agcggtgacc ggcctgcaaa ccatcaataa acaagtgctg   3480
tatttcgacc aggatggtaa acaagtcaaa ggtaaggtgg tcacgctggc tgataagtct   3540
atccgctact tcgacgcgaa cagcggtgag atggcagtgg gcaaattcgc cgaaggcgca   3600
aagaatgagt ggtattactt tgaccaggcg ggcaaggctg ttaccggtct gcaaaagatc   3660
ggccaacaga cgctgtattt cgaccagaac ggtaaacagg ttaagggtaa agtggtcacc   3720
ctggcggata agagcatccg ctatttcgac gctaactctg gcgaaatggc aagcaataag   3780
ttcgttgagg gtgccaaaaa tgaatggtac tatttcgatc aggctggcaa ggcagtgacg   3840
ggtctgcaac aaattggcca gcagaccctg tattttgacc agaatggcaa acaggtgaag   3900
ggtaagattg tgtatgttaa tggtgcgaat cgctactttg atgccaatag cggtgaaatg   3960
gcgcgtaaca agtggattca gctggaagat ggcagctgga tgtattttga ccgcaatggt   4020
```

```
cgtggtcgtc gtttcggttg gaactaa                                     4047


<210> SEQ ID NO 18
<211> LENGTH: 1348
<212> TYPE: PRT
<213> ORGANISM: Streptococcus sanguinis

<400> SEQUENCE: 18

Met Ile Asp Gly Lys Lys Tyr Tyr Val Gln Asp Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365
```

```
Val Glu Pro Thr Ile Thr Asn Ser Leu Asn Asp Arg Ser Thr Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
            740                 745                 750

Lys Tyr Gly Ser Leu Asn Asp Leu Leu Asn Ala Leu Arg Ala Leu His
        755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
```

```
785                 790                 795                 800

Gly Thr Tyr Arg Glu Gly Ser Glu Ile Lys Glu Asn Leu Tyr Val Ala
                805                 810                 815

Asn Thr Lys Thr Asn Gly Thr Asp Tyr Gln Gly Lys Tyr Gly Gly Ala
            820                 825                 830

Phe Leu Asp Glu Leu Lys Ala Lys Tyr Pro Glu Ile Phe Glu Arg Val
        835                 840                 845

Gln Ile Ser Asn Gly Gln Lys Met Thr Thr Asp Glu Lys Ile Thr Lys
    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
            900                 905                 910

Thr Gly Phe Val Ser Asp Ala Ser Gly Thr Lys Tyr Tyr Ser Thr Ser
        915                 920                 925

Gly Tyr Gln Ala Arg Asn Ser Phe Ile Gln Asp Glu Asn Gly Asn Trp
    930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                965                 970                 975

Ser Leu Arg Glu Asp Glu Asn Gly Asn Gln Tyr Tyr Tyr Asp Lys Thr
            980                 985                 990

Gly Ala Gln Val Leu Asn Arg Tyr  Tyr Thr Thr Asp Gly  Gln Asn Trp
        995                 1000                1005

Arg Tyr  Phe Asp Val Lys Gly  Val Met Ala Arg Gly  Leu Val Thr
    1010                1015                1020

Met Gly  Gly Asn Gln Gln Phe  Phe Asp Gln Asn Gly  Tyr Gln Val
    1025                1030                1035

Lys Gly  Lys Ile Ala Arg Ala  Lys Asp Gly Lys Leu  Arg Tyr Phe
    1040                1045                1050

Asp Lys  Asp Ser Gly Asn Ala  Ala Ala Asn Arg Phe  Ala Gln Gly
    1055                1060                1065

Asp Asn  Pro Ser Asp Trp Tyr  Tyr Phe Gly Ala Asp  Gly Val Ala
    1070                1075                1080

Val Thr  Gly Leu Gln Lys Val  Gly Gln Gln Thr Leu  Tyr Phe Asp
    1085                1090                1095

Gln Asp  Gly Lys Gln Val Lys  Gly Lys Val Val Thr  Leu Ala Asp
    1100                1105                1110

Lys Ser  Ile Arg Tyr Phe Asp  Ala Asn Ser Gly Glu  Met Ala Val
    1115                1120                1125

Asn Lys  Phe Val Glu Gly Ala  Lys Asn Val Trp Tyr  Tyr Phe Asp
    1130                1135                1140

Gln Ala  Gly Lys Ala Val Thr  Gly Leu Gln Thr Ile  Asn Lys Gln
    1145                1150                1155

Val Leu  Tyr Phe Asp Gln Asp  Gly Lys Gln Val Lys  Gly Lys Val
    1160                1165                1170

Val Thr  Leu Ala Asp Lys Ser  Ile Arg Tyr Phe Asp  Ala Asn Ser
    1175                1180                1185

Gly Glu  Met Ala Val Gly Lys  Phe Ala Glu Gly Ala  Lys Asn Glu
    1190                1195                1200
```

```
Trp Tyr  Tyr Phe Asp Gln Ala  Gly Lys Ala Val Thr  Gly Leu Gln
    1205                 1210                 1215

Lys Ile  Gly Gln Gln Thr Leu  Tyr Phe Asp Gln Asn  Gly Lys Gln
    1220                 1225                 1230

Val Lys  Gly Lys Val Val Thr  Leu Ala Asp Lys Ser  Ile Arg Tyr
    1235                 1240                 1245

Phe Asp  Ala Asn Ser Gly Glu  Met Ala Ser Asn Lys  Phe Val Glu
    1250                 1255                 1260

Gly Ala  Lys Asn Glu Trp Tyr  Tyr Phe Asp Gln Ala  Gly Lys Ala
    1265                 1270                 1275

Val Thr  Gly Leu Gln Gln Ile  Gly Gln Gln Thr Leu  Tyr Phe Asp
    1280                 1285                 1290

Gln Asn  Gly Lys Gln Val Lys  Gly Lys Ile Val Tyr  Val Asn Gly
    1295                 1300                 1305

Ala Asn  Arg Tyr Phe Asp Ala  Asn Ser Gly Glu Met  Ala Arg Asn
    1310                 1315                 1320

Lys Trp  Ile Gln Leu Glu Asp  Gly Ser Trp Met Tyr  Phe Asp Arg
    1325                 1330                 1335

Asn Gly  Arg Gly Arg Arg Phe  Gly Trp Asn
    1340                 1345
```

<210> SEQ ID NO 19
<211> LENGTH: 4023
<212> TYPE: DNA
<213> ORGANISM: Unknown
<220> FEATURE:
<223> OTHER INFORMATION: unknown Streptococcus species

<400> SEQUENCE: 19

```
atgatcgacg gcaaatacta ctacgtaaac gaggacggca gccacaaaga gaatttcgcg     60

atcacggtta atggtcaact gctgtatttt ggtaaggatg gcgcgctgac cagcagcagc    120

acgtacagct tcacccaagg cactaccaat attgtggacg gttttagcat taacaaccgt    180

gcgtatgact ccagcgaggc ctctttcgag ctgattgacg gttatctgac tgcggactct    240

tggtaccgtc cggcgagcat tatcaaagac ggtgtgacgt ggcaagcatc caccgccgag    300

gacttccgcc cgttgctgat ggcgtggtgg ccgaacgttg atactcaggt gaactacctg    360

aactacatgt ccaaagtctt taatctggat gctaaataca gctcgactga taaacaggaa    420

accctgaagg tggcggcgaa agatatccag atcaaaattg aacaaaagat tcaggcggaa    480

aagtccacgc aatggctgcg tgaaacgatc agcgcctttg taaaaaccca gccgcaatgg    540

aacaaagaga ctgagaacta cagcaagggc ggtggtgagg accatctgca aggtggtgcc    600

ctgctgtatg ttaatgactc tcgtaccccg tgggcgaaca gcaactatcg tttgctgaac    660

cgcacggcga ccaaccagac cggtacgatc gacaagagca tcctggacga gcagagcgat    720

ccgaatcaca tgggtggttt tgatttcttg ctggctaatg acgttgactt gagcaatccg    780

gtcgtccagg cggaacaact gaatcagatc cactacctga tgaattgggg ttctattgtc    840

atgggtgata aagacgcgaa ttttgacggt attcgtgtag acgcggtgga taatgttgat    900

gcggacatgc tgcaattgta caccaactat ttccgcgaat actatggtgt caacaaaagc    960

gaggcaaacg cgctggcgca cattagcgtc ctggaagcct ggagcctgaa tgacaaccat   1020

tacaatgata agactgatgt tgcggcgctg gcaatggaga ataagcagcg cttggcactg   1080

ttgtttagcc tggcgaaacc gattaaagaa cgcacgcctg ccgtgtctcc gctgtacaac   1140
```

-continued

```
aatacgttta acaccactca gcgtgatgaa aagacggact ggatcaataa agatggttcg   1200
aaagcctaca atgaggatgg cactgtcaag aaaagcacca tcggcaagta taacgagaag   1260
tatggtgatg ctagcggcaa ctacgttttc atccgcgctc acgacaataa cgtgcaagac   1320
atcatcgcgg agatcattaa gaaagagatt aacgagaaat ctgacggttt taccattacg   1380
gattcggaga tgaagcgtgc atttgagatc tataacaaag acatgctgtc taatgacaaa   1440
aagtacacgc tgaataacat cccggcggcg tacgcggtta tgctgcaaaa catggaaacg   1500
attacccgcg tgtattacgg cgatctgtac acggacgacg gtaattacat ggaagcgaaa   1560
agcccgtact acgatacgat tgttaacttg atgaagtctc gcatcaaata cgtgagcggt   1620
ggccaggcgc agcgcagcta ctggctgccg accgatggta agatggataa gtcggatgtt   1680
gagctgtacc gtacgaacga agtgtacacg agcgtccgtt acggcaaaga cattatgacc   1740
gccgatgaca cgcaaggtag caaatacagc cgtaccagcg gtcaggtgac cctggtcgtc   1800
aacaacccaa aactgacctt ggaccaaagc gcaaagctga acgtggttat gggcaagatt   1860
catgctaatc agaagtaccg cgcactgatt gtcggtaccc cgaacggtat taagaatttc   1920
accagcgacg cagaggctat tgccgcaggc tatgtcaaag aaaccgatgg caatggcgtg   1980
ctgaccttcg gtgcaaacga catcaagggt tatgaaactt tcgatatgag cggcttcgtc   2040
gctgtttggg ttccggtcgg tgcgagcgac gaccaagata ttcgtgtggc ggcgtctacg   2100
gcagcaaaga aagagggtga gctgacgctg aaagcgaccg aagcctatga ctcccaactg   2160
atctatgaag gctttagcaa tttccagacc atcccagatg gcagcgatcc ttctgtttat   2220
accaatcgta agatcgcgga aaatgttgat ttgttcaaga gctggggtgt cacgagcttc   2280
gaaatggctc cgcagttcgt ttctgcggac gatggcacgt ttctggacag cgtcattcaa   2340
aacggctatg cgttcgcaga ccgttatgat ctggccatga gcaaaaacaa taagtacggt   2400
agcaaagaag atctgcgtaa cgcgctgaag gcactgcaca aagcaggcat tcaggcgatt   2460
gcagattggg tgccagacca aatctaccag ctgcctggca aagaagttgt tactgccacc   2520
cgcacggacg gtgctggtcg caaaatcagc gatgcaatca tcgatcattc cctgtacgtt   2580
gcgaactcca agagctccgg taaggactac caagcgaagt acggtggcga gttcttggcg   2640
gaactgaagg cgaaataccc ggaaatgttc aaagtgaaca tgattagcac cggcaaaccg   2700
attgatgata gcgtgaaact gaagcagtgg aaagcagaat acttcaacgg caccaatgtg   2760
ctggatcgcg gtgtcggtta tgttctgagc gatgaggcaa ccggtaagta tttcaccgtt   2820
accaaagagg gtaactttat cccgttgcag ctgaagggta acaagaaggt gattaccggc   2880
ttttccagcg acggtaaggg cattacctat ttcggtacta gcggtaacca agctaaatcc   2940
gcgttcgtca cttttaacgg taacacgtac tacttcgacg cacgtggcca catggttacc   3000
aacggtgagt actcgccgaa tggtaaagat gtgtatcgtt ttctgccgaa cggcattatg   3060
ctgagcaacg cgttctatgt tgacggcaat ggcaacacct acctgtacaa ctccaaaggc   3120
caaatgtata aaggtggcta tagcaaattt gacgtcacgg aaacgaagga cggtaaagag   3180
agcaaagttg tcaagttccg ctactttacg aacgagggcg tgatggcgaa aggtgtcacg   3240
gttgtggatg gcttcactca gtactttaac gaggatggca ttcaaagcaa agacgagctg   3300
gtcacttaca atggcaagac ctattacttc gaagcacaca cgggcaatgc cattaagaat   3360
acgtggcgta atatcaaggg caaatggtac cattttgatg ctaacggtgt cgcggctact   3420
ggcgcacagg ttatcaacgg tcagcacctg tacttcaatg aagatggctc tcaagtaaaa   3480
ggtagcatcg tcaaaaacgc tgatggtacg ttcagcaagt acaaggacag ctctggcgat   3540
```

```
ctggtggtga acgagttttt cacgacgggt gataacgtct ggtactatgc tggtgccaat   3600

ggcaaaacgg ttactggtgc acaggtgatt aatggccagc acttgttctt caaagaggat   3660

ggcagccagg tcaagggcga ctttgtgaag aatagcgacg gcacctactc caagtatgac   3720

gctgcgagcg gcgaacgtct gaccaacgag ttcttcacta cgggcgacaa tcattggtac   3780

tatattggcg ccaacggtaa gaccgttacc ggtgaagtta agattggtga cgacacgtat   3840

ttcttcgcaa aagacggtaa gcaactgaaa ggtcaaatcg ttaccacccg tagcggtcgt   3900

atcagctact actttggtga tagcggtaag aaggctatta gcacgtgggt ggagatccag   3960

ccgggtgtgt ttgttttctt cgacaaaaac ggcctggctt acccaccgga gaatatgaac   4020

tga                                                                  4023
```

<210> SEQ ID NO 20
<211> LENGTH: 1340
<212> TYPE: PRT
<213> ORGANISM: Unknown
<220> FEATURE:
<223> OTHER INFORMATION: unknown Streptococcus species

<400> SEQUENCE: 20

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270
```

```
Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Glu Lys Ser Asp Gly Phe Thr Ile Thr Asp Ser Glu Met
    450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Thr Leu Asp
        595                 600                 605

Gln Ser Ala Lys Leu Asn Val Val Met Gly Lys Ile His Ala Asn Gln
    610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685
```

```
Ser Asp Asp Gln Asp Ile Arg Val Ala Ala Ser Thr Ala Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
    930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
        995                 1000                1005

Lys Asp  Val Tyr Arg Phe Leu  Pro Asn Gly Ile Met  Leu Ser Asn
    1010                1015                1020

Ala Phe  Tyr Val Asp Gly Asn  Gly Asn Thr Tyr Leu  Tyr Asn Ser
    1025                1030                1035

Lys Gly  Gln Met Tyr Lys Gly  Gly Tyr Ser Lys Phe  Asp Val Thr
    1040                1045                1050

Glu Thr  Lys Asp Gly Lys Glu  Ser Lys Val Val Lys  Phe Arg Tyr
    1055                1060                1065

Phe Thr  Asn Glu Gly Val Met  Ala Lys Gly Val Thr  Val Val Asp
    1070                1075                1080

Gly Phe  Thr Gln Tyr Phe Asn  Glu Asp Gly Ile Gln  Ser Lys Asp
    1085                1090                1095

Glu Leu  Val Thr Tyr Asn Gly  Lys Thr Tyr Tyr Phe  Glu Ala His
```

```
    1100                1105                1110

Thr Gly  Asn Ala Ile Lys Asn  Thr Trp Arg Asn Ile  Lys Gly Lys
    1115                1120                1125

Trp Tyr  His Phe Asp Ala Asn  Gly Val Ala Ala Thr  Gly Ala Gln
    1130                1135                1140

Val Ile  Asn Gly Gln His Leu  Tyr Phe Asn Glu Asp  Gly Ser Gln
    1145                1150                1155

Val Lys  Gly Ser Ile Val Lys  Asn Ala Asp Gly Thr  Phe Ser Lys
    1160                1165                1170

Tyr Lys  Asp Ser Ser Gly Asp  Leu Val Val Asn Glu  Phe Phe Thr
    1175                1180                1185

Thr Gly  Asp Asn Val Trp Tyr  Tyr Ala Gly Ala Asn  Gly Lys Thr
    1190                1195                1200

Val Thr  Gly Ala Gln Val Ile  Asn Gly Gln His Leu  Phe Phe Lys
    1205                1210                1215

Glu Asp  Gly Ser Gln Val Lys  Gly Asp Phe Val Lys  Asn Ser Asp
    1220                1225                1230

Gly Thr  Tyr Ser Lys Tyr Asp  Ala Ala Ser Gly Glu  Arg Leu Thr
    1235                1240                1245

Asn Glu  Phe Phe Thr Thr Gly  Asp Asn His Trp Tyr  Tyr Ile Gly
    1250                1255                1260

Ala Asn  Gly Lys Thr Val Thr  Gly Glu Val Lys Ile  Gly Asp Asp
    1265                1270                1275

Thr Tyr  Phe Phe Ala Lys Asp  Gly Lys Gln Leu Lys  Gly Gln Ile
    1280                1285                1290

Val Thr  Thr Arg Ser Gly Arg  Ile Ser Tyr Tyr Phe  Gly Asp Ser
    1295                1300                1305

Gly Lys  Lys Ala Ile Ser Thr  Trp Val Glu Ile Gln  Pro Gly Val
    1310                1315                1320

Phe Val  Phe Phe Asp Lys Asn  Gly Leu Ala Tyr Pro  Pro Glu Asn
    1325                1330                1335

Met Asn
    1340


<210> SEQ ID NO 21
<211> LENGTH: 4479
<212> TYPE: DNA
<213> ORGANISM: Leuconostoc mesenteroides

<400> SEQUENCE: 21

atgaccccat ccgtattagg tgattcttcc gtcccagatg tatcggctaa caatgtgcaa     60

tccgcgagcg ataatacgac ggacacccag caaaatacca ccatcaccga ggaaaatgat    120

aaggtccaga gcgctgcgac caacgataac gtgaccacgg cagcgtccga cacgacgcag    180

agcgccgata acaacgttac cgagaaacaa tctgatgatc acgcgctgga taatgaaaag    240

gttgacaata agcaggacga ggtcgcccag accaacgtga ctagcaaaaa cgaggagagc    300

gcggtggcct ctaccgacac cgatccggca gagactacca cggacgaaac gcaacaggtt    360

agcggcaagt atgtggaaaa ggatggttct tggtattact actttgacga cggtaagaac    420

gcgaagggtc tgagcacgat tgacaacaat atccaatact ttgatgaaag cggtaagcag    480

gtcaaaggtc agtatgtgac gattgataac cagacctatt actttgataa agatagcggt    540

gatgaactga ccggcctgca atctattgac ggtaacattg ttgccttcaa tgacgagggc    600

cagcagatct ttaatcaata ctaccagagc gagaacggta cgacctacta ttttgatgat    660
```

```
aagggccacg ctgccaccgg tattaagaat attgagggca agaactacta ttttgacaat    720
ctgggtcaac tgaaaaaggg cttctccggc gtgatcgacg gtcagattat gacgtttgac    780
caggaaactg gtcaagaggt ttccaatacc acgtccgaga tcaaagaggg cctgacgact    840
cagaacactg attactctga acataatgcg gcgcacggta ccgacgccga agattttgag    900
aacatcgatg gctatctgac cgccagctcc tggtaccgtc cgacggacat tctgcgcaat    960
ggcactgact gggaaccgag caccgacacg gactttcgtc caatcttgag cgtttggtgg   1020
ccggataaga atacgcaggt caactatctg aactacatgg cggacctggg cttcattagc   1080
aacgcagaca gcttcgaaac gggtgactct cagagcctgc tgaacgaggc gtccaattac   1140
gtccagaaaa gcatcgagat gaaaatctcc gcgcaacaga gcaccgagtg gctgaaagac   1200
gccatggccg cgtttattgt tacgcagccg caatggaatg aaacttccga agatatgagc   1260
aacgaccact tgcaaaacgg tgcgctgacc tacgttaaca gcccgctgac cccggacgca   1320
aacagcaact ttcgcctgct gaatcgtacc cctaccaacc agaccggcga acaggcgtac   1380
aacctggata attctaaagg tggctttgag ctgctgctgg caaatgatgt ggataacagc   1440
aacccggtgg ttcaagcgga acaactgaat tggctgtact acctgatgaa tttcggtacg   1500
attaccgcca atgacgcgga tgccaacttt gacggcattc gcgtcgatgc agtggataac   1560
gtggatgctg atctgttgca gattgcggca gactacttta aactggccta cggtgtggac   1620
cagaatgata gcaccgcaaa ccaacacctg tctatcctgg aagattggag ccacaacgac   1680
ccgctgtatg tcacggatca aggcagcgac cagctgacta tggacgacta cgtgcatacg   1740
caattgattt ggagcctgac caaaagcagc gatatccgtg gtaccatgca acgttttgtg   1800
gattactata tggtggaccg ttccaatgac tccacggaga atgaagcgat cccgaattac   1860
agctttgtcc gcgcacacga tagcgaagtt caaaccgtta tcgcgcaaat cgtgagcgat   1920
ctgtatccag atgttgagaa tagcctggct ccgaccaccg agcagctggc agcagcattc   1980
aaggtgtata atgaagatga gaaattggcc gacaaaaagt atacccaata caacatggcg   2040
agcgcctatg cgatgctgct gaccaataaa gacacggtgc cgcgtgtcta ctatggcgac   2100
ctgtataccg atgacggtca atacatggca acgaagagcc cgtattacga cgcgattaac   2160
accctgctga aagctcgtgt tcaatatgtc gcgggtggcc aaagcatgag cgtggatagc   2220
aacgatgtgc tgaccagcgt tcgctatggc aaagacgcga tgacggcgag cgacacgggc   2280
accagcgaga ctcgtaccga gggcgtcggt gtcattgtgt ccaacaatgc ggagctgcaa   2340
ctggaagatg gtcatacggt taccctgcac atgggtgccg cgcacaaaaa tcaggcatac   2400
cgtgcgttgt tgtccaccac ggccgacggt ctggcgtatt atgatacgga cgagaatgcc   2460
ccggtggcat atacggatgc gaacggtgac ttgattttca ccaatgagtc catctacggc   2520
gttcagaatc cgcaagtcag cggttacctg gcggtgtggg tcccggttgg tgcacaacag   2580
gaccaggacg cgcgcacggc aagcgatacc accactaaca ccagcgataa agttttccac   2640
agcaacgcgg ctctggacag ccaagtgatc tacgagggct tcagcaactt ccaagcgttt   2700
gcgactgatt ccagcgaata caccaatgtt gttattgctc agaacgctga tcaattcaaa   2760
caatggggcg tgacctcgtt tcagctggct ccgcagtacc gcagcagcac ggacacttcc   2820
ttcctggata gcatcatcca aaatggttac gcgtttacgg accgctatga tctgggttat   2880
ggcacgccga cgaagtacgg taccgcggac caactgcgtg atgcaatcaa agcactgcat   2940
gcgagcggca tccaagcgat tgcagattgg gttccggacc agatttacaa tctgccggag   3000
```

```
caagaactgg cgactgtcac gcgcacgaat agcttcggtg atgatgatac tgacagcgac   3060

attgataatg ctctgtatgt ggttcaaagc cgcggtggtg gtcagtacca agagatgtat   3120

ggcggtgcgt ttctggagga gttgcaagcg ctgtacccta gcctgtttaa ggtgaaccag   3180

atttctactg gtgtcccgat cgatggtagc gtgaagatta ccgagtgggc tgcgaaatac   3240

ttcaacggca gcaatatcca gggtaagggt gcgggttacg tgttgaaaga catgggtagc   3300

aataagtact tcaaggtcgt gagcaatacc gaggacggcg actatctgcc gaaacagctg   3360

accaacgacc tgagcgaaac cggtttcacc cacgacgaca agggtatcat ctactacacc   3420

ctgagcggct atcgtgcaca gaacgccttc attcaagacg atgataacaa ttactattac   3480

tttgacaaga ccggtcacct ggtcacgggt ttgcagaaaa tcaacaacca tacgtacttc   3540

ttcctgccga atggcattga gctggtgaaa tccttcttgc agaacgagga tggcacgatc   3600

gtttacttcg ataagaaagg tcatcaagtc tttgatcaat acattacgga tcaaaatggc   3660

aacgcgtact atttcgacga tgccggtgtt atgctgaagt ctggtctggc aacgattgat   3720

ggtcatcagc agtacttcga tcagaatggc gttcaagtta aggacaagtt cgttatcggt   3780

acggatggct acaagtacta cttcgagccg ggttgcggca atttggcaat tttgcgttac   3840

gtgcaaaata gcaagaacca atggttctat ttcgatggca atggccacgc agtcacgggt   3900

ttccaaacca tcaacggcaa gaagcagtat ttctacaacg atggtcacca aagcaagggc   3960

gaatttatca atgcggacgg tgacaccttc tacaccagcg ccaccgacgg tcgtttggtg   4020

acgggtgttc agaagatcaa cggtatcacc tacgcgtttg acaataccgg caacctgatc   4080

acgaaccagt attatcagct ggcggacggt aagtacatgc tgctggacga ctctggtcgc   4140

gcaaaaacgg gctttgtcct gcaagacggt gtcctgcgtt atttcgacca gaacggtgaa   4200

caagtgaagg acgccattat cgtcgacccg gacaccaacc tgtcttatta ctttaacgcg   4260

acccagggtg tcgcggtgaa aaacgattac ttcgagtacc aaggcaactg gtacctgacc   4320

gatgcaaact accagctgat taaaggcttc aaagcagttg acgactcgct gcaacacttc   4380

gacgaagtta cgggtgtgca gaccaaggaa agcgctctga ttagcgcaca gggcaaagtt   4440

taccagttcg acaacaatgg taacgcggtg agcgcataa                          4479
```

```
<210> SEQ ID NO 22
<211> LENGTH: 1492
<212> TYPE: PRT
<213> ORGANISM: Leuconostoc mesenteroides

<400> SEQUENCE: 22

Met Thr Pro Ser Val Leu Gly Asp Ser Ser Val Pro Asp Val Ser Ala
1               5                   10                  15

Asn Asn Val Gln Ser Ala Ser Asp Asn Thr Thr Asp Thr Gln Gln Asn
            20                  25                  30

Thr Thr Ile Thr Glu Glu Asn Asp Lys Val Gln Ser Ala Ala Thr Asn
        35                  40                  45

Asp Asn Val Thr Thr Ala Ala Ser Asp Thr Thr Gln Ser Ala Asp Asn
    50                  55                  60

Asn Val Thr Glu Lys Gln Ser Asp Asp His Ala Leu Asp Asn Glu Lys
65                  70                  75                  80

Val Asp Asn Lys Gln Asp Glu Val Ala Gln Thr Asn Val Thr Ser Lys
                85                  90                  95

Asn Glu Glu Ser Ala Val Ala Ser Thr Asp Thr Asp Pro Ala Glu Thr
            100                 105                 110
```

```
Thr Thr Asp Glu Thr Gln Gln Val Ser Gly Lys Tyr Val Glu Lys Asp
        115                 120                 125

Gly Ser Trp Tyr Tyr Tyr Phe Asp Asp Gly Lys Asn Ala Lys Gly Leu
    130                 135                 140

Ser Thr Ile Asp Asn Asn Ile Gln Tyr Phe Asp Glu Ser Gly Lys Gln
145                 150                 155                 160

Val Lys Gly Gln Tyr Val Thr Ile Asp Asn Gln Thr Tyr Tyr Phe Asp
                165                 170                 175

Lys Asp Ser Gly Asp Glu Leu Thr Gly Leu Gln Ser Ile Asp Gly Asn
            180                 185                 190

Ile Val Ala Phe Asn Asp Glu Gly Gln Gln Ile Phe Asn Gln Tyr Tyr
        195                 200                 205

Gln Ser Glu Asn Gly Thr Thr Tyr Tyr Phe Asp Asp Lys Gly His Ala
    210                 215                 220

Ala Thr Gly Ile Lys Asn Ile Glu Gly Lys Asn Tyr Tyr Phe Asp Asn
225                 230                 235                 240

Leu Gly Gln Leu Lys Lys Gly Phe Ser Gly Val Ile Asp Gly Gln Ile
                245                 250                 255

Met Thr Phe Asp Gln Glu Thr Gly Gln Glu Val Ser Asn Thr Thr Ser
            260                 265                 270

Glu Ile Lys Glu Gly Leu Thr Thr Gln Asn Thr Asp Tyr Ser Glu His
        275                 280                 285

Asn Ala Ala His Gly Thr Asp Ala Glu Asp Phe Glu Asn Ile Asp Gly
    290                 295                 300

Tyr Leu Thr Ala Ser Ser Trp Tyr Arg Pro Thr Asp Ile Leu Arg Asn
305                 310                 315                 320

Gly Thr Asp Trp Glu Pro Ser Thr Asp Thr Asp Phe Arg Pro Ile Leu
                325                 330                 335

Ser Val Trp Trp Pro Asp Lys Asn Thr Gln Val Asn Tyr Leu Asn Tyr
            340                 345                 350

Met Ala Asp Leu Gly Phe Ile Ser Asn Ala Asp Ser Phe Glu Thr Gly
        355                 360                 365

Asp Ser Gln Ser Leu Leu Asn Glu Ala Ser Asn Tyr Val Gln Lys Ser
    370                 375                 380

Ile Glu Met Lys Ile Ser Ala Gln Gln Ser Thr Glu Trp Leu Lys Asp
385                 390                 395                 400

Ala Met Ala Ala Phe Ile Val Thr Gln Pro Gln Trp Asn Glu Thr Ser
                405                 410                 415

Glu Asp Met Ser Asn Asp His Leu Gln Asn Gly Ala Leu Thr Tyr Val
            420                 425                 430

Asn Ser Pro Leu Thr Pro Asp Ala Asn Ser Asn Phe Arg Leu Leu Asn
        435                 440                 445

Arg Thr Pro Thr Asn Gln Thr Gly Glu Gln Ala Tyr Asn Leu Asp Asn
    450                 455                 460

Ser Lys Gly Gly Phe Glu Leu Leu Leu Ala Asn Asp Val Asp Asn Ser
465                 470                 475                 480

Asn Pro Val Val Gln Ala Glu Gln Leu Asn Trp Leu Tyr Tyr Leu Met
                485                 490                 495

Asn Phe Gly Thr Ile Thr Ala Asn Asp Ala Asp Ala Asn Phe Asp Gly
            500                 505                 510

Ile Arg Val Asp Ala Val Asp Asn Val Asp Ala Asp Leu Leu Gln Ile
        515                 520                 525

Ala Ala Asp Tyr Phe Lys Leu Ala Tyr Gly Val Asp Gln Asn Asp Ser
```

```
    530                 535                 540

Thr Ala Asn Gln His Leu Ser Ile Leu Glu Asp Trp Ser His Asn Asp
545                 550                 555                 560

Pro Leu Tyr Val Thr Asp Gln Gly Ser Asp Gln Leu Thr Met Asp Asp
                565                 570                 575

Tyr Val His Thr Gln Leu Ile Trp Ser Leu Thr Lys Ser Ser Asp Ile
            580                 585                 590

Arg Gly Thr Met Gln Arg Phe Val Asp Tyr Tyr Met Val Asp Arg Ser
        595                 600                 605

Asn Asp Ser Thr Glu Asn Glu Ala Ile Pro Asn Tyr Ser Phe Val Arg
    610                 615                 620

Ala His Asp Ser Glu Val Gln Thr Val Ile Ala Gln Ile Val Ser Asp
625                 630                 635                 640

Leu Tyr Pro Asp Val Glu Asn Ser Leu Ala Pro Thr Thr Glu Gln Leu
                645                 650                 655

Ala Ala Ala Phe Lys Val Tyr Asn Glu Asp Glu Lys Leu Ala Asp Lys
            660                 665                 670

Lys Tyr Thr Gln Tyr Asn Met Ala Ser Ala Tyr Ala Met Leu Leu Thr
        675                 680                 685

Asn Lys Asp Thr Val Pro Arg Val Tyr Tyr Gly Asp Leu Tyr Thr Asp
    690                 695                 700

Asp Gly Gln Tyr Met Ala Thr Lys Ser Pro Tyr Tyr Asp Ala Ile Asn
705                 710                 715                 720

Thr Leu Leu Lys Ala Arg Val Gln Tyr Val Ala Gly Gly Gln Ser Met
                725                 730                 735

Ser Val Asp Ser Asn Asp Val Leu Thr Ser Val Arg Tyr Gly Lys Asp
            740                 745                 750

Ala Met Thr Ala Ser Asp Thr Gly Thr Ser Glu Thr Arg Thr Glu Gly
        755                 760                 765

Val Gly Val Ile Val Ser Asn Asn Ala Glu Leu Gln Leu Glu Asp Gly
    770                 775                 780

His Thr Val Thr Leu His Met Gly Ala Ala His Lys Asn Gln Ala Tyr
785                 790                 795                 800

Arg Ala Leu Leu Ser Thr Thr Ala Asp Gly Leu Ala Tyr Tyr Asp Thr
                805                 810                 815

Asp Glu Asn Ala Pro Val Ala Tyr Thr Asp Ala Asn Gly Asp Leu Ile
            820                 825                 830

Phe Thr Asn Glu Ser Ile Tyr Gly Val Gln Asn Pro Gln Val Ser Gly
        835                 840                 845

Tyr Leu Ala Val Trp Val Pro Val Gly Ala Gln Gln Asp Gln Asp Ala
    850                 855                 860

Arg Thr Ala Ser Asp Thr Thr Thr Asn Thr Ser Asp Lys Val Phe His
865                 870                 875                 880

Ser Asn Ala Ala Leu Asp Ser Gln Val Ile Tyr Glu Gly Phe Ser Asn
                885                 890                 895

Phe Gln Ala Phe Ala Thr Asp Ser Ser Glu Tyr Thr Asn Val Val Ile
            900                 905                 910

Ala Gln Asn Ala Asp Gln Phe Lys Gln Trp Gly Val Thr Ser Phe Gln
        915                 920                 925

Leu Ala Pro Gln Tyr Arg Ser Ser Thr Asp Thr Ser Phe Leu Asp Ser
    930                 935                 940

Ile Ile Gln Asn Gly Tyr Ala Phe Thr Asp Arg Tyr Asp Leu Gly Tyr
945                 950                 955                 960
```

```
Gly Thr Pro Thr Lys Tyr Gly Thr Ala Asp Gln Leu Arg Asp Ala Ile
                965                 970                 975

Lys Ala Leu His Ala Ser Gly Ile Gln Ala Ile Ala Asp Trp Val Pro
            980                 985                 990

Asp Gln Ile Tyr Asn Leu Pro Glu  Gln Glu Leu Ala Thr  Val Thr Arg
        995                 1000                 1005

Thr Asn  Ser Phe Gly Asp Asp  Asp Thr Asp Ser Asp  Ile Asp Asn
    1010                 1015                 1020

Ala Leu  Tyr Val Val Gln Ser  Arg Gly Gly Gly Gln  Tyr Gln Glu
    1025                 1030                 1035

Met Tyr  Gly Gly Ala Phe Leu  Glu Glu Leu Gln Ala  Leu Tyr Pro
    1040                 1045                 1050

Ser Leu  Phe Lys Val Asn Gln  Ile Ser Thr Gly Val  Pro Ile Asp
    1055                 1060                 1065

Gly Ser  Val Lys Ile Thr Glu  Trp Ala Ala Lys Tyr  Phe Asn Gly
    1070                 1075                 1080

Ser Asn  Ile Gln Gly Lys Gly  Ala Gly Tyr Val Leu  Lys Asp Met
    1085                 1090                 1095

Gly Ser  Asn Lys Tyr Phe Lys  Val Val Ser Asn Thr  Glu Asp Gly
    1100                 1105                 1110

Asp Tyr  Leu Pro Lys Gln Leu  Thr Asn Asp Leu Ser  Glu Thr Gly
    1115                 1120                 1125

Phe Thr  His Asp Asp Lys Gly  Ile Ile Tyr Tyr Thr  Leu Ser Gly
    1130                 1135                 1140

Tyr Arg  Ala Gln Asn Ala Phe  Ile Gln Asp Asp Asp  Asn Asn Tyr
    1145                 1150                 1155

Tyr Tyr  Phe Asp Lys Thr Gly  His Leu Val Thr Gly  Leu Gln Lys
    1160                 1165                 1170

Ile Asn  Asn His Thr Tyr Phe  Phe Leu Pro Asn Gly  Ile Glu Leu
    1175                 1180                 1185

Val Lys  Ser Phe Leu Gln Asn  Glu Asp Gly Thr Ile  Val Tyr Phe
    1190                 1195                 1200

Asp Lys  Lys Gly His Gln Val  Phe Asp Gln Tyr Ile  Thr Asp Gln
    1205                 1210                 1215

Asn Gly  Asn Ala Tyr Tyr Phe  Asp Asp Ala Gly Val  Met Leu Lys
    1220                 1225                 1230

Ser Gly  Leu Ala Thr Ile Asp  Gly His Gln Gln Tyr  Phe Asp Gln
    1235                 1240                 1245

Asn Gly  Val Gln Val Lys Asp  Lys Phe Val Ile Gly  Thr Asp Gly
    1250                 1255                 1260

Tyr Lys  Tyr Tyr Phe Glu Pro  Gly Cys Gly Asn Leu  Ala Ile Leu
    1265                 1270                 1275

Arg Tyr  Val Gln Asn Ser Lys  Asn Gln Trp Phe Tyr  Phe Asp Gly
    1280                 1285                 1290

Asn Gly  His Ala Val Thr Gly  Phe Gln Thr Ile Asn  Gly Lys Lys
    1295                 1300                 1305

Gln Tyr  Phe Tyr Asn Asp Gly  His Gln Ser Lys Gly  Glu Phe Ile
    1310                 1315                 1320

Asn Ala  Asp Gly Asp Thr Phe  Tyr Thr Ser Ala Thr  Asp Gly Arg
    1325                 1330                 1335

Leu Val  Thr Gly Val Gln Lys  Ile Asn Gly Ile Thr  Tyr Ala Phe
    1340                 1345                 1350
```

```
Asp Asn  Thr Gly Asn Leu Ile  Thr Asn Gln Tyr Tyr  Gln Leu Ala
    1355                 1360                 1365

Asp Gly  Lys Tyr Met Leu Leu  Asp Asp Ser Gly Arg  Ala Lys Thr
    1370                 1375                 1380

Gly Phe  Val Leu Gln Asp Gly  Val Leu Arg Tyr Phe  Asp Gln Asn
    1385                 1390                 1395

Gly Glu  Gln Val Lys Asp Ala  Ile Ile Val Asp Pro  Asp Thr Asn
    1400                 1405                 1410

Leu Ser  Tyr Tyr Phe Asn Ala  Thr Gln Gly Val Ala  Val Lys Asn
    1415                 1420                 1425

Asp Tyr  Phe Glu Tyr Gln Gly  Asn Trp Tyr Leu Thr  Asp Ala Asn
    1430                 1435                 1440

Tyr Gln  Leu Ile Lys Gly Phe  Lys Ala Val Asp Asp  Ser Leu Gln
    1445                 1450                 1455

His Phe  Asp Glu Val Thr Gly  Val Gln Thr Lys Glu  Ser Ala Leu
    1460                 1465                 1470

Ile Ser  Ala Gln Gly Lys Val  Tyr Gln Phe Asp Asn  Asn Gly Asn
    1475                 1480                 1485

Ala Val  Ser Ala
    1490
```

<210> SEQ ID NO 23
<211> LENGTH: 3972
<212> TYPE: DNA
<213> ORGANISM: Streptococcus criceti

<400> SEQUENCE: 23

```
atggttgatg gcaaatacta ctactacgac gcagatggca acgttaagaa gaatttcgcg     60

attagcgtcg gtgacgcaat cttctacttt gacgaaaccg gtgcttacaa ggacaccagc    120

aaagttggtg cggataaaac cagcagcagc gcgaatcaaa ccacggccac cttcgcggca    180

aacaaccgtg cctatagcac tgcggcggag aactttgagg caattgacaa ctatttgacc    240

gcagacagct ggtatcgtcc gaagagcatt ctgaaagatg gtaagacgtg gaccgaatcc    300

accaaagacg acttccgtcc gctgctgatg gcttggtggc cggataccga aactaaacgc    360

aactatgtca actatatgaa taaggtcgtc ggcattgata aaacctatac cgcggagact    420

agccaagccg acctgacggc agctgcggag ctggttcaag cgcgcattga gcaacgcatc    480

acgtctgaga agaacacgaa atggctgcgc gaggctatta gcgcgtttgt caagacccag    540

ccgcaatgga atggcgagtc cgaaaagccg tatgatgatc atttgcagaa cggtgcactg    600

aagttcgaca acgaaacctc tctgaccccg gacacccagt ctggttatcg tatcttgaat    660

cgcacgccga ccaatcaaac gggcagcctg gacccgcgtt tcacctttaa tcaaaatgat    720

ccgctgggtg gctatgaata tctgctggca aacgacgtgg ataatagcaa cccggtggtg    780

caagcggaga gcttgaattg gctgcactac ctgctgaact tcggcagcat ctacgcgaat    840

gatccggaag cgaatttcga ttccattcgt gtagacgccg tggataacgt ggatgcggat    900

ctgttgcaga ttagcagcga ctacctgaaa tctgcgtaca aaatcgataa gaacaacaaa    960

aatgcgaatg accacgtgag catcgttgag gcgtggagcg ataacgacac cccgtacctg   1020

cacgatgaag gcgataactt gatgaatatg gacaataagt ttcgcctgag catgttgcgc   1080

tccctggcga agcctctgga caaacgtagc ggcctgaacc ctctgatcca taatagcgtc   1140

gttgatcgcg aggtggatga ccgtgaggtt gagaaaattc cgagctactc ttttgcacgc   1200

gctcacgaca gcgaggttca ggatctgatt cgtgacatca ttaaggcaga aatcaatccg   1260
```

```
aacagcttcg gctacagctt tacccaagaa gaaatcgatc aagcgttcaa gatctacaac   1320
gaggacctga agaaaaccaa caagaagtac acccattaca atgtcccgct gtcttacacc   1380
ttgctgctga cgaataaggg tagcattccg cgtatttact acggcgacat gtttaccgac   1440
gatggccagt atatggcgaa caaaacggtg aattacaatg ctattgagag cctgctgaag   1500
gctcgtatga agtatgtgag cggtggtcag gcgatgcaaa actatcaaat tggtaatggt   1560
gaaattctga cgtcggtgcg ctacggtaaa ggtgcgctga agcaatcgga caagggcgac   1620
gcaacgacgc gtacctctgg tattggtatt gtcatgggca accagccgaa tttctcgctg   1680
gaaggtaaag tcgttgccct gaacatgggt gcagcgcatg ccaatcagga gtatcgtgcc   1740
ctgatggtga gcactaaaga cggcgtggcg acctatgcga cggatgcaga cgcgagcaaa   1800
gcgggtatga cgaaacgtac cgacgagaac ggctacttgt atttcctgaa tgacgacttg   1860
aagggtgttg caaatccaca gatctccggt tttctgcaag tatgggtgcc ggtcggtgct   1920
cctgccgacc aggatattcg cgttgccgcg acgaacgctg caagcacgga tggtaagtcc   1980
ctgcaccaag atgcggcgat ggatagccgt gttatgttcg agggtttttc caactttcag   2040
gcgttcgcaa cgaaagaaga tgagtatgct aatgttgtta ttgcgaaaaa tgtggataag   2100
tttgttagct ggggcatcac tgactttgag atggcaccgc agtatacctc tagcgatgac   2160
ggtcagttcc tggatagcgt tattcagaat ggttatgcat tcacggaccg ttatgatctg   2220
ggtatgagca aggcaaacaa atatggtacg gcggaacacc tggtcaaagc tatcaaagcg   2280
ttgcacaaag caggtctgaa agttatggcg gattgggtcc cggaccagat gtataccttt   2340
ccgaagaaag aggttgtcac cgttacgcgt acggacaagt tcggtaaacc ggttgcgggc   2400
agccaaatca atcataccct gtatgtgact gacaccaaag gtagcggtga tgactatcag   2460
gccaaatacg gtggtgcgtt tctggacgag ctgaaagaga aatacccgga attgtttacg   2520
aaaaagcaga tttctacggg ccaagcaatc gacccaagcg tcaagattaa gcagtggagc   2580
gcgaaatact ttaacggcag caatatcttg ggtcgtggtg caaattacgt cctgagcgac   2640
caggccagca acaagtattt caatgtggcg gaaggtaagg tttttctgcc aggcgccatg   2700
ctgggcaagg tggtggaaag cggcatccgt tttgacggca agggctacat ctataacagc   2760
tcgaccaccg gcgaacaagt caaagatagc ttcatcacgg aagcaggtaa tttgtattac   2820
ttcggtaaag acggttacat ggtcatgggt gcgcagaaca ttcaaggcgc caattactac   2880
ttcctggcca acggtgcggc actgcgtaat agcatcctga ccgatcaaga cggcaagtcc   2940
cactactacg cgaacgacgg caaacgttat gaaaacggct attatcagtt tggtaacgat   3000
tcctggcgct acttcgagaa tggtgtaatg gccgtcggcg tgacccgtgt ggctggccat   3060
gaccagtact tcgataagga tggtattcaa gcgaagaaca agatcatcgt tacccgcgat   3120
ggtaaggttc gttacttcga tgagcacaat ggcaatgcag tcaccaacac gttcattagc   3180
gatcaggcag gtcactggta ctatctgggt aaggacggtg tggcggtgac gggtgcccaa   3240
acggtgggca aacagcacct gtatttcgag gccaacggcc agcaggtcaa aggcgatttt   3300
gtgaccgcga aagacggtaa actgtatttc ttcgatggcg atagcggtga catgtggacc   3360
gacacgttcg tccaagacaa aactggccat tggttttacc tgggtaaaga tggtgcggcg   3420
gtcaccggtg cacagaccgt gcgcggtcag aaattgtact ttaaagccaa cggtcagcaa   3480
gttaagggcg acattgtcaa aggtgctgat ggtaaaatcc gttactatga tgcaaattcg   3540
ggcgatcagg tctacaaccg tactgtgaag ggttccgacg gtaaaaccta catcatcggc   3600
```

```
aaagacggtg ttgccattac gcagaccatc gcgaagggtc aaaccattaa ggacggcagc   3660

gttctgcgtt tctacagcat ggaaggccag ctggttaccg gtagcggctg gtattctaac   3720

gcgaaaggtc agtggctgta cgtgaagaat ggtcaggttc tgaccggtct gcaaaccgtt   3780

ggttcccaac gtgtgtactt cgacgctaac ggtatccaag cgaagggcaa ggccgtgcgc   3840

accagcgacg gtaagctgcg ttactttgat gcgaacagcg gtagcatgat cactaaccag   3900

tggaaagagg tgaacggtca atactattac tttgacaaca atggcgtcgc catctaccgc   3960

ggctggaact aa                                                       3972


<210> SEQ ID NO 24
<211> LENGTH: 1323
<212> TYPE: PRT
<213> ORGANISM: Streptococcus criceti

<400> SEQUENCE: 24

Met Val Asp Gly Lys Tyr Tyr Tyr Tyr Asp Ala Asp Gly Asn Val Lys
1               5                   10                  15

Lys Asn Phe Ala Ile Ser Val Gly Asp Ala Ile Phe Tyr Phe Asp Glu
            20                  25                  30

Thr Gly Ala Tyr Lys Asp Thr Ser Lys Val Gly Ala Asp Lys Thr Ser
        35                  40                  45

Ser Ser Ala Asn Gln Thr Thr Ala Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Arg Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300
```

```
Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu His Asp Glu Gly Asp Asn Leu Met Asn Met Asp Asn
            340                 345                 350

Lys Phe Arg Leu Ser Met Leu Arg Ser Leu Ala Lys Pro Leu Asp Lys
        355                 360                 365

Arg Ser Gly Leu Asn Pro Leu Ile His Asn Ser Val Val Asp Arg Glu
    370                 375                 380

Val Asp Asp Arg Glu Val Glu Lys Ile Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asn Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Ile Gly Ile Val Met Gly Asn Gln Pro Asn Phe Ser Leu
545                 550                 555                 560

Glu Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Met Thr Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Ile Ser Gly Phe Leu Gln Val Trp Val Pro Val Gly Ala
625                 630                 635                 640

Pro Ala Asp Gln Asp Ile Arg Val Ala Ala Thr Asn Ala Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ala Phe Ala Thr Lys Glu Asp Glu
        675                 680                 685

Tyr Ala Asn Val Val Ile Ala Lys Asn Val Asp Lys Phe Val Ser Trp
    690                 695                 700

Gly Ile Thr Asp Phe Glu Met Ala Pro Gln Tyr Thr Ser Ser Asp Asp
705                 710                 715                 720

Gly Gln Phe Leu Asp Ser Val Ile Gln Asn Gly Tyr Ala Phe Thr Asp
```

```
                725                 730                 735

Arg Tyr Asp Leu Gly Met Ser Lys Ala Asn Lys Tyr Gly Thr Ala Glu
            740                 745                 750

His Leu Val Lys Ala Ile Lys Ala Leu His Lys Ala Gly Leu Lys Val
        755                 760                 765

Met Ala Asp Trp Val Pro Asp Gln Met Tyr Thr Phe Pro Lys Lys Glu
    770                 775                 780

Val Val Thr Val Thr Arg Thr Asp Lys Phe Gly Lys Pro Val Ala Gly
785                 790                 795                 800

Ser Gln Ile Asn His Thr Leu Tyr Val Thr Asp Thr Lys Gly Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
                885                 890                 895

Pro Gly Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
        915                 920                 925

Asp Ser Phe Ile Thr Glu Ala Gly Asn Leu Tyr Tyr Phe Gly Lys Asp
    930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp  Ser Trp Arg Tyr Phe  Glu Asn Gly
        995                 1000                1005

Val Met  Ala Val Gly Val Thr  Arg Val Ala Gly His  Asp Gln Tyr
    1010                 1015                 1020

Phe Asp  Lys Asp Gly Ile Gln  Ala Lys Asn Lys Ile  Ile Val Thr
    1025                 1030                 1035

Arg Asp  Gly Lys Val Arg Tyr  Phe Asp Glu His Asn  Gly Asn Ala
    1040                 1045                 1050

Val Thr  Asn Thr Phe Ile Ser  Asp Gln Ala Gly His  Trp Tyr Tyr
    1055                 1060                 1065

Leu Gly  Lys Asp Gly Val Ala  Val Thr Gly Ala Gln  Thr Val Gly
    1070                 1075                 1080

Lys Gln  His Leu Tyr Phe Glu  Ala Asn Gly Gln Gln  Val Lys Gly
    1085                 1090                 1095

Asp Phe  Val Thr Ala Lys Asp  Gly Lys Leu Tyr Phe  Phe Asp Gly
    1100                 1105                 1110

Asp Ser  Gly Asp Met Trp Thr  Asp Thr Phe Val Gln  Asp Lys Thr
    1115                 1120                 1125

Gly His  Trp Phe Tyr Leu Gly  Lys Asp Gly Ala Ala  Val Thr Gly
    1130                 1135                 1140
```

```
Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Ile Ile Gly Lys Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Glu Val Asn Gly Gln Tyr
    1295                1300                1305

Tyr Tyr Phe Asp Asn Asn Gly Val Ala Ile Tyr Arg Gly Trp Asn
    1310                1315                1320
```

<210> SEQ ID NO 25
<211> LENGTH: 4308
<212> TYPE: DNA
<213> ORGANISM: Streptococcus sobrinus

<400> SEQUENCE: 25

```
atggttgacg gcaaatacta ctattatgat caggatggca acgttaagaa gaatttcgcg     60

gttagcgttg gtgacaagat ctactacttt gacgagactg gtgcctacaa agacacctct    120

aaagtggacg cggacaagtc tagcagcgcc gttagccaaa atgcgacgat ctttgcggct    180

aacaatcgtg cgtatagcac ctctgctgag aactttgagg ccgttgataa ctatctgacg    240

gcagatagct ggtatcgtcc taaatctatt ctgaaagatg gcaagacgtg gaccgagtcg    300

ggtaaggacg acttccgtcc gctgctgatg gcgtggtggc cggacacgga gactaaacgc    360

aattacgtga attacatgaa cctggttgtc ggcatcgaca agacgtacac cgcggaaacc    420

tctcaagcag atttgaccgc agcggcggag ctggtccagg cgcgtattga acagaaaatc    480

accacggaac agaatacgaa atggctgcgc gaggcgatct ctgctttcgt caagacccag    540

ccgcagtgga atggtgaaag cgagaagccg tatgacgacc acctgcaaaa cggtgctctg    600

aaattcgata atcagagcga cctgaccccg gacacccaga gcaactatcg cctgctgaat    660

cgcaccccga ctaaccagac tggcagcctg gacagccgtt tcacctataa tgcgaacgat    720

ccgttgggtg gctacgaatt tctgctggct aacgacgtgg ataatagcaa ccctgtggtg    780

caggcagaac aactgaactg gttgcattac ctgttgaatt ttggtagcat ttacgcgaaa    840

gatgcggatg caaacttcga ttccatccgt gtggacgccg tggacaacgt cgatgcagat    900

ctgttgcaga ttagcagcga ttacctgaag gcagcctatg gcattgacaa gaacaataag    960

aacgcgaaca accatgttag cattgttgag gcttggagcg ataacgatac gccgtacctg   1020
```

```
cacgatgacg gtgataacct gatgaacatg gacaataagt tccgcttgag catgctgtgg   1080
agcctggcca agccgctgga caagcgcagc ggtctgaatc ctctgattca taacagcctg   1140
gtggaccgtg aggttgatga ccgtgaagtg gaaacggttc cgagctactc ttttgcgcgt   1200
gcgcatgatt ccgaggtcca agacattatc cgcgacatta tcaaggccga aatcaacccg   1260
aatagctttg gttatagctt cacccaagaa gagattgacc aggcgtttaa gatctataat   1320
gaagatctga agaaaaccga caagaaatac acccactata atgtcccgtt gagctatact   1380
ttgctgctga cgaataaagg ttcgattccg cgtgtgtatt acggtgatat gttcaccgat   1440
gatggtcaat acatggcgaa caaaacggtt aactatgatg ccattgagtc gctgctgaaa   1500
gcgcgcatga agtacgttag cggcggtcaa gcgatgcaaa actatcaaat cggcaatggt   1560
gagattctga ccagcgttcg ttatggtaag ggtgcattga agcaatccga caagggtgac   1620
gcgaccacgc gtacgtccgg tgtgggcgtc gtgatgggca accagccgaa ctttagcctg   1680
gacggcaagg tggtggcatt gaacatgggt gccgctcatg caaatcagga gtatcgtgcg   1740
ctgatggtga gcaccaagga tggcgttgcc acgtatgcca ccgacgcgga cgcaagcaag   1800
gcaggtctgg tcaaacgcac cgatgaaaat ggttatttgt actttctgaa cgacgatctg   1860
aagggtgtgg caaacccaca agtcagcggt ttcttgcagg tgtgggtccc agtgggtgcg   1920
gctgacgatc aggacattcg tgttgcagcg agcgacacgg ctagcacgga cggtaagtcc   1980
ctgcatcaag atgcggcaat ggatagccgt gttatgtttg agggttttag caacttccag   2040
agctttgcaa ccaaagaaga agagtacacc aacgtagtta ttgcgaacaa cgtggacaaa   2100
ttcgttagct ggggtattac cgactttgag atggcaccgc aatatgtcag ctccaccgat   2160
ggccagtttc tggatagcgt tatccagaat ggttacgcgt tcaccgaccg ttatgatctg   2220
ggtatgagca aagccaacaa atacggtacc gcggatcagc tggttaaagc aatcaaagcg   2280
ttgcacgcga agggtctgaa ggtgatggcg gactgggttc cagaccagat gtacacgttt   2340
ccgaagcagg aagttgtcac tgtcacgcgc accgacaaat ttggtaagcc gattgcgggc   2400
agccaaatca atcacagcct gtacgtgacg gacaccaaat ccagcggtga tgattaccag   2460
gccaaatatg gtggtgcgtt cctggatgag ctgaaagaga aatacccgga gctgttcacc   2520
aaaaagcaga tctcgaccgg tcaggcgatc gacccgagcg tgaagattaa gcagtggagc   2580
gcgaaatact ttaatggtag caacattctg ggtcgtggtg ccgactacgt cctgtccgat   2640
caagttagca acaagtattt caatgtggcc agcgacacgc tgtttctgcc gtctagcctg   2700
ttgggtaagg ttgtcgaaag cggtattcgt tacgatggca aaggttatat ctataacagc   2760
agcgcgactg gcgaccaagt caaggcgtct tttatcacgg aagcaggcaa tctgtactac   2820
ttcggcaaag acggttacat ggttactggt gcgcagacca ttaacggtgc gaattacttc   2880
ttcttggaaa atggtacggc cctgcgtaat accatctaca ccgatgcaca gggcaactcc   2940
cactattatg ctaatgatgg caagcgttac gagaacggtt accagcagtt cggcaacgat   3000
tggcgttact tcaaagatgg taacatggcc gtcggtctga ccacggtgga tggtaacgtt   3060
cagtatttcg acaaggacgg tgtccaagct aaagacaaga ttattgtgac ccgcgatggt   3120
aaggtgcgct actttgatca acacaatggc aacgcggtca cgaatacctt tatcgccgac   3180
aagaccggtc actggtacta cctgggcaaa gatggcgtcg cggtcaccgg cgctcaaacc   3240
gtcggtaagc aaaaactgta ttttgaggcg aacggtgagc aggtgaaagg cgactttgtg   3300
actagccatg aaggcaaact gtacttttat gatgttgaca gcggcgacat gtggaccgat   3360
accttcatcg aggataaggc cggcaactgg ttctacctgg gtaaagacgg cgcagcagtt   3420
```

```
agcggtgcac agaccattcg cggtcaaaag ctgtacttca aggcgtacgg tcaacaggtc   3480

aaaggtgaca tcgttaaagg caccgacggc aagatccgtt actacgatgc gaaatccggc   3540

gagcaggttt tcaataagac ggtcaaagcc gctgatggca aaacctatgt gatcggcaac   3600

aatggtgtgg cggtcgatcc gagcgttgtt aagggtcaga cgttcaaaga cgccagcggc   3660

gcactgcgtt tttacaatct gaaaggtcaa ctggttacgg gctccggttg gtatgaaacg   3720

gccaatcacg attgggtgta tattcagagc ggtaaagcac tgaccggtga gcaaaccatc   3780

aatggtcagc acctgtactt taaagaagat ggccaccaag ttaaaggtca gctggtcacc   3840

cgtacggacg gcaaagtgcg ttactatgac gcaaattctg gcgatcaagc gttcaacaag   3900

tccgtgacgg ttaacggcaa aacgtattac ttcggtaatg atggtaccgc gcaaaccgcg   3960

ggtaacccga aaggccaaat cttcaaggac ggcagcgttc tgcgtttcta tagcatggaa   4020

ggccagctgg taattggcag cggctggtat tccaacgcgc aaggccaatg gctgtatgtg   4080

aagaatggta aagtgttgac cggtttgcag accgtcggtt cccagcgcgt gtactttgat   4140

gagaatggca ttcaagcaaa aggcaaagcg gttcgcacga gcgacggcaa aattcgctac   4200

ttcgacgaga acagcggtag catgatcacc aatcaatgga agtttgttta cggtcaatac   4260

tattactttg gtaatgacgg tgcggcaatc taccgtggtt ggaattaa               4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
```

```
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640
```

```
Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
        915                 920                 925

Ala Ser Phe Ile Thr Glu Ala Gly Asn Leu Tyr Tyr Phe Gly Lys Asp
    930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp  Trp Arg Tyr Phe Lys  Asp Gly Asn
        995                 1000                 1005

Met Ala  Val Gly Leu Thr Thr  Val Asp Gly Asn Val  Gln Tyr Phe
    1010                 1015                 1020

Asp Lys  Asp Gly Val Gln Ala  Lys Asp Lys Ile Ile  Val Thr Arg
    1025                 1030                 1035

Asp Gly  Lys Val Arg Tyr Phe  Asp Gln His Asn Gly  Asn Ala Val
    1040                 1045                 1050
```

```
Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Glu Gln Val Lys Gly Asp
    1085                1090                1095

Phe Val Thr Ser His Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Ser Gly Ala
    1130                1135                1140

Gln Thr Ile Arg Gly Gln Lys Leu Tyr Phe Lys Ala Tyr Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asn Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Arg Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Ile Phe Lys Asp Gly Ser Val Leu Arg Phe Tyr Ser
    1325                1330                1335

Met Glu Gly Gln Leu Val Ile Gly Ser Gly Trp Tyr Ser Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Tyr Phe Gly Asn Asp Gly Ala
    1415                1420                1425

Ala Ile Tyr Arg Gly Trp Asn
    1430                1435
```

<210> SEQ ID NO 27
<211> LENGTH: 4023
<212> TYPE: DNA
<213> ORGANISM: Streptococcus salivarius

<400> SEQUENCE: 27

```
atgattgacg gcaaatacta ctacgtaaac aaagatggct cgcacaaaga gaatttcgca     60
attaccgtga atggtcagtt gttgtatttc ggtaaggacg gtgcattgac gtctagcagc    120
acctacagct ttacgcaggg caccaccaac atcgttgatg gctttagcaa aaacaaccgt    180
gcgtacgatt ccagcgaggc gagctttgaa ctgatcgacg gttatctgac cgcggactcc    240
tggtatcgtc cggtgagcat tatcaaggac ggcgttacgt ggcaagccag caccaaagag    300
gactttcgcc cgctgctgat ggcctggtgg ccgaatgttg acacccaggt caactacctg    360
aattacatgt cgaaggtgtt taacctggac gcgaagtata cgagcaccga caaacaggtt    420
gacctgaatc gcgcagccaa ggacattcag gttaagattg agcaaaagat tcaggccgag    480
aagagcactc aatggctgcg tgaagcgatt tcggccttcg tcaaaaccca gccgcagtgg    540
aataaagaaa cggagaactt ctccaagggt ggtggtgagg atcatctgca aggtggtgca    600
ctgctgtacg ttaacgaccc gcgtaccccg tgggctaact ccaactaccg cctgctgaat    660
cgtactgcga ccaaccagac cggcacgatc gacaagagcg ttctggacga acagagcgat    720
cctaaccaca tgggcggctt cgattttctg ctggcgaatg acgtcgatac cagcaatccg    780
gtggtgcagg cggaacaact gaatcagatc cactacctga tgaattgggg ttccattgtt    840
atgggcgaca aagatgcaaa cttcgatggt atccgcgtgg acgcggtcga taacgttgac    900
gcagatatgc tgcaactgta caccaactac tttcgtgagt attatggcgt gaacaaaagc    960
gaggcaaacg ctttggcgca catctcggtg ctggaagcgt ggagcttgaa tgataatcac   1020
tataatgaca agactgacgg tgcggccctg gcgatggaga acaaacagcg tttggccctg   1080
ctgtttagct tggcgaaacc gatcaaagaa cgtacccctg cggtgagccc gctgtacaac   1140
aacactttca acacgacgca gcgtgacgaa aagaccgatt ggattaacaa agacggtagc   1200
aaagcctata atgaggacgg caccgtcaag cagtccacca tcggcaagta caacgagaaa   1260
tacggcgacg cgtccggcaa ttatgtgttc attcgcgccc acgataacaa cgtccaagac   1320
attattgcag agatcattaa gaaagaaatc aatccgaaaa gcgacggttt caccattacc   1380
gacgccgaaa tgaaaaaggc attcgaaatc tacaacaaag atatgctgtc ctctgataag   1440
aaatacaccc tgaacaacat cccagcggcc tacgcggtga tgctgcaaaa catggaaacc   1500
attactcgtg tgtattacgg cgatctgtat accgacgatg gccattacat ggaaaccaag   1560
agcccgtact acgacaccat tgtgaacctg atgaagaacc gtatcaaata cgtgtccggt   1620
ggtcaagcgc aacgttccta ttggctgccg accgacggta agatggataa aagcgatgtc   1680
gaactgtatc gcaccaacga ggtgtacacc agcgtccgtt acggtaagga catcatgact   1740
gccgatgaca cccaaggtag caagtacagc cgtaccagcg gtcaggtgac cctggtggtg   1800
aacaacccga agctgtcttt ggataagagc gcgaagctgg acgtcgaaat gggcaagatc   1860
catgcaaacc agaaataccg tgctctgatc gtgggtacgc cgaacggcat caaaaacttc   1920
acgagcgacg ccgaggcaat cgcggctggc tacgtgaaag aaaccgacgg caatggtgtg   1980
ctgaccttcg gtgcaaatga catcaaaggt tacgaaacgt ttgacatgag cggtttcgtt   2040
gcagtttggg ttccggtagg tgcaagcgat gatcaagaca tccgtgtcgc cgcaagcacc   2100
gcggcaaaga aagaaggtga gctgactttg aaggcaactg aggcgtatga ctctcagctg   2160
```

```
atttacgaag gtttttcgaa ttttcagacc attccggatg gtagcgatcc gagcgtttac   2220
accaatcgta agatcgcgga aaatgttgat ttgttcaaga gctggggtgt gacctctttc   2280
gaaatggcgc cacagtttgt gagcgcagac gacggtacgt ttctggacag cgttatccag   2340
aacggctatg cgtttgcgga ccgttatgat ctggcgatgt ccaaaaacaa taagtacggt   2400
tcgaaagaag atctgcgtaa cgcgttgaag gctttgcaca aggccggcat ccaagccatt   2460
gcggactggg ttccggatca gatctaccaa ctgccgggca aagaagtagt gaccgccact   2520
cgtaccgatg gtgccggtcg taagattagc gatgcaatta tcgatcacag cctgtacgtc   2580
gcaaacagca agtcgtctgg caaagactat caagctaaat acggtggtga gttcctggcc   2640
gagctgaaag caaagtaccc ggaaatgttt aaagtcaaca tgattagcac gggtaaaccg   2700
atcgacgact ctgtcaaact gaagcaatgg aaggcggagt actttaacgg tacgaatgtt   2760
ctggaccgtg gtgttggtta cgtcctgagc gatgaggcga cgggcaagta ctttaccgtt   2820
acgaaagagg gtaactttat cccactgcaa ttgaaaggta acgagaaagt tatcacgggc   2880
ttcagctctg acggcaaggg cattacctat ttcggcacct cgggtaatca agcgaaaagc   2940
gcttttgtca cgttcaatgg taatacctac tattttgacg cgcgtggcca catggttacc   3000
aacggcgaat atagccctaa tggtaaggat gtgtatcgtt tcctgccgaa tggtattatg   3060
ttgagcaatg cattctacgt tgacggtaac ggcaatacct acctgtacaa ctccaagggc   3120
caaatgtaca aggtggtta tagcaaattc gacgttacgg aaaccaaaga tggtaaagag   3180
agcaaagtgg tgaaatttcg ctactttacc aatgaaggtg tgatggcaaa aggtgttacc   3240
gtggtggacg gcttcactca atacttcaac gaagatggca ttcagagcaa ggacgaactg   3300
gtgacctaca atggtaaaac ctattacttc gaagcgcata ccggtaatgc gatcaaaaac   3360
acgtggcgca atatcaaggg taagtggtat cactttgatg cgaatggcgt ggcggcaacg   3420
ggtgcacagg ttatcaatgg tcagcacctg tactttaatg aggatggttc ccaggtgaag   3480
ggtggcgtcg tgaagaatgc ggatggtacc ttcagcaagt ataaagatgg ttccggtgac   3540
ctggtggtca atgagttctt cactactggt gataacgtgt ggtactacgc tggtgccaac   3600
ggcaaaactg tgacgggtgc ccaggtcatc aatggccaac acctgttttt caaagaggac   3660
ggtagccagg ttaagggtga tttcgttaag aacagcgacg gcacctactc taagtatgat   3720
gcggccagcg gcgaacgcct gacgaatgag tttttcacga ccggtgacaa ccactggtac   3780
tatattggtg ccaatggcaa aaccgttacc ggcgaagtca agatcggtga tgatacgtac   3840
ttcttcgcaa aagatggcaa gcagctgaag ggccagatcg tgacgacccg cagcggtcgt   3900
atcagctact acttcggcga ctctggtaag aaggcgatta gcacctgggt ggagattcag   3960
ccgggtgttt tcgtgttttt cgacaaaaat ggcctggcat atccgccgga aaacatgaat   4020
taa                                                                4023
```

<210> SEQ ID NO 28
<211> LENGTH: 1340
<212> TYPE: PRT
<213> ORGANISM: Streptococcus salivarius

<400> SEQUENCE: 28

```
Met Ile Asp Gly Lys Tyr Tyr Tyr Val Asn Lys Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Gln Gly Thr
```

```
        35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Val Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly Gly
            180                 185                 190

Glu Asp His Leu Gln Gly Gly Ala Leu Leu Tyr Val Asn Asp Pro Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460
```

```
Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
    610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
    850                 855                 860

Ser Ser Gly Lys Asp Tyr Gln Ala Lys Tyr Gly Gly Glu Phe Leu Ala
865                 870                 875                 880
```

```
Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
        900                 905                 910

Glu Tyr Phe Asn Gly Thr Asn Val Leu Asp Arg Gly Val Gly Tyr Val
    915                 920                 925

Leu Ser Asp Glu Ala Thr Gly Lys Tyr Phe Thr Val Thr Lys Glu Gly
    930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
        980                 985                 990

Asp Ala Arg Gly His Met Val Thr  Asn Gly Glu Tyr Ser  Pro Asn Gly
    995                 1000                1005

Lys Asp  Val Tyr Arg Phe Leu  Pro Asn Gly Ile Met  Leu Ser Asn
    1010                1015                1020

Ala Phe  Tyr Val Asp Gly Asn  Gly Asn Thr Tyr Leu  Tyr Asn Ser
    1025                1030                1035

Lys Gly  Gln Met Tyr Lys Gly  Gly Tyr Ser Lys Phe  Asp Val Thr
    1040                1045                1050

Glu Thr  Lys Asp Gly Lys Glu  Ser Lys Val Val Lys  Phe Arg Tyr
    1055                1060                1065

Phe Thr  Asn Glu Gly Val Met  Ala Lys Gly Val Thr  Val Val Asp
    1070                1075                1080

Gly Phe  Thr Gln Tyr Phe Asn  Glu Asp Gly Ile Gln  Ser Lys Asp
    1085                1090                1095

Glu Leu  Val Thr Tyr Asn Gly  Lys Thr Tyr Tyr Phe  Glu Ala His
    1100                1105                1110

Thr Gly  Asn Ala Ile Lys Asn  Thr Trp Arg Asn Ile  Lys Gly Lys
    1115                1120                1125

Trp Tyr  His Phe Asp Ala Asn  Gly Val Ala Ala Thr  Gly Ala Gln
    1130                1135                1140

Val Ile  Asn Gly Gln His Leu  Tyr Phe Asn Glu Asp  Gly Ser Gln
    1145                1150                1155

Val Lys  Gly Gly Val Val Lys  Asn Ala Asp Gly Thr  Phe Ser Lys
    1160                1165                1170

Tyr Lys  Asp Gly Ser Gly Asp  Leu Val Val Asn Glu  Phe Phe Thr
    1175                1180                1185

Thr Gly  Asp Asn Val Trp Tyr  Tyr Ala Gly Ala Asn  Gly Lys Thr
    1190                1195                1200

Val Thr  Gly Ala Gln Val Ile  Asn Gly Gln His Leu  Phe Phe Lys
    1205                1210                1215

Glu Asp  Gly Ser Gln Val Lys  Gly Asp Phe Val Lys  Asn Ser Asp
    1220                1225                1230

Gly Thr  Tyr Ser Lys Tyr Asp  Ala Ala Ser Gly Glu  Arg Leu Thr
    1235                1240                1245

Asn Glu  Phe Phe Thr Thr Gly  Asp Asn His Trp Tyr  Tyr Ile Gly
    1250                1255                1260

Ala Asn  Gly Lys Thr Val Thr  Gly Glu Val Lys Ile  Gly Asp Asp
    1265                1270                1275

Thr Tyr  Phe Phe Ala Lys Asp  Gly Lys Gln Leu Lys  Gly Gln Ile
```

```
    1280                1285                1290

Val Thr  Thr Arg Ser Gly Arg  Ile Ser Tyr Tyr Phe  Gly Asp Ser
    1295                1300                1305

Gly Lys  Lys Ala Ile Ser Thr  Trp Val Glu Ile Gln  Pro Gly Val
    1310                1315                1320

Phe Val  Phe Phe Asp Lys Asn  Gly Leu Ala Tyr Pro  Pro Glu Asn
    1325                1330                1335

Met Asn
    1340


<210> SEQ ID NO 29
<211> LENGTH: 4026
<212> TYPE: DNA
<213> ORGANISM: Streptococcus salivarius

<400> SEQUENCE: 29

atgacggacg gtaaatacta ttatgtaaat gaggacggca gccacaaaga gaatttcgca     60

attacggtaa acggtcaact gttgtacttt ggcaaggacg gcgctctgac gagcagcagc    120

acgcacagct tcacgccggg tactacgaat attgtggacg gtttctcgat caacaaccgt    180

gcgtacgata gcagcgaagc gagctttgag ctgatcaacg gttacctgac ggcggattcc    240

tggtatcgcc cggtttctat catcaaggat ggcgtcacgt ggcaggcaag cactgccgag    300

gattttcgtc cgctgttgat ggcctggtgg ccgaacgttg atacccaggt gaactatctg    360

aactatatgt ccaaggtctt taacctggaa gccaagtaca ccagcaccga taaacaggct    420

gatctgaacc gtgctgcaaa ggatatccag gtcaagatcg aacagaagat ccaggcggaa    480

aagagcacgc agtggctgcg tgagactatc tccgcgtttg ttaaaaccca gccgcaatgg    540

aacaaagaga ctgagaatta ctccaagggt ggtggcgaag atcatctgca aggcggtgcg    600

ctgttgtacg tgaacgacag ccgtaccccg tgggcgaata gcaattaccg cctgctgaat    660

cgcacggcaa cgaaccagac cggtaccatt aacaagtcgg tgttggacga gcaatccgat    720

ccaaatcaca tgggtggctt cgacttcctg ctggcaaacg atgtggatct gagcaatcct    780

gttgtgcagg ccgagcagct gaatcaaatc cattatctga tgaactgggg cagcattgtt    840

atgggtgaca aagacgcgaa ttttgatggt atccgtgtgg acgccgttga caacgtgaac    900

gctgacatgt tgcagctgta cacgaactac tttcgtgagt attacggcgt caacaaaagc    960

gaagcgcaag cgctggcgca cattagcgtt ctggaagcgt ggagcttgaa cgataaccac   1020

tataacgaca aaaccgatgg tgcggcactg gcgatggaga ataagcaacg tctggccttg   1080

ctgttctctc tggccaagcc gatcaaagat cgtactccgg cagtgagccc actgtataac   1140

aatactttca ataccaccca acgtgacttc aagacggatt ggattaacaa ggacggtagc   1200

accgcctaca atgaggatgg caccgcgaaa caatctacca tcggtaagta caatgagaaa   1260

tatggtgatg caagcggtaa ctatgtgttt attcgtgccc atgacaataa cgtccaagac   1320

attattgcgg agatcattaa gaaagaaatc aataagaaga gcgatggttt taccatcagc   1380

gatagcgaaa tgaaacaggc gttcgaaatc tacaacaaag atatgctgag cagcaataag   1440

aaatacactc tgaataacat tccggcagcg tacgccgtga tgctgcaaaa catggagact   1500

atcacccgtg tgtattatgg tgacctgtac accgacgacg gtcactatat ggaaaccaag   1560

agcccgtatc atgacaccat tgtgaacctg atgaaaaacc gtatcaagta cgtttctggt   1620

ggccaggccc aacgctccta ttggctgccg accgacggta aaatggacaa tagcgatgtc   1680

gaactgtacc gtactagcga ggtctatacc agcgttcgct acggtaagga cattatgacg   1740
```

```
gcggatgaca ccgagggtag caagtactcc cgcacgagcg gtcaggttac cctggttgtt   1800

aacaacccga agctgactct gcatgaaagc gccaaactga acgtcgagat gggtaagatc   1860

cacgcaaacc agaaataccg tgcgctgatt gtgggtaccg ccgatggcat caaaaacttt   1920

acgtctgatg ccgaagcgat cgcggcaggc tacgtaaaag aaacggacag caatggtgtt   1980

ctgaccttcg gcgcaaatga tatcaaaggt tacgagactt tcgatatgag cggtttcgtc   2040

gcagtttggg tgccggtggg tgcgagcgat gatcaggaca tccgcgtggc gccgtcgacg   2100

gaagcgaaga aagaaggtga actgacgctg aaagccacgg aagcgtatga tagccagttg   2160

atttatgaag gcttctccaa tttccagacc attccggatg gcagcgaccc gagcgtttat   2220

accaaccgca aaattgctga gaatgttgat ctgtttaagt cctggggtgt cactagcttc   2280

gaaatggctc cgcagtttgt ttcggcggac gacggcacct tcctggatag cgttatccag   2340

aacggttacg cctttgcgga ccgttatgat ttggccatga gcaagaacaa caagtacggt   2400

tctaaagagg atctgcgcga cgcactgaaa gcgctgcaca aagctggcat tcaggcaatc   2460

gcggactggg tcccagacca aatctaccaa ctgccaggca aagaagtggt tacggcgacg   2520

cgcacggacg gtgcgggtcg caagatcgcg gacgccatca ttgatcatag cctgtatgtt   2580

gctaactcca agagctccgg tcgcgattac caagcgcagt atggtggcga gtttctggca   2640

gagctgaaag cgaagtaccc gaaaatgttc acggaaaaca tgattagcac gggtaagccg   2700

atcgatgaca gcgtcaaact gaagcaatgg aaagccaagt atttcaatgg tacgaatgtg   2760

ctggaccgtg gtgtcggtta cgtcctgtcc gacgaggcga ccggcaaata cttcaccgtt   2820

accaaagagg gtaacttcat tccgctgcaa ctgaccggca atgaaaaagc ggtgaccggt   2880

ttcagcaacg acggcaaggg tatcacctac tttggtacga gcggtaatca ggccaagagc   2940

gcgttcgtca cctttaacgg caatacgtac tatttcgacg cgcgtggcca catggtcacg   3000

aacggcgagt atagcccgaa cggcaaagat gtctaccgtt ttctgccaaa tggtattatg   3060

ttgtcgaacg cgttttatgt cgacgcaaac ggtaatacgt acttgtacaa ctacaagggc   3120

cagatgtaca aggtggttta tacgaaattt gatgtcaccg aaactgataa agatggtaat   3180

gagagcaagg tggtcaagtt tcgttatttc accaatgagg gcgtcatggc taagggtctg   3240

accgtcattg acggtagcac ccagtacttt ggtgaggatg gttttcaaac gaaggacaag   3300

ctggcgacct ataaaggtaa gacttattac ttcgaggcac acacgggcaa tgcgatcaaa   3360

aacacctggc gtaacatcga cggtaagtgg tatcacttcg atgagaatgg cgttgccgcg   3420

accggtgcac aagtgattaa cggtcaaaaa ctgtatttca acgaggatgg ctcgcaagtg   3480

aagggcggtg ttgttaagaa cgccgacggt acctacagca aatacaaaga gggcagcggt   3540

gagctggtta ccaacgagtt tttcacgacc gacggtaatg tgtggtacta tgctggtgcg   3600

gatggcaaga ctgtgaccgg tgctcaggtc attaatggtc agcacctgta ctttaaagaa   3660

gatggcagcc aggtgaaagg tggtgtggtg aaaaacgcgg acggtacgta cagcaagtat   3720

gacgccgcca ccggtgaacg cttgaccaat gagttcttta ccacgggcga taacaattgg   3780

tactatattg gttctaatgg taagaccgta accggtgaag tcaaaatcgg tgcggacacc   3840

tattactttg ccaaagatgg caaacaggtc aagggccaaa ccgtcaccgc aggcaatggc   3900

cgcatctcct attactacgg cgattctggt aagaaagcaa tcagcacgtg gatcgaaatt   3960

caaccgggta tctatgtcta ttttgataag acgggcatcg cgtacccacc gcgtgtgctg   4020

aattaa                                                              4026
```

<210> SEQ ID NO 30
<211> LENGTH: 1341
<212> TYPE: PRT
<213> ORGANISM: Streptococcus salivarius

<400> SEQUENCE: 30

Met Thr Asp Gly Lys Tyr Tyr Tyr Val Asn Glu Asp Gly Ser His Lys
1 5 10 15

Glu Asn Phe Ala Ile Thr Val Asn Gly Gln Leu Leu Tyr Phe Gly Lys
20 25 30

Asp Gly Ala Leu Thr Ser Ser Ser Thr His Ser Phe Thr Pro Gly Thr
35 40 45

Thr Asn Ile Val Asp Gly Phe Ser Ile Asn Asn Arg Ala Tyr Asp Ser
50 55 60

Ser Glu Ala Ser Phe Glu Leu Ile Asn Gly Tyr Leu Thr Ala Asp Ser
65 70 75 80

Trp Tyr Arg Pro Val Ser Ile Ile Lys Asp Gly Val Thr Trp Gln Ala
85 90 95

Ser Thr Ala Glu Asp Phe Arg Pro Leu Leu Met Ala Trp Trp Pro Asn
100 105 110

Val Asp Thr Gln Val Asn Tyr Leu Asn Tyr Met Ser Lys Val Phe Asn
115 120 125

Leu Glu Ala Lys Tyr Thr Ser Thr Asp Lys Gln Ala Asp Leu Asn Arg
130 135 140

Ala Ala Lys Asp Ile Gln Val Lys Ile Glu Gln Lys Ile Gln Ala Glu
145 150 155 160

Lys Ser Thr Gln Trp Leu Arg Glu Thr Ile Ser Ala Phe Val Lys Thr
165 170 175

Gln Pro Gln Trp Asn Lys Glu Thr Glu Asn Tyr Ser Lys Gly Gly Gly
180 185 190

Glu Asp His Leu Gln Gly Gly Ala Leu Leu Tyr Val Asn Asp Ser Arg
195 200 205

Thr Pro Trp Ala Asn Ser Asn Tyr Arg Leu Leu Asn Arg Thr Ala Thr
210 215 220

Asn Gln Thr Gly Thr Ile Asn Lys Ser Val Leu Asp Glu Gln Ser Asp
225 230 235 240

Pro Asn His Met Gly Gly Phe Asp Phe Leu Leu Ala Asn Asp Val Asp
245 250 255

Leu Ser Asn Pro Val Val Gln Ala Glu Gln Leu Asn Gln Ile His Tyr
260 265 270

Leu Met Asn Trp Gly Ser Ile Val Met Gly Asp Lys Asp Ala Asn Phe
275 280 285

Asp Gly Ile Arg Val Asp Ala Val Asp Asn Val Asn Ala Asp Met Leu
290 295 300

Gln Leu Tyr Thr Asn Tyr Phe Arg Glu Tyr Tyr Gly Val Asn Lys Ser
305 310 315 320

Glu Ala Gln Ala Leu Ala His Ile Ser Val Leu Glu Ala Trp Ser Leu
325 330 335

Asn Asp Asn His Tyr Asn Asp Lys Thr Asp Gly Ala Ala Leu Ala Met
340 345 350

Glu Asn Lys Gln Arg Leu Ala Leu Leu Phe Ser Leu Ala Lys Pro Ile
355 360 365

Lys Asp Arg Thr Pro Ala Val Ser Pro Leu Tyr Asn Asn Thr Phe Asn
370 375 380

```
Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Lys Lys Ser Asp Gly Phe Thr Ile Ser Asp Ser Glu Met
    450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800
```

```
Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Ser Lys
    850                 855                 860

Ser Ser Gly Arg Asp Tyr Gln Ala Gln Tyr Gly Gly Glu Phe Leu Ala
865                 870                 875                 880

Glu Leu Lys Ala Lys Tyr Pro Lys Met Phe Thr Glu Asn Met Ile Ser
                885                 890                 895

Thr Gly Lys Pro Ile Asp Asp Ser Val Lys Leu Lys Gln Trp Lys Ala
            900                 905                 910

Lys Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
    930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
        995                 1000                 1005

Lys Asp  Val Tyr Arg Phe Leu  Pro Asn Gly Ile Met  Leu Ser Asn
    1010                 1015                 1020

Ala Phe  Tyr Val Asp Ala Asn  Gly Asn Thr Tyr Leu  Tyr Asn Tyr
    1025                 1030                 1035

Lys Gly  Gln Met Tyr Lys Gly  Gly Tyr Thr Lys Phe  Asp Val Thr
    1040                 1045                 1050

Glu Thr  Asp Lys Asp Gly Asn  Glu Ser Lys Val Val  Lys Phe Arg
    1055                 1060                 1065

Tyr Phe  Thr Asn Glu Gly Val  Met Ala Lys Gly Leu  Thr Val Ile
    1070                 1075                 1080

Asp Gly  Ser Thr Gln Tyr Phe  Gly Glu Asp Gly Phe  Gln Thr Lys
    1085                 1090                 1095

Asp Lys  Leu Ala Thr Tyr Lys  Gly Lys Thr Tyr Tyr  Phe Glu Ala
    1100                 1105                 1110

His Thr  Gly Asn Ala Ile Lys  Asn Thr Trp Arg Asn  Ile Asp Gly
    1115                 1120                 1125

Lys Trp  Tyr His Phe Asp Glu  Asn Gly Val Ala Ala  Thr Gly Ala
    1130                 1135                 1140

Gln Val  Ile Asn Gly Gln Lys  Leu Tyr Phe Asn Glu  Asp Gly Ser
    1145                 1150                 1155

Gln Val  Lys Gly Gly Val Val  Lys Asn Ala Asp Gly  Thr Tyr Ser
    1160                 1165                 1170

Lys Tyr  Lys Glu Gly Ser Gly  Glu Leu Val Thr Asn  Glu Phe Phe
    1175                 1180                 1185

Thr Thr  Asp Gly Asn Val Trp  Tyr Tyr Ala Gly Ala  Asp Gly Lys
    1190                 1195                 1200

Thr Val  Thr Gly Ala Gln Val  Ile Asn Gly Gln His  Leu Tyr Phe
```

```
    1205                1210                1215

Lys Glu  Asp Gly Ser Gln Val  Lys Gly Gly Val Val  Lys Asn Ala
    1220                1225                1230

Asp Gly  Thr Tyr Ser Lys Tyr  Asp Ala Ala Thr Gly  Glu Arg Leu
    1235                1240                1245

Thr Asn  Glu Phe Phe Thr Thr  Gly Asp Asn Asn Trp  Tyr Tyr Ile
    1250                1255                1260

Gly Ser  Asn Gly Lys Thr Val  Thr Gly Glu Val Lys  Ile Gly Ala
    1265                1270                1275

Asp Thr  Tyr Tyr Phe Ala Lys  Asp Gly Lys Gln Val  Lys Gly Gln
    1280                1285                1290

Thr Val  Thr Ala Gly Asn Gly  Arg Ile Ser Tyr Tyr  Tyr Gly Asp
    1295                1300                1305

Ser Gly  Lys Lys Ala Ile Ser  Thr Trp Ile Glu Ile  Gln Pro Gly
    1310                1315                1320

Ile Tyr  Val Tyr Phe Asp Lys  Thr Gly Ile Ala Tyr  Pro Pro Arg
    1325                1330                1335

Val Leu  Asn
    1340


<210> SEQ ID NO 31
<211> LENGTH: 3918
<212> TYPE: DNA
<213> ORGANISM: Streptococcus salivarius

<400> SEQUENCE: 31

atgatcgacg gcaaacagta ttatgtagag aacggtgtgg ttaagaaaaa tgcggcaatt     60

gaactggatg gccgcctgta ctactttgat gagactggcg caatggtcga tcagagcaaa    120

ccgttgtatc gtgcggacgc gattccgaac aactctatct acgccgtgta caaccaagcg    180

tatgatacca gcagcaaatc cttcgagcat ttggataact tcctgaccgc ggatagctgg    240

tatcgcccga aacagattct gaaggacggt aaaaactgga ccgcaagcac tgagaaagac    300

tatcgtcctc tgctgatgac ctggtggccg gacaaggtga cccaggtgaa ttacctgaac    360

tatatgtctc aacagggttt tggtaacaaa acgtacacca cggatatgat gagctacgac    420

ctggcggctg cggcagaaac ggtgcagcgt ggcatcgaag agcgtatcgg tcgcgagggt    480

aacaccacgt ggctgcgcca gctgatgagc gatttcatca aaacccagcc gggttggaat    540

agcgagagcg aggacaatct gctggttggt aaggaccatc tgcaaggtgg tgcgctgacc    600

tttctgaaca atagcgcaac gagccacgcg aatagcgact ttcgtctgat gaaccgtacc    660

ccgaccaatc agaccggtac ccgtaaatac cacatcgatc gtagcaatgg cggctatgag    720

ctgctgctgg ctaacgacat tgataatagc aatccggcag ttcaagcaga gcaactgaat    780

tggctgcact acattatgaa tattggcagc atcttgggta atgacccgag cgcgaatttt    840

gacggtgttc gtatcgatgc ggtggataat gtggacgcgg atttgctgca aatcgcgtct    900

gattacttca aagagaagta ccgtgtcgcg gacaacgagg caaacgcgat tgcccacctg    960

agcattctgg aagcgtggag ctataatgat catcagtaca acaaggacac gaagggcgca   1020

cagctgtcca tcgataaccc gctgcgcgaa accctgctga ctaccttcct gcgtaaaagc   1080

aattatcgtg gtagcttgga gcgcgttatt accaactccc tgaataaccg ctctagcgag   1140

caaaagcaca ctccgcgcga cgcgaactac atctttgtac gtgcgcatga cagcgaagtt   1200

caagacgtgc tggcgaatat cattagcaaa cagatcaacc caaagacgga tggcttcacg   1260
```

```
ttcaccatgg atgaactgaa gcaggcgttc gagatctaca atgcggatat tgcgaaggcg   1320
gacaagaagt atacccaata caacattccg gcagcttacg caaccatgct gacgaacaag   1380
gatagcatta cccgcgttta ctacggcgac ctgtttacgg atgacggtca gtatatggcc   1440
gagaaatccc cgtactataa cgcaattgac gctctgctgc gtgcgcgcat taagtacgtc   1500
gcgggtggtc aggacatgaa ggtgactaaa ctgaatggtt atgagattat gagcagcgtg   1560
cgttatggta aaggtgcaga agaggctaac cagctgggta cggcagaaac ccgcaatcaa   1620
ggtatgctgg ttctgacggc taaccgtccg gacatgaaac tgggtgcaaa cgatcgcctg   1680
gtcgtgaata tgggcgctgc ccacaaaaac caggcctacc gcccgttgct gttgtccaaa   1740
tctactggcc tggcgacgta tctgaaagat agcgacgttc cggcaggcct ggtgcgttat   1800
accgataacc agggtaatct gacctttacg gcggacgata ttgcaggcca tagcacggtt   1860
gaagtgagcg gttacttggc ggtctgggtt ccggtcggcg cgagcgagaa ccaggacgcg   1920
cgcacgaagg ccagctctac caagaagggc gagcaagttt tcgaatctag cgccgctctg   1980
gacagccagg ttatctacga aggtttctcc aatttccaag attttgtcaa gaccccgagc   2040
cagtacacca accgcgtgat cgcgcaaaat gcgaagctgt ttaaagaatg gggcatcact   2100
agctttgagt tcgcgcctca gtatgtttct agccaagacg gcaccttttt ggatagcatc   2160
attgaaaacg gctacgcgtt cgaggatcgt tacgatatcg caatgagcaa gaacaataag   2220
tatggcagcc tgaaagattt gatggacgca ctgcgtgcgt tgcatgcgga aggcatcagc   2280
gcaatcgccg attgggtccc ggaccaaatc tataatctgc cgggtaaaga agttgtcacg   2340
gcgagccgta ccaacagcta tggtaccccg cgtccgaatg cggaaatcta caatagcctg   2400
tacgctgcta aaacgcgcac gttcggtaat gacttccagg gtaagtatgg tggcgcattt   2460
ctggacgaac tgaaagcaaa gtacccggcc atctttgagc gtgttcaaat cagcaacggt   2520
cgtaaattga ccacgaatga gaagattacc cagtggagcg ccaaatactt taatggtagc   2580
aatattcagg gcacgggtgc gcgttacgtt ttgcaggaca acgctaccaa tcagtacttt   2640
agcgttaagg cgggtcagac tttcctgccg aagcagatga ccgaaattac cggcagcggt   2700
ttccgtcgtg tcggtgacga tgtccaatat ctgagcattg gtggttatct ggcgaagaat   2760
acctttatcc aggtcggtgc gaatcagtgg tattattttg acaaaaacgg caatatggtt   2820
acgggtgaac aggtgatcga tggtaaaaag tacttcttct tggataacgg tctgcaactg   2880
cgtcatgttc tgcgccaggg ctccgatggt cacgtctatt actatgaccc taaaggtgtg   2940
caagcgttca atggtttcta cgactttgca ggccctcgcc aagacgttcg ttacttcgat   3000
ggcaatggtc agatgtatcg cggcctgcac gatatgtacg gtacgacctt ttacttcgac   3060
gagaaaaccg gcatccaagc aaaagacaag ttcattcgct tcgcagacgg tcgtacccgt   3120
tacttcattc cggacaccgg taatctggca gtgaatcgtt tcgcccaaaa cccggagaac   3180
aaagcctggt attacctgga tagcaacggt tacgctgtca ccggcttgca gacgattaat   3240
ggcaagcagt attactttga caacgaaggc cgtcaggtta aaggccactt tgtgaccatt   3300
aacaaccagc gttactttct ggatggtgac tcgggcgaga tcgcgccatc gcgtttcgtt   3360
accgagaaca acaagtggta ctacgtcgac ggtaatggta agctggtcaa gggtgcacag   3420
gtgattaacg gtaaccacta ctacttcaat aacgactata gccaggtgaa gggtgcatgg   3480
gcgaacggtc gttactacga tggcgacagc ggtcaagcgg tcagcaacca gtttattcaa   3540
attgcggcga accaatgggc atatctgaat caagatggcc acaaggtcac gggtctgcaa   3600
aacatcaaca ataaagtgta ctattttggc tctaatggcg cgcaagttaa gggtaaactg   3660
```

```
ctgaccgtgc aaggcaagaa atgctacttt gacgcccaca ccggtgagca agtcgttaat   3720

cgcttcgtgg aagctgcccg tggttgctgg tactatttca attccgctgg ccaggccgtt   3780

accggccaac aagtcatcaa cggtaagcag ttgtattttg atggttctgg tcgtcaagtc   3840

aaaggccgtt atgtgtacgt gggtggtaaa cgtttgttct gtgatgcgaa aacgggcgag   3900

ctgcgtcaac gccgttaa                                                 3918
```

<210> SEQ ID NO 32
<211> LENGTH: 1305
<212> TYPE: PRT
<213> ORGANISM: Streptococcus salivarius

<400> SEQUENCE: 32

```
Met Ile Asp Gly Lys Gln Tyr Tyr Val Glu Asn Gly Val Val Lys Lys
1               5                   10                  15

Asn Ala Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175

Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Ala Thr Ser
        195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
        275                 280                 285

Asp Asn Val Asp Ala Asp Leu Leu Gln Ile Ala Ser Asp Tyr Phe Lys
    290                 295                 300

Glu Lys Tyr Arg Val Ala Asp Asn Glu Ala Asn Ala Ile Ala His Leu
305                 310                 315                 320
```

```
Ser Ile Leu Glu Ala Trp Ser Tyr Asn Asp His Gln Tyr Asn Lys Asp
                325                 330                 335

Thr Lys Gly Ala Gln Leu Ser Ile Asp Asn Pro Leu Arg Glu Thr Leu
            340                 345                 350

Leu Thr Thr Phe Leu Arg Lys Ser Asn Tyr Arg Gly Ser Leu Glu Arg
        355                 360                 365

Val Ile Thr Asn Ser Leu Asn Asn Arg Ser Ser Glu Gln Lys His Thr
    370                 375                 380

Pro Arg Asp Ala Asn Tyr Ile Phe Val Arg Ala His Asp Ser Glu Val
385                 390                 395                 400

Gln Asp Val Leu Ala Asn Ile Ile Ser Lys Gln Ile Asn Pro Lys Thr
                405                 410                 415

Asp Gly Phe Thr Phe Thr Met Asp Glu Leu Lys Gln Ala Phe Glu Ile
            420                 425                 430

Tyr Asn Ala Asp Ile Ala Lys Ala Asp Lys Lys Tyr Thr Gln Tyr Asn
        435                 440                 445

Ile Pro Ala Ala Tyr Ala Thr Met Leu Thr Asn Lys Asp Ser Ile Thr
    450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
                485                 490                 495

Ile Lys Tyr Val Ala Gly Gly Gln Asp Met Lys Val Thr Lys Leu Asn
            500                 505                 510

Gly Tyr Glu Ile Met Ser Ser Val Arg Tyr Gly Lys Gly Ala Glu Glu
        515                 520                 525

Ala Asn Gln Leu Gly Thr Ala Glu Thr Arg Asn Gln Gly Met Leu Val
    530                 535                 540

Leu Thr Ala Asn Arg Pro Asp Met Lys Leu Gly Ala Asn Asp Arg Leu
545                 550                 555                 560

Val Val Asn Met Gly Ala Ala His Lys Asn Gln Ala Tyr Arg Pro Leu
                565                 570                 575

Leu Leu Ser Lys Ser Thr Gly Leu Ala Thr Tyr Leu Lys Asp Ser Asp
            580                 585                 590

Val Pro Ala Gly Leu Val Arg Tyr Thr Asp Asn Gln Gly Asn Leu Thr
        595                 600                 605

Phe Thr Ala Asp Asp Ile Ala Gly His Ser Thr Val Glu Val Ser Gly
    610                 615                 620

Tyr Leu Ala Val Trp Val Pro Val Gly Ala Ser Glu Asn Gln Asp Ala
625                 630                 635                 640

Arg Thr Lys Ala Ser Ser Thr Lys Lys Gly Glu Gln Val Phe Glu Ser
                645                 650                 655

Ser Ala Ala Leu Asp Ser Gln Val Ile Tyr Glu Gly Phe Ser Asn Phe
            660                 665                 670

Gln Asp Phe Val Lys Thr Pro Ser Gln Tyr Thr Asn Arg Val Ile Ala
        675                 680                 685

Gln Asn Ala Lys Leu Phe Lys Glu Trp Gly Ile Thr Ser Phe Glu Phe
    690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                725                 730                 735

Lys Asn Asn Lys Tyr Gly Ser Leu Lys Asp Leu Met Asp Ala Leu Arg
```

```
            740                 745                 750

Ala Leu His Ala Glu Gly Ile Ser Ala Ile Ala Asp Trp Val Pro Asp
        755                 760                 765

Gln Ile Tyr Asn Leu Pro Gly Lys Glu Val Val Thr Ala Ser Arg Thr
    770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
                805                 810                 815

Gly Gly Ala Phe Leu Asp Glu Leu Lys Ala Lys Tyr Pro Ala Ile Phe
            820                 825                 830

Glu Arg Val Gln Ile Ser Asn Gly Arg Lys Leu Thr Thr Asn Glu Lys
        835                 840                 845

Ile Thr Gln Trp Ser Ala Lys Tyr Phe Asn Gly Ser Asn Ile Gln Gly
    850                 855                 860

Thr Gly Ala Arg Tyr Val Leu Gln Asp Asn Ala Thr Asn Gln Tyr Phe
865                 870                 875                 880

Ser Val Lys Ala Gly Gln Thr Phe Leu Pro Lys Gln Met Thr Glu Ile
                885                 890                 895

Thr Gly Ser Gly Phe Arg Arg Val Gly Asp Asp Val Gln Tyr Leu Ser
            900                 905                 910

Ile Gly Gly Tyr Leu Ala Lys Asn Thr Phe Ile Gln Val Gly Ala Asn
        915                 920                 925

Gln Trp Tyr Tyr Phe Asp Lys Asn Gly Asn Met Val Thr Gly Glu Gln
    930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                965                 970                 975

Pro Lys Gly Val Gln Ala Phe Asn Gly Phe Tyr Asp Phe Ala Gly Pro
            980                 985                 990

Arg Gln Asp Val Arg Tyr Phe Asp  Gly Asn Gly Gln Met  Tyr Arg Gly
        995                 1000                1005

Leu His  Asp Met Tyr Gly Thr  Thr Phe Tyr Phe Asp  Glu Lys Thr
    1010                1015                1020

Gly Ile  Gln Ala Lys Asp Lys  Phe Ile Arg Phe Ala  Asp Gly Arg
    1025                1030                1035

Thr Arg  Tyr Phe Ile Pro Asp  Thr Gly Asn Leu Ala  Val Asn Arg
    1040                1045                1050

Phe Ala  Gln Asn Pro Glu Asn  Lys Ala Trp Tyr Tyr  Leu Asp Ser
    1055                1060                1065

Asn Gly  Tyr Ala Val Thr Gly  Leu Gln Thr Ile Asn  Gly Lys Gln
    1070                1075                1080

Tyr Tyr  Phe Asp Asn Glu Gly  Arg Gln Val Lys Gly  His Phe Val
    1085                1090                1095

Thr Ile  Asn Asn Gln Arg Tyr  Phe Leu Asp Gly Asp  Ser Gly Glu
    1100                1105                1110

Ile Ala  Pro Ser Arg Phe Val  Thr Glu Asn Asn Lys  Trp Tyr Tyr
    1115                1120                1125

Val Asp  Gly Asn Gly Lys Leu  Val Lys Gly Ala Gln  Val Ile Asn
    1130                1135                1140

Gly Asn  His Tyr Tyr Phe Asn  Asn Asp Tyr Ser Gln  Val Lys Gly
    1145                1150                1155
```

```
Ala Trp  Ala Asn Gly Arg Tyr  Tyr Asp Gly Asp Ser  Gly Gln Ala
    1160                 1165                 1170

Val Ser  Asn Gln Phe Ile Gln  Ile Ala Ala Asn Gln  Trp Ala Tyr
    1175                 1180                 1185

Leu Asn  Gln Asp Gly His Lys  Val Thr Gly Leu Gln  Asn Ile Asn
    1190                 1195                 1200

Asn Lys  Val Tyr Tyr Phe Gly  Ser Asn Gly Ala Gln  Val Lys Gly
    1205                 1210                 1215

Lys Leu  Leu Thr Val Gln Gly  Lys Lys Cys Tyr Phe  Asp Ala His
    1220                 1225                 1230

Thr Gly  Glu Gln Val Val Asn  Arg Phe Val Glu Ala  Ala Arg Gly
    1235                 1240                 1245

Cys Trp  Tyr Tyr Phe Asn Ser  Ala Gly Gln Ala Val  Thr Gly Gln
    1250                 1255                 1260

Gln Val  Ile Asn Gly Lys Gln  Leu Tyr Phe Asp Gly  Ser Gly Arg
    1265                 1270                 1275

Gln Val  Lys Gly Arg Tyr Val  Tyr Val Gly Gly Lys  Arg Leu Phe
    1280                 1285                 1290

Cys Asp  Ala Lys Thr Gly Glu  Leu Arg Gln Arg Arg
    1295                 1300                 1305
```

<210> SEQ ID NO 33
<211> LENGTH: 4026
<212> TYPE: DNA
<213> ORGANISM: Streptococcus salivarius

<400> SEQUENCE: 33

```
atgatcgacg gcaaatacta ctatgtaaac gaggacggca gccacaaaga gaatttcgcg     60

attacggtaa acggtcagct gctgtacttt ggtaaggacg gtgctctgac gagcagctcc    120

acgtacagct ttaccccggg tacgaccaat attgtcgatg gcttcagcat taacaaccgt    180

gcgtatgaca gcagcgaggc atcctttgag ctgatcgatg gttatttgac cgcggatagc    240

tggtatcgtc cggcgagcat cattaaggac ggcgttacgt ggcaggcctc gaccgcagaa    300

gattttcgtc cgctgctgat ggcttggtgg ccgaatgttg acacccaggt gaattatctg    360

aattacatgt ccaaggtttt caacctggat gcaaagtaca ccagcaccga caagcaggaa    420

accctgaacg tggctgcgaa agatatccaa gtcaagattg agcaaaagat tcaggcagag    480

aaatctaccc agtggctgcg tgaaacgatt agcgcgtttg ttaaaactca gccgcaatgg    540

aataaagaaa cggaaaacta ttccaagggt ggtggcgagg accatctgca aggcggtgcc    600

ctgttgtacg ttaacgattc gcgcaccccg tgggcgaact cgaactatcg cttgctgaac    660

cataccgcta ccaatcaaaa aggcactatt gacaaatctg tcctggacga gcagagcgac    720

ccgaaccaca tgggcggttt cgattttctg ctggcgaacg acgtcgacct gagcaacccg    780

gtggtgcagg ccgaacaact gaaccagatt cactacctga tgaattgggg tagcatcgtg    840

atgggtgata aagatgcgaa ctttgacggc attcgtgtcg atgcggtcga taacgtggac    900

gccgacatgt tgcagctgta cacgaactac tttcgtgagt actacggcgt taacaagagc    960

gaagcaaatg ccctggcgca tatcagcgtt ctggaagcgt ggagcctgaa tgacaatcac   1020

tataacgata agacggacgg tgcggccctg gcaatggaga ataaacaacg tctggcgctg   1080

ctgttcagcc tggcgaaacc gatcaaagag cgtacgccgg ctgtgagccc actgtataac   1140

aacaccttca atactacgca gcgtgacgag aaaacggact ggattaacaa agacggtagc   1200
```

```
aaagcgtata acgaggatgg taccgtcaag caatcgacca ttggtaagta caatgagaag   1260
tatggcgacg caagcggtaa ttacgtgttc attcgtgccc acgacaacaa tgttcaagac   1320
atcatcgccg aaatcatcaa gaaagagatc aaccctaaga gcgacggttt caccatcacc   1380
gacgcagaga tgaagaaggc ctttgaaatc tacaacaagg acatgttgag cagcgataag   1440
aagtatactc tgaacaacat tccggctgcg tacgcggtga tgttgcagaa tatggaaacc   1500
atcacgcgtg tttactatgg tgatctgtat accgataatg gcaactacat ggaaacgaaa   1560
agcccgtact atgacaccat tgttaatctg atgaagaatc gcatcaagta tgtgtctggc   1620
ggtcaagcgc agcgttctta ctggctgccg accgatggta agatggacaa tagcgatgtg   1680
gaactgtacc gcaccaacga ggtatacgct tctgtgcgct atggtaaaga cattatgacc   1740
gccgatgata ccgagggttc caagtactcc cgtacgagcg gccaagttac cttggtggca   1800
aacaacccga aattgaccct ggaccaaagc gcgaaactga aagtggagat gggtaagatc   1860
cacgcaaatc aaaagtaccg tgcactgatt gtcggtaccg ccgacggtat caagaatttc   1920
accagcgatg cggatgcgat tgcagcaggc tatgttaaag agactgatag caatggtgtg   1980
ctgacgtttg gtgcgaacga cattaaaggc tatgaaacgt ttgacatgag cggtttcgtt   2040
gcggtgtggg tgcctgtggg tgctagcgat gatcaggata tccgtgtcgc gccgagcacc   2100
gaggcaaaga aagaaggtga gctgacgttg aaagcgaccg aggcctatga cagccagttg   2160
atttacgaag gtttcagcaa tttccaaacc attccagacg gttccgatcc gagcgtctac   2220
accaatcgca aaatcgcgga aaacgttgat ctgttcaaaa gctggggtgt gaccagcttc   2280
gaaatggcac cgcaattcgt tagcgcggac gatggtacgt tcttggacag cgttatccaa   2340
aatggctatg cgttcgccga tcgttatgac ttggcgatga gcaaaaacaa caaatacggc   2400
agcaaagagg atctgcgcga cgccctgaaa gcgctgcata aagcgggtat tcaagccatc   2460
gctgactggg ttccggacca gatctaccag ctgccgggta aagaagtcgt taccgcgacc   2520
cgcaccgatg gcgctggccg taagatcgcg gatgcaatta tcgatcatag cttgtatgtg   2580
gccaatacta aaagctccgg taaggattac caggcgaaat atggtggtga atttctggct   2640
gagctgaagg ccaaataccc ggagatgttc aaggtcaaca tgattagcac cggcaaacct   2700
attgatgact ctgtcaaatt gaaacaatgg aaggcagagt atttcaatgg cactaacgtc   2760
ctggaacgtg gtgttggtta cgtgctgagc gacgaggcga ccggtaaata cttcaccgtt   2820
acgaaggacg gcaatttcat cccgctgcaa ctgaccggta atgagaaggt tgtgacgggt   2880
ttttctaatg acggtaaggg cattacctac ttcggtacct cgggtaccca ggcaaagagc   2940
gcattcgtga cgtttaacgg taacacctac tactttgatg cacgcggcca catggtgacg   3000
aacggcgagt acagcccgaa cggcaaggat gtttatcgct tcctgccgaa tggcatcatg   3060
ctgtccaatg cgttttacgt cgatgcaaat ggtaatactt acctgtacaa cagcaagggt   3120
cagatgtata agggcggtta taccaagttc gacgttactg aaacggacaa ggacggtaaa   3180
gagagcaaag tagtgaagtt tcgttatttc acgaacgaag gcgtcatggc gaaaggtgtc   3240
accgttattg atggctttac ccagtatttc ggtgaagatg gctttcaagc gaaggacaag   3300
ctggtgacct ttaagggcaa aacctactat tttgacgcgc acacgggcaa cgccatcaag   3360
aacacctggc gtaatatcga cggtaagtgg tatcattttg atgcgaacgg tgtggcggcg   3420
accggcgcac aggtcattaa tggtcaaaaa ctgtacttta atgaggacgg tagccaagtc   3480
aaaggtggcg tcgtcaagaa tgcagatggc acctatagca aatacaaaga gggctccggt   3540
gagctggtta ccaacgagtt ctttaccacg gatggtaacg tctggtacta tgctggtgcg   3600
```

```
aatggcaaga ccgttaccgg tgcacaggtt atcaacggcc agcacctgta cttcaatgcg   3660

gatggctctc aagtgaaggg cggtgtcgtc aaaaacgcgg acggtacgta ctccaaatac   3720

gatgccgcga ccggtgaacg tctgaccaat gagtttttca cgactggtga caacaattgg   3780

tactacatcg gcgccaacgg taagacggtt acgggcgaag tgaaaattgg cgacgatacg   3840

tactacttcg caaaagatgg taaacaggtg aaaggtcaga cggtttccgc tggtaatggc   3900

cgcatcagct actattacgg tgactctggt aaacgtgcgg ttagcacgtg ggttgaaatt   3960

caaccgggcg tgtatgtcta ttttgataag aatggcctgg catatccacc gcgcgttttg   4020

aattaa                                                              4026
```

```
<210> SEQ ID NO 34
<211> LENGTH: 1341
<212> TYPE: PRT
<213> ORGANISM: Streptococcus salivarius

<400> SEQUENCE: 34

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285
```

```
Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asn Gly Asn Tyr Met Glu Thr Lys Ser Pro Tyr Tyr Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Ala Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Lys Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
```

```
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
        995                 1000                1005

Lys Asp  Val Tyr Arg Phe Leu  Pro Asn Gly Ile Met  Leu Ser Asn
    1010                 1015                 1020

Ala Phe  Tyr Val Asp Ala Asn  Gly Asn Thr Tyr Leu  Tyr Asn Ser
    1025                 1030                 1035

Lys Gly  Gln Met Tyr Lys Gly  Gly Tyr Thr Lys Phe  Asp Val Thr
    1040                 1045                 1050

Glu Thr  Asp Lys Asp Gly Lys  Glu Ser Lys Val Val  Lys Phe Arg
    1055                 1060                 1065

Tyr Phe  Thr Asn Glu Gly Val  Met Ala Lys Gly Val  Thr Val Ile
    1070                 1075                 1080

Asp Gly  Phe Thr Gln Tyr Phe  Gly Glu Asp Gly Phe  Gln Ala Lys
    1085                 1090                 1095

Asp Lys  Leu Val Thr Phe Lys  Gly Lys Thr Tyr Tyr  Phe Asp Ala
    1100                 1105                 1110

His Thr  Gly Asn Ala Ile Lys  Asn Thr Trp Arg Asn  Ile Asp Gly
    1115                 1120                 1125
```

```
Lys Trp  Tyr His Phe Asp Ala  Asn Gly Val Ala Ala  Thr Gly Ala
    1130                 1135                 1140

Gln Val  Ile Asn Gly Gln Lys  Leu Tyr Phe Asn Glu  Asp Gly Ser
    1145                 1150                 1155

Gln Val  Lys Gly Gly Val Val  Lys Asn Ala Asp Gly  Thr Tyr Ser
    1160                 1165                 1170

Lys Tyr  Lys Glu Gly Ser Gly  Glu Leu Val Thr Asn  Glu Phe Phe
    1175                 1180                 1185

Thr Thr  Asp Gly Asn Val Trp  Tyr Tyr Ala Gly Ala  Asn Gly Lys
    1190                 1195                 1200

Thr Val  Thr Gly Ala Gln Val  Ile Asn Gly Gln His  Leu Tyr Phe
    1205                 1210                 1215

Asn Ala  Asp Gly Ser Gln Val  Lys Gly Gly Val Val  Lys Asn Ala
    1220                 1225                 1230

Asp Gly  Thr Tyr Ser Lys Tyr  Asp Ala Ala Thr Gly  Glu Arg Leu
    1235                 1240                 1245

Thr Asn  Glu Phe Phe Thr Thr  Gly Asp Asn Asn Trp  Tyr Tyr Ile
    1250                 1255                 1260

Gly Ala  Asn Gly Lys Thr Val  Thr Gly Glu Val Lys  Ile Gly Asp
    1265                 1270                 1275

Asp Thr  Tyr Tyr Phe Ala Lys  Asp Gly Lys Gln Val  Lys Gly Gln
    1280                 1285                 1290

Thr Val  Ser Ala Gly Asn Gly  Arg Ile Ser Tyr Tyr  Tyr Gly Asp
    1295                 1300                 1305

Ser Gly  Lys Arg Ala Val Ser  Thr Trp Val Glu Ile  Gln Pro Gly
    1310                 1315                 1320

Val Tyr  Val Tyr Phe Asp Lys  Asn Gly Leu Ala Tyr  Pro Pro Arg
    1325                 1330                 1335

Val Leu  Asn
    1340
```

<210> SEQ ID NO 35
<211> LENGTH: 3996
<212> TYPE: DNA
<213> ORGANISM: Streptococcus salivarius

<400> SEQUENCE: 35

```
atggtcgacg gcaaatacta ctacgtgaaa gaggatggca gctacaaaac gaacttcgca     60

gtttccgtca acggccaact gctgtatttc ggcaaggatg gcgcgctgac gtccaccagc    120

acccatagct ttacgccagg cactaccaat ctggttgatg cgttcagctc ccataaccgc    180

gcctacgact ccaaaaagga gagcttcgaa ctggtggatg gttatctgac gccgaactct    240

tggtatcgtc cggtcactat cctggaaaat ggtgaaaaat ggcgtgttag caccgagaag    300

gactttcgcc cgttgttgat ggcctggtgg ccggatgtcg acacgcaagt tgcctatctg    360

aacacctttt ctaaacactt caacctgaac gcgacgtact ctacttctca gagccaaagc    420

gagctgaatg cggcagctaa aaccatccaa atcaaaatcg aacaggagat tagcgcgaaa    480

aagagcacgg agtggctgcg ccaggcaatt gagtcctttg tcaaggagca ggatcagtgg    540

aacaccacga ccgagaacta caccctggcg gatcatttgc agggcggtgc gctgctgtat    600

gtgaacaatg acaagacgcc gtgggcgaac agcgactatc gtctgctgaa ccgtactccg    660

agcaaccagg acggcagcct gaacggtact ggccgttatc tgggtggtta cgagtttctg    720

ctggcgaatg acgtggacaa tagcaatccg gtggtccagg ctgagcagct gaatcaaatt    780
```

```
cactatctgg tcaactgggg cagcattgtc atgggtgaca aggacgcgaa tttcgacggc     840
attcgtgttg acgccgttga caatgtggac gccgatctgt tgcaggttta cacgaactac     900
ttccgtgcgg cgtttggtgt ggataaaagc gaagcgaacg cactggccca catcagcatt     960
ctggaggcgt gggatctgaa cgacaatgcg tacaaccaga aacatgacgg tgcggccttg    1020
gcaatggata acaacctgcg ttacgcgatc atgggtgcac tgtatggtag cggtagctcg    1080
ctgaaagatc tgattaccag cagcctgacc gaccgtacga ataactccaa atatggtgat    1140
acccaagcaa actacatctt cgcccgtgct catgataatc tggtccagga cattattcgt    1200
gacatcgtgc agaaagagat caatccgaag agcgacggct acacgatgac cgatgcggag    1260
ctgaagcgtg cgtttgaaat ctacaacgag gatatgaaaa aggccgaaaa acgctacact    1320
atcaacaaca tcccggcagc gtatgcactg attttgcaga acatggaaca ggttactcgt    1380
gtgtactacg gtgatctgta taccgacaat ggtcagtaca tggcgaccaa aagcccgtac    1440
tacgacgcga ttacgaccct gctgaaaaat cgtatgaagt atgtgagcgg cggtcagagc    1500
atgaaagttg acactttcaa cggtaaagaa attctgtcgt ctgttcgtta cggtaaggac    1560
atcatgaccg cggaccaaac gaccggtgtc gcagaaacca gcaagcacag cggcatgctg    1620
accctgatcg ccaataacca ggatttttct ctgggcgatg gcaccttgaa agtgaacatg    1680
ggcaagctgc acgcgaacca ggcgtatcgc ccgctgctgc tgggcacgga taagggcatc    1740
gttacctatg aaaatgacgc ggctgcggca ggcaaaatca agtacacgga cgcagagggt    1800
aatctgacct tcagcggtga cgagatcaag ggctatcgca ccgtggacat gcgcggctac    1860
ctgggtgtgt gggtcccggt cggcgcaccg gacaatcaag acattcgcgt taagggtagc    1920
gataagaaac tggacaagac tttcagcgca accgaagctc tggatagcca ggtgatttac    1980
gaaggtttta gcaactttca ggacttcgtg gaaaaagaca gccagtacac caacaagctg    2040
attgcggaaa acgcggaact gtttaagagc tggggtatta ctagctttga aatggcccct    2100
cagtttgtca gcgcagacga tcgtaccttc ctggatagcg ttatccaaaa cggttatgcg    2160
tttaccgatc gttacgatct ggccatgtct aagaataaca agtatggcag caaagaagat    2220
ctgcgtgatg cgctgaaggc gctgcacaag cagggcattc aagcaattgc cgactgggtt    2280
ccggatcaac tgtaccaact gccgggtcaa gaggttgtca ccgctacccg tgcaaatagc    2340
tacggcaccc cgaaggccaa tgcctacatt aacaatacgc tgtatgttgc caatagcaag    2400
agcagcggta aagacttcca ggctcaatac ggtggcgagt tcctggatga attgcagaag    2460
aagtacccgc agttgttcga ggatgtgatg atcagcacgg gtaaaaagat tgacccgagc    2520
gtgaaaatca agcagtggag cgccaaatac atgaatggca ccaacattct gggtcgtggc    2580
aaccgttacg ttctgtcgaa tgacgccacc ggtcgctatt atcaagtgac cgacaacggc    2640
attttcttgc cgaagccgct gacggatcag ggtggtaaga ccggcttcta ttacgatggt    2700
aagggcatgg cctatttcga caattccggc tttcaagcga aaaatgcgtt catcaagtac    2760
gcgggtaact actactactt cgataaagag ggctatatgc tgacgggccg tcaagatatt    2820
gacagcaaga cgtatttctt tctgccgaat ggtatccaac tgcgtgatag catttaccaa    2880
caagatggca agtactacta ttttggtagc ttcggcgaac aatacaaaga cggttatttc    2940
gtctttgacg tgccaaaaga gggcaccagc gaaaccgagg ctaagttccg ctacttttct    3000
ccgacgggtg agatggcagt gggtttgacc tatgcgggtg gtggtctgca atactttgat    3060
gagaacggtt tccaggcgaa gggtacgaag tatgttacgc cggatggtaa gttgtatttc    3120
```

```
ttcgacaaga atagcggcaa cgcgtacacc aatcgttggg cggagatcga tggtatttgg   3180

tacgagttta atgaccaagg ttacgcgcag gcgaagaaag gtgagtttta caccacggat   3240

ggtagcacgt ggttttaccg cgacgcagca ggtaaaaacg ttaccggtgc cctgaccctg   3300

gacggtcacg agtattactt tcgtgcgaac ggtgcgcagg tgaaaggcga gttcgtcacc   3360

gaaaacggta agattagcta ttacaccgtt gataacggtt acaaggtaaa agacaagttc   3420

ttcgaagtca atggtaagtg gtatcacgct gataaggacg gtaatttggc gacgggtcgt   3480

cagaccatcg accatctgaa ttactacttc aacgcggacg gctcccaggt taagtccgat   3540

ttcttcactc tggatggtgg taaaacctgg tattatgcca aagacaacgg tgagattgtg   3600

accggtgcgt actcggtgcg tggcaagaac tattacttca aagaggacgg tagccaagtt   3660

aagggcgatt tcgtcaaaaa tgcggacggt tccctgagct attatgacaa ggatagcggc   3720

gaacgtctga acaaccgttt cttgaccacg ggtaacaatg tctggtatta ctttaaggat   3780

ggtaaagcgg tcacgggtcg ccagaacatc gacggtaagg agtactactt tgatcacctg   3840

ggtcgtcaag tcaaaggctc cccgattagc actccgaagg gcgttgagta ttatgagtct   3900

gtgctgggtg agcgtgtcac caacacctgg atcaccttcc aagacggcaa aaccgtgttc   3960

tttgatgaaa atggctacgc ggactttgat aagtaa                             3996

<210> SEQ ID NO 36
<211> LENGTH: 1331
<212> TYPE: PRT
<213> ORGANISM: Streptococcus salivarius

<400> SEQUENCE: 36

Met Val Asp Gly Lys Tyr Tyr Tyr Val Lys Glu Asp Gly Ser Tyr Lys
1               5                   10                  15

Thr Asn Phe Ala Val Ser Val Asn Gly Gln Leu Leu Tyr Phe Gly Lys
            20                  25                  30

Asp Gly Ala Leu Thr Ser Thr Ser Thr His Ser Phe Thr Pro Gly Thr
        35                  40                  45

Thr Asn Leu Val Asp Ala Phe Ser Ser His Asn Arg Ala Tyr Asp Ser
    50                  55                  60

Lys Lys Glu Ser Phe Glu Leu Val Asp Gly Tyr Leu Thr Pro Asn Ser
65                  70                  75                  80

Trp Tyr Arg Pro Val Thr Ile Leu Glu Asn Gly Glu Lys Trp Arg Val
                85                  90                  95

Ser Thr Glu Lys Asp Phe Arg Pro Leu Leu Met Ala Trp Trp Pro Asp
            100                 105                 110

Val Asp Thr Gln Val Ala Tyr Leu Asn Thr Phe Ser Lys His Phe Asn
        115                 120                 125

Leu Asn Ala Thr Tyr Ser Thr Ser Gln Ser Gln Ser Glu Leu Asn Ala
    130                 135                 140

Ala Ala Lys Thr Ile Gln Ile Lys Ile Glu Gln Glu Ile Ser Ala Lys
145                 150                 155                 160

Lys Ser Thr Glu Trp Leu Arg Gln Ala Ile Glu Ser Phe Val Lys Glu
                165                 170                 175

Gln Asp Gln Trp Asn Thr Thr Thr Glu Asn Tyr Thr Leu Ala Asp His
            180                 185                 190

Leu Gln Gly Gly Ala Leu Leu Tyr Val Asn Asn Asp Lys Thr Pro Trp
        195                 200                 205

Ala Asn Ser Asp Tyr Arg Leu Leu Asn Arg Thr Pro Ser Asn Gln Asp
    210                 215                 220
```

```
Gly Ser Leu Asn Gly Thr Gly Arg Tyr Leu Gly Gly Tyr Glu Phe Leu
225                 230                 235                 240

Leu Ala Asn Asp Val Asp Asn Ser Asn Pro Val Val Gln Ala Glu Gln
                245                 250                 255

Leu Asn Gln Ile His Tyr Leu Val Asn Trp Gly Ser Ile Val Met Gly
            260                 265                 270

Asp Lys Asp Ala Asn Phe Asp Gly Ile Arg Val Asp Ala Val Asp Asn
        275                 280                 285

Val Asp Ala Asp Leu Leu Gln Val Tyr Thr Asn Tyr Phe Arg Ala Ala
    290                 295                 300

Phe Gly Val Asp Lys Ser Glu Ala Asn Ala Leu Ala His Ile Ser Ile
305                 310                 315                 320

Leu Glu Ala Trp Asp Leu Asn Asp Asn Ala Tyr Asn Gln Lys His Asp
                325                 330                 335

Gly Ala Ala Leu Ala Met Asp Asn Asn Leu Arg Tyr Ala Ile Met Gly
            340                 345                 350

Ala Leu Tyr Gly Ser Gly Ser Ser Leu Lys Asp Leu Ile Thr Ser Ser
        355                 360                 365

Leu Thr Asp Arg Thr Asn Asn Ser Lys Tyr Gly Asp Thr Gln Ala Asn
    370                 375                 380

Tyr Ile Phe Ala Arg Ala His Asp Asn Leu Val Gln Asp Ile Ile Arg
385                 390                 395                 400

Asp Ile Val Gln Lys Glu Ile Asn Pro Lys Ser Asp Gly Tyr Thr Met
                405                 410                 415

Thr Asp Ala Glu Leu Lys Arg Ala Phe Glu Ile Tyr Asn Glu Asp Met
            420                 425                 430

Lys Lys Ala Glu Lys Arg Tyr Thr Ile Asn Asn Ile Pro Ala Ala Tyr
        435                 440                 445

Ala Leu Ile Leu Gln Asn Met Glu Gln Val Thr Arg Val Tyr Tyr Gly
    450                 455                 460

Asp Leu Tyr Thr Asp Asn Gly Gln Tyr Met Ala Thr Lys Ser Pro Tyr
465                 470                 475                 480

Tyr Asp Ala Ile Thr Thr Leu Leu Lys Asn Arg Met Lys Tyr Val Ser
                485                 490                 495

Gly Gly Gln Ser Met Lys Val Asp Thr Phe Asn Gly Lys Glu Ile Leu
            500                 505                 510

Ser Ser Val Arg Tyr Gly Lys Asp Ile Met Thr Ala Asp Gln Thr Thr
        515                 520                 525

Gly Val Ala Glu Thr Ser Lys His Ser Gly Met Leu Thr Leu Ile Ala
    530                 535                 540

Asn Asn Gln Asp Phe Ser Leu Gly Asp Gly Thr Leu Lys Val Asn Met
545                 550                 555                 560

Gly Lys Leu His Ala Asn Gln Ala Tyr Arg Pro Leu Leu Leu Gly Thr
                565                 570                 575

Asp Lys Gly Ile Val Thr Tyr Glu Asn Asp Ala Ala Ala Ala Gly Lys
            580                 585                 590

Ile Lys Tyr Thr Asp Ala Glu Gly Asn Leu Thr Phe Ser Gly Asp Glu
        595                 600                 605

Ile Lys Gly Tyr Arg Thr Val Asp Met Arg Gly Tyr Leu Gly Val Trp
    610                 615                 620

Val Pro Val Gly Ala Pro Asp Asn Gln Asp Ile Arg Val Lys Gly Ser
625                 630                 635                 640
```

```
Asp Lys Lys Leu Asp Lys Thr Phe Ser Ala Thr Glu Ala Leu Asp Ser
                645                 650                 655

Gln Val Ile Tyr Glu Gly Phe Ser Asn Phe Gln Asp Phe Val Glu Lys
            660                 665                 670

Asp Ser Gln Tyr Thr Asn Lys Leu Ile Ala Glu Asn Ala Glu Leu Phe
        675                 680                 685

Lys Ser Trp Gly Ile Thr Ser Phe Glu Met Ala Pro Gln Phe Val Ser
    690                 695                 700

Ala Asp Asp Arg Thr Phe Leu Asp Ser Val Ile Gln Asn Gly Tyr Ala
705                 710                 715                 720

Phe Thr Asp Arg Tyr Asp Leu Ala Met Ser Lys Asn Asn Lys Tyr Gly
                725                 730                 735

Ser Lys Glu Asp Leu Arg Asp Ala Leu Lys Ala Leu His Lys Gln Gly
            740                 745                 750

Ile Gln Ala Ile Ala Asp Trp Val Pro Asp Gln Leu Tyr Gln Leu Pro
        755                 760                 765

Gly Gln Glu Val Val Thr Ala Thr Arg Ala Asn Ser Tyr Gly Thr Pro
    770                 775                 780

Lys Ala Asn Ala Tyr Ile Asn Asn Thr Leu Tyr Val Ala Asn Ser Lys
785                 790                 795                 800

Ser Ser Gly Lys Asp Phe Gln Ala Gln Tyr Gly Gly Glu Phe Leu Asp
                805                 810                 815

Glu Leu Gln Lys Lys Tyr Pro Gln Leu Phe Glu Asp Val Met Ile Ser
            820                 825                 830

Thr Gly Lys Lys Ile Asp Pro Ser Val Lys Ile Lys Gln Trp Ser Ala
        835                 840                 845

Lys Tyr Met Asn Gly Thr Asn Ile Leu Gly Arg Gly Asn Arg Tyr Val
    850                 855                 860

Leu Ser Asn Asp Ala Thr Gly Arg Tyr Tyr Gln Val Thr Asp Asn Gly
865                 870                 875                 880

Ile Phe Leu Pro Lys Pro Leu Thr Asp Gln Gly Gly Lys Thr Gly Phe
                885                 890                 895

Tyr Tyr Asp Gly Lys Gly Met Ala Tyr Phe Asp Asn Ser Gly Phe Gln
            900                 905                 910

Ala Lys Asn Ala Phe Ile Lys Tyr Ala Gly Asn Tyr Tyr Tyr Phe Asp
        915                 920                 925

Lys Glu Gly Tyr Met Leu Thr Gly Arg Gln Asp Ile Asp Ser Lys Thr
    930                 935                 940

Tyr Phe Phe Leu Pro Asn Gly Ile Gln Leu Arg Asp Ser Ile Tyr Gln
945                 950                 955                 960

Gln Asp Gly Lys Tyr Tyr Tyr Phe Gly Ser Phe Gly Glu Gln Tyr Lys
                965                 970                 975

Asp Gly Tyr Phe Val Phe Asp Val Pro Lys Glu Gly Thr Ser Glu Thr
            980                 985                 990

Glu Ala Lys Phe Arg Tyr Phe Ser  Pro Thr Gly Glu Met  Ala Val Gly
        995                 1000                1005

Leu Thr  Tyr Ala Gly Gly Gly  Leu Gln Tyr Phe Asp  Glu Asn Gly
    1010                1015                1020

Phe Gln  Ala Lys Gly Thr Lys  Tyr Val Thr Pro Asp  Gly Lys Leu
    1025                1030                1035

Tyr Phe  Phe Asp Lys Asn Ser  Gly Asn Ala Tyr Thr  Asn Arg Trp
    1040                1045                1050

Ala Glu  Ile Asp Gly Ile Trp  Tyr Glu Phe Asn Asp  Gln Gly Tyr
```

```
    1055                1060                1065

Ala Gln  Ala Lys Lys Gly Glu  Phe Tyr Thr Thr Asp  Gly Ser Thr
    1070                1075                1080

Trp Phe  Tyr Arg Asp Ala Ala  Gly Lys Asn Val Thr  Gly Ala Leu
    1085                1090                1095

Thr Leu  Asp Gly His Glu Tyr  Tyr Phe Arg Ala Asn  Gly Ala Gln
    1100                1105                1110

Val Lys  Gly Glu Phe Val Thr  Glu Asn Gly Lys Ile  Ser Tyr Tyr
    1115                1120                1125

Thr Val  Asp Asn Gly Tyr Lys  Val Lys Asp Lys Phe  Phe Glu Val
    1130                1135                1140

Asn Gly  Lys Trp Tyr His Ala  Asp Lys Asp Gly Asn  Leu Ala Thr
    1145                1150                1155

Gly Arg  Gln Thr Ile Asp His  Leu Asn Tyr Tyr Phe  Asn Ala Asp
    1160                1165                1170

Gly Ser  Gln Val Lys Ser Asp  Phe Phe Thr Leu Asp  Gly Gly Lys
    1175                1180                1185

Thr Trp  Tyr Tyr Ala Lys Asp  Asn Gly Glu Ile Val  Thr Gly Ala
    1190                1195                1200

Tyr Ser  Val Arg Gly Lys Asn  Tyr Tyr Phe Lys Glu  Asp Gly Ser
    1205                1210                1215

Gln Val  Lys Gly Asp Phe Val  Lys Asn Ala Asp Gly  Ser Leu Ser
    1220                1225                1230

Tyr Tyr  Asp Lys Asp Ser Gly  Glu Arg Leu Asn Asn  Arg Phe Leu
    1235                1240                1245

Thr Thr  Gly Asn Asn Val Trp  Tyr Tyr Phe Lys Asp  Gly Lys Ala
    1250                1255                1260

Val Thr  Gly Arg Gln Asn Ile  Asp Gly Lys Glu Tyr  Tyr Phe Asp
    1265                1270                1275

His Leu  Gly Arg Gln Val Lys  Gly Ser Pro Ile Ser  Thr Pro Lys
    1280                1285                1290

Gly Val  Glu Tyr Tyr Glu Ser  Val Leu Gly Glu Arg  Val Thr Asn
    1295                1300                1305

Thr Trp  Ile Thr Phe Gln Asp  Gly Lys Thr Val Phe  Phe Asp Glu
    1310                1315                1320

Asn Gly  Tyr Ala Asp Phe Asp  Lys
    1325                1330
```

```
<210> SEQ ID NO 37
<211> LENGTH: 3918
<212> TYPE: DNA
<213> ORGANISM: Streptococcus salivarius

<400> SEQUENCE: 37

atgattgacg gcaaacagta ttatgtagag aacggtgtgg ttaagaagaa tacggcgatt     60

gaactggatg gccgtctgta ttactttgac gaaaccggtg caatggttga tcaatctaag    120

ccgctgtatc gcgcggatgc aatcccgaac aactctatct acgcagttta caaccaggct    180

tacgacacca gcagcaagag ctttgaacac ctggacaact ttctgacggc cgatagctgg    240

taccgtccga agcagatttt gaaagacggc aagaattgga ccgcctcgac ggagaaggac    300

tatcgtcctt tgctgatgac gtggtggccg gataaagtca cgcaagtcaa ctacctgaac    360

tatatgtccc aacagggctt tggtaacaag acctacacca cggatatgat gagctacgac    420

ctggcggcag cggcggaaac ggttcagcgt ggcatcgaag agcgtattgg tcgtgagggt    480
```

```
aatacgacgt ggctgcgtca gttgatgagc gacttcatca aaacccagcc gggctggaat    540
agcgagagcg aagataatct gctggtcggt aaggatcatc tgcaaggtgg tgcactgacg    600
tttctgaaca atagcaccac gagccatgcg aacagcgatt tccgcctgat gaatcgtacc    660
ccgacgaacc agaccggcac ccgcaaatac cacatcgatc gtagcaatgg tggctacgaa    720
ctgctgctgg cgaacgacat cgacaatagc aatccggccg tccaagcgga acagctgaac    780
tggctgcatt acatcatgaa catcggctct atcctgggca atgacccaag cgcgaatttt    840
gatggcgtcc gtatcgatgc agttgacaat gtggatgcgg acttgttgca aattgcgtct    900
gactacttta aggaaaagta ccgtgttgcc gataacgagg caaacgctat tgcgcacctg    960
tcgattctgg aggcatggtc ctacaatgat catcaataca acaaagacac gaagggcgct   1020
caactgagca ttgataatcc gctgcgtgag actttgctga cgaccttcct gcgcaagtct   1080
aactaccgtg gttccctgga gcgtgtgatc accaactcgt tgaacaaccg tagcagcgaa   1140
cagaagcaca cgccgcgtga cgccaactac atttttgtgc gtgctcacga cagcgaagtt   1200
caagcggtgc tggcaaacat catctctaaa cagatcaacc cgaaaaccga cggttttacc   1260
tttacgatgg atgagctgaa gcaggcgttt gagatttaca acgcagacat gcgtaaggcg   1320
gataagaagt acacgcagta caacattccg gcagcttacg ccaccatgct gaccaataag   1380
gatagcatca cccgtgtgta ctatggtgat ttgtttaccg acgacggtca atacatggcg   1440
gagaaaagcc cgtactataa cgcaattgac gccctgctgc gtgctcgcat caaatacgtc   1500
gcgggtggtc aggacatgaa ggtgaccaaa ttgaacggct atgagatcat gtcctccgtt   1560
cgctacggta aaggcgcaga ggaagctaat cagctgggca ccgcagaaac ccgcaatcaa   1620
ggcatgctgg tcctgaccgc gaatcgccca gacatgaagc tgggtacgaa tgatcgcctg   1680
gtcgtcaata tgggtgcagc ccacaagaat caggcgtatc gtccgctgct gctgtccaag   1740
tccaccggct tggcaaccta cctgaaagac agcgacgtcc ctgcgggcct ggtgcgttac   1800
acggacaatc aaggtaatct gaccttcacg gcggacgaca tcaccggcca tagcaccgta   1860
gaggtgagcg gttacctggc ggtttgggtg ccggtgggtg cgagcgagaa ccaagatgcg   1920
cgcacgaaag cgagcacgac gaaaaagggc gaacaagttt ttgaaagctc cgcagcgctg   1980
gatagccagg tcatctatga gggtttctcc aacttccagg attttgttaa gacccccttcc   2040
cagtacacga atcgcgttat cgcacagaac gcgaagcgct ttaaggagtg gggtatcacc   2100
agctttgagt tcgcgcctca atatgttagc agccaagacg gtacctttct ggatagcatt   2160
attgagaacg gctacgcgtt cgaggaccgt tacgatatcg cgatgagcaa aaacaacaag   2220
tacggcagcc tgaaggatct gatggacgcg ctgcgtgcac tgcacgcgga gggtatcagc   2280
gccattgctg actgggttcc ggaccaaatc tataacctgc cgggtaagga agttgtaacc   2340
gcaagccgca cgaatagcta cggtacgccg cgtccgaacg cggaaatcta taacagcctg   2400
tatgcggcga aaacgcgtac gtttggcaat gattttcagg gtaaatacgg tggcgcgttt   2460
ctggatgaac tgaaagcaaa gtacccggcg atcttcgagc gtgtgcaaat ttcgaatggt   2520
cgtaagctga ctaccaatga gaaaatcacg caatggagcg cgaagtactt taatggcagc   2580
aacattcaag gtaccggtgc gcgttacgtt ctgcaagata atgccacgaa ccagtatttc   2640
aacctgaagg ccggtcaaac ctttctgcca aagcagatga ccgagattac cgcaacgggc   2700
ttccgtcgtg tcggtgacaa agtgcaatac ctgtccacgt ccggctacct ggcgaagaat   2760
acctttatcc agattggtgc gaaccagtgg tattacttcg acaagaatgg caacatggtg   2820
```

```
accggtgagc aagtgattga tggtaaaaag tatttcttcc tggataacgg tctgcaactg   2880

cgtcatgtct tgcgtcaagg ttctgacggt cacgtgtatt actacgatcc gaaaggcgtc   2940

caggcgttta atggtttcta tgactttgcg ggtccgcgcc aagatgtccg ttatttcgac   3000

ggtaatggtc agatgtaccg tggtctgcat gatatgtatg gtaccacgtt ctactttgat   3060

gaaaagacgg gtatccaggc taaggataag tttatccgtt tcgccgacgg ccgtacccgt   3120

tactttattc cggacaccgg caatttggct gtgaatcgct tcgctcagaa tccggaaaac   3180

aaggcgtggt actacctgga cagcaacggt tatgcagtga cgggtttgca gaccattaat   3240

ggcaaacaat actatttcga caacgagggc cgtcaggtca agggccactt cgttactatc   3300

aacaatcagc gctacttctt ggacggtgac tcgggtgaga tcgcacgtag ccgcttcgtg   3360

acggagaaca acaaatggta ctatgtggat ggtaacggta aattggtcaa gggtgcacaa   3420

gtcatcaacg gtaaccacta ttacttcaat aatgattatt ctcaggtgaa aggtgcttgg   3480

gccaatggcc gctactacga cggcgatagc ggccaggcgg tcacgaatcg tttcgtgcag   3540

gtcggtgcaa accagtgggc ctatctgaat cagaacggtc agaaggttgt gggcttgcaa   3600

cacatcaatg gcaagctgta ctactttgaa ggcaacggtg tccaagcaaa aggcaagctg   3660

ctgacctata agggtaagaa atactacttc gatgctaaca gcggtgaggc agtcaccaac   3720

cgctttattc aaatctctcg cggtgtttgg tactatttca atgcgagcgg tcaagcagtg   3780

accggcgagc aagttatcaa tggtcaacac ctgtacttcg acgcaagcgg tcgccaggtt   3840

aaaggccgct atgtctggat taaaggccag cgccgttatt acgacgcgaa cactggtgcc   3900

tgggtacgta atcgttaa                                                 3918
```

<210> SEQ ID NO 38
<211> LENGTH: 1305
<212> TYPE: PRT
<213> ORGANISM: Streptococcus salivarius

<400> SEQUENCE: 38

```
Met Ile Asp Gly Lys Gln Tyr Tyr Val Glu Asn Gly Val Val Lys Lys
1               5                   10                  15

Asn Thr Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175
```

```
Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Thr Thr Ser
        195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
        275                 280                 285

Asp Asn Val Asp Ala Asp Leu Leu Gln Ile Ala Ser Asp Tyr Phe Lys
    290                 295                 300

Glu Lys Tyr Arg Val Ala Asp Asn Glu Ala Asn Ala Ile Ala His Leu
305                 310                 315                 320

Ser Ile Leu Glu Ala Trp Ser Tyr Asn Asp His Gln Tyr Asn Lys Asp
                325                 330                 335

Thr Lys Gly Ala Gln Leu Ser Ile Asp Asn Pro Leu Arg Glu Thr Leu
            340                 345                 350

Leu Thr Thr Phe Leu Arg Lys Ser Asn Tyr Arg Gly Ser Leu Glu Arg
        355                 360                 365

Val Ile Thr Asn Ser Leu Asn Asn Arg Ser Ser Glu Gln Lys His Thr
    370                 375                 380

Pro Arg Asp Ala Asn Tyr Ile Phe Val Arg Ala His Asp Ser Glu Val
385                 390                 395                 400

Gln Ala Val Leu Ala Asn Ile Ile Ser Lys Gln Ile Asn Pro Lys Thr
                405                 410                 415

Asp Gly Phe Thr Phe Thr Met Asp Glu Leu Lys Gln Ala Phe Glu Ile
            420                 425                 430

Tyr Asn Ala Asp Met Arg Lys Ala Asp Lys Lys Tyr Thr Gln Tyr Asn
        435                 440                 445

Ile Pro Ala Ala Tyr Ala Thr Met Leu Thr Asn Lys Asp Ser Ile Thr
    450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
                485                 490                 495

Ile Lys Tyr Val Ala Gly Gly Gln Asp Met Lys Val Thr Lys Leu Asn
            500                 505                 510

Gly Tyr Glu Ile Met Ser Ser Val Arg Tyr Gly Lys Gly Ala Glu Glu
        515                 520                 525

Ala Asn Gln Leu Gly Thr Ala Glu Thr Arg Asn Gln Gly Met Leu Val
    530                 535                 540

Leu Thr Ala Asn Arg Pro Asp Met Lys Leu Gly Thr Asn Asp Arg Leu
545                 550                 555                 560

Val Val Asn Met Gly Ala Ala His Lys Asn Gln Ala Tyr Arg Pro Leu
                565                 570                 575

Leu Leu Ser Lys Ser Thr Gly Leu Ala Thr Tyr Leu Lys Asp Ser Asp
            580                 585                 590

Val Pro Ala Gly Leu Val Arg Tyr Thr Asp Asn Gln Gly Asn Leu Thr
```

```
        595                 600                 605

Phe Thr Ala Asp Asp Ile Thr Gly His Ser Thr Val Glu Val Ser Gly
    610                 615                 620

Tyr Leu Ala Val Trp Val Pro Val Gly Ala Ser Glu Asn Gln Asp Ala
625                 630                 635                 640

Arg Thr Lys Ala Ser Thr Thr Lys Lys Gly Glu Gln Val Phe Glu Ser
                645                 650                 655

Ser Ala Ala Leu Asp Ser Gln Val Ile Tyr Glu Gly Phe Ser Asn Phe
            660                 665                 670

Gln Asp Phe Val Lys Thr Pro Ser Gln Tyr Thr Asn Arg Val Ile Ala
        675                 680                 685

Gln Asn Ala Lys Arg Phe Lys Glu Trp Gly Ile Thr Ser Phe Glu Phe
    690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                725                 730                 735

Lys Asn Asn Lys Tyr Gly Ser Leu Lys Asp Leu Met Asp Ala Leu Arg
            740                 745                 750

Ala Leu His Ala Glu Gly Ile Ser Ala Ile Ala Asp Trp Val Pro Asp
        755                 760                 765

Gln Ile Tyr Asn Leu Pro Gly Lys Glu Val Val Thr Ala Ser Arg Thr
    770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
                805                 810                 815

Gly Gly Ala Phe Leu Asp Glu Leu Lys Ala Lys Tyr Pro Ala Ile Phe
            820                 825                 830

Glu Arg Val Gln Ile Ser Asn Gly Arg Lys Leu Thr Thr Asn Glu Lys
        835                 840                 845

Ile Thr Gln Trp Ser Ala Lys Tyr Phe Asn Gly Ser Asn Ile Gln Gly
    850                 855                 860

Thr Gly Ala Arg Tyr Val Leu Gln Asp Asn Ala Thr Asn Gln Tyr Phe
865                 870                 875                 880

Asn Leu Lys Ala Gly Gln Thr Phe Leu Pro Lys Gln Met Thr Glu Ile
                885                 890                 895

Thr Ala Thr Gly Phe Arg Arg Val Gly Asp Lys Val Gln Tyr Leu Ser
            900                 905                 910

Thr Ser Gly Tyr Leu Ala Lys Asn Thr Phe Ile Gln Ile Gly Ala Asn
        915                 920                 925

Gln Trp Tyr Tyr Phe Asp Lys Asn Gly Asn Met Val Thr Gly Glu Gln
    930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                965                 970                 975

Pro Lys Gly Val Gln Ala Phe Asn Gly Phe Tyr Asp Phe Ala Gly Pro
            980                 985                 990

Arg Gln Asp Val Arg Tyr Phe Asp  Gly Asn Gly Gln Met  Tyr Arg Gly
        995                 1000                1005

Leu His  Asp Met Tyr Gly Thr  Thr Phe Tyr Phe Asp  Glu Lys Thr
    1010                1015                1020
```

```
Gly Ile  Gln Ala Lys Asp Lys  Phe Ile Arg Phe Ala  Asp Gly Arg
    1025                 1030                 1035

Thr Arg  Tyr Phe Ile Pro Asp  Thr Gly Asn Leu Ala  Val Asn Arg
    1040                 1045                 1050

Phe Ala  Gln Asn Pro Glu Asn  Lys Ala Trp Tyr Tyr  Leu Asp Ser
    1055                 1060                 1065

Asn Gly  Tyr Ala Val Thr Gly  Leu Gln Thr Ile Asn  Gly Lys Gln
    1070                 1075                 1080

Tyr Tyr  Phe Asp Asn Glu Gly  Arg Gln Val Lys Gly  His Phe Val
    1085                 1090                 1095

Thr Ile  Asn Asn Gln Arg Tyr  Phe Leu Asp Gly Asp  Ser Gly Glu
    1100                 1105                 1110

Ile Ala  Arg Ser Arg Phe Val  Thr Glu Asn Asn Lys  Trp Tyr Tyr
    1115                 1120                 1125

Val Asp  Gly Asn Gly Lys Leu  Val Lys Gly Ala Gln  Val Ile Asn
    1130                 1135                 1140

Gly Asn  His Tyr Tyr Phe Asn  Asn Asp Tyr Ser Gln  Val Lys Gly
    1145                 1150                 1155

Ala Trp  Ala Asn Gly Arg Tyr  Tyr Asp Gly Asp Ser  Gly Gln Ala
    1160                 1165                 1170

Val Thr  Asn Arg Phe Val Gln  Val Gly Ala Asn Gln  Trp Ala Tyr
    1175                 1180                 1185

Leu Asn  Gln Asn Gly Gln Lys  Val Val Gly Leu Gln  His Ile Asn
    1190                 1195                 1200

Gly Lys  Leu Tyr Tyr Phe Glu  Gly Asn Gly Val Gln  Ala Lys Gly
    1205                 1210                 1215

Lys Leu  Leu Thr Tyr Lys Gly  Lys Lys Tyr Tyr Phe  Asp Ala Asn
    1220                 1225                 1230

Ser Gly  Glu Ala Val Thr Asn  Arg Phe Ile Gln Ile  Ser Arg Gly
    1235                 1240                 1245

Val Trp  Tyr Tyr Phe Asn Ala  Ser Gly Gln Ala Val  Thr Gly Glu
    1250                 1255                 1260

Gln Val  Ile Asn Gly Gln His  Leu Tyr Phe Asp Ala  Ser Gly Arg
    1265                 1270                 1275

Gln Val  Lys Gly Arg Tyr Val  Trp Ile Lys Gly Gln  Arg Arg Tyr
    1280                 1285                 1290

Tyr Asp  Ala Asn Thr Gly Ala  Trp Val Arg Asn Arg
    1295                 1300                 1305
```

<210> SEQ ID NO 39
<211> LENGTH: 3933
<212> TYPE: DNA
<213> ORGANISM: Streptococcus gallolyticus

<400> SEQUENCE: 39

```
atgatcgacg gcaaatacta ctatgttcag gcagatggca gcgttaagaa gaatttcgcg     60

attacggtca acggtcagct gctgtacttt gatgctgaga ctggcgctct gacgagcacg    120

agcacttata gctttaccga aggcctgacc aatctggtgg ataactttag caagaacaat    180

caagcgtatg acagcacgga gaaatccttt gagctggttg atggctacct gacggcgaac    240

agctggtatc gtccgactaa agttttggag aatggcgaaa cctgggttga cagcaccgaa    300

gagagcttcc gtccactggt gatggcttgg tggcctgacg tcgataccca gattaactac    360

ctgaacagca tgagcgaata ctttggtttg aataagaagt attctgcatc ggatagccaa    420
```

```
gcatctctga atgtggcggc tgaagcgatc caggtgaaaa ttgagcagga gattgcgcgt    480

cgtggttcga ccgagtggtt gcgtgaggtc attagctctt ttgttacgac ccaagataag    540

tggaatatga acagcgaaga tcgcgacact gaccacctgc aaggtggcgc actgctgtat    600

gtcaacagcg atctgactga gtgggccaat agcgattacc gcctgctgaa ccgcgctccg    660

acctatcaaa ctggtgaaac taagtaccac aaagccgacc gcacgggtgg ctacgacttc    720

ctgctggcga atgatgttga caatagcaat ccggttgttc aggccgaaca actgaatcag    780

ctgtactacc tgatgaactg ggtaagatt gtgttcggtg acgcagatgc aaacttcgat    840

ggcgtccgtg ttgacgcggt ggacaacgtg gatgctgatc tgttgcaaat ctacacgaat    900

ctgtttgaag cggcctacgg cgtcgataag accgaagcac aagcgctggc gcatattagc    960

atcttggaag cgtggagctt caacgacccg gactataatc acgacaccaa cggtgcagca   1020

ctggccatcg acaacggtct gcgtatggcc ttcctggatg ctctgactcg tcctctggac   1080

tcccgcacta atttggagag cctgattcac aacgatctgg gcatgactga ccgtaccgtc   1140

gatagcgcgt atggtgatgc tatgccgagc tatgccttcg tccgtgccca cgactctgaa   1200

gttcagggca tcattgcatc tatcatcgcc ggtcagatca atccgaaaac ggacggtttt   1260

acctttacct tggatgagct gcaaaaggca ttcgaaatct acaacgccga catgaactcc   1320

gtgcacaaga agtataccca tttcaatatc ccagcagcat acgctttgct gctgaccaac   1380

atggagagcg ttccgcgtgt atactatggc gatttgttca ccgataacgg tcagtacatg   1440

gccgttaaaa gcccgtacta cgaccagatc accgcgctgc tgaagtctcg tatcaagtac   1500

gcggcaggcg gtcaagccat gaatgtgcaa tacccggatg gtgcgggtgc gggtatcctg   1560

acttctgtgc gcttcggcta tggcattatg acggcggatc aaaaagcgac cgacgacagc   1620

gttactacca gcggcattgt caccattgtt tccaacaacc cgaacctgaa actgaatagc   1680

agcgacaaaa ttgcggtgca agttggtctg gcacacgcag gccaatacta ccgtccgctg   1740

ctgtctccga cggagaatgg tctgcaagtg ttcctgaatg attccgacac cgacatcacc   1800

aagctggtcg atgataacgg ttacatctat ttcacgggtg atgagatcaa aggtttcgag   1860

actgtggaca tgaatggctt cctgaccgtt tgggttccgg tgggtgcggc agccgatcag   1920

gatattcgcg tcaaggcgag cacggaagcg aagaaggatg gtgagctgac ctatgaaacc   1980

tctgcggcgc tggattctca ggtcattttt gaaggcttta gcaactttca agactttgtt   2040

caggacccaa gccagtacac caataaggtg attgcggaga atgcggatct gttcgcgagc   2100

tggggcatca cgtctttcga gctggcaccg cagtatgtta gcagcacgga cggtacgttc   2160

ctggacagca ttattcagaa cggttatgct tttacggatc gttatgactt ggcgatgtct   2220

aagaacaata agtatggtag cgcagaagat ttgcgcaatg cgattaaagc gctgcacgca   2280

cgcggtattc aagtgattgc tgattgggtc cctgaccaga tttatgcgct gcctggtgaa   2340

gagattgtga cggcgacccg tgttaatgac tacggcgaag aacgtgaagg cgcgcaaatc   2400

aagaacaaac cgtatgcggc gaatacgaaa agctccggtg aggattacca agcccaatac   2460

ggtggcgagt tcttggaata tctgcaagag aattacccgg agttgtttga aaaggtcatg   2520

attagcacgg gtaagaccat tgacccatcg acgaagatca aggtctggaa agcggagtat   2580

ttcaacggca cgaatattct gggtaagggt gccgattacg tcctgaacga tgcggccacc   2640

ggcacctact tcaccgtaac ggagaacggc gccttcctgc cgaaacaaat gacgagcgat   2700

accgcccaaa cgggtttcta ttatgatggc accggcatga cgtactattc tacctcgggt   2760
```

```
taccaagcta agtctagctt cgtgctgtac aacggcaacc gttactattt cgatgaaaac   2820

ggtcacatgg ttacgggtat gcgcgatatt gatggtcaga cgtactactt tctgccgaat   2880

ggtatcgaac tgcgtgacgc gatctatgag gacgcgaacg gtaatcagta ttactttggc   2940

aaatcgggta accgctacgc gggtcattac tacgcctttg aaaccacgag caccgttgac   3000

ggtgtcacca agaccactac taactggcgc tattttgatg aaaacggcgt tatggcacgc   3060

ggcctggtga aaatcggtaa tgattatcaa tactacgacg ataacggcaa tcagatcaag   3120

ggtcaactgg tgacggacaa ggacggcaac acccgttact ttaaagctga cagcggtgca   3180

atggttacgg gtgagtttgc actggtgaat ggtggttggt actacttcga tgacaatggt   3240

gttgcagtca aggtgctcca gaccattaac ggtcaacagt tgtacttcga cgagaatggt   3300

gtccaagcaa aggtgtgtt cgtgaccaat gaggatggca cccgtagcta ttacgacgcc   3360

aagtccggtg agaagtttgt tggcgacttc tttacgaccg gcgacaacca ttggtactat   3420

gccgacgaga acggcaattt ggcaacgggt agccaggtta tccgtggtca gaagttgtat   3480

tttgcagccg atggtttgca ggcgaaaggt atctttacca ccgacgccga aggtaaccgc   3540

cacttctacg acccggactc cggcgatctg gcggaaaaca agtttatcgc ggatggtgac   3600

gactggtact attttgacga aacgggtcat gttgttaccg gcgagcaagt gatcaacggc   3660

caacagctgt atttcgacga aaatggcgtt caggcgaagg gtgttttcgt gaccgatgat   3720

aatggtaata agcgttacta tgatgcacag acgggtgaga tggtggtgaa ccagacgctg   3780

acggtggatg gtgtggaata tacctttggt gcggatggcg tcgcggtggt taatgcacaa   3840

gatagcgacg aacaaagcga aagcacggat gaaacgcaag tgaccagcga tgacgcgacg   3900

gttgcaaaga cggaaaccag ctctgctgaa taa                                3933
```

```
<210> SEQ ID NO 40
<211> LENGTH: 1310
<212> TYPE: PRT
<213> ORGANISM: Streptococcus gallolyticus

<400> SEQUENCE: 40

Met Ile Asp Gly Lys Tyr Tyr Tyr Val Gln Ala Asp Gly Ser Val Lys
1               5                   10                  15

Lys Asn Phe Ala Ile Thr Val Asn Gly Gln Leu Leu Tyr Phe Asp Ala
            20                  25                  30

Glu Thr Gly Ala Leu Thr Ser Thr Ser Thr Tyr Ser Phe Thr Glu Gly
        35                  40                  45

Leu Thr Asn Leu Val Asp Asn Phe Ser Lys Asn Asn Gln Ala Tyr Asp
    50                  55                  60

Ser Thr Glu Lys Ser Phe Glu Leu Val Asp Gly Tyr Leu Thr Ala Asn
65                  70                  75                  80

Ser Trp Tyr Arg Pro Thr Lys Val Leu Glu Asn Gly Glu Thr Trp Val
                85                  90                  95

Asp Ser Thr Glu Glu Ser Phe Arg Pro Leu Val Met Ala Trp Trp Pro
            100                 105                 110

Asp Val Asp Thr Gln Ile Asn Tyr Leu Asn Ser Met Ser Glu Tyr Phe
        115                 120                 125

Gly Leu Asn Lys Lys Tyr Ser Ala Ser Asp Ser Gln Ala Ser Leu Asn
    130                 135                 140

Val Ala Ala Glu Ala Ile Gln Val Lys Ile Glu Gln Glu Ile Ala Arg
145                 150                 155                 160

Arg Gly Ser Thr Glu Trp Leu Arg Glu Val Ile Ser Ser Phe Val Thr
```

```
                165                 170                 175

Thr Gln Asp Lys Trp Asn Met Asn Ser Glu Asp Arg Asp Thr Asp His
            180                 185                 190

Leu Gln Gly Gly Ala Leu Leu Tyr Val Asn Ser Asp Leu Thr Glu Trp
        195                 200                 205

Ala Asn Ser Asp Tyr Arg Leu Leu Asn Arg Ala Pro Thr Tyr Gln Thr
    210                 215                 220

Gly Glu Thr Lys Tyr His Lys Ala Asp Arg Thr Gly Gly Tyr Asp Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Lys Ile Val Phe
            260                 265                 270

Gly Asp Ala Asp Ala Asn Phe Asp Gly Val Arg Val Asp Ala Val Asp
        275                 280                 285

Asn Val Asp Ala Asp Leu Leu Gln Ile Tyr Thr Asn Leu Phe Glu Ala
    290                 295                 300

Ala Tyr Gly Val Asp Lys Thr Glu Ala Gln Ala Leu Ala His Ile Ser
305                 310                 315                 320

Ile Leu Glu Ala Trp Ser Phe Asn Asp Pro Asp Tyr Asn His Asp Thr
                325                 330                 335

Asn Gly Ala Ala Leu Ala Ile Asp Asn Gly Leu Arg Met Ala Phe Leu
            340                 345                 350

Asp Ala Leu Thr Arg Pro Leu Asp Ser Arg Thr Asn Leu Glu Ser Leu
        355                 360                 365

Ile His Asn Asp Leu Gly Met Thr Asp Arg Thr Val Asp Ser Ala Tyr
    370                 375                 380

Gly Asp Ala Met Pro Ser Tyr Ala Phe Val Arg Ala His Asp Ser Glu
385                 390                 395                 400

Val Gln Gly Ile Ile Ala Ser Ile Ile Ala Gly Gln Ile Asn Pro Lys
                405                 410                 415

Thr Asp Gly Phe Thr Phe Thr Leu Asp Glu Leu Gln Lys Ala Phe Glu
            420                 425                 430

Ile Tyr Asn Ala Asp Met Asn Ser Val His Lys Lys Tyr Thr His Phe
        435                 440                 445

Asn Ile Pro Ala Ala Tyr Ala Leu Leu Leu Thr Asn Met Glu Ser Val
    450                 455                 460

Pro Arg Val Tyr Tyr Gly Asp Leu Phe Thr Asp Asn Gly Gln Tyr Met
465                 470                 475                 480

Ala Val Lys Ser Pro Tyr Tyr Asp Gln Ile Thr Ala Leu Leu Lys Ser
                485                 490                 495

Arg Ile Lys Tyr Ala Ala Gly Gly Gln Ala Met Asn Val Gln Tyr Pro
            500                 505                 510

Asp Gly Ala Gly Ala Gly Ile Leu Thr Ser Val Arg Phe Gly Tyr Gly
        515                 520                 525

Ile Met Thr Ala Asp Gln Lys Ala Thr Asp Asp Ser Val Thr Thr Ser
    530                 535                 540

Gly Ile Val Thr Ile Val Ser Asn Asn Pro Asn Leu Lys Leu Asn Ser
545                 550                 555                 560

Ser Asp Lys Ile Ala Val Gln Val Gly Leu Ala His Ala Gly Gln Tyr
                565                 570                 575

Tyr Arg Pro Leu Leu Ser Pro Thr Glu Asn Gly Leu Gln Val Phe Leu
            580                 585                 590
```

```
Asn Asp Ser Asp Thr Asp Ile Thr Lys Leu Val Asp Asp Asn Gly Tyr
        595                 600                 605

Ile Tyr Phe Thr Gly Asp Glu Ile Lys Gly Phe Glu Thr Val Asp Met
    610                 615                 620

Asn Gly Phe Leu Thr Val Trp Val Pro Val Gly Ala Ala Ala Asp Gln
625                 630                 635                 640

Asp Ile Arg Val Lys Ala Ser Thr Glu Ala Lys Lys Asp Gly Glu Leu
                645                 650                 655

Thr Tyr Glu Thr Ser Ala Ala Leu Asp Ser Gln Val Ile Phe Glu Gly
            660                 665                 670

Phe Ser Asn Phe Gln Asp Phe Val Gln Asp Pro Ser Gln Tyr Thr Asn
        675                 680                 685

Lys Val Ile Ala Glu Asn Ala Asp Leu Phe Ala Ser Trp Gly Ile Thr
    690                 695                 700

Ser Phe Glu Leu Ala Pro Gln Tyr Val Ser Ser Thr Asp Gly Thr Phe
705                 710                 715                 720

Leu Asp Ser Ile Ile Gln Asn Gly Tyr Ala Phe Thr Asp Arg Tyr Asp
                725                 730                 735

Leu Ala Met Ser Lys Asn Asn Lys Tyr Gly Ser Ala Glu Asp Leu Arg
            740                 745                 750

Asn Ala Ile Lys Ala Leu His Ala Arg Gly Ile Gln Val Ile Ala Asp
        755                 760                 765

Trp Val Pro Asp Gln Ile Tyr Ala Leu Pro Gly Glu Glu Ile Val Thr
    770                 775                 780

Ala Thr Arg Val Asn Asp Tyr Gly Glu Glu Arg Glu Gly Ala Gln Ile
785                 790                 795                 800

Lys Asn Lys Pro Tyr Ala Ala Asn Thr Lys Ser Ser Gly Glu Asp Tyr
                805                 810                 815

Gln Ala Gln Tyr Gly Gly Glu Phe Leu Glu Tyr Leu Gln Glu Asn Tyr
            820                 825                 830

Pro Glu Leu Phe Glu Lys Val Met Ile Ser Thr Gly Lys Thr Ile Asp
        835                 840                 845

Pro Ser Thr Lys Ile Lys Val Trp Lys Ala Glu Tyr Phe Asn Gly Thr
    850                 855                 860

Asn Ile Leu Gly Lys Gly Ala Asp Tyr Val Leu Asn Asp Ala Ala Thr
865                 870                 875                 880

Gly Thr Tyr Phe Thr Val Thr Glu Asn Gly Ala Phe Leu Pro Lys Gln
                885                 890                 895

Met Thr Ser Asp Thr Ala Gln Thr Gly Phe Tyr Tyr Asp Gly Thr Gly
            900                 905                 910

Met Thr Tyr Tyr Ser Thr Ser Gly Tyr Gln Ala Lys Ser Ser Phe Val
        915                 920                 925

Leu Tyr Asn Gly Asn Arg Tyr Tyr Phe Asp Glu Asn Gly His Met Val
    930                 935                 940

Thr Gly Met Arg Asp Ile Asp Gly Gln Thr Tyr Tyr Phe Leu Pro Asn
945                 950                 955                 960

Gly Ile Glu Leu Arg Asp Ala Ile Tyr Glu Asp Ala Asn Gly Asn Gln
                965                 970                 975

Tyr Tyr Phe Gly Lys Ser Gly Asn Arg Tyr Ala Gly His Tyr Tyr Ala
            980                 985                 990

Phe Glu Thr Thr Ser Thr Val Asp  Gly Val Thr Lys Thr  Thr Thr Asn
        995                 1000                1005
```

```
Trp Arg  Tyr Phe Asp Glu Asn  Gly Val Met Ala Arg  Gly Leu Val
    1010                 1015                 1020

Lys Ile  Gly Asn Asp Tyr Gln  Tyr Tyr Asp Asp Asn  Gly Asn Gln
    1025                 1030                 1035

Ile Lys  Gly Gln Leu Val Thr  Asp Lys Asp Gly Asn  Thr Arg Tyr
    1040                 1045                 1050

Phe Lys  Ala Asp Ser Gly Ala  Met Val Thr Gly Glu  Phe Ala Leu
    1055                 1060                 1065

Val Asn  Gly Gly Trp Tyr Tyr  Phe Asp Asp Asn Gly  Val Ala Val
    1070                 1075                 1080

Lys Gly  Ala Gln Thr Ile Asn  Gly Gln Gln Leu Tyr  Phe Asp Glu
    1085                 1090                 1095

Asn Gly  Val Gln Ala Lys Gly  Val Phe Val Thr Asn  Glu Asp Gly
    1100                 1105                 1110

Thr Arg  Ser Tyr Tyr Asp Ala  Lys Ser Gly Glu Lys  Phe Val Gly
    1115                 1120                 1125

Asp Phe  Phe Thr Thr Gly Asp  Asn His Trp Tyr Tyr  Ala Asp Glu
    1130                 1135                 1140

Asn Gly  Asn Leu Ala Thr Gly  Ser Gln Val Ile Arg  Gly Gln Lys
    1145                 1150                 1155

Leu Tyr  Phe Ala Ala Asp Gly  Leu Gln Ala Lys Gly  Ile Phe Thr
    1160                 1165                 1170

Thr Asp  Ala Glu Gly Asn Arg  His Phe Tyr Asp Pro  Asp Ser Gly
    1175                 1180                 1185

Asp Leu  Ala Glu Asn Lys Phe  Ile Ala Asp Gly Asp  Asp Trp Tyr
    1190                 1195                 1200

Tyr Phe  Asp Glu Thr Gly His  Val Val Thr Gly Glu  Gln Val Ile
    1205                 1210                 1215

Asn Gly  Gln Gln Leu Tyr Phe  Asp Glu Asn Gly Val  Gln Ala Lys
    1220                 1225                 1230

Gly Val  Phe Val Thr Asp Asp  Asn Gly Asn Lys Arg  Tyr Tyr Asp
    1235                 1240                 1245

Ala Gln  Thr Gly Glu Met Val  Val Asn Gln Thr Leu  Thr Val Asp
    1250                 1255                 1260

Gly Val  Glu Tyr Thr Phe Gly  Ala Asp Gly Val Ala  Val Val Asn
    1265                 1270                 1275

Ala Gln  Asp Ser Asp Glu Gln  Ser Glu Ser Thr Asp  Glu Thr Gln
    1280                 1285                 1290

Val Thr  Ser Asp Asp Ala Thr  Val Ala Lys Thr Glu  Thr Ser Ser
    1295                 1300                 1305

Ala Glu
    1310
```

<210> SEQ ID NO 41
<211> LENGTH: 3804
<212> TYPE: DNA
<213> ORGANISM: Streptococcus mutans

<400> SEQUENCE: 41

```
atggtcaatg gcaaatacta ctactacaaa gaggacggta cgttgcagaa gaactacgca      60

ctgaacatta acggcaagac ctttttcttt gacgagactg gcgccctgag caataacacc     120

ctgccgagca agaaaggtaa catcaccaat aacgacaata ccaatagctt cgcgcaatac     180

aatcaggtgt attcgacgga tgcagcgaac ttcgaacatg tcgatcacta cctgacggcg     240
```

```
gagtcctggt atcgcccgaa gtatattctg aaagatggca agacgtggac tcagtccacg    300
gagaaagatt ttcgcccgtt gttgatgacc tggtggccgg atcaggaaac ccagcgtcag    360
tatgtaaact atatgaatgc ccagctgggt attcaccaga cctacaacac ggcgaccagc    420
ccgttgcaac tgaatctggc ggcacagacg atccagacca agattgaaga gaagatcacg    480
gcggagaaga acactaattg gctgcgtcaa acgatttcgg cctttgtcaa aacccagagc    540
gcgtggaact cggacagcga aaaaccgttt gacgatcatc tgcaaaaggg tgcactgctg    600
tactctaaca atagcaagtt gacctctcaa gctaatagca actaccgtat tctgaaccgt    660
accccaacca accaaaccgg caagaaagat ccgcgttata ccgctgaccg taccatcggt    720
ggttatgagt tcttgctggc gaacgatgtg gataatagca atcctgttgt tcaagcggaa    780
cagctgaact ggctgcactt cctgatgaac tttggcaata tctatgcaaa cgaccctgac    840
gccaactttg acagcatccg tgtagacgcc gtggacaacg tggatgcaga tttgttgcaa    900
atcgctggtg actatctgaa ggctgcaaag ggcatccata agaacgacaa agcagcgaac    960
gaccacctgt cgatcctgga agcatggagc tataatgaca ccccgtatct gcacgacgac   1020
ggtgacaaca tgatcaatat ggacaaccgt ctgcgtctga gcctgctgta tagcctggcg   1080
aagccgttga accagcgttc gggcatgaac ccgctgatca cgaacagcct ggttaaccgt   1140
accgatgaca acgcagaaac cgcagcggtc ccgagctaca gctttatccg tgcacacgat   1200
agcgaggttc aagacctgat tcgtaacatt attcgtgctg agattaatcc gaacgtcgtc   1260
ggttatagct tcacgatgga agagatcaag aaggcctttg agatttacaa caaggatctg   1320
ctggcgacgg aaaagaaata cacccactat aacaccgcgc tgagctacgc gctgctgctg   1380
accaataaga gcagcgttcc gcgtgtgtat tacggtgata tgtttactga cgacggtcag   1440
tacatggcac ataaaacgat caactacgag gctatcgaaa cgctgttgaa ggcgcgcatt   1500
aagtacgtgt ctggtggcca agcgatgcgt aatcaacagg tgggtaatag cgaaatcatt   1560
acgagcgtcc gctatggcaa gggcgcactg aaagcgacgg ataccggcga tcgtaccacg   1620
cgcaccagcg gcgttgcggt tattgaaggc aataacccga gcctgcgctt gaaggcgagc   1680
gaccgcgtcg ttgttaacat gggtgcagca cacaagaacc aggcatatcg tccgctgttg   1740
ctgaccactg ataatggcat caaagcgtat cacagcgatc aggaagctgc gggcctggtg   1800
cgctatacca atgatcgtgg tgaattgatc ttcacggcag ctgacattaa aggttatgca   1860
aatccgcaag tcagcggtta tctgggcgtc tgggtgccgg tcggcgcagc ggctgatcaa   1920
gacgtgcgtg tggccgcgag caccgcgcca tcgaccgacg gtaaaagcgt gcaccagaat   1980
gcggcgctgg acagccgtgt catgtttgag ggttttagca actttcaagc ctttgcaacg   2040
aagaaagaag agtacaccaa cgtcgtcatc gcgaagaacg tcgataagtt cgcggaatgg   2100
ggcgttaccg atttcgaaat ggcaccgcag tatgtgtcta gcaccgatgg ctcgtttctg   2160
gattccgtga tccaaaatgg ttatgcattt accgaccgct atgacctggg cattagcaag   2220
ccgaataagt atggtacggc ggatgatctg gttaaagcga tcaaggcgct gcattctaaa   2280
ggtattaagg ttatggccga ctgggttcca gatcagatgt atgctttccc ggaaaaagaa   2340
gtggtgacgg ccacccgcgt ggacaaatat ggtacgccgg tcgcgggcag ccagatcaaa   2400
aacactctgt atgtcgtgga tggcaaaagc tccggtaaag atcagcaagc gaaatatggc   2460
ggtgccttcc tggaagagtt gcaggcgaaa tacccggaac tgttcgcgcg taagcagatc   2520
agcactggtg ttccgatgga cccgagcgtg aagattaaac aatggtccgc gaaatacttt   2580
aacggcacga acatcctggg tcgtggtgcc ggctacgtgc tgaaagacca ggcaacgaat   2640
```

```
acgtacttta gcttggtgtc cgacaatacg tttctgccga agtctctggt caacccgaac   2700

cacggtacga gcagctctgt gaccggcctg gtgttcgatg gtaagggcta cgtgtactac   2760

tctaccagcg gttaccaggc caagaatacg ttcatcagcc tgggtaacaa ctggtattac   2820

ttcgacaata acggttacat ggtcacgggt gcgcagagca tcaacggtgc caactactat   2880

tttctgagca acggcattca gctgcgtaat gcgatttacg acaatggcaa taaggttctg   2940

agctactacg gtaatgacgg tcgtcgttat gagaatggct attacctgtt tggccaacag   3000

tggcgctact ttcaaaatgg tattatggcc gtcggtctga cccgtgtcca cggtgcggtg   3060

cagtattttg acgccagcgg cttccaagcc aagggccagt tcatcaccac tgcggacggt   3120

aaactgcgtt actttgaccg tgacagcggc aaccaaatca gcaatcgttt tgttcgtaac   3180

agcaagggtg aatggttttt gttcgatcat aacggcgtgg cggttaccgg caccgttact   3240

ttcaatggtc aacgtctgta ctttaagccg aacggtgttc aggcaaaggg tgagttcatt   3300

cgcgacgcgg atggtcactt gcgttactac gaccctaatt ccggtaatga ggttcgtaac   3360

cgtttcgtcc gcaactctaa gggcgaatgg ttcctgtttg accacaatgg catcgcagtc   3420

accggcgctc gtgtggtcaa cggccaacgc ttgtacttca aagcaatggg cgtccaagct   3480

aagggtgagc tgattaccga acgtaagggc cgtattaagt attatgatcc taacagcggt   3540

aacgaagtgc gtaaccgcta cgtccgcacc agcagcggta attggtacta ttttggtaac   3600

gatggttacg cgctgatcgg ctggcatgtt gttgagggtc gtcgtgtgta ctttgatgag   3660

aacggtgtct atcgttacgc gagccacgac cagcgtaatc attggaacta cgactatcgt   3720

cgcgatttcg gtcgtggtag cagctccgct atccgttttc gccatagccg taacggcttt   3780

ttcgacaact tcttccgctt ctaa                                          3804
```

<210> SEQ ID NO 42
<211> LENGTH: 1267
<212> TYPE: PRT
<213> ORGANISM: Streptococcus mutans

<400> SEQUENCE: 42

```
Met Val Asn Gly Lys Tyr Tyr Tyr Tyr Lys Glu Asp Gly Thr Leu Gln
1               5                   10                  15

Lys Asn Tyr Ala Leu Asn Ile Asn Gly Lys Thr Phe Phe Phe Asp Glu
            20                  25                  30

Thr Gly Ala Leu Ser Asn Asn Thr Leu Pro Ser Lys Lys Gly Asn Ile
        35                  40                  45

Thr Asn Asn Asp Asn Thr Asn Ser Phe Ala Gln Tyr Asn Gln Val Tyr
    50                  55                  60

Ser Thr Asp Ala Ala Asn Phe Glu His Val Asp His Tyr Leu Thr Ala
65                  70                  75                  80

Glu Ser Trp Tyr Arg Pro Lys Tyr Ile Leu Lys Asp Gly Lys Thr Trp
                85                  90                  95

Thr Gln Ser Thr Glu Lys Asp Phe Arg Pro Leu Leu Met Thr Trp Trp
            100                 105                 110

Pro Asp Gln Glu Thr Gln Arg Gln Tyr Val Asn Tyr Met Asn Ala Gln
        115                 120                 125

Leu Gly Ile His Gln Thr Tyr Asn Thr Ala Thr Ser Pro Leu Gln Leu
    130                 135                 140

Asn Leu Ala Ala Gln Thr Ile Gln Thr Lys Ile Glu Glu Lys Ile Thr
145                 150                 155                 160
```

```
Ala Glu Lys Asn Thr Asn Trp Leu Arg Gln Thr Ile Ser Ala Phe Val
                165                 170                 175

Lys Thr Gln Ser Ala Trp Asn Ser Asp Ser Glu Lys Pro Phe Asp Asp
            180                 185                 190

His Leu Gln Lys Gly Ala Leu Leu Tyr Ser Asn Asn Ser Lys Leu Thr
        195                 200                 205

Ser Gln Ala Asn Ser Asn Tyr Arg Ile Leu Asn Arg Thr Pro Thr Asn
    210                 215                 220

Gln Thr Gly Lys Lys Asp Pro Arg Tyr Thr Ala Asp Arg Thr Ile Gly
225                 230                 235                 240

Gly Tyr Glu Phe Leu Leu Ala Asn Asp Val Asp Asn Ser Asn Pro Val
                245                 250                 255

Val Gln Ala Glu Gln Leu Asn Trp Leu His Phe Leu Met Asn Phe Gly
            260                 265                 270

Asn Ile Tyr Ala Asn Asp Pro Asp Ala Asn Phe Asp Ser Ile Arg Val
        275                 280                 285

Asp Ala Val Asp Asn Val Asp Ala Asp Leu Leu Gln Ile Ala Gly Asp
    290                 295                 300

Tyr Leu Lys Ala Ala Lys Gly Ile His Lys Asn Asp Lys Ala Ala Asn
305                 310                 315                 320

Asp His Leu Ser Ile Leu Glu Ala Trp Ser Tyr Asn Asp Thr Pro Tyr
                325                 330                 335

Leu His Asp Asp Gly Asp Asn Met Ile Asn Met Asp Asn Arg Leu Arg
            340                 345                 350

Leu Ser Leu Leu Tyr Ser Leu Ala Lys Pro Leu Asn Gln Arg Ser Gly
        355                 360                 365

Met Asn Pro Leu Ile Thr Asn Ser Leu Val Asn Arg Thr Asp Asp Asn
    370                 375                 380

Ala Glu Thr Ala Ala Val Pro Ser Tyr Ser Phe Ile Arg Ala His Asp
385                 390                 395                 400

Ser Glu Val Gln Asp Leu Ile Arg Asn Ile Ile Arg Ala Glu Ile Asn
                405                 410                 415

Pro Asn Val Val Gly Tyr Ser Phe Thr Met Glu Glu Ile Lys Lys Ala
            420                 425                 430

Phe Glu Ile Tyr Asn Lys Asp Leu Leu Ala Thr Glu Lys Lys Tyr Thr
        435                 440                 445

His Tyr Asn Thr Ala Leu Ser Tyr Ala Leu Leu Leu Thr Asn Lys Ser
    450                 455                 460

Ser Val Pro Arg Val Tyr Tyr Gly Asp Met Phe Thr Asp Asp Gly Gln
465                 470                 475                 480

Tyr Met Ala His Lys Thr Ile Asn Tyr Glu Ala Ile Glu Thr Leu Leu
                485                 490                 495

Lys Ala Arg Ile Lys Tyr Val Ser Gly Gly Gln Ala Met Arg Asn Gln
            500                 505                 510

Gln Val Gly Asn Ser Glu Ile Ile Thr Ser Val Arg Tyr Gly Lys Gly
        515                 520                 525

Ala Leu Lys Ala Thr Asp Thr Gly Asp Arg Thr Thr Arg Thr Ser Gly
    530                 535                 540

Val Ala Val Ile Glu Gly Asn Asn Pro Ser Leu Arg Leu Lys Ala Ser
545                 550                 555                 560

Asp Arg Val Val Val Asn Met Gly Ala Ala His Lys Asn Gln Ala Tyr
                565                 570                 575

Arg Pro Leu Leu Leu Thr Thr Asp Asn Gly Ile Lys Ala Tyr His Ser
```

```
            580                 585                 590

Asp Gln Glu Ala Ala Gly Leu Val Arg Tyr Thr Asn Asp Arg Gly Glu
        595                 600                 605

Leu Ile Phe Thr Ala Ala Asp Ile Lys Gly Tyr Ala Asn Pro Gln Val
    610                 615                 620

Ser Gly Tyr Leu Gly Val Trp Val Pro Val Gly Ala Ala Ala Asp Gln
625                 630                 635                 640

Asp Val Arg Val Ala Ala Ser Thr Ala Pro Ser Thr Asp Gly Lys Ser
                645                 650                 655

Val His Gln Asn Ala Ala Leu Asp Ser Arg Val Met Phe Glu Gly Phe
            660                 665                 670

Ser Asn Phe Gln Ala Phe Ala Thr Lys Lys Glu Glu Tyr Thr Asn Val
        675                 680                 685

Val Ile Ala Lys Asn Val Asp Lys Phe Ala Glu Trp Gly Val Thr Asp
    690                 695                 700

Phe Glu Met Ala Pro Gln Tyr Val Ser Ser Thr Asp Gly Ser Phe Leu
705                 710                 715                 720

Asp Ser Val Ile Gln Asn Gly Tyr Ala Phe Thr Asp Arg Tyr Asp Leu
                725                 730                 735

Gly Ile Ser Lys Pro Asn Lys Tyr Gly Thr Ala Asp Asp Leu Val Lys
            740                 745                 750

Ala Ile Lys Ala Leu His Ser Lys Gly Ile Lys Val Met Ala Asp Trp
        755                 760                 765

Val Pro Asp Gln Met Tyr Ala Phe Pro Glu Lys Glu Val Val Thr Ala
    770                 775                 780

Thr Arg Val Asp Lys Tyr Gly Thr Pro Val Ala Gly Ser Gln Ile Lys
785                 790                 795                 800

Asn Thr Leu Tyr Val Val Asp Gly Lys Ser Ser Gly Lys Asp Gln Gln
                805                 810                 815

Ala Lys Tyr Gly Gly Ala Phe Leu Glu Glu Leu Gln Ala Lys Tyr Pro
            820                 825                 830

Glu Leu Phe Ala Arg Lys Gln Ile Ser Thr Gly Val Pro Met Asp Pro
        835                 840                 845

Ser Val Lys Ile Lys Gln Trp Ser Ala Lys Tyr Phe Asn Gly Thr Asn
    850                 855                 860

Ile Leu Gly Arg Gly Ala Gly Tyr Val Leu Lys Asp Gln Ala Thr Asn
865                 870                 875                 880

Thr Tyr Phe Ser Leu Val Ser Asp Asn Thr Phe Leu Pro Lys Ser Leu
                885                 890                 895

Val Asn Pro Asn His Gly Thr Ser Ser Ser Val Thr Gly Leu Val Phe
            900                 905                 910

Asp Gly Lys Gly Tyr Val Tyr Tyr Ser Thr Ser Gly Tyr Gln Ala Lys
        915                 920                 925

Asn Thr Phe Ile Ser Leu Gly Asn Asn Trp Tyr Tyr Phe Asp Asn Asn
    930                 935                 940

Gly Tyr Met Val Thr Gly Ala Gln Ser Ile Asn Gly Ala Asn Tyr Tyr
945                 950                 955                 960

Phe Leu Ser Asn Gly Ile Gln Leu Arg Asn Ala Ile Tyr Asp Asn Gly
                965                 970                 975

Asn Lys Val Leu Ser Tyr Tyr Gly Asn Asp Gly Arg Arg Tyr Glu Asn
            980                 985                 990

Gly Tyr Tyr Leu Phe Gly Gln Gln  Trp Arg Tyr Phe Gln  Asn Gly Ile
        995                 1000                1005
```

```
Met Ala  Val Gly Leu Thr Arg  Val His Gly Ala Val  Gln Tyr Phe
    1010                 1015                 1020

Asp Ala  Ser Gly Phe Gln Ala  Lys Gly Gln Phe Ile  Thr Thr Ala
    1025                 1030                 1035

Asp Gly  Lys Leu Arg Tyr Phe  Asp Arg Asp Ser Gly  Asn Gln Ile
    1040                 1045                 1050

Ser Asn  Arg Phe Val Arg Asn  Ser Lys Gly Glu Trp  Phe Leu Phe
    1055                 1060                 1065

Asp His  Asn Gly Val Ala Val  Thr Gly Thr Val Thr  Phe Asn Gly
    1070                 1075                 1080

Gln Arg  Leu Tyr Phe Lys Pro  Asn Gly Val Gln Ala  Lys Gly Glu
    1085                 1090                 1095

Phe Ile  Arg Asp Ala Asp Gly  His Leu Arg Tyr Tyr  Asp Pro Asn
    1100                 1105                 1110

Ser Gly  Asn Glu Val Arg Asn  Arg Phe Val Arg Asn  Ser Lys Gly
    1115                 1120                 1125

Glu Trp  Phe Leu Phe Asp His  Asn Gly Ile Ala Val  Thr Gly Ala
    1130                 1135                 1140

Arg Val  Val Asn Gly Gln Arg  Leu Tyr Phe Lys Ser  Asn Gly Val
    1145                 1150                 1155

Gln Ala  Lys Gly Glu Leu Ile  Thr Glu Arg Lys Gly  Arg Ile Lys
    1160                 1165                 1170

Tyr Tyr  Asp Pro Asn Ser Gly  Asn Glu Val Arg Asn  Arg Tyr Val
    1175                 1180                 1185

Arg Thr  Ser Ser Gly Asn Trp  Tyr Tyr Phe Gly Asn  Asp Gly Tyr
    1190                 1195                 1200

Ala Leu  Ile Gly Trp His Val  Val Glu Gly Arg Arg  Val Tyr Phe
    1205                 1210                 1215

Asp Glu  Asn Gly Val Tyr Arg  Tyr Ala Ser His Asp  Gln Arg Asn
    1220                 1225                 1230

His Trp  Asn Tyr Asp Tyr Arg  Arg Asp Phe Gly Arg  Gly Ser Ser
    1235                 1240                 1245

Ser Ala  Ile Arg Phe Arg His  Ser Arg Asn Gly Phe  Phe Asp Asn
    1250                 1255                 1260

Phe Phe  Arg Phe
    1265
```

<210> SEQ ID NO 43
<211> LENGTH: 3864
<212> TYPE: DNA
<213> ORGANISM: Streptococcus mutans

<400> SEQUENCE: 43

```
atgattgacg gcaaatacta ctacatcggc agcgacggtc agccaaagaa gaattttgcg     60

ttgacggtta acaataaagt cctgtatttt gacaagaaca cgggtgcgct gaccgacacc    120

agccaatatc agttcaaaca aggtctgacg aagctgaaca acgactacac ccctcacaat    180

cagattgtca actttgaaaa tactagcctg gaaactattg ataactatgt tactgccgac    240

tcttggtatc gtccgaaaga cattctgaag aacggtaaga cgtggaccgc gtcctctgag    300

agcgatctgc gtccgctgct gatgtcctgg tggcctgata agcagaccca gatcgcatac    360

ctgaactaca tgaaccaaca aggcttgggc actggcgaga actataccgc tgatagctct    420

caagagagcc tgaacctggc ggcacaaacc gttcaagtca aaatcgaaac caagatcagc    480
```

```
caaacgcaac agactcagtg gctgcgtgac atcattaact ctttcgttaa gacgcaaccg    540
aactggaata gccaaaccga gtctgacacg agcgctggtg aaaaagatca tttgcagggc    600
ggtgccctgc tgtatagcaa ttcggacaaa accgcatacg caaatagcga ctatcgtctg    660
ctgaaccgta ccccgaccag ccagactggt aagccgaaat acttcgagga caatagcagc    720
ggtggttacg acttcctgtt ggcaaacgat attgataatt ccaatccggt ggtgcaggct    780
gagcagctga attggctgca ttacctgatg aattacggta gcattgtcgc aaatgacccg    840
gaagcgaatt tcgatggtgt ccgtgttgac gcggtggata acgtgaacgc agacctgttg    900
cagatcgcaa gcgattatct gaaagcccat tatggtgttg ataagagcga gaagaatgcg    960
atcaaccacc tgagcatcct ggaagcgtgg tctgacaacg acccacagta taacaaagac   1020
accaaaggtg cccagctgcc gatcgacaac aaactgcgtc tgtcgttgct gtacgcactg   1080
acccgtccgc tggagaagga tgcaagcaac aaaaatgaga ttcgtagcgg tctggagccg   1140
gttattacca attccctgaa taatcgttcc gctgagggca agaactctga acgcatggcg   1200
aattacatct tcatccgtgc tcacgattct gaagttcaaa cggtgatcgc aaagatcatc   1260
aaagcgcaga ttaacccgaa aacggatggc ctgaccttca ccctggatga gctgaaacag   1320
gcgttcaaaa tctataacga ggatatgcgc caggcgaaga agaagtatac ccagagcaat   1380
atcccgacgg catacgccct gatgctgagc aataaggact ccatcacgcg cctgtattac   1440
ggtgatatgt acagcgatga tggccaatac atggcgacca aatccccgta ctacgatgcg   1500
attgacaccc tgctgaaggc gcgcattaag tatgccgctg gcggtcagga tatgaagatc   1560
acctacgttg agggtgacaa aagccacatg gactgggact atacgggtgt cctgacgagc   1620
gttcgctacg gcacgggcgc aaacgaagcg accgaccagg gcagcgaagc taccaagacg   1680
caaggtatgg ccgtcatcac ttctaacaac ccgtccctga agctgaatca gaacgacaag   1740
gtcattgtca atatgggcac cgctcacaaa aatcaggaat accgtccgtt gctgctgacc   1800
accaaagacg gtctgaccag ctacaccagc gacgccgctg ccaagagcct gtaccgtaaa   1860
acgaacgata agggcgagtt ggtgttcgat gcaagcgaca ttcagggcta tctgaatccg   1920
caagtgagcg gttacctggc tgtttgggtg cctgtgggtg cgagcgacaa ccaggatgtg   1980
cgtgtcgcgg ccagcaataa agccaatgcg accggccaag tctatgaaag cagcagcgca   2040
ctggatagcc aactgattta tgagggtttt tccaactttc aggacttcgt caccaaggat   2100
tctgattaca ccaataaaaa gatcgcgcaa aatgtccagc tgtttaagag ctggggcgtc   2160
accagctttg agatggctcc gcaatacgtc agcagcgagg acggcagctt tttggacagc   2220
attatccaga acggctatgc gttcgaggat cgttacgacc tggcgatgag caaaaacaac   2280
aaatacggct cccagcagga catgatcaac gcggttaagg cgctgcataa gagcggtatc   2340
caagtgatcg cggactgggt cccggatcaa atctacaatt tgccgggtaa agaggtcgtc   2400
accgcgaccc gtgtgaacga ctacggcgag tatcgcaagg actccgaaat caaaaacacc   2460
ctgtacgccg ccaacaccaa aagcaacggt aaagattatc aagcaaagta cggtggcgcc   2520
tttttgagcg agctggccgc caaatatccg agcatcttta accgcactca gattagcaat   2580
ggcaagaaga tcgacccgtc tgaaaagatc accgcctgga aggccaaata cttcaatggt   2640
acgaacattt tgggtcgcgg cgttggttac gtcttgaaag acaatgccag cgacaagtat   2700
tttgagctga agggcaatca gacttatctg ccgaagcaaa tgacgaataa agaagcctcg   2760
actggtttcg ttaatgacgg caatggtatg accttttaca gcacgagcgg ttatcaagcg   2820
aagaacagct tcgttcagga cgcaaaaggc aactggtact actttgacaa caatggccac   2880
```

```
atggtttacg gtctgcaaca tctgaacggc gaggtgcaat acttcctgag caatggcgtg   2940

caactgcgtg aatccttctt ggaaaatgcc gacggcagca aaaactattt cggtcacctg   3000

ggcaaccgtt atagcaatgg ttactacagc ttcgataatg atagcaaatg gcgctatttc   3060

gatgcgagcg gtgttatggc agtgggtctg aaaactatta acggtaacac ccagtatttc   3120

gatcaagacg gctaccaagt gaagggtgca tggattaccg gcagcgatgg taagaagcgt   3180

tacttcgacg acggtagcgg caatatggca gttaatcgct ttgctaacga caagaatggc   3240

gattggtatt acctgaatag cgacggtatt gcactggtgg gtgttcagac catcaacggc   3300

aaaacgtatt actttggcca agatggtaaa caaatcaaag gcaaaatcat taccgataat   3360

ggtaaactga aatactttct ggcgaacagc ggtgagctgg cgcgtaacat tttgcgacc    3420

gacagccaga acaactggta ttacttcggc tcggatggtg ttgcggttac gggttcgcag   3480

acgattgcgg gtaaaaagtt gtactttgcg tccgacggta aacaggtgaa gggtagcttt   3540

gttacttaca atggtaaagt gcactattac catgcggaca gcggcgaact gcaagtcaac   3600

cgtttcgagg cggataaaga cggtaattgg tactatctgg acagcaacgg tgaggcactg   3660

acgggtagcc agcgtatcaa tggtcaacgt gtgtttttca cccgcgaggg caaacaggtt   3720

aagggtgatg tcgcgtatga tgaacgcggc ttgctgcgct attacgacaa aaacagcggt   3780

aatatggtgt acaacaaggt ggtcacgctg gcgaacggtc gtcgtattgg tattgaccgc   3840

tggggtattg ctcgctatta ctaa                                          3864
```

```
<210> SEQ ID NO 44
<211> LENGTH: 1287
<212> TYPE: PRT
<213> ORGANISM: Streptococcus mutans

<400> SEQUENCE: 44

Met Ile Asp Gly Lys Tyr Tyr Tyr Ile Gly Ser Asp Gly Gln Pro Lys
1               5                   10                  15

Lys Asn Phe Ala Leu Thr Val Asn Asn Lys Val Leu Tyr Phe Asp Lys
            20                  25                  30

Asn Thr Gly Ala Leu Thr Asp Thr Ser Gln Tyr Gln Phe Lys Gln Gly
        35                  40                  45

Leu Thr Lys Leu Asn Asn Asp Tyr Thr Pro His Asn Gln Ile Val Asn
    50                  55                  60

Phe Glu Asn Thr Ser Leu Glu Thr Ile Asp Asn Tyr Val Thr Ala Asp
65                  70                  75                  80

Ser Trp Tyr Arg Pro Lys Asp Ile Leu Lys Asn Gly Lys Thr Trp Thr
                85                  90                  95

Ala Ser Ser Glu Ser Asp Leu Arg Pro Leu Leu Met Ser Trp Trp Pro
            100                 105                 110

Asp Lys Gln Thr Gln Ile Ala Tyr Leu Asn Tyr Met Asn Gln Gln Gly
        115                 120                 125

Leu Gly Thr Gly Glu Asn Tyr Thr Ala Asp Ser Ser Gln Glu Ser Leu
    130                 135                 140

Asn Leu Ala Ala Gln Thr Val Gln Val Lys Ile Glu Thr Lys Ile Ser
145                 150                 155                 160

Gln Thr Gln Gln Thr Gln Trp Leu Arg Asp Ile Ile Asn Ser Phe Val
                165                 170                 175

Lys Thr Gln Pro Asn Trp Asn Ser Gln Thr Glu Ser Asp Thr Ser Ala
            180                 185                 190
```

```
Gly Glu Lys Asp His Leu Gln Gly Gly Ala Leu Leu Tyr Ser Asn Ser
        195                 200                 205

Asp Lys Thr Ala Tyr Ala Asn Ser Asp Tyr Arg Leu Leu Asn Arg Thr
    210                 215                 220

Pro Thr Ser Gln Thr Gly Lys Pro Lys Tyr Phe Glu Asp Asn Ser Ser
225                 230                 235                 240

Gly Gly Tyr Asp Phe Leu Leu Ala Asn Asp Ile Asp Asn Ser Asn Pro
                245                 250                 255

Val Val Gln Ala Glu Gln Leu Asn Trp Leu His Tyr Leu Met Asn Tyr
            260                 265                 270

Gly Ser Ile Val Ala Asn Asp Pro Glu Ala Asn Phe Asp Gly Val Arg
        275                 280                 285

Val Asp Ala Val Asp Asn Val Asn Ala Asp Leu Leu Gln Ile Ala Ser
    290                 295                 300

Asp Tyr Leu Lys Ala His Tyr Gly Val Asp Lys Ser Glu Lys Asn Ala
305                 310                 315                 320

Ile Asn His Leu Ser Ile Leu Glu Ala Trp Ser Asp Asn Asp Pro Gln
                325                 330                 335

Tyr Asn Lys Asp Thr Lys Gly Ala Gln Leu Pro Ile Asp Asn Lys Leu
            340                 345                 350

Arg Leu Ser Leu Leu Tyr Ala Leu Thr Arg Pro Leu Glu Lys Asp Ala
        355                 360                 365

Ser Asn Lys Asn Glu Ile Arg Ser Gly Leu Glu Pro Val Ile Thr Asn
    370                 375                 380

Ser Leu Asn Asn Arg Ser Ala Glu Gly Lys Asn Ser Glu Arg Met Ala
385                 390                 395                 400

Asn Tyr Ile Phe Ile Arg Ala His Asp Ser Glu Val Gln Thr Val Ile
                405                 410                 415

Ala Lys Ile Ile Lys Ala Gln Ile Asn Pro Lys Thr Asp Gly Leu Thr
            420                 425                 430

Phe Thr Leu Asp Glu Leu Lys Gln Ala Phe Lys Ile Tyr Asn Glu Asp
        435                 440                 445

Met Arg Gln Ala Lys Lys Lys Tyr Thr Gln Ser Asn Ile Pro Thr Ala
    450                 455                 460

Tyr Ala Leu Met Leu Ser Asn Lys Asp Ser Ile Thr Arg Leu Tyr Tyr
465                 470                 475                 480

Gly Asp Met Tyr Ser Asp Asp Gly Gln Tyr Met Ala Thr Lys Ser Pro
                485                 490                 495

Tyr Tyr Asp Ala Ile Asp Thr Leu Leu Lys Ala Arg Ile Lys Tyr Ala
            500                 505                 510

Ala Gly Gly Gln Asp Met Lys Ile Thr Tyr Val Glu Gly Asp Lys Ser
        515                 520                 525

His Met Asp Trp Asp Tyr Thr Gly Val Leu Thr Ser Val Arg Tyr Gly
    530                 535                 540

Thr Gly Ala Asn Glu Ala Thr Asp Gln Gly Ser Glu Ala Thr Lys Thr
545                 550                 555                 560

Gln Gly Met Ala Val Ile Thr Ser Asn Asn Pro Ser Leu Lys Leu Asn
                565                 570                 575

Gln Asn Asp Lys Val Ile Val Asn Met Gly Thr Ala His Lys Asn Gln
            580                 585                 590

Glu Tyr Arg Pro Leu Leu Leu Thr Thr Lys Asp Gly Leu Thr Ser Tyr
        595                 600                 605

Thr Ser Asp Ala Ala Ala Lys Ser Leu Tyr Arg Lys Thr Asn Asp Lys
```

```
    610                 615                 620

Gly Glu Leu Val Phe Asp Ala Ser Asp Ile Gln Gly Tyr Leu Asn Pro
625                 630                 635                 640

Gln Val Ser Gly Tyr Leu Ala Val Trp Val Pro Val Gly Ala Ser Asp
                645                 650                 655

Asn Gln Asp Val Arg Val Ala Ala Ser Asn Lys Ala Asn Ala Thr Gly
            660                 665                 670

Gln Val Tyr Glu Ser Ser Ser Ala Leu Asp Ser Gln Leu Ile Tyr Glu
        675                 680                 685

Gly Phe Ser Asn Phe Gln Asp Phe Val Thr Lys Asp Ser Asp Tyr Thr
    690                 695                 700

Asn Lys Lys Ile Ala Gln Asn Val Gln Leu Phe Lys Ser Trp Gly Val
705                 710                 715                 720

Thr Ser Phe Glu Met Ala Pro Gln Tyr Val Ser Ser Glu Asp Gly Ser
                725                 730                 735

Phe Leu Asp Ser Ile Ile Gln Asn Gly Tyr Ala Phe Glu Asp Arg Tyr
            740                 745                 750

Asp Leu Ala Met Ser Lys Asn Asn Lys Tyr Gly Ser Gln Gln Asp Met
        755                 760                 765

Ile Asn Ala Val Lys Ala Leu His Lys Ser Gly Ile Gln Val Ile Ala
    770                 775                 780

Asp Trp Val Pro Asp Gln Ile Tyr Asn Leu Pro Gly Lys Glu Val Val
785                 790                 795                 800

Thr Ala Thr Arg Val Asn Asp Tyr Gly Glu Tyr Arg Lys Asp Ser Glu
                805                 810                 815

Ile Lys Asn Thr Leu Tyr Ala Ala Asn Thr Lys Ser Asn Gly Lys Asp
            820                 825                 830

Tyr Gln Ala Lys Tyr Gly Gly Ala Phe Leu Ser Glu Leu Ala Ala Lys
        835                 840                 845

Tyr Pro Ser Ile Phe Asn Arg Thr Gln Ile Ser Asn Gly Lys Lys Ile
    850                 855                 860

Asp Pro Ser Glu Lys Ile Thr Ala Trp Lys Ala Lys Tyr Phe Asn Gly
865                 870                 875                 880

Thr Asn Ile Leu Gly Arg Gly Val Gly Tyr Val Leu Lys Asp Asn Ala
                885                 890                 895

Ser Asp Lys Tyr Phe Glu Leu Lys Gly Asn Gln Thr Tyr Leu Pro Lys
            900                 905                 910

Gln Met Thr Asn Lys Glu Ala Ser Thr Gly Phe Val Asn Asp Gly Asn
        915                 920                 925

Gly Met Thr Phe Tyr Ser Thr Ser Gly Tyr Gln Ala Lys Asn Ser Phe
    930                 935                 940

Val Gln Asp Ala Lys Gly Asn Trp Tyr Tyr Phe Asp Asn Asn Gly His
945                 950                 955                 960

Met Val Tyr Gly Leu Gln His Leu Asn Gly Glu Val Gln Tyr Phe Leu
                965                 970                 975

Ser Asn Gly Val Gln Leu Arg Glu Ser Phe Leu Glu Asn Ala Asp Gly
            980                 985                 990

Ser Lys Asn Tyr Phe Gly His Leu  Gly Asn Arg Tyr Ser  Asn Gly Tyr
        995                 1000                1005

Tyr Ser  Phe Asp Asn Asp Ser  Lys Trp Arg Tyr Phe  Asp Ala Ser
    1010                1015                1020

Gly Val  Met Ala Val Gly Leu  Lys Thr Ile Asn Gly  Asn Thr Gln
    1025                1030                1035
```

```
Tyr Phe  Asp Gln Asp Gly Tyr  Gln Val Lys Gly Ala  Trp Ile Thr
    1040                 1045                 1050

Gly Ser  Asp Gly Lys Lys Arg  Tyr Phe Asp Asp Gly  Ser Gly Asn
    1055                 1060                 1065

Met Ala  Val Asn Arg Phe Ala  Asn Asp Lys Asn Gly  Asp Trp Tyr
    1070                 1075                 1080

Tyr Leu  Asn Ser Asp Gly Ile  Ala Leu Val Gly Val  Gln Thr Ile
    1085                 1090                 1095

Asn Gly  Lys Thr Tyr Tyr Phe  Gly Gln Asp Gly Lys  Gln Ile Lys
    1100                 1105                 1110

Gly Lys  Ile Ile Thr Asp Asn  Gly Lys Leu Lys Tyr  Phe Leu Ala
    1115                 1120                 1125

Asn Ser  Gly Glu Leu Ala Arg  Asn Ile Phe Ala Thr  Asp Ser Gln
    1130                 1135                 1140

Asn Asn  Trp Tyr Tyr Phe Gly  Ser Asp Gly Val Ala  Val Thr Gly
    1145                 1150                 1155

Ser Gln  Thr Ile Ala Gly Lys  Lys Leu Tyr Phe Ala  Ser Asp Gly
    1160                 1165                 1170

Lys Gln  Val Lys Gly Ser Phe  Val Thr Tyr Asn Gly  Lys Val His
    1175                 1180                 1185

Tyr Tyr  His Ala Asp Ser Gly  Glu Leu Gln Val Asn  Arg Phe Glu
    1190                 1195                 1200

Ala Asp  Lys Asp Gly Asn Trp  Tyr Tyr Leu Asp Ser  Asn Gly Glu
    1205                 1210                 1215

Ala Leu  Thr Gly Ser Gln Arg  Ile Asn Gly Gln Arg  Val Phe Phe
    1220                 1225                 1230

Thr Arg  Glu Gly Lys Gln Val  Lys Gly Asp Val Ala  Tyr Asp Glu
    1235                 1240                 1245

Arg Gly  Leu Leu Arg Tyr Tyr  Asp Lys Asn Ser Gly  Asn Met Val
    1250                 1255                 1260

Tyr Asn  Lys Val Val Thr Leu  Ala Asn Gly Arg Arg  Ile Gly Ile
    1265                 1270                 1275

Asp Arg  Trp Gly Ile Ala Arg  Tyr Tyr
    1280                 1285
```

<210> SEQ ID NO 45
<211> LENGTH: 4068
<212> TYPE: DNA
<213> ORGANISM: Streptococcus gallolyticus

<400> SEQUENCE: 45

```
atgatcgacg gcaaatacta ctatattgac gaggacggta acgtaaagaa gaatttcgcg     60

attacggtgg atggtcagtt gctgtacttc gacgctgaaa cgggtgctct gaccagcacg    120

tccacctata gcttctccga gggcctgact aatctggtcg ataacttcag cattaacaac    180

cagtcctacg acagcaccga agagtcgttt gagctgatcg acggttacct gaccgtcaat    240

acttggtacc gtccgaccaa aattctggaa aacggtgaaa cctgggtcga tagcaccgaa    300

acggatttcc gtccgctgct gatggcctgg tggccggatg ttgacaccca aattgactac    360

ttgaactaca tgagcgatta cttcgatctg ggtacgacct atagcgctga cgattcccaa    420

gcgagcctga atctggcagc tgaggcggtt caggtgaaaa ttgaacaaga aattacccgt    480

caagagaaca ccgcctggct gcgcgagatc atctctagct ttgttaccac ccaggataaa    540

tggaatatca ataccgagaa tgagggcacc gaccatctgc aaggtggtgc cctgctgtac    600
```

```
gttaacagcg acttgactcc gtgggcaaac agcgattatc gcctgctgaa ccgcaccccg    660
acgtaccaga cgggtgagac taattacttt aaagcagatc gtactggtgg ctacgaattt    720
ctgctggcaa atgacgtgga taattctaac ccggtcgttc aagccgaaca gttgaaccag    780
ctgtactact tgatgaattg gggctctatt gtattcggtg atgacgacgc caattttgat    840
ggcgtgcgtg ttgacgcggt ggacaatgtg aacgctgacc tgttgcagat ttacacgaac    900
ctgttcgaag cggcgtatgg tgttaacgag tctgaggcgc aggccctggc tcacattagc    960
atcctggaag cgtggtctta taacgacccg gactacaacc acgacacgaa tggcgctgcc   1020
ctggcaatcg acaatggtct gcgtctgagc tttctgtact ctttgacgcg ccctacggac   1080
gagcgcagcg gtttggagcc actgatcacc tctgagattg gcctgaccga tcgttccgag   1140
gactctgcat acggtgacac catgccgagc tatgttttcg tccgtgcaca tgacagcgag   1200
gttcagacca ttattgcgag cattatcgca gaacagatca acccggaaac cgatggctat   1260
accttcaccc tggacgagct gaaccaggcg tttgagattt acaacgcgga tatgaacagc   1320
gtggataaag agtatacgca ttacaatatc ccggctgcgt atagcctgct gctgaccaac   1380
atggaaagcg tcccgcgtgt ttactacggt gacctgtata cggataacgg tcagtacatg   1440
gcgactaaga gcccgtatta tgaccagatc accaccctgc tgcaagcgcg cattcgttac   1500
gcggcgggtg gccaatctat ggctgttacg tactacaccc ctgcgtcgag catgtctacc   1560
gacaatgcgg atagcgtcct gaatgagact ggtgtgctga cttctgtgcg ttacggctat   1620
ggcatcatga ccgccgacca agaggccacg gacgactccg ttctgacctc tggtattgtt   1680
actattatca gcaacaaccc taatttgcag ctggatgatt ccgaagtgat tgcagtccag   1740
gttggtgtgg cgcacgctgg tcagtattat cgtccgctgt tgtacccgac ggcggatggt   1800
ctgcaaagct acctgaacga tagcgatacc gacattacta agctggtcga tgataatggt   1860
tatatctact ttacggcaga tgagattaaa ggctacgaaa cggttgacat gaatggctac   1920
ctgagcgttt gggtcccggt tggtgcagac gagaatcagg acatccgtgt cagcgcagac   1980
accagcgcgt acaccgaggg tgaattgatc tatcaagcaa ccgcagcgct ggatagccaa   2040
gtgatctacg agggtttcag caacttccaa gatttcgtta cctctaacag cgagtacact   2100
aacaagctga tcgcggagaa cgtcgatctg tttaccagct ggggcattac gagctttgag   2160
atggcgccac agtatgtgag caccgatgac ggtacttttc tggatagcat cattcaaaac   2220
ggttatgcat ttgacgatcg ctacgacctg gcaatgagcc agaataacaa gtatggtagc   2280
gctgaagatt tgcgtaatgc catcaaggcc ctgcacgctg ctggcattca ggtcattgct   2340
gactgggtgc cggatcaaat ctattcgctg ccaggcgaag aagtcgttac ggcgactcgc   2400
gtgaatgact atggcgaaga aaccgaaggc gcgtacatta acaatacgtt gtatgtggcg   2460
aacagcaaaa gcagcggcga ggactaccag gcacagtatg gtggtgagtt cctggattac   2520
ttgcaagaaa cctacccgga aatgttcgaa gttgcgatga ttagcacggg tgagccgatt   2580
gatccgagca ccaagatcaa gatttggaaa gcagaatact ttaatggtac gaacattctg   2640
ggtaagggcg ctggttacgt gctgagcgat gccgcgactg gcacgtactt taccgtgact   2700
gagaatggca cgtttctgcc gaagcagctg accaccgact ccgccattac gggtttctat   2760
tacgacggta cgggtatgtc ttactttagc acctcgggtt atcgcgctaa agcgagcttc   2820
attgtttaca acggctacta ctactatttt gatgataacg gctacatggt cactggcacg   2880
gtggaaatca acggtaagac ctactatttc ctgccgaatg gtattcagct gcgtgatgcg   2940
```

```
atttacgaag acgagaacgg taatcagtac tatttcggtc cgttgggcaa ccagtatttc   3000

aacaactatt acagctttga cgttgaagag gtggtggacg gtgtaacgac tacggtaacg   3060

aagtggcgtc attttgacga gaacggcgtg atggcgcgtg gtttggtcga gattgatggt   3120

gtctaccagt attacgatga aaacggctac caggtcaaag gtgagctgat caccgatgct   3180

gatggtaatt tgcgttattt caaagaagat agcggtgaaa tggttgttag cgattttgtg   3240

aagatcggcg ataacaactg gtactacttt gacgaaaacg gtattgcagt cacgggtgcc   3300

caaaccattg ccggccagaa cttgtatttc gatgacaacg gtgtgcaggc gaaaggtgcc   3360

tttgtcacga acgccgatgg cacgcgcagc tattatgacg cggacagcgg tgagaagatc   3420

gtggcagatt tcttcactac gggcgataat gactggtatt atgcagatga aaatggcaat   3480

ctggtgactg gtagccaaac tatcaatggt caaaacctgt actttgctga ggacggtttg   3540

caggccaagg gtgtgtttgt taccgatacg gctggtaaca ttcactatta tgatgcgaac   3600

tctggcgagt tggcggttaa taccttcgtt ggtgatggcg acgactggta ttactttgat   3660

gagaatggca tcgcagttac cggcgcacaa gtcattaacg gtcaacacct gtatttcgca   3720

gacaacggca tccaagtgaa aggtgaaatc gtcaccgacg caaacggcaa ccgctattac   3780

tacgatgcag attccggcga aatggcagtt aacacctttg tggagattga cggtgtttgg   3840

tactattttg gtgccgatgg tatcgcggtg acgggtgcac aagtaattga tggtcagaat   3900

ttgtacttta acgcagacgg tagccaagtc aagggtgacg ttgtccgtat caacggtttg   3960

cgttactact acgacgctaa tagcggcgaa caggtgcgca atcagtgggt cacgctgccg   4020

gatggtactg ttgttttctt taatgcgcgt ggctatactt ggggctaa                4068
```

<210> SEQ ID NO 46
<211> LENGTH: 1355
<212> TYPE: PRT
<213> ORGANISM: Streptococcus gallolyticus

<400> SEQUENCE: 46

```
Met Ile Asp Gly Lys Tyr Tyr Tyr Ile Asp Glu Asp Gly Asn Val Lys
1               5                   10                  15

Lys Asn Phe Ala Ile Thr Val Asp Gly Gln Leu Leu Tyr Phe Asp Ala
            20                  25                  30

Glu Thr Gly Ala Leu Thr Ser Thr Ser Thr Tyr Ser Phe Ser Glu Gly
        35                  40                  45

Leu Thr Asn Leu Val Asp Asn Phe Ser Ile Asn Asn Gln Ser Tyr Asp
    50                  55                  60

Ser Thr Glu Glu Ser Phe Glu Leu Ile Asp Gly Tyr Leu Thr Val Asn
65                  70                  75                  80

Thr Trp Tyr Arg Pro Thr Lys Ile Leu Glu Asn Gly Glu Thr Trp Val
                85                  90                  95

Asp Ser Thr Glu Thr Asp Phe Arg Pro Leu Leu Met Ala Trp Trp Pro
            100                 105                 110

Asp Val Asp Thr Gln Ile Asp Tyr Leu Asn Tyr Met Ser Asp Tyr Phe
        115                 120                 125

Asp Leu Gly Thr Thr Tyr Ser Ala Asp Asp Ser Gln Ala Ser Leu Asn
    130                 135                 140

Leu Ala Ala Glu Ala Val Gln Val Lys Ile Glu Gln Glu Ile Thr Arg
145                 150                 155                 160

Gln Glu Asn Thr Ala Trp Leu Arg Glu Ile Ile Ser Ser Phe Val Thr
                165                 170                 175
```

```
Thr Gln Asp Lys Trp Asn Ile Asn Thr Glu Asn Glu Gly Thr Asp His
            180                 185                 190

Leu Gln Gly Gly Ala Leu Leu Tyr Val Asn Ser Asp Leu Thr Pro Trp
        195                 200                 205

Ala Asn Ser Asp Tyr Arg Leu Leu Asn Arg Thr Pro Thr Tyr Gln Thr
    210                 215                 220

Gly Glu Thr Asn Tyr Phe Lys Ala Asp Arg Thr Gly Gly Tyr Glu Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Ser Ile Val Phe
            260                 265                 270

Gly Asp Asp Asp Ala Asn Phe Asp Gly Val Arg Val Asp Ala Val Asp
        275                 280                 285

Asn Val Asn Ala Asp Leu Leu Gln Ile Tyr Thr Asn Leu Phe Glu Ala
    290                 295                 300

Ala Tyr Gly Val Asn Glu Ser Glu Ala Gln Ala Leu Ala His Ile Ser
305                 310                 315                 320

Ile Leu Glu Ala Trp Ser Tyr Asn Asp Pro Asp Tyr Asn His Asp Thr
                325                 330                 335

Asn Gly Ala Ala Leu Ala Ile Asp Asn Gly Leu Arg Leu Ser Phe Leu
            340                 345                 350

Tyr Ser Leu Thr Arg Pro Thr Asp Glu Arg Ser Gly Leu Glu Pro Leu
        355                 360                 365

Ile Thr Ser Glu Ile Gly Leu Thr Asp Arg Ser Glu Asp Ser Ala Tyr
    370                 375                 380

Gly Asp Thr Met Pro Ser Tyr Val Phe Val Arg Ala His Asp Ser Glu
385                 390                 395                 400

Val Gln Thr Ile Ile Ala Ser Ile Ile Ala Glu Gln Ile Asn Pro Glu
                405                 410                 415

Thr Asp Gly Tyr Thr Phe Thr Leu Asp Glu Leu Asn Gln Ala Phe Glu
            420                 425                 430

Ile Tyr Asn Ala Asp Met Asn Ser Val Asp Lys Glu Tyr Thr His Tyr
        435                 440                 445

Asn Ile Pro Ala Ala Tyr Ser Leu Leu Leu Thr Asn Met Glu Ser Val
    450                 455                 460

Pro Arg Val Tyr Tyr Gly Asp Leu Tyr Thr Asp Asn Gly Gln Tyr Met
465                 470                 475                 480

Ala Thr Lys Ser Pro Tyr Tyr Asp Gln Ile Thr Thr Leu Leu Gln Ala
                485                 490                 495

Arg Ile Arg Tyr Ala Ala Gly Gly Gln Ser Met Ala Val Thr Tyr Tyr
            500                 505                 510

Thr Pro Ala Ser Ser Met Ser Thr Asp Asn Ala Asp Ser Val Leu Asn
        515                 520                 525

Glu Thr Gly Val Leu Thr Ser Val Arg Tyr Gly Tyr Gly Ile Met Thr
    530                 535                 540

Ala Asp Gln Glu Ala Thr Asp Asp Ser Val Leu Thr Ser Gly Ile Val
545                 550                 555                 560

Thr Ile Ile Ser Asn Asn Pro Asn Leu Gln Leu Asp Asp Ser Glu Val
                565                 570                 575

Ile Ala Val Gln Val Gly Val Ala His Ala Gly Gln Tyr Tyr Arg Pro
            580                 585                 590

Leu Leu Tyr Pro Thr Ala Asp Gly Leu Gln Ser Tyr Leu Asn Asp Ser
```

```
        595                 600                 605

Asp Thr Asp Ile Thr Lys Leu Val Asp Asp Asn Gly Tyr Ile Tyr Phe
    610                 615                 620

Thr Ala Asp Glu Ile Lys Gly Tyr Glu Thr Val Asp Met Asn Gly Tyr
625                 630                 635                 640

Leu Ser Val Trp Val Pro Val Gly Ala Asp Glu Asn Gln Asp Ile Arg
                645                 650                 655

Val Ser Ala Asp Thr Ser Ala Tyr Thr Glu Gly Glu Leu Ile Tyr Gln
            660                 665                 670

Ala Thr Ala Ala Leu Asp Ser Gln Val Ile Tyr Glu Gly Phe Ser Asn
        675                 680                 685

Phe Gln Asp Phe Val Thr Ser Asn Ser Glu Tyr Thr Asn Lys Leu Ile
    690                 695                 700

Ala Glu Asn Val Asp Leu Phe Thr Ser Trp Gly Ile Thr Ser Phe Glu
705                 710                 715                 720

Met Ala Pro Gln Tyr Val Ser Thr Asp Asp Gly Thr Phe Leu Asp Ser
                725                 730                 735

Ile Ile Gln Asn Gly Tyr Ala Phe Asp Asp Arg Tyr Asp Leu Ala Met
            740                 745                 750

Ser Gln Asn Asn Lys Tyr Gly Ser Ala Glu Asp Leu Arg Asn Ala Ile
        755                 760                 765

Lys Ala Leu His Ala Ala Gly Ile Gln Val Ile Ala Asp Trp Val Pro
    770                 775                 780

Asp Gln Ile Tyr Ser Leu Pro Gly Glu Glu Val Val Thr Ala Thr Arg
785                 790                 795                 800

Val Asn Asp Tyr Gly Glu Glu Thr Glu Gly Ala Tyr Ile Asn Asn Thr
                805                 810                 815

Leu Tyr Val Ala Asn Ser Lys Ser Ser Gly Glu Asp Tyr Gln Ala Gln
            820                 825                 830

Tyr Gly Gly Glu Phe Leu Asp Tyr Leu Gln Glu Thr Tyr Pro Glu Met
        835                 840                 845

Phe Glu Val Ala Met Ile Ser Thr Gly Glu Pro Ile Asp Pro Ser Thr
    850                 855                 860

Lys Ile Lys Ile Trp Lys Ala Glu Tyr Phe Asn Gly Thr Asn Ile Leu
865                 870                 875                 880

Gly Lys Gly Ala Gly Tyr Val Leu Ser Asp Ala Ala Thr Gly Thr Tyr
                885                 890                 895

Phe Thr Val Thr Glu Asn Gly Thr Phe Leu Pro Lys Gln Leu Thr Thr
            900                 905                 910

Asp Ser Ala Ile Thr Gly Phe Tyr Tyr Asp Gly Thr Gly Met Ser Tyr
        915                 920                 925

Phe Ser Thr Ser Gly Tyr Arg Ala Lys Ala Ser Phe Ile Val Tyr Asn
    930                 935                 940

Gly Tyr Tyr Tyr Tyr Phe Asp Asp Asn Gly Tyr Met Val Thr Gly Thr
945                 950                 955                 960

Val Glu Ile Asn Gly Lys Thr Tyr Tyr Phe Leu Pro Asn Gly Ile Gln
                965                 970                 975

Leu Arg Asp Ala Ile Tyr Glu Asp Glu Asn Gly Asn Gln Tyr Tyr Phe
            980                 985                 990

Gly Pro Leu Gly Asn Gln Tyr Phe  Asn Asn Tyr Tyr Ser  Phe Asp Val
        995                 1000                 1005

Glu Glu  Val Val Asp Gly Val  Thr Thr Thr Val Thr  Lys Trp Arg
    1010                 1015                 1020
```

```
His Phe  Asp Glu Asn Gly Val  Met Ala Arg Gly Leu  Val Glu Ile
    1025                 1030                 1035

Asp Gly  Val Tyr Gln Tyr Tyr  Asp Glu Asn Gly Tyr  Gln Val Lys
    1040                 1045                 1050

Gly Glu  Leu Ile Thr Asp Ala  Asp Gly Asn Leu Arg  Tyr Phe Lys
    1055                 1060                 1065

Glu Asp  Ser Gly Glu Met Val  Val Ser Asp Phe Val  Lys Ile Gly
    1070                 1075                 1080

Asp Asn  Asn Trp Tyr Tyr Phe  Asp Glu Asn Gly Ile  Ala Val Thr
    1085                 1090                 1095

Gly Ala  Gln Thr Ile Ala Gly  Gln Asn Leu Tyr Phe  Asp Asp Asn
    1100                 1105                 1110

Gly Val  Gln Ala Lys Gly Ala  Phe Val Thr Asn Ala  Asp Gly Thr
    1115                 1120                 1125

Arg Ser  Tyr Tyr Asp Ala Asp  Ser Gly Glu Lys Ile  Val Ala Asp
    1130                 1135                 1140

Phe Phe  Thr Thr Gly Asp Asn  Asp Trp Tyr Tyr Ala  Asp Glu Asn
    1145                 1150                 1155

Gly Asn  Leu Val Thr Gly Ser  Gln Thr Ile Asn Gly  Gln Asn Leu
    1160                 1165                 1170

Tyr Phe  Ala Glu Asp Gly Leu  Gln Ala Lys Gly Val  Phe Val Thr
    1175                 1180                 1185

Asp Thr  Ala Gly Asn Ile His  Tyr Tyr Asp Ala Asn  Ser Gly Glu
    1190                 1195                 1200

Leu Ala  Val Asn Thr Phe Val  Gly Asp Gly Asp Asp  Trp Tyr Tyr
    1205                 1210                 1215

Phe Asp  Glu Asn Gly Ile Ala  Val Thr Gly Ala Gln  Val Ile Asn
    1220                 1225                 1230

Gly Gln  His Leu Tyr Phe Ala  Asp Asn Gly Ile Gln  Val Lys Gly
    1235                 1240                 1245

Glu Ile  Val Thr Asp Ala Asn  Gly Asn Arg Tyr Tyr  Tyr Asp Ala
    1250                 1255                 1260

Asp Ser  Gly Glu Met Ala Val  Asn Thr Phe Val Glu  Ile Asp Gly
    1265                 1270                 1275

Val Trp  Tyr Tyr Phe Gly Ala  Asp Gly Ile Ala Val  Thr Gly Ala
    1280                 1285                 1290

Gln Val  Ile Asp Gly Gln Asn  Leu Tyr Phe Asn Ala  Asp Gly Ser
    1295                 1300                 1305

Gln Val  Lys Gly Asp Val Val  Arg Ile Asn Gly Leu  Arg Tyr Tyr
    1310                 1315                 1320

Tyr Asp  Ala Asn Ser Gly Glu  Gln Val Arg Asn Gln  Trp Val Thr
    1325                 1330                 1335

Leu Pro  Asp Gly Thr Val Val  Phe Phe Asn Ala Arg  Gly Tyr Thr
    1340                 1345                 1350

Trp Gly
    1355

<210> SEQ ID NO 47
<211> LENGTH: 4047
<212> TYPE: DNA
<213> ORGANISM: Streptococcus sanguinis

<400> SEQUENCE: 47

atgatcgatg gcaagaaata ctatgttcag gacgacggta cggtaaagaa gaatttcgcg     60
```

```
gttgaactga acggcaaggt cctgtatttc gatgcagaaa ccggtgccct ggtcgacagc    120

gcggagtacc agtttcaaca gggtacgagc tccctgaata acgagttcag ccgcatgaat    180

gcgttccatg gcacgacgga gaaagatatt gaaaccgtcg atggctatct gaccgcagat    240

acgtggtacc gcccgaaggc catcctgaaa gatggcaaaa cctggactca gagcaccgaa    300

accgatctgc gtccgctgct gatggcatgg tggccggaca aacaaacgca ggtaagctac    360

ttgaactata tgaaccagca gggtctgggt gcgggtgcgt ttgagaacaa agttgagcag    420

gcaatcttga cgggcgcaag ccagcaggtg cagcgcaaga tcgaagaacg tattggcaaa    480

gacggcgata ccaaatggct gcgtaccctg atgggtgcat ttgtgaaaac ccagccgaat    540

tggaatatca agacggagag cgaaaccacg ggtactaata aggatcatct gcaaggtggt    600

gcgctgctgt acaccaactc tgaaaagacg agccacgcga acagcaaata ccgtattctg    660

aatcgtaccc cgaccaatca gaccggtacg ccgaagtatt tcatcgacaa atcgaatggt    720

ggttacgagt tcttgctggc aaatgatttt gataatagca acccagcagt ccaagcggaa    780

cagctgaatt ggctgcactt tatgatgaat ttcggcagca ttgttgcaaa tgacccgacc    840

gcaaacttcg atggcgtgcg tgtggatgcg gtggacaatg ttaatgccga tttgctgcaa    900

attgccagcg actatttcaa atctcgttac aaagtgggcg agagcgaaga acaagcgatt    960

aaacatctga gcatcctgga agcctggagc gacaacgatc cggactataa caaagacacc   1020

aaaggcgccc aactgccgat cgacaataag ctgcgtctga gcctgttgta cagctttatg   1080

cgtaagctga gcattcgcag cggtgtcgaa ccgacgatta ccaacagcct gaacgaccgt   1140

tctgcggaga agaagaacgg tgagcgcatg gcaaactata tctttgttcg tgcgcatgat   1200

tccgaagtgc agacggtcat tgccgacatt attcgcgaga atatcaatcc gaacacggat   1260

ggtctgacct ttaccatgga cgagctgaaa caggcgttca agatctacaa tgaagatatg   1320

cgcaaggcgg ataagaagta tacccaattc aatattccga ccgctcacgc gttgatgttg   1380

agcaacaagg attccattac gcgtgtgtac tacggtgacc tgtatacgga tgatggtcag   1440

tatatggaaa agaaaagccc ttattacgac gcgatcgacg cgctgctgcg cgcacgcatt   1500

aagtacgttg cgggtggcca ggacatgaaa gttacctaca tgggtgtgcc gcgtgaaacc   1560

gacaaatgga gctacaacgg catcctgacc agcgtccgct acggcaccgg cgcaaatgag   1620

gctacggacg agggtactgc cgagactcgc acccagggta tggccgtcat cgcaagcaac   1680

aatccgaatt tgaaactgaa cgagtgggat aagttgcagg tcaacatggg tgcggcacac   1740

aagaaccaat actatcgtcc ggtgctgctg accaccaagg acggtattag ccgttacctg   1800

accgacgaag aagttccgca aagcctgtgg aagaaaaccg atgcaaacgg catcttgacg   1860

ttcgacatga acgatatcgc aggttacagc aatgtccaag tatctggcta cttggctgtg   1920

tgggtgccgg ttggtgccaa agcggatcaa gacgcgcgtg ttactgcgtc gaagaagaaa   1980

aacgccagcg gtcaggtgta tgagtccagc gctgcactgg acagccaact gatttatgaa   2040

ggcttctcta acttccaaga cttcgcgacc cgcgacgatc aatacaccaa caaagttatt   2100

gccaaaaatg ttaatctgtt taaagagtgg ggtgtgacca gctttgagct gccacctcag   2160

tatgtttcca gccaggatgg cacgtttttg gatagcatca tccagaatgg ctacgcattt   2220

gaagatcgtt atgacatggc gatgagcaaa aacaataagt acggtagcct ggacgacctg   2280

ctgaacgcgc tgcgtgcctt gcacagcgtc aacatccaag cgatcgcgga ctgggtcccg   2340

gatcagattt acaacctgcc gggcaaagaa gtggttacgg ctacgcgtgt caacaattat   2400
```

```
ggtacctatc gtgagggtgc ggaaatcaaa gaaaatctgt acgtggcaaa cacgaaaacc   2460

aacggcaccg actatcaagg caaatacggt ggtgcgttcc tggacgaact gaaagcgaaa   2520

tatcctgaga tcttcgaacg tgttcaaatt tccaatggtc aaaagatgac caccgatgag   2580

aagattacga aatggagcgc gaaacacttc aatggtacca acattctggg ccgtggtgca   2640

tactacgtgc tgaaagattg ggccagcaat gagtatctga acaataagaa tggtgagatg   2700

gtgttgccga agcaactggt taacaaaaac gcgtacaccg gctttgttaa ggacaccacc   2760

ggttttaagt actatagcac ctcgggctat caagcgcgta atagcttcat ccaagatgag   2820

aacggtaatt ggtactactt tgacaaacgt ggttacctgg cgactggtgc acacgaaatc   2880

gacggcaagc aggtctattt cctgaaaaac ggcattcaac tgcgcgactc tctgcgtgag   2940

gacgagaacg gcaatcagta ctattacgac aagaccggtg cgcaggtgct gaaccgctac   3000

tacaccaccg acggccagaa ctggcgttac ttcgacgcca aaggtgttat ggcgcgtggc   3060

ctggttacca tgggtggtaa ccaacaattc ttcgaccaga acggttatca ggtgaaaggc   3120

aagatcgcgc gtgccaagga tggtaaactg cgctacttcg acaaagacag cggtaacgca   3180

gcggcgaatc gctttgcaca gggcgataat ccgagcgatt ggtattactt tggtgccgat   3240

ggcgtcgctg ttaccggttt gcaaaaactg ggtcaacaaa ctctgtactt tgatcaagaa   3300

ggtaaacaag tgaagggcaa gattgtcacg ctggctgata agtccatccg ttacttcgat   3360

gcgaacagcg gcgagatggc tgtcggtaag tttgctgagg gtagcaagaa cgaatggtac   3420

tatttcgatc agacgggcaa agcggttacg ggtctgcaaa agattggcca gcagaccctg   3480

tattttgacc aagatggtaa gcaggtaaag ggtaaagtgg taaccctggc agataagtcg   3540

attcgctact ttgatgcaaa ctccggcgaa atggcggtgg gtaagttcgc cgagggtgct   3600

aagaatgagt ggtactactt tgaccaggcg ggcaaggcgg tgaccggctt gcagaaaatt   3660

ggtcagcaaa cgctgtattt tgatcaggac ggcaaacaag tcaaaggcca actggtgacg   3720

ctggcggaca agagcattcg ttatttcgac gcaaacagcg gtgagatggc ctctaacaag   3780

ttcgttgagg gtgccaaaaa cgaatggtac tatttcgacc aagccggtaa agcagtgacc   3840

ggtctgcaac aaatcggtca gcagaccttg tacttcgacc aaaacggtaa acaggtcaaa   3900

ggtaaaatcg tgtatgttaa cggtgccaat cgttactttg acgccaattc gggtgaaatg   3960

gcgcgcaata agtggatcca actggaagat ggtagctgga tgtacttcga tcgtaacggt   4020

cgtggtcgtc gtttcggctg gaattaa                                       4047
```

```
<210> SEQ ID NO 48
<211> LENGTH: 1348
<212> TYPE: PRT
<213> ORGANISM: Streptococcus sanguinis

<400> SEQUENCE: 48

Met Ile Asp Gly Lys Lys Tyr Tyr Val Gln Asp Asp Gly Thr Val Lys
1               5                   10                  15

Lys Asn Phe Ala Val Glu Leu Asn Gly Lys Val Leu Tyr Phe Asp Ala
            20                  25                  30

Glu Thr Gly Ala Leu Val Asp Ser Ala Glu Tyr Gln Phe Gln Gln Gly
        35                  40                  45

Thr Ser Ser Leu Asn Asn Glu Phe Ser Arg Met Asn Ala Phe His Gly
    50                  55                  60

Thr Thr Glu Lys Asp Ile Glu Thr Val Asp Gly Tyr Leu Thr Ala Asp
65                  70                  75                  80
```

```
Thr Trp Tyr Arg Pro Lys Ala Ile Leu Lys Asp Gly Lys Thr Trp Thr
                85                  90                  95

Gln Ser Thr Glu Thr Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Asp Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Thr Asn Ser Glu
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Gln Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365

Val Glu Pro Thr Ile Thr Asn Ser Leu Asn Asp Arg Ser Ala Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr Tyr Asp Ala Ile Asp Ala Leu Leu
                485                 490                 495

Arg Ala Arg Ile Lys Tyr Val Ala Gly Gly Gln Asp Met Lys Val Thr
```

```
            500                 505                 510

Tyr Met Gly Val Pro Arg Glu Thr Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
            740                 745                 750

Lys Tyr Gly Ser Leu Asp Asp Leu Leu Asn Ala Leu Arg Ala Leu His
        755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Asn Leu Tyr Val Ala
                805                 810                 815

Asn Thr Lys Thr Asn Gly Thr Asp Tyr Gln Gly Lys Tyr Gly Gly Ala
            820                 825                 830

Phe Leu Asp Glu Leu Lys Ala Lys Tyr Pro Glu Ile Phe Glu Arg Val
        835                 840                 845

Gln Ile Ser Asn Gly Gln Lys Met Thr Thr Asp Glu Lys Ile Thr Lys
    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
            900                 905                 910

Thr Gly Phe Val Lys Asp Thr Thr Gly Phe Lys Tyr Tyr Ser Thr Ser
        915                 920                 925
```

```
Gly Tyr Gln Ala Arg Asn Ser Phe Ile Gln Asp Glu Asn Gly Asn Trp
    930                 935                 940

Tyr Tyr Phe Asp Lys Arg Gly Tyr Leu Ala Thr Gly Ala His Glu Ile
945                 950                 955                 960

Asp Gly Lys Gln Val Tyr Phe Leu Lys Asn Gly Ile Gln Leu Arg Asp
                965                 970                 975

Ser Leu Arg Glu Asp Glu Asn Gly Asn Gln Tyr Tyr Tyr Asp Lys Thr
            980                 985                 990

Gly Ala Gln Val Leu Asn Arg Tyr  Tyr Thr Thr Asp Gly  Gln Asn Trp
        995                 1000                1005

Arg Tyr  Phe Asp Ala Lys Gly  Val Met Ala Arg Gly  Leu Val Thr
    1010                1015                1020

Met Gly  Gly Asn Gln Gln Phe  Phe Asp Gln Asn Gly  Tyr Gln Val
    1025                1030                1035

Lys Gly  Lys Ile Ala Arg Ala  Lys Asp Gly Lys Leu  Arg Tyr Phe
    1040                1045                1050

Asp Lys  Asp Ser Gly Asn Ala  Ala Ala Asn Arg Phe  Ala Gln Gly
    1055                1060                1065

Asp Asn  Pro Ser Asp Trp Tyr  Tyr Phe Gly Ala Asp  Gly Val Ala
    1070                1075                1080

Val Thr  Gly Leu Gln Lys Leu  Gly Gln Gln Thr Leu  Tyr Phe Asp
    1085                1090                1095

Gln Glu  Gly Lys Gln Val Lys  Gly Lys Ile Val Thr  Leu Ala Asp
    1100                1105                1110

Lys Ser  Ile Arg Tyr Phe Asp  Ala Asn Ser Gly Glu  Met Ala Val
    1115                1120                1125

Gly Lys  Phe Ala Glu Gly Ser  Lys Asn Glu Trp Tyr  Tyr Phe Asp
    1130                1135                1140

Gln Thr  Gly Lys Ala Val Thr  Gly Leu Gln Lys Ile  Gly Gln Gln
    1145                1150                1155

Thr Leu  Tyr Phe Asp Gln Asp  Gly Lys Gln Val Lys  Gly Lys Val
    1160                1165                1170

Val Thr  Leu Ala Asp Lys Ser  Ile Arg Tyr Phe Asp  Ala Asn Ser
    1175                1180                1185

Gly Glu  Met Ala Val Gly Lys  Phe Ala Glu Gly Ala  Lys Asn Glu
    1190                1195                1200

Trp Tyr  Tyr Phe Asp Gln Ala  Gly Lys Ala Val Thr  Gly Leu Gln
    1205                1210                1215

Lys Ile  Gly Gln Gln Thr Leu  Tyr Phe Asp Gln Asp  Gly Lys Gln
    1220                1225                1230

Val Lys  Gly Gln Leu Val Thr  Leu Ala Asp Lys Ser  Ile Arg Tyr
    1235                1240                1245

Phe Asp  Ala Asn Ser Gly Glu  Met Ala Ser Asn Lys  Phe Val Glu
    1250                1255                1260

Gly Ala  Lys Asn Glu Trp Tyr  Tyr Phe Asp Gln Ala  Gly Lys Ala
    1265                1270                1275

Val Thr  Gly Leu Gln Gln Ile  Gly Gln Gln Thr Leu  Tyr Phe Asp
    1280                1285                1290

Gln Asn  Gly Lys Gln Val Lys  Gly Lys Ile Val Tyr  Val Asn Gly
    1295                1300                1305

Ala Asn  Arg Tyr Phe Asp Ala  Asn Ser Gly Glu Met  Ala Arg Asn
    1310                1315                1320
```

```
Lys Trp  Ile Gln Leu Glu Asp  Gly Ser Trp Met Tyr  Phe Asp Arg
    1325                 1330                 1335

Asn Gly  Arg Gly Arg Arg Phe  Gly Trp Asn
    1340                 1345


<210> SEQ ID NO 49
<211> LENGTH: 4284
<212> TYPE: DNA
<213> ORGANISM: Streptococcus salivarius

<400> SEQUENCE: 49

atgaaggatg gcaaatacta ctacttgttg gaagatggct cgcacaaaaa gaatttcgca     60

atcaccgtca atggtcaagt gctgtatttt gacgagaacg gtgcgctgag cagcaccagc    120

acgtacagct tcacgcagga aaccaccaat ctggttacgg actttacgaa gaataatgcg    180

gcgtatgact ccacgaaagc gtctttcgaa ttggtggacg gctatctgac cgcagacagc    240

tggtatcgcc cgaaagagat tctggaagcc ggcaccacct ggaaggcgag caccgaaaag    300

gacttccgtc cgctgctgat gtcctggtgg ccggataagg acacgcaagt tgcttatctg    360

aattacatga cgaaagcact gtcgaacggc gaagaaacca aggatgtctt tacgatcgaa    420

aacagccaag cgagcctgaa tgcggcagcg caaatcctgc aacgtaagat tgaggtcaag    480

attgcggcca acaagagcac cgactggctg cgccaaagca tcgaggcgtt tgtcaaagac    540

caagataagt ggaatatcaa tagcgaaagc cctggcaaag agcatttcca gaagggtgcg    600

ctgctgtttg ttaatagcga cagcaccaag tgggcgaact ccgattatcg taaactgaat    660

cagaccgcga cgtcttacat caagaatcat aagatcgtga acggtagcga tggtggttac    720

gagttcttgc tgagcaacga catcgacaac agcaacccgg tggtccaggc agagatgctg    780

aatcaactgt actactttat gaactggggt cagattgtgt tcggcgataa agataaagac    840

gcacatttcg atggcatccg tgtggacgcg gtggacaatg ttagcgttga catgctgcaa    900

ctggtcagca gctacatgaa ggcggcatac aaggtcaatg aatctgaagc ccgtgcgctg    960

gcgaatatca gcattttgga agcgtggagc cataatgacc cgtattatgt gaacgagcac   1020

aatacggcag cactgagcat ggataacggt ctgcgtctgt ctattgtgca tggtctgacg   1080

cgtccggtga ctaacaaagg cacgggtgct cgtaacgcca gcatgaagga cctgatcaac   1140

ggcggttact ttggcttgag caaccgtgcg gaagttacta gctacgacca gctgggcttt   1200

gccacttacc tgtttgtgcg tgcgcatgac agcgaggttc agacggttat cgctgatatt   1260

atttctaaaa agattgaccc gaccaccgac ggttttacct ttaccctgga ccagctgaag   1320

caggcttttg atatttataa cgcggacatg ttgaaggttg ataaagagta tacgcatagc   1380

aacatcccgg ctgcgtatgc gctgatgctg caaacgatgg gtgcagcgac ccgcgtgtat   1440

tacggcgatc tgtacactga taacggccaa tacatggcga aaaagagccc gtattttgat   1500

cagattacca cgctgttgaa ggcccgtccg aagtacgtgg cgggtggcca gacgagctac   1560

atccacaacc tggcaggcga tggtgtcagc tcggccaaag ataacaaaga ggttctggtt   1620

agcgtgcgct acggtcagga tctgatgagc aaaacggata ctgagggcgg taaatacggt   1680

cgtaacagcg gtatgctgac tctgatcgcg aacaacccgg acctgaagct ggccgatggt   1740

gagactatca cggttaacat gggtgctgcc cacaaaaatc aggcgtatcg tccgttgctg   1800

ctgggcacgg aaaagggtat tgtcagcagc ctgaacgata gcgacaccaa aatcgtgaag   1860

tatacggacg cccaaggtaa cctggttttc accgccgacg agatcaaggg cttcaaaacc   1920

gtggacatgt ctggctacct gtctgtttgg gttccggttg gtgccacgga tgaccagaac   1980
```

```
gtcctggcga aaccgagcac caaagcatac aaagaaggtg ataaggttta cagcagcagc   2040
gcggctctgg aagctcaggt tatctatgaa ggttttagca atttccagga tttcgtgaaa   2100
gaagatagcc agtataccaa taagctgatt gcggctaatg cggacctgtt taagagctgg   2160
ggtatcacga gctttgagat cgcaccgcaa tatgtgagca gcaaagatgg tacttttctg   2220
gacagcatca ttgaaaatgg ttacgcgttc accgatcgtt atgacttcgc gatgagcaag   2280
aacaataagt atggtagcaa agaggatctg cgcgacgcgc tgaaggcact gcacaaacaa   2340
ggcatccaag tcatcgcgga ttgggtgccg gatcagctgt ataccctgcc gggcaaagag   2400
gtggttacgg caacccgtac cgatacgcac ggtaaagtgc tggatgacac gagcctggtg   2460
aataaactgt atgtgaccaa tacgaagtct agcggtaacg atttccaggc acagtatggt   2520
ggtgcgttcc tggataaact gcaaaagctg tacccagaga ttttcaaaga agttatggaa   2580
gcgtccggca agaccatcga cccaagcgtc aagattaaac aatgggaagc taaatacttt   2640
aatggcacga atattcaaaa gcgtggttcc gattatgttc tgagcgatgg caaactgtac   2700
tttacggtta acgataaggg caccttcctg cctgctgccc tgacgggtga caccaaggct   2760
aaaacgggtt ttgcctacga tggtacgggt gtcacgtatt acactaccag cggtactcaa   2820
gctaagagcc agtttgtgac gtataatggt aagcaatact acttcaacga caagggttac   2880
ttggttaccg gcgagcagac gattgatggc tccaactatt tcttcctgcc gaatggtgtt   2940
atgtttaccg atggtgtgcg taaaaacgcg aagggtcaga gcctggttta tggcaagtct   3000
ggtaagctga ccacgcaaac gggctggaaa gaagtgaccg ttaaagatga tagcggcaaa   3060
gaagaaaagt tttaccagta tttcttcaag ggtggcatca tggcgaccgg cctgacggaa   3120
gttgaaggta aagagaagta tttctatgac aatggctacc aggctaaagg cgtctttgtc   3180
ccgaccaaag acggccacct gatgttcttt tgcggcgaca gcggtgagcg taaatacagc   3240
ggtttctttg aacaagacgg taactggtac tatgcgaatg acaagggcta cgtcgcgacc   3300
ggctttacca aggtgggtaa acaaaatctg tatttcaatg agaaaggcgt ccaggtcaaa   3360
aaccgctttt tccaagtggg tgacgccacc tattacgcga ataacgaggg cgacgtgctg   3420
cgtggtgcgc aaaccatcaa tggtgatgag ctgtacttcg acgaaagcgg caaacaagtt   3480
aagggtgagt tcgtgaataa cccagacggc acgacctctt actatgatgc gatcacgggc   3540
gttaagctgg tcgatacctc gctggttgtt gatggtcaga cgttcaacgt ggatgcgaag   3600
ggtgtcgtaa ccaaggcgca cacgccgggt ttctacacca cgggcgacaa caactggttc   3660
tacgcagata gctatggtcg taatgttacc ggtgcgcaag taatcaacgg ccaacacctg   3720
tatttcgatg caaatggtcg tcaagtgaaa ggcggctttg tcacgaacac ggacggtagc   3780
cgtagctttt accactggaa taccggcgac aaactggtgt ccacgttctt tgcgacgggt   3840
cacgatcgct ggtactacgc tgatgatcgt ggcaacgtcg tcacgggtgc acaggtcatc   3900
aacggtcaga agctgttctt tgacaccgat ggtaaacaag tcaaaggtgc tttcgcgacc   3960
aacgcgaatg gttcccgtag ctattatcat tggaatacgg gcaacaagct ggtgagcacc   4020
ttcttcacct cgggtgacaa taactggtat tacgcggacg ccaaaggtga ggttgtggtc   4080
ggtgaacaga cgattaatgg ccagcacctg tactttgacc agactggcaa gcaagtgaag   4140
ggcgcgactg caacgaaccc ggacggctcg atcagctatt atgatgtgca cacgggtgaa   4200
aaggctatca atcgttgggt gaagattccg agcggtcaat gggtgtactt caatgcgcag   4260
ggcaaaggtt acgtcagcaa ctaa                                          4284
```

<210> SEQ ID NO 50
<211> LENGTH: 1427
<212> TYPE: PRT
<213> ORGANISM: Streptococcus salivarius

<400> SEQUENCE: 50

```
Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
        115                 120                 125

Asn Gly Glu Glu Thr Lys Asp Val Phe Thr Ile Glu Asn Ser Gln Ala
    130                 135                 140

Ser Leu Asn Ala Ala Ala Gln Ile Leu Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Ser
        195                 200                 205

Thr Lys Trp Ala Asn Ser Asp Tyr Arg Lys Leu Asn Gln Thr Ala Thr
    210                 215                 220

Ser Tyr Ile Lys Asn His Lys Ile Val Asn Gly Ser Asp Gly Gly Tyr
225                 230                 235                 240

Glu Phe Leu Leu Ser Asn Asp Ile Asp Asn Ser Asn Pro Val Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
        275                 280                 285

Asp Ala Val Asp Asn Val Ser Val Asp Met Leu Gln Leu Val Ser Ser
    290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser His Asn Asp Pro Tyr Tyr
                325                 330                 335

Val Asn Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
        355                 360                 365

Gly Ala Arg Asn Ala Ser Met Lys Asp Leu Ile Asn Gly Gly Tyr Phe
    370                 375                 380
```

```
Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
            420                 425                 430

Thr Phe Thr Leu Asp Gln Leu Lys Gln Ala Phe Asp Ile Tyr Asn Ala
        435                 440                 445

Asp Met Leu Lys Val Asp Lys Glu Tyr Thr His Ser Asn Ile Pro Ala
    450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
                485                 490                 495

Pro Tyr Phe Asp Gln Ile Thr Thr Leu Leu Lys Ala Arg Pro Lys Tyr
            500                 505                 510

Val Ala Gly Gly Gln Thr Ser Tyr Ile His Asn Leu Ala Gly Asp Gly
        515                 520                 525

Val Ser Ser Ala Lys Asp Asn Lys Glu Val Leu Val Ser Val Arg Tyr
    530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Leu Gly Thr Glu Lys Gly Ile Val
        595                 600                 605

Ser Ser Leu Asn Asp Ser Asp Thr Lys Ile Val Lys Tyr Thr Asp Ala
    610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Asp Asp Gln Asn Val Leu Ala Lys Pro Ser Thr Lys Ala Tyr Lys Glu
            660                 665                 670

Gly Asp Lys Val Tyr Ser Ser Ser Ala Ala Leu Glu Ala Gln Val Ile
        675                 680                 685

Tyr Glu Gly Phe Ser Asn Phe Gln Asp Phe Val Lys Glu Asp Ser Gln
    690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Asn Lys Tyr Gly Ser Lys Glu
        755                 760                 765

Asp Leu Arg Asp Ala Leu Lys Ala Leu His Lys Gln Gly Ile Gln Val
    770                 775                 780

Ile Ala Asp Trp Val Pro Asp Gln Leu Tyr Thr Leu Pro Gly Lys Glu
785                 790                 795                 800
```

```
Val Val Thr Ala Thr Arg Thr Asp Thr His Gly Lys Val Leu Asp Asp
            805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
        835                 840                 845

Lys Leu Tyr Pro Glu Ile Phe Lys Glu Val Met Glu Ala Ser Gly Lys
    850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
            885                 890                 895

Gly Lys Leu Tyr Phe Thr Val Asn Asp Lys Gly Thr Phe Leu Pro Ala
            900                 905                 910

Ala Leu Thr Gly Asp Thr Lys Ala Lys Thr Gly Phe Ala Tyr Asp Gly
        915                 920                 925

Thr Gly Val Thr Tyr Tyr Thr Thr Ser Gly Thr Gln Ala Lys Ser Gln
    930                 935                 940

Phe Val Thr Tyr Asn Gly Lys Gln Tyr Tyr Phe Asn Asp Lys Gly Tyr
945                 950                 955                 960

Leu Val Thr Gly Glu Gln Thr Ile Asp Gly Ser Asn Tyr Phe Phe Leu
            965                 970                 975

Pro Asn Gly Val Met Phe Thr Asp Gly Val Arg Lys Asn Ala Lys Gly
            980                 985                 990

Gln Ser Leu Val Tyr Gly Lys Ser  Gly Lys Leu Thr Thr  Gln Thr Gly
        995                 1000                1005

Trp Lys  Glu Val Thr Val Lys  Asp Asp Ser Gly Lys  Glu Glu Lys
    1010                1015                1020

Phe Tyr  Gln Tyr Phe Phe Lys  Gly Gly Ile Met Ala  Thr Gly Leu
    1025                1030                1035

Thr Glu  Val Glu Gly Lys Glu  Lys Tyr Phe Tyr Asp  Asn Gly Tyr
    1040                1045                1050

Gln Ala  Lys Gly Val Phe Val  Pro Thr Lys Asp Gly  His Leu Met
    1055                1060                1065

Phe Phe  Cys Gly Asp Ser Gly  Glu Arg Lys Tyr Ser  Gly Phe Phe
    1070                1075                1080

Glu Gln  Asp Gly Asn Trp Tyr  Tyr Ala Asn Asp Lys  Gly Tyr Val
    1085                1090                1095

Ala Thr  Gly Phe Thr Lys Val  Gly Lys Gln Asn Leu  Tyr Phe Asn
    1100                1105                1110

Glu Lys  Gly Val Gln Val Lys  Asn Arg Phe Phe Gln  Val Gly Asp
    1115                1120                1125

Ala Thr  Tyr Tyr Ala Asn Asn  Glu Gly Asp Val Leu  Arg Gly Ala
    1130                1135                1140

Gln Thr  Ile Asn Gly Asp Glu  Leu Tyr Phe Asp Glu  Ser Gly Lys
    1145                1150                1155

Gln Val  Lys Gly Glu Phe Val  Asn Asn Pro Asp Gly  Thr Thr Ser
    1160                1165                1170

Tyr Tyr  Asp Ala Ile Thr Gly  Val Lys Leu Val Asp  Thr Ser Leu
    1175                1180                1185

Val Val  Asp Gly Gln Thr Phe  Asn Val Asp Ala Lys  Gly Val Val
    1190                1195                1200

Thr Lys  Ala His Thr Pro Gly  Phe Tyr Thr Thr Gly  Asp Asn Asn
```

```
    1205                1210                1215

Trp Phe  Tyr Ala Asp Ser Tyr  Gly Arg Asn Val Thr  Gly Ala Gln
    1220                1225                1230

Val Ile  Asn Gly Gln His Leu  Tyr Phe Asp Ala Asn  Gly Arg Gln
    1235                1240                1245

Val Lys  Gly Gly Phe Val Thr  Asn Thr Asp Gly Ser  Arg Ser Phe
    1250                1255                1260

Tyr His  Trp Asn Thr Gly Asp  Lys Leu Val Ser Thr  Phe Phe Ala
    1265                1270                1275

Thr Gly  His Asp Arg Trp Tyr  Tyr Ala Asp Asp Arg  Gly Asn Val
    1280                1285                1290

Val Thr  Gly Ala Gln Val Ile  Asn Gly Gln Lys Leu  Phe Phe Asp
    1295                1300                1305

Thr Asp  Gly Lys Gln Val Lys  Gly Ala Phe Ala Thr  Asn Ala Asn
    1310                1315                1320

Gly Ser  Arg Ser Tyr Tyr His  Trp Asn Thr Gly Asn  Lys Leu Val
    1325                1330                1335

Ser Thr  Phe Phe Thr Ser Gly  Asp Asn Asn Trp Tyr  Tyr Ala Asp
    1340                1345                1350

Ala Lys  Gly Glu Val Val Val  Gly Glu Gln Thr Ile  Asn Gly Gln
    1355                1360                1365

His Leu  Tyr Phe Asp Gln Thr  Gly Lys Gln Val Lys  Gly Ala Thr
    1370                1375                1380

Ala Thr  Asn Pro Asp Gly Ser  Ile Ser Tyr Tyr Asp  Val His Thr
    1385                1390                1395

Gly Glu  Lys Ala Ile Asn Arg  Trp Val Lys Ile Pro  Ser Gly Gln
    1400                1405                1410

Trp Val  Tyr Phe Asn Ala Gln  Gly Lys Gly Tyr Val  Ser Asn
    1415                1420                1425
```

<210> SEQ ID NO 51
<211> LENGTH: 4182
<212> TYPE: DNA
<213> ORGANISM: Unknown
<220> FEATURE:
<223> OTHER INFORMATION: unknown Streptococcus species

<400> SEQUENCE: 51

```
atgatcaatg gcaaacagta ctatgtaaat tcggacggta gcgtgcgtaa gaatttcgtt      60

tttgaacagg atggtaagag ctactacttt gacgcggaaa ctggcgcgct ggccactaaa     120

agccaagatg aatttagcac ggagccgatt aaagcagcag tggacttctc tagcggcaac     180

cagctgtaca aaaatgacaa caaatcgctg gatcagctgg atacgtttat caccgctgac     240

gcatggtacc gccctaagtc tattctgaag gatggcaaaa cctggaccgc gtctaccgaa     300

gctgataagc gtccgttgct gatggtgtgg tggccggaca agtccaccca agttaactac     360

ctgaactaca tgcagaacca gggtttgggt gcgggtagct tcagcaccaa tagcagccaa     420

gaatccctga atctggctgc gaaagcagtt cagaccaaga tcgaagaacg catcgcacgt     480

gagggtaaca ccaattggct gcgtaccagc attgaccaat tcattaagac gcagccaggc     540

tggaacagca gcactgagaa tagcagctat gatcacttgc agggtggtca actgctgttc     600

aataacagca aaggtgatac gggtaaccgc accagctatg cgaatagcga ctatcgtctg     660

ctgaaccgta ccccaactaa tcaaagcggc acccgtaagt actttaagga taattccatc     720

ggtggtctgg aatttctgct ggcaaacgac atcgacaaca gcaaccctgc cgttcaggcg     780
```

```
gagcagctga actggctgca cttcatgatg aacattggtt ctatcatggc gaatgacccg    840
acggcgaact ttgatggttt gcgtgtggac gcgttggata acgtggatgc ggacctgttg    900
cagatcgcga gcgattactt caaggcagtc tacggtgttg ataaatccga ggcgaatgcg    960
atcaagcacc tgagctatct ggaggcgtgg agcgccaatg acccgtatta caacaaggat   1020
accaaaggcg cgcaactgcc gattgacaac gcgctgcgca acgcactgac caacctgttg   1080
atgcgtgaca agaatacgcg catgcagctg ggtgacatga cggcgtttat gaatagctct   1140
ctgaacccac gtggtgcgaa tgacaaaaac ggcgagcgta tggcgaatta cattttcacc   1200
cgcgcacacg ataccgaggc gcagaccatc attcagcgta ttatccgcga tcgtatcaat   1260
ccgaacctgt ttggctacaa tttcacccgc gatgaaatca aaaaggcgtt tgagatctac   1320
aacgcggaca ttaacacggc gcataagacg tacgcgagct acaatctgcc gtccgtctac   1380
gcactgatgc tgacgaataa ggacagcgtg acccgtgtgt attacggtga cctgtatcgt   1440
gaggacggtc actacatggc caagaaaacg ccttatttcg atgcaatcga taccctgctg   1500
cgtgcgcgca tcaaatacgt ggcgggtggt caagacatgg aggtgaagaa agttggtaat   1560
gacggcttgc tgacgagcgt ccgctatggc aagggtgcga acaatagcac cgactggggc   1620
acgactgaaa cccgtaccca aggtatgggc gttatcctga cgaacaacta tgatttccgc   1680
ctgggcagca acgaaaccgt cacgatgaac atgggccgtg cgcatcgcaa tcagctgtat   1740
cgtccgctgc tgctgacgac caaggatggt ctggccacgt acctgaatga tagcgacgtg   1800
ccttcgaatt tgctgaaacg cacggactgg aatggtaact tgacctttaa tgccaacgat   1860
gtgtttggtg tagagaacgt ccaggtcagc ggttacctgg gtgtttgggt accggttggt   1920
gctaaagcta accaggatgc gcgtacccaa ccgagcaacc gtgcgaacag cgatggtcag   1980
gtctataagt cgtctgcggc attggacagc caggtcatgt atgaggcgtt tagcaatttt   2040
caggcatttg cggacgatca accggaactg tacatgaacc gcgttctggc gaagaacacc   2100
gatctgctga aagcgtgggg cgttactagc gttggcttgc cgccacaata cgttagcagc   2160
aaagacggca ccttcctgga tagcactatt gataacggct atgcgttcga tgatcgttac   2220
gacatggcgc tgagccagaa caacaaatac ggttctctgg aggacttgct gaacgttctg   2280
cgcgctctgc acaaagacgg tattcaggcg attgcggact gggtcccgga tcaaatctac   2340
aatttgccgg gtaaagaggt tgttaatgcg acgcgtgtta acggttacgg ttaccatcag   2400
cagggctacc agattgttga ccaggcgtac gttgcaaaca cccgtacgga tggtaccgat   2460
tatcagggtc gttacggtgg tgcttttctg gacgaactga aggcgaagta cccgagcatt   2520
ttcaatcgtg tccagattag caacggtaaa cagctgccaa ccaatgagaa aatcacgaaa   2580
tggtccgcga aatacttcaa tggcacgaac atcctgggcc gtggtattaa ctatgtgctg   2640
cgcgacgaca agaccaatca gtatttcaac accagcgcaa acggccaact gctgccgacg   2700
ccactgcgcg acaccggtgc catcaccagc acgcaagttt tccagcgtcg tggccaagac   2760
gtctattttc tgcgtgataa ccaggttatc aaaaacgagt ttgtgcaaga tggtaacggt   2820
aattggtact acttcggtgc cgacggtaaa atgacgaagg gtgcacaaaa catcaatagc   2880
aaggattact atttcttcga taatggcgtc cagctgcgta atgcgctgcg tcgcgcgtcc   2940
aatggttaca cctactatta tggcctggac ggtgccatga tcaagaacgc tttcgtcgat   3000
tttgatgata agcaccaaca ggtgcgtgcg tttactacgc agggcacgat ggtggtcggt   3060
aatttgcact ggagcggtca ccacttctat tttgaccgcg aaacgggtat ccaagccaaa   3120
```

```
gaccgcattg tgcgtaccga tgatggcaag ctgcactatt atgtcgcaca aaccggcgat   3180

atgggccgca atgtgtttgc gaccgacagc cgcacgggca agcgctatta ctttgatgcg   3240

gacggcaaca ccgttacggg ctcccgtgtc atcgacggca agacctacta cttcaaccag   3300

gacggttcgg tcggtaccgc gtacagcaat cgtgcggata gcattatctt tgagaatggc   3360

aaggctcgct atatcactcc ggctggcgag attggccgtt ccatttttgt ctacaacccg   3420

gcgaccaaag cgtggaatta cttcgacaag gaaggtaacc gtgtcaccgg tcgtcagtat   3480

attgacggca atctgtacta ctttaaagag gacggctccc aagtgaaagg tgcgattgtt   3540

gaagagaacg gtatcaagta ctactacgaa ccgggcagcg gtatcctggc gagcggtcgt   3600

tatctgcaag tcggtgacga ccaatggatc tacttcaaac acgacggtag cctggcgatc   3660

ggtcaggttc gtgcagacgg tggttacttg aaatactttg ataagaatgg catccaggtc   3720

aagggccaaa ccattgtgga ggatggtcat acctattact acgatgccga ctccggtgct   3780

ctggtgacct ctagcttcgc ggagattgct ccgaaccagt gggcctactt caataccgag   3840

ggccaagccc tgaagggcaa atggaccatc aatggtaaag agtactattt tgatcagaac   3900

ggcattcagt ataaaggcaa ggcagttaag gtcggcagcc gttacaaata ctatgacgag   3960

aatgacggtc aaccggtcac taaccgtttt gcccagattg agccgaacgt ctgggcgtac   4020

tttggtgccg atggctacgc agttactggc gaacaggtga ttaatggcca gcacctgtac   4080

ttcgatcagt cgggtcgtca ggttaaaggt gcgtacgtca ccgtgaatgg tcaacgtcgt   4140

tactacgacg caaacacggg tgaatacatt ccgggtcgtt aa                      4182
```

```
<210> SEQ ID NO 52
<211> LENGTH: 1393
<212> TYPE: PRT
<213> ORGANISM: Unknown
<220> FEATURE:
<223> OTHER INFORMATION: unknown Streptococcus species

<400> SEQUENCE: 52

Met Ile Asn Gly Lys Gln Tyr Tyr Val Asn Ser Asp Gly Ser Val Arg
1               5                   10                  15

Lys Asn Phe Val Phe Glu Gln Asp Gly Lys Ser Tyr Tyr Phe Asp Ala
            20                  25                  30

Glu Thr Gly Ala Leu Ala Thr Lys Ser Gln Asp Glu Phe Ser Thr Glu
        35                  40                  45

Pro Ile Lys Ala Ala Val Asp Phe Ser Ser Gly Asn Gln Leu Tyr Lys
    50                  55                  60

Asn Asp Asn Lys Ser Leu Asp Gln Leu Asp Thr Phe Ile Thr Ala Asp
65                  70                  75                  80

Ala Trp Tyr Arg Pro Lys Ser Ile Leu Lys Asp Gly Lys Thr Trp Thr
                85                  90                  95

Ala Ser Thr Glu Ala Asp Lys Arg Pro Leu Leu Met Val Trp Trp Pro
            100                 105                 110

Asp Lys Ser Thr Gln Val Asn Tyr Leu Asn Tyr Met Gln Asn Gln Gly
        115                 120                 125

Leu Gly Ala Gly Ser Phe Ser Thr Asn Ser Ser Gln Glu Ser Leu Asn
    130                 135                 140

Leu Ala Ala Lys Ala Val Gln Thr Lys Ile Glu Glu Arg Ile Ala Arg
145                 150                 155                 160

Glu Gly Asn Thr Asn Trp Leu Arg Thr Ser Ile Asp Gln Phe Ile Lys
                165                 170                 175
```

```
Thr Gln Pro Gly Trp Asn Ser Ser Thr Glu Asn Ser Ser Tyr Asp His
            180                 185                 190

Leu Gln Gly Gly Gln Leu Leu Phe Asn Asn Ser Lys Gly Asp Thr Gly
        195                 200                 205

Asn Arg Thr Ser Tyr Ala Asn Ser Asp Tyr Arg Leu Leu Asn Arg Thr
    210                 215                 220

Pro Thr Asn Gln Ser Gly Thr Arg Lys Tyr Phe Lys Asp Asn Ser Ile
225                 230                 235                 240

Gly Gly Leu Glu Phe Leu Leu Ala Asn Asp Ile Asp Asn Ser Asn Pro
                245                 250                 255

Ala Val Gln Ala Glu Gln Leu Asn Trp Leu His Phe Met Met Asn Ile
            260                 265                 270

Gly Ser Ile Met Ala Asn Asp Pro Thr Ala Asn Phe Asp Gly Leu Arg
        275                 280                 285

Val Asp Ala Leu Asp Asn Val Asp Ala Asp Leu Leu Gln Ile Ala Ser
    290                 295                 300

Asp Tyr Phe Lys Ala Val Tyr Gly Val Asp Lys Ser Glu Ala Asn Ala
305                 310                 315                 320

Ile Lys His Leu Ser Tyr Leu Glu Ala Trp Ser Ala Asn Asp Pro Tyr
                325                 330                 335

Tyr Asn Lys Asp Thr Lys Gly Ala Gln Leu Pro Ile Asp Asn Ala Leu
            340                 345                 350

Arg Asn Ala Leu Thr Asn Leu Leu Met Arg Asp Lys Asn Thr Arg Met
        355                 360                 365

Gln Leu Gly Asp Met Thr Ala Phe Met Asn Ser Ser Leu Asn Pro Arg
    370                 375                 380

Gly Ala Asn Asp Lys Asn Gly Glu Arg Met Ala Asn Tyr Ile Phe Thr
385                 390                 395                 400

Arg Ala His Asp Thr Glu Ala Gln Thr Ile Ile Gln Arg Ile Ile Arg
                405                 410                 415

Asp Arg Ile Asn Pro Asn Leu Phe Gly Tyr Asn Phe Thr Arg Asp Glu
            420                 425                 430

Ile Lys Lys Ala Phe Glu Ile Tyr Asn Ala Asp Ile Asn Thr Ala His
        435                 440                 445

Lys Thr Tyr Ala Ser Tyr Asn Leu Pro Ser Val Tyr Ala Leu Met Leu
    450                 455                 460

Thr Asn Lys Asp Ser Val Thr Arg Val Tyr Tyr Gly Asp Leu Tyr Arg
465                 470                 475                 480

Glu Asp Gly His Tyr Met Ala Lys Lys Thr Pro Tyr Phe Asp Ala Ile
                485                 490                 495

Asp Thr Leu Leu Arg Ala Arg Ile Lys Tyr Val Ala Gly Gly Gln Asp
            500                 505                 510

Met Glu Val Lys Lys Val Gly Asn Asp Gly Leu Leu Thr Ser Val Arg
        515                 520                 525

Tyr Gly Lys Gly Ala Asn Asn Ser Thr Asp Trp Gly Thr Thr Glu Thr
    530                 535                 540

Arg Thr Gln Gly Met Gly Val Ile Leu Thr Asn Asn Tyr Asp Phe Arg
545                 550                 555                 560

Leu Gly Ser Asn Glu Thr Val Thr Met Asn Met Gly Arg Ala His Arg
                565                 570                 575

Asn Gln Leu Tyr Arg Pro Leu Leu Leu Thr Thr Lys Asp Gly Leu Ala
            580                 585                 590

Thr Tyr Leu Asn Asp Ser Asp Val Pro Ser Asn Leu Leu Lys Arg Thr
```

```
        595                 600                 605

Asp Trp Asn Gly Asn Leu Thr Phe Asn Ala Asn Asp Val Phe Gly Val
    610                 615                 620

Glu Asn Val Gln Val Ser Gly Tyr Leu Gly Val Trp Val Pro Val Gly
625                 630                 635                 640

Ala Lys Ala Asn Gln Asp Ala Arg Thr Gln Pro Ser Asn Arg Ala Asn
                645                 650                 655

Ser Asp Gly Gln Val Tyr Lys Ser Ser Ala Ala Leu Asp Ser Gln Val
            660                 665                 670

Met Tyr Glu Ala Phe Ser Asn Phe Gln Ala Phe Ala Asp Asp Gln Pro
        675                 680                 685

Glu Leu Tyr Met Asn Arg Val Leu Ala Lys Asn Thr Asp Leu Leu Lys
    690                 695                 700

Ala Trp Gly Val Thr Ser Val Gly Leu Pro Pro Gln Tyr Val Ser Ser
705                 710                 715                 720

Lys Asp Gly Thr Phe Leu Asp Ser Thr Ile Asp Asn Gly Tyr Ala Phe
                725                 730                 735

Asp Asp Arg Tyr Asp Met Ala Leu Ser Gln Asn Asn Lys Tyr Gly Ser
            740                 745                 750

Leu Glu Asp Leu Leu Asn Val Leu Arg Ala Leu His Lys Asp Gly Ile
        755                 760                 765

Gln Ala Ile Ala Asp Trp Val Pro Asp Gln Ile Tyr Asn Leu Pro Gly
    770                 775                 780

Lys Glu Val Val Asn Ala Thr Arg Val Asn Gly Tyr Gly Tyr His Gln
785                 790                 795                 800

Gln Gly Tyr Gln Ile Val Asp Gln Ala Tyr Val Ala Asn Thr Arg Thr
                805                 810                 815

Asp Gly Thr Asp Tyr Gln Gly Arg Tyr Gly Gly Ala Phe Leu Asp Glu
            820                 825                 830

Leu Lys Ala Lys Tyr Pro Ser Ile Phe Asn Arg Val Gln Ile Ser Asn
        835                 840                 845

Gly Lys Gln Leu Pro Thr Asn Glu Lys Ile Thr Lys Trp Ser Ala Lys
    850                 855                 860

Tyr Phe Asn Gly Thr Asn Ile Leu Gly Arg Gly Ile Asn Tyr Val Leu
865                 870                 875                 880

Arg Asp Asp Lys Thr Asn Gln Tyr Phe Asn Thr Ser Ala Asn Gly Gln
                885                 890                 895

Leu Leu Pro Thr Pro Leu Arg Asp Thr Gly Ala Ile Thr Ser Thr Gln
            900                 905                 910

Val Phe Gln Arg Arg Gly Gln Asp Val Tyr Phe Leu Arg Asp Asn Gln
        915                 920                 925

Val Ile Lys Asn Glu Phe Val Gln Asp Gly Asn Gly Asn Trp Tyr Tyr
    930                 935                 940

Phe Gly Ala Asp Gly Lys Met Thr Lys Gly Ala Gln Asn Ile Asn Ser
945                 950                 955                 960

Lys Asp Tyr Tyr Phe Phe Asp Asn Gly Val Gln Leu Arg Asn Ala Leu
                965                 970                 975

Arg Arg Ala Ser Asn Gly Tyr Thr Tyr Tyr Tyr Gly Leu Asp Gly Ala
            980                 985                 990

Met Ile Lys Asn Ala Phe Val Asp  Phe Asp Asp Lys His  Gln Gln Val
        995                 1000                1005

Arg Ala  Phe Thr Thr Gln Gly  Thr Met Val Val Gly  Asn Leu His
    1010                1015                1020
```

```
Trp Ser  Gly His His Phe Tyr  Phe Asp Arg Glu Thr  Gly Ile Gln
    1025                 1030                 1035

Ala Lys  Asp Arg Ile Val Arg  Thr Asp Asp Gly Lys  Leu His Tyr
    1040                 1045                 1050

Tyr Val  Ala Gln Thr Gly Asp  Met Gly Arg Asn Val  Phe Ala Thr
    1055                 1060                 1065

Asp Ser  Arg Thr Gly Lys Arg  Tyr Tyr Phe Asp Ala  Asp Gly Asn
    1070                 1075                 1080

Thr Val  Thr Gly Ser Arg Val  Ile Asp Gly Lys Thr  Tyr Tyr Phe
    1085                 1090                 1095

Asn Gln  Asp Gly Ser Val Gly  Thr Ala Tyr Ser Asn  Arg Ala Asp
    1100                 1105                 1110

Ser Ile  Ile Phe Glu Asn Gly  Lys Ala Arg Tyr Ile  Thr Pro Ala
    1115                 1120                 1125

Gly Glu  Ile Gly Arg Ser Ile  Phe Val Tyr Asn Pro  Ala Thr Lys
    1130                 1135                 1140

Ala Trp  Asn Tyr Phe Asp Lys  Glu Gly Asn Arg Val  Thr Gly Arg
    1145                 1150                 1155

Gln Tyr  Ile Asp Gly Asn Leu  Tyr Tyr Phe Lys Glu  Asp Gly Ser
    1160                 1165                 1170

Gln Val  Lys Gly Ala Ile Val  Glu Glu Asn Gly Ile  Lys Tyr Tyr
    1175                 1180                 1185

Tyr Glu  Pro Gly Ser Gly Ile  Leu Ala Ser Gly Arg  Tyr Leu Gln
    1190                 1195                 1200

Val Gly  Asp Asp Gln Trp Ile  Tyr Phe Lys His Asp  Gly Ser Leu
    1205                 1210                 1215

Ala Ile  Gly Gln Val Arg Ala  Asp Gly Gly Tyr Leu  Lys Tyr Phe
    1220                 1225                 1230

Asp Lys  Asn Gly Ile Gln Val  Lys Gly Gln Thr Ile  Val Glu Asp
    1235                 1240                 1245

Gly His  Thr Tyr Tyr Tyr Asp  Ala Asp Ser Gly Ala  Leu Val Thr
    1250                 1255                 1260

Ser Ser  Phe Ala Glu Ile Ala  Pro Asn Gln Trp Ala  Tyr Phe Asn
    1265                 1270                 1275

Thr Glu  Gly Gln Ala Leu Lys  Gly Lys Trp Thr Ile  Asn Gly Lys
    1280                 1285                 1290

Glu Tyr  Tyr Phe Asp Gln Asn  Gly Ile Gln Tyr Lys  Gly Lys Ala
    1295                 1300                 1305

Val Lys  Val Gly Ser Arg Tyr  Lys Tyr Tyr Asp Glu  Asn Asp Gly
    1310                 1315                 1320

Gln Pro  Val Thr Asn Arg Phe  Ala Gln Ile Glu Pro  Asn Val Trp
    1325                 1330                 1335

Ala Tyr  Phe Gly Ala Asp Gly  Tyr Ala Val Thr Gly  Glu Gln Val
    1340                 1345                 1350

Ile Asn  Gly Gln His Leu Tyr  Phe Asp Gln Ser Gly  Arg Gln Val
    1355                 1360                 1365

Lys Gly  Ala Tyr Val Thr Val  Asn Gly Gln Arg Arg  Tyr Tyr Asp
    1370                 1375                 1380

Ala Asn  Thr Gly Glu Tyr Ile  Pro Gly Arg
    1385                 1390
```

<210> SEQ ID NO 53
<211> LENGTH: 3789

<212> TYPE: DNA
<213> ORGANISM: Leuconostoc citreum

<400> SEQUENCE: 53

```
atgattaacg gccacaatta ctatttcgac agcttgggtc aactgaagaa aggtttcacg     60
ggcgtgatcg acggtcaggt ccgttacttc gaccaggagt ccggtcagga agttagcacc    120
accgacagcc aaatcaaaga gggcttgacg agccaaacga ccgactacac cgcccataac    180
gcggtccaca gcacggactc cgcagatttt gacaacttca atggttacct gaccgcgagc    240
agctggtatc gtcctaagga cgttctgcgt aacggccaac attgggaagc caccaccgcg    300
aatgacttcc gtcctatcgt cagcgtgtgg tggccgagca agcaaacgca ggtcaactac    360
ctgaactata tgagccagat gggtttgatc gataaccgtc aaatgttctc gttgaaagat    420
aaccaagcga tgctgaacat cgcgtgcacg accgtgcaac aagcaatcga aactaaaatc    480
ggtgtggcga atagcaccgc gtggctgaaa accgcgatcg atgactttat ccgtacccag    540
ccgcagtgga acatgagcag cgaagatccg aagaatgacc atctgcaaaa tggcgccctg    600
acgtttgtta acagcccgct gaccccggat acgaatagca atttccgcct gctgaatcgt    660
accccgacca atcaaaccgg tgttccgaaa tacaccatcg accaaagcaa aggtggtttt    720
gaactgctgc tggcgaatga cgtggataat tcgaacccgg ttgtgcaggc cgagcagttg    780
aactggctgc actacctgat gaactttggt agcattactg cgaatgacag cgcagcaaac    840
ttcgacggta ttcgcgttga cgcagtggat aacgtggatg cggacctgct gcaaattgcg    900
gcagattact tcaaagcagc atacggtgtg gacaagaacg acgcaacggc aaatcagcat    960
ctgtcgatcc tggaagattg gagccacaac gacccggagt acgttaaaga cttcggcaat   1020
aaccaactga ccatggacga ttacatgcac acgcagctga tctggagcct gacgaaagac   1080
atgcgtatgc gtggtacgat gcagcgcttt atggactact atctggttaa ccgcaatcac   1140
gacagcaccg agaatactgc cattccgaat tacagctttg tccgtgccca tgacagcgaa   1200
gttcaaacgg ttattgcgca gatcatttct gagctgcatc cagacgtgaa gaatagcctg   1260
gcgccgaccg cggatcaact ggctgaggcg ttcaaaatct acaacaacga cgagaagcaa   1320
gctgataaga agtataccca atacaatatg ccaagcgcgt acgcaatgct gttgaccaat   1380
aaagataccg ttccgcgtgt ttactacggt gacctgtata ccgatgacgg tcagtatatg   1440
gctaacaaat ccccgtattt tgacgctatc aacggtctgc tgaagagccg tatcaaatat   1500
gtggcaggcg gtcaaagcat ggcggtggat cagaatgata tcctgacgaa tgtgcgctat   1560
ggcaaaggtg ccatgagcgt gacggatagc ggcaacgcgg atacgcgtac ccagggcatc   1620
ggcgttattg ttagcaacaa agaaaacctg gctctgaaat ccggcgacac cgttaccctg   1680
cacatgggcg cagcgcacaa gaaccaggcg tttcgcctgc tgttgggtac gacggcggac   1740
aacctgagct actacgacaa tgacaatgcg ccggtgaagt acaccaatga tcaaggtgat   1800
ctgattttcg ataataccga gatttatggt gttcgcaatc cgcaagtctc tggttttctg   1860
gcggtgtggg tcccggttgg tgccgatagc catcaagatg ctcgcacttt gagcgacgat   1920
acggcacacc acgacggcaa gaccttccac tcgaacgcag cactggatag ccaggtgatt   1980
tacgaaggtt ttagcaactt ccaagcattt gcaacgaata cggaagatta cactaacgct   2040
gtgatcgcca aaaacggcca gctgttcaag gattggggca tcacctcgtt ccagctggct   2100
ccgcagtatc gcagctccac cgatacgagc ttcctggata gcattattca gaacggctat   2160
gccttcacgg accgttatga cctgggctat ggcaccccga cgaagtatgg caccgtggac   2220
```

```
cagctgcgcg atgcaatcaa ggctctgcac gccaatggca tccaagcaat tgccgactgg   2280

gttccggacc agatctacaa cctgccgggt caggagctgg ccacggtgac ccgtacgaac   2340

tcctatggtg ataaagacac caatagcgat attgatcaga gcttgtacgt gatccaatcg   2400

cgcggtggcg gtaagtatca agcccaatac ggtggtgcat tcctgagcga cattcaaaag   2460

aagtatccgg ctctgttcga gactaaacag atcagcacgg gtctgccgat ggacccgagc   2520

caaaagatta ccgagtggag cggcaagtac ttcaacggta gcaatattca aggtaagggc   2580

gctggttacg tcctgaagga cagcggcacc gaccagtact ataaagtgac gagcaacaat   2640

aacaaccgtg atttcctgcc gaaacagctg acggatgatc tgtctgaaac cggttttgtg   2700

cgtgacaata ttggcatggt ctattacacc ctgtctggct acctggcacg caataccttc   2760

atccaggacg acaacggtaa ctattactac tttgatagca ccggtcacct ggttacgggt   2820

ttccagaaca ttaacaacca ccactacttt ttcttgccga acggcattga actggttcag   2880

agctttctgc aaaacgctga tggtagcacg atctacttcg atcaaaaggg tcgtcaagtt   2940

ttcaaccagt atatcactga tcagactggt accgcgtact acttccagaa cgacggcacc   3000

atggtcactt ctggctttac tgagatcgat ggccacaagc agtatttcta taagaatggc   3060

actcaggtta agggtcagtt tgtgagcgac accgatggtc acgtctttta cctggaagcg   3120

ggtaatggta atgtcgccac gcaacgtttc gcacagaaca gccagggtca atggttctac   3180

ttgggtaatg atggcattgc gttgacgggt ttgcagacga tcaacggtgt tcagaactac   3240

ttttatgcgg acggtcatca aagcaagggt gacttcatca ccatccagaa tcatgtcctg   3300

tacaccaacc cgctgacggg tgccatcacg accggcatgc aacagatcgg cgacaaaatc   3360

ttcgtgtttg ataatacggg taatatgctg acgaaccagt attatcagac gctggatggt   3420

cagtggctgc acctgagcac ccagggtcca gcagatacgg gtctggtcaa tatcaatggt   3480

aatctgaagt attttcaggc aaatggtcgt caggtgaaag gccaattcgt caccgacccg   3540

attaccaacg tcagctacta catgaacgcg acggacggta gcgcagtgtt caatgactat   3600

ttcacctatc agggccaatg gtatttgacg gactccaact atcagttggt caaaggcttc   3660

aaagtggtga acaacaaact gcaacatttc gatgaaatca ccggtgtgca aaccaagagc   3720

gctcacatta ttgttaacaa tcgtacctac atttttgacg accagggcta ttttgtcagc   3780

gtggcataa                                                           3789
```

```
<210> SEQ ID NO 54
<211> LENGTH: 1262
<212> TYPE: PRT
<213> ORGANISM: Leuconostoc citreum

<400> SEQUENCE: 54

Met Ile Asn Gly His Asn Tyr Tyr Phe Asp Ser Leu Gly Gln Leu Lys
1               5                   10                  15

Lys Gly Phe Thr Gly Val Ile Asp Gly Gln Val Arg Tyr Phe Asp Gln
            20                  25                  30

Glu Ser Gly Gln Glu Val Ser Thr Thr Asp Ser Gln Ile Lys Glu Gly
        35                  40                  45

Leu Thr Ser Gln Thr Thr Asp Tyr Thr Ala His Asn Ala Val His Ser
    50                  55                  60

Thr Asp Ser Ala Asp Phe Asp Asn Phe Asn Gly Tyr Leu Thr Ala Ser
65                  70                  75                  80

Ser Trp Tyr Arg Pro Lys Asp Val Leu Arg Asn Gly Gln His Trp Glu
                85                  90                  95
```

```
Ala Thr Thr Ala Asn Asp Phe Arg Pro Ile Val Ser Val Trp Trp Pro
            100                 105                 110

Ser Lys Gln Thr Gln Val Asn Tyr Leu Asn Tyr Met Ser Gln Met Gly
        115                 120                 125

Leu Ile Asp Asn Arg Gln Met Phe Ser Leu Lys Asp Asn Gln Ala Met
    130                 135                 140

Leu Asn Ile Ala Cys Thr Thr Val Gln Gln Ala Ile Glu Thr Lys Ile
145                 150                 155                 160

Gly Val Ala Asn Ser Thr Ala Trp Leu Lys Thr Ala Ile Asp Asp Phe
                165                 170                 175

Ile Arg Thr Gln Pro Gln Trp Asn Met Ser Ser Glu Asp Pro Lys Asn
            180                 185                 190

Asp His Leu Gln Asn Gly Ala Leu Thr Phe Val Asn Ser Pro Leu Thr
        195                 200                 205

Pro Asp Thr Asn Ser Asn Phe Arg Leu Leu Asn Arg Thr Pro Thr Asn
    210                 215                 220

Gln Thr Gly Val Pro Lys Tyr Thr Ile Asp Gln Ser Lys Gly Gly Phe
225                 230                 235                 240

Glu Leu Leu Leu Ala Asn Asp Val Asp Asn Ser Asn Pro Val Val Gln
                245                 250                 255

Ala Glu Gln Leu Asn Trp Leu His Tyr Leu Met Asn Phe Gly Ser Ile
            260                 265                 270

Thr Ala Asn Asp Ser Ala Ala Asn Phe Asp Gly Ile Arg Val Asp Ala
        275                 280                 285

Val Asp Asn Val Asp Ala Asp Leu Leu Gln Ile Ala Ala Asp Tyr Phe
    290                 295                 300

Lys Ala Ala Tyr Gly Val Asp Lys Asn Asp Ala Thr Ala Asn Gln His
305                 310                 315                 320

Leu Ser Ile Leu Glu Asp Trp Ser His Asn Asp Pro Glu Tyr Val Lys
                325                 330                 335

Asp Phe Gly Asn Asn Gln Leu Thr Met Asp Asp Tyr Met His Thr Gln
            340                 345                 350

Leu Ile Trp Ser Leu Thr Lys Asp Met Arg Met Arg Gly Thr Met Gln
        355                 360                 365

Arg Phe Met Asp Tyr Tyr Leu Val Asn Arg Asn His Asp Ser Thr Glu
    370                 375                 380

Asn Thr Ala Ile Pro Asn Tyr Ser Phe Val Arg Ala His Asp Ser Glu
385                 390                 395                 400

Val Gln Thr Val Ile Ala Gln Ile Ile Ser Glu Leu His Pro Asp Val
                405                 410                 415

Lys Asn Ser Leu Ala Pro Thr Ala Asp Gln Leu Ala Glu Ala Phe Lys
            420                 425                 430

Ile Tyr Asn Asn Asp Glu Lys Gln Ala Asp Lys Lys Tyr Thr Gln Tyr
        435                 440                 445

Asn Met Pro Ser Ala Tyr Ala Met Leu Leu Thr Asn Lys Asp Thr Val
    450                 455                 460

Pro Arg Val Tyr Tyr Gly Asp Leu Tyr Thr Asp Asp Gly Gln Tyr Met
465                 470                 475                 480

Ala Asn Lys Ser Pro Tyr Phe Asp Ala Ile Asn Gly Leu Leu Lys Ser
                485                 490                 495

Arg Ile Lys Tyr Val Ala Gly Gly Gln Ser Met Ala Val Asp Gln Asn
            500                 505                 510
```

```
Asp Ile Leu Thr Asn Val Arg Tyr Gly Lys Gly Ala Met Ser Val Thr
        515                 520                 525

Asp Ser Gly Asn Ala Asp Thr Arg Thr Gln Gly Ile Gly Val Ile Val
    530                 535                 540

Ser Asn Lys Glu Asn Leu Ala Leu Lys Ser Gly Asp Thr Val Thr Leu
545                 550                 555                 560

His Met Gly Ala Ala His Lys Asn Gln Ala Phe Arg Leu Leu Leu Gly
                565                 570                 575

Thr Thr Ala Asp Asn Leu Ser Tyr Tyr Asp Asn Asp Asn Ala Pro Val
            580                 585                 590

Lys Tyr Thr Asn Asp Gln Gly Asp Leu Ile Phe Asp Asn Thr Glu Ile
        595                 600                 605

Tyr Gly Val Arg Asn Pro Gln Val Ser Gly Phe Leu Ala Val Trp Val
    610                 615                 620

Pro Val Gly Ala Asp Ser His Gln Asp Ala Arg Thr Leu Ser Asp Asp
625                 630                 635                 640

Thr Ala His His Asp Gly Lys Thr Phe His Ser Asn Ala Ala Leu Asp
                645                 650                 655

Ser Gln Val Ile Tyr Glu Gly Phe Ser Asn Phe Gln Ala Phe Ala Thr
            660                 665                 670

Asn Thr Glu Asp Tyr Thr Asn Ala Val Ile Ala Lys Asn Gly Gln Leu
        675                 680                 685

Phe Lys Asp Trp Gly Ile Thr Ser Phe Gln Leu Ala Pro Gln Tyr Arg
    690                 695                 700

Ser Ser Thr Asp Thr Ser Phe Leu Asp Ser Ile Ile Gln Asn Gly Tyr
705                 710                 715                 720

Ala Phe Thr Asp Arg Tyr Asp Leu Gly Tyr Gly Thr Pro Thr Lys Tyr
                725                 730                 735

Gly Thr Val Asp Gln Leu Arg Asp Ala Ile Lys Ala Leu His Ala Asn
            740                 745                 750

Gly Ile Gln Ala Ile Ala Asp Trp Val Pro Asp Gln Ile Tyr Asn Leu
        755                 760                 765

Pro Gly Gln Glu Leu Ala Thr Val Thr Arg Thr Asn Ser Tyr Gly Asp
    770                 775                 780

Lys Asp Thr Asn Ser Asp Ile Asp Gln Ser Leu Tyr Val Ile Gln Ser
785                 790                 795                 800

Arg Gly Gly Gly Lys Tyr Gln Ala Gln Tyr Gly Gly Ala Phe Leu Ser
                805                 810                 815

Asp Ile Gln Lys Lys Tyr Pro Ala Leu Phe Glu Thr Lys Gln Ile Ser
            820                 825                 830

Thr Gly Leu Pro Met Asp Pro Ser Gln Lys Ile Thr Glu Trp Ser Gly
        835                 840                 845

Lys Tyr Phe Asn Gly Ser Asn Ile Gln Gly Lys Gly Ala Gly Tyr Val
    850                 855                 860

Leu Lys Asp Ser Gly Thr Asp Gln Tyr Tyr Lys Val Thr Ser Asn Asn
865                 870                 875                 880

Asn Asn Arg Asp Phe Leu Pro Lys Gln Leu Thr Asp Asp Leu Ser Glu
                885                 890                 895

Thr Gly Phe Val Arg Asp Asn Ile Gly Met Val Tyr Tyr Thr Leu Ser
            900                 905                 910

Gly Tyr Leu Ala Arg Asn Thr Phe Ile Gln Asp Asp Asn Gly Asn Tyr
        915                 920                 925

Tyr Tyr Phe Asp Ser Thr Gly His Leu Val Thr Gly Phe Gln Asn Ile
```

```
    930                 935                 940

Asn Asn His His Tyr Phe Phe Leu Pro Asn Gly Ile Glu Leu Val Gln
945                 950                 955                 960

Ser Phe Leu Gln Asn Ala Asp Gly Ser Thr Ile Tyr Phe Asp Gln Lys
                965                 970                 975

Gly Arg Gln Val Phe Asn Gln Tyr Ile Thr Asp Gln Thr Gly Thr Ala
            980                 985                 990

Tyr Tyr Phe Gln Asn Asp Gly Thr  Met Val Thr Ser Gly  Phe Thr Glu
        995                 1000                 1005

Ile Asp  Gly His Lys Gln Tyr  Phe Tyr Lys Asn Gly  Thr Gln Val
    1010                 1015                 1020

Lys Gly  Gln Phe Val Ser Asp  Thr Asp Gly His Val  Phe Tyr Leu
    1025                 1030                 1035

Glu Ala  Gly Asn Gly Asn Val  Ala Thr Gln Arg Phe  Ala Gln Asn
    1040                 1045                 1050

Ser Gln  Gly Gln Trp Phe Tyr  Leu Gly Asn Asp Gly  Ile Ala Leu
    1055                 1060                 1065

Thr Gly  Leu Gln Thr Ile Asn  Gly Val Gln Asn Tyr  Phe Tyr Ala
    1070                 1075                 1080

Asp Gly  His Gln Ser Lys Gly  Asp Phe Ile Thr Ile  Gln Asn His
    1085                 1090                 1095

Val Leu  Tyr Thr Asn Pro Leu  Thr Gly Ala Ile Thr  Thr Gly Met
    1100                 1105                 1110

Gln Gln  Ile Gly Asp Lys Ile  Phe Val Phe Asp Asn  Thr Gly Asn
    1115                 1120                 1125

Met Leu  Thr Asn Gln Tyr Tyr  Gln Thr Leu Asp Gly  Gln Trp Leu
    1130                 1135                 1140

His Leu  Ser Thr Gln Gly Pro  Ala Asp Thr Gly Leu  Val Asn Ile
    1145                 1150                 1155

Asn Gly  Asn Leu Lys Tyr Phe  Gln Ala Asn Gly Arg  Gln Val Lys
    1160                 1165                 1170

Gly Gln  Phe Val Thr Asp Pro  Ile Thr Asn Val Ser  Tyr Tyr Met
    1175                 1180                 1185

Asn Ala  Thr Asp Gly Ser Ala  Val Phe Asn Asp Tyr  Phe Thr Tyr
    1190                 1195                 1200

Gln Gly  Gln Trp Tyr Leu Thr  Asp Ser Asn Tyr Gln  Leu Val Lys
    1205                 1210                 1215

Gly Phe  Lys Val Val Asn Asn  Lys Leu Gln His Phe  Asp Glu Ile
    1220                 1225                 1230

Thr Gly  Val Gln Thr Lys Ser  Ala His Ile Ile Val  Asn Asn Arg
    1235                 1240                 1245

Thr Tyr  Ile Phe Asp Asp Gln  Gly Tyr Phe Val Ser  Val Ala
    1250                 1255                 1260
```

<210> SEQ ID NO 55
<211> LENGTH: 4284
<212> TYPE: DNA
<213> ORGANISM: Streptococcus salivarius

<400> SEQUENCE: 55

```
atgaaagacg gcaagtacta ttacctgttg gaggacggta gccacaagaa aaactttgcg     60

atcacggtca acggccaagt gctgtatttc gatgagaacg gtgcactgag cagcacgtct    120

acctattcgt ttacccagga gactaccaac ctggttaccg atttcactaa gaataatgct    180
```

```
gcgtacgaca gcaccaaggc ttccttcgag ctggttgatg gctacctgac tgcggacagc    240
tggtatcgtc cgaaggaaat cctggaggct ggcaccacct ggaaagcgag caccgagaaa    300
gactttcgtc cgctgctgat gagctggtgg ccggataaag acacccaggt tgcgtacctg    360
aattacatga cgaaggcgct gagcaatggc gaggaaacga aagacgtgtt tacgatcgag    420
aactcccaag catctctgaa cgcagccgct cagatcatcc aacgcaagat cgaggtcaag    480
attgcagcga acaaaagcac ggactggctg cgccagagca tcgaggcgtt cgtgaaagat    540
caagacaagt ggaatatcaa ttcggagagc ccgggtaaag agcatttcca aaaaggtgct    600
ctgctgttcg ttaacagcga cctgaccaaa tgggcgaata gcgactatcg taaactggac    660
caaacggcga ccagccgtct gccgaaagac aagattaaga gcggcagcga tgcgggctac    720
gagtttttgc tgtcctctga cattgataac agcaacccga ttgttcaggc ggagatgctg    780
aaccaactgt actatttcat gaactggggt cagattgtgt ttggcgacaa agataaggat    840
gcccatttcg acggtatccg cgtcgacgcc gtagacaacg ttagcattga tatgctgcaa    900
ctggttagct cttatatgaa ggcggcatac aaagttaatg aaagcgaagc gcgtgcactg    960
gcaaacattt ccattctgga ggcttggagc cagaacgatc cgtactacgt tgatgaacac   1020
aacacggctg cgctgtctat ggacaacggt ctgcgcctga gcatcgttca cggtttgacc   1080
cgtccggtta ctaacaaggg taccggtgcc cgtaatgcaa gcatgaaaga cctgatcaac   1140
ggtggctact tcggcttgtc caatcgtgca gaagttacga gctacgatca gctgggcttc   1200
gccacctacc tgtttgtgcg tgcccatgac tctgaagttc agaccgttat cgcggacatt   1260
atctcgaaga aaatcgatcc aaccacggac ggtttcacgt tcaccctgga ccagttgaaa   1320
caagccttcg acatctacaa cgccgatatg ctgaaggttg ataaggagta cacgcacagc   1380
aacatcccgg ctgcgtatgc cctgatgctg caaactatgg gtgcggctac gcgcgtgtat   1440
tatggtgatt tgtatacgga caatggccag tacatggcga aaaagagccc gtactttgat   1500
cagatcacga ccctgctgaa ggcgcgtagc aagtacgttg cgggtggcca gaccagctac   1560
atccataacc tggcgggtga tggtgtcagc agcgcgaagg ataacaaaga ggtgttggtc   1620
agcgtccgct acggtcagga tttgatgagc aaaaccgaca ccgagggtgg taagtatggt   1680
cgtaacagcg gtatgctgac cctgatcgcc aacaaccctg atctgaagct ggcagacggt   1740
gaaaccatca ccgtcaacat gggcgcagcg cacaagaatc aagcatatcg tccgttgttg   1800
ctgggcaccg aaaagggcat tgtgagcagc ctgaatgatt ccgacacgaa aattgttaag   1860
tataccgacg cgcaaggcaa tctggttttt accgctgatg agatcaaagg tttcaaaacc   1920
gtggatatga gcggttacct gtccgtgtgg gtgccggttg gcgcgaccga ggaccaaaac   1980
gtgctggcca agccgagcac gaaggtctac aaagagggtg ataaagttta ttcgagcagc   2040
gcggcactgg aagcacaggt gatctacgag ggttttagca attttcaaga cttcgtgaag   2100
gaagatagcc agtataccaa caagctgatt gcggccaatg cggacctgtt caaaagctgg   2160
ggtattacga gctttgaaat cgctccgcag tatgttagct ccaaggatgg caccttcctg   2220
gatagcatca ttgagaatgg ctacgcgttt accgatcgtt acgacttcgc gatgtcgaaa   2280
aacaataagt acggctccaa agaggatctg cgtgacgcgt tgaaagccct gcacaaacaa   2340
ggcattcaag ttattgcaga ttgggtcccg gaccagctgt acaccctgcc gggtaaggaa   2400
gtggtcacgg cgacccgcac ggacacccac ggtaaagtcc tggatgacac ctccctggtc   2460
aataaactgt acgttaccaa taccaaatct agcggtaacg acttccaggc gcaatacggc   2520
ggtgcattcc tggacaaact gcaaaagttg tacccggaga ttttcaagga agtgatggag   2580
```

```
gctagcggca aaaccattga tccgtccgtc aaaatcaagc agtgggaggc aaagtatttc   2640

aacggtacga acattcagaa acgcggtagc gactacgttc tgagcgacgg caaactgtat   2700

ttcacggtaa acgacaaagg taccttcttg ccggcagctc tgaccggtga cacgaaggca   2760

aagaccggtt tcgcctatga cggtactggc gtcacttact atacgacctc cggcacgcag   2820

gcaaagagcc aatttgtcac ctacaatggc aagcagtact atttcaatga caaaggttat   2880

ctggtcacgg gtgaacaggc gattgacggt agcaactact tcttcctgcc gaacggcgtt   2940

atgtttacgg acggtgtgat caaaaatgct aaaggtcagt ctctggtcta cggcaaatct   3000

ggtaagctga ccacgcaaac cggttggaag gaagttacgg tgaaggatga tagcggcaag   3060

gaagagaaat tctaccaata cttctttaag ggtggcatta tggcgacggg tctgaccgag   3120

gttgaaggta aagagaaata cttttatgat aatggttatc aggctaaagg tattttcatc   3180

cctaccaaag acggccatct gatgtttttc tgcggtgata gcggtgagcg taaatacagc   3240

ggtttcttcg aacaagacgg taactggtat tacgcaaacg ataaaggtta cgtcgcgacc   3300

ggttttacca aagtgggtaa gcagaacttg tactttaacg agaaaggtgt gcaggtcaag   3360

aaccgtttct ttcaggttgg tgatgctact tattacgcga ataacgaggg tgatgtactg   3420

cgtggtgcac agacgatcaa cggcgacgaa ctgtacttcg acgaaagcgg caagcaagtc   3480

aaaggtgaat ttgtgaataa cccggacggt accacgagct attatgacgc aattaccggt   3540

gtgaaactgg tggacaccag cttggtcgtt aatggtcaaa cgttcaacat tgacgctaaa   3600

ggcgttgtca ccaaggcgca cacgccgggt ttctatacca ctggcgacaa caattggttt   3660

tatgcagata gccacggtcg caatgtcact ggcgcacaga tcattaacgg ccaacacctg   3720

tatttcgatg cgaatggccg tcaggtgaag ggcggctttg ttatgaacac tgatggttct   3780

cgttcgttct atcattggaa taccggtgat aaactggtga gcacgttctt tacgaccggc   3840

cacgatcgtt ggtactacgc cgacgacaaa ggtaacgtgg tgaccggcgc acaagtcatc   3900

aacggtcaga aattgttctt cgcgaccgac ggtaaacaag ttaagggcga tttcgcgacc   3960

aacgcaaatg gttcccgttc ttactatcac ggtgccacgg gtaataagct ggtcagcacc   4020

ttctttacca cgggcgataa caactggtac tatgcagacg cgaagggcga ggttgtcgtt   4080

ggtgaacaaa cgattaacgg tcaaaatctg tattttgatc agaccggtaa gcaagtgaaa   4140

ggtgcgaccg cgaccaatcc agatggcagc atttcttatt acgatgttca cacgggcgag   4200

aaggtcatca accgctgggt caaaattccg agcggtcaat gggtgtactt caacgcgcag   4260

ggtaagggtt acgtcagcaa ttaa                                          4284
```

<210> SEQ ID NO 56
<211> LENGTH: 1427
<212> TYPE: PRT
<213> ORGANISM: Streptococcus salivarius

<400> SEQUENCE: 56

```
Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60
```

```
Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
        115                 120                 125

Asn Gly Glu Glu Thr Lys Asp Val Phe Thr Ile Glu Asn Ser Gln Ala
    130                 135                 140

Ser Leu Asn Ala Ala Ala Gln Ile Ile Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Leu
        195                 200                 205

Thr Lys Trp Ala Asn Ser Asp Tyr Arg Lys Leu Asp Gln Thr Ala Thr
    210                 215                 220

Ser Arg Leu Pro Lys Asp Lys Ile Lys Ser Gly Ser Asp Ala Gly Tyr
225                 230                 235                 240

Glu Phe Leu Leu Ser Ser Asp Ile Asp Asn Ser Asn Pro Ile Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
        275                 280                 285

Asp Ala Val Asp Asn Val Ser Ile Asp Met Leu Gln Leu Val Ser Ser
    290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser Gln Asn Asp Pro Tyr Tyr
                325                 330                 335

Val Asp Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
        355                 360                 365

Gly Ala Arg Asn Ala Ser Met Lys Asp Leu Ile Asn Gly Gly Tyr Phe
    370                 375                 380

Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
            420                 425                 430

Thr Phe Thr Leu Asp Gln Leu Lys Gln Ala Phe Asp Ile Tyr Asn Ala
        435                 440                 445

Asp Met Leu Lys Val Asp Lys Glu Tyr Thr His Ser Asn Ile Pro Ala
    450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
```

```
                485                 490                 495

Pro Tyr Phe Asp Gln Ile Thr Thr Leu Leu Lys Ala Arg Ser Lys Tyr
            500                 505                 510

Val Ala Gly Gly Gln Thr Ser Tyr Ile His Asn Leu Ala Gly Asp Gly
        515                 520                 525

Val Ser Ser Ala Lys Asp Asn Lys Glu Val Leu Val Ser Val Arg Tyr
    530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Leu Gly Thr Glu Lys Gly Ile Val
        595                 600                 605

Ser Ser Leu Asn Asp Ser Asp Thr Lys Ile Val Lys Tyr Thr Asp Ala
    610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Glu Asp Gln Asn Val Leu Ala Lys Pro Ser Thr Lys Val Tyr Lys Glu
            660                 665                 670

Gly Asp Lys Val Tyr Ser Ser Ser Ala Ala Leu Glu Ala Gln Val Ile
        675                 680                 685

Tyr Glu Gly Phe Ser Asn Phe Gln Asp Phe Val Lys Glu Asp Ser Gln
    690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Asn Lys Tyr Gly Ser Lys Glu
        755                 760                 765

Asp Leu Arg Asp Ala Leu Lys Ala Leu His Lys Gln Gly Ile Gln Val
    770                 775                 780

Ile Ala Asp Trp Val Pro Asp Gln Leu Tyr Thr Leu Pro Gly Lys Glu
785                 790                 795                 800

Val Val Thr Ala Thr Arg Thr Asp Thr His Gly Lys Val Leu Asp Asp
                805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
        835                 840                 845

Lys Leu Tyr Pro Glu Ile Phe Lys Glu Val Met Glu Ala Ser Gly Lys
    850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
                885                 890                 895

Gly Lys Leu Tyr Phe Thr Val Asn Asp Lys Gly Thr Phe Leu Pro Ala
            900                 905                 910
```

```
Ala Leu Thr Gly Asp Thr Lys Ala Lys Thr Gly Phe Ala Tyr Asp Gly
        915                 920                 925

Thr Gly Val Thr Tyr Tyr Thr Thr Ser Gly Thr Gln Ala Lys Ser Gln
    930                 935                 940

Phe Val Thr Tyr Asn Gly Lys Gln Tyr Tyr Phe Asn Asp Lys Gly Tyr
945                 950                 955                 960

Leu Val Thr Gly Glu Gln Ala Ile Asp Gly Ser Asn Tyr Phe Phe Leu
                965                 970                 975

Pro Asn Gly Val Met Phe Thr Asp Gly Val Ile Lys Asn Ala Lys Gly
            980                 985                 990

Gln Ser Leu Val Tyr Gly Lys Ser  Gly Lys Leu Thr Thr  Gln Thr Gly
        995                 1000                 1005

Trp Lys  Glu Val Thr Val Lys  Asp Asp Ser Gly Lys  Glu Glu Lys
    1010                 1015                 1020

Phe Tyr  Gln Tyr Phe Phe Lys  Gly Gly Ile Met Ala  Thr Gly Leu
    1025                 1030                 1035

Thr Glu  Val Glu Gly Lys Glu  Lys Tyr Phe Tyr Asp  Asn Gly Tyr
    1040                 1045                 1050

Gln Ala  Lys Gly Ile Phe Ile  Pro Thr Lys Asp Gly  His Leu Met
    1055                 1060                 1065

Phe Phe  Cys Gly Asp Ser Gly  Glu Arg Lys Tyr Ser  Gly Phe Phe
    1070                 1075                 1080

Glu Gln  Asp Gly Asn Trp Tyr  Tyr Ala Asn Asp Lys  Gly Tyr Val
    1085                 1090                 1095

Ala Thr  Gly Phe Thr Lys Val  Gly Lys Gln Asn Leu  Tyr Phe Asn
    1100                 1105                 1110

Glu Lys  Gly Val Gln Val Lys  Asn Arg Phe Phe Gln  Val Gly Asp
    1115                 1120                 1125

Ala Thr  Tyr Tyr Ala Asn Asn  Glu Gly Asp Val Leu  Arg Gly Ala
    1130                 1135                 1140

Gln Thr  Ile Asn Gly Asp Glu  Leu Tyr Phe Asp Glu  Ser Gly Lys
    1145                 1150                 1155

Gln Val  Lys Gly Glu Phe Val  Asn Asn Pro Asp Gly  Thr Thr Ser
    1160                 1165                 1170

Tyr Tyr  Asp Ala Ile Thr Gly  Val Lys Leu Val Asp  Thr Ser Leu
    1175                 1180                 1185

Val Val  Asn Gly Gln Thr Phe  Asn Ile Asp Ala Lys  Gly Val Val
    1190                 1195                 1200

Thr Lys  Ala His Thr Pro Gly  Phe Tyr Thr Thr Gly  Asp Asn Asn
    1205                 1210                 1215

Trp Phe  Tyr Ala Asp Ser His  Gly Arg Asn Val Thr  Gly Ala Gln
    1220                 1225                 1230

Ile Ile  Asn Gly Gln His Leu  Tyr Phe Asp Ala Asn  Gly Arg Gln
    1235                 1240                 1245

Val Lys  Gly Gly Phe Val Met  Asn Thr Asp Gly Ser  Arg Ser Phe
    1250                 1255                 1260

Tyr His  Trp Asn Thr Gly Asp  Lys Leu Val Ser Thr  Phe Phe Thr
    1265                 1270                 1275

Thr Gly  His Asp Arg Trp Tyr  Tyr Ala Asp Asp Lys  Gly Asn Val
    1280                 1285                 1290

Val Thr  Gly Ala Gln Val Ile  Asn Gly Gln Lys Leu  Phe Phe Ala
    1295                 1300                 1305
```

```
Thr Asp  Gly Lys Gln Val Lys  Gly Asp Phe Ala Thr  Asn Ala Asn
    1310                 1315                 1320

Gly Ser  Arg Ser Tyr Tyr His  Gly Ala Thr Gly Asn  Lys Leu Val
    1325                 1330                 1335

Ser Thr  Phe Phe Thr Thr Gly  Asp Asn Asn Trp Tyr  Tyr Ala Asp
    1340                 1345                 1350

Ala Lys  Gly Glu Val Val Val  Gly Glu Gln Thr Ile  Asn Gly Gln
    1355                 1360                 1365

Asn Leu  Tyr Phe Asp Gln Thr  Gly Lys Gln Val Lys  Gly Ala Thr
    1370                 1375                 1380

Ala Thr  Asn Pro Asp Gly Ser  Ile Ser Tyr Tyr Asp  Val His Thr
    1385                 1390                 1395

Gly Glu  Lys Val Ile Asn Arg  Trp Val Lys Ile Pro  Ser Gly Gln
    1400                 1405                 1410

Trp Val  Tyr Phe Asn Ala Gln  Gly Lys Gly Tyr Val  Ser Asn
    1415                 1420                 1425
```

<210> SEQ ID NO 57
<211> LENGTH: 5208
<212> TYPE: DNA
<213> ORGANISM: Lactobacillus reuteri

<400> SEQUENCE: 57

```
atggatcagc aagtacaaag cagcaccacc caggagcaga cgagcacggt taacgcggac     60

acgactaaaa ccgtcaatct ggataccaac actgaccagc cggctcagac gaccgataag    120

aatcaggtcg cgaatgatac caccaccaac caaagcaaga cggacagcac cagcacgacg    180

gttaagaatc cgacgtttat tcctgttagc actttgtcca gctccgataa cgaaaagcag    240

agccagaatt acaataaacc agataacggt aattacggta atgttgatgc ggcctacttc    300

aataacaatc agctgcacat tagcggttgg cacgcaacca acgcgagcca gggtacggat    360

agccgccaag taatcgtacg cgacattacc accaagaccg agctgggtcg tactaatgtg    420

accaacaatg ttctgcgtcc ggacgtgaaa aatgttcaca acgtctacaa cgctgacaac    480

agcggctttg atgtgaatat caatattgat ttcagcaaga tgaaagacta tcgtgacagc    540

atcgagatcg tttctcgtta tagcggcaac ggcaagagcg ttgactggtg gtcgcagccg    600

atcacgtttg acaaaaacaa ttatgcttat ctggacactt tcgaggtgaa gaacggtgaa    660

ctgcatgcaa cgggctggaa tgccaccaac aaggctatca attacaatca ccacttcgtt    720

attctgtttg atcgtacgaa tggcaaagaa gtcacccgcc aagaggtgcg tgatggtcaa    780

agccgtccgg atgtggcgaa ggtataccg caagtcgttg gcgcgaacaa tagcggtttt    840

gacgttacgt ttaacattgg tgatttggac tacacccatc agtaccagat cctgtctcgt    900

tacagcaacg cagacaacgg tgaaggcgat tatgtgacct attggtttgc gccgcagagc    960

atcgctccgg cgaatcaaag caaccaaggt tacctggaca gcttcgatat ttcgaaaaac   1020

ggtgaggtga ccgtgacggg ttggaatgcg acggatctga gcgagttgca aacgaatcac   1080

tacgtgatcc tgtttgatca gacggcgggt caacaggttg catccgctaa ggtcgacctg   1140

atcagccgtc cagacgtcgc gaaggcgtac cctaccgtta aaacggcaga aacctccggt   1200

ttcaaggtca cgtttaaggt tagcaatctg caaccgggcc accaatacag cgtcgttagc   1260

cgctttagcg ccgatgaaaa cggtaatggc aacgacaaac gccacacgga ctactggtac   1320

tctccggtta ccctgaacca aacggctagc aacattgaca ctatcaccat gacttccaac   1380

ggtctgcaca tcaccggctg gatggcgagc gataatagca ttaacgaagc gaccccgtac   1440
```

```
gcgattatcc tgaacaacgg tcgcgaggtg acgcgccaga aactgaccct gatcgcgcgt   1500
ccggatgttg cggcagtgta tccgagcctg tacaatagcg cggttagcgg cttcgacacc   1560
accatcaagc tgactaacgc gcaatatcaa gcattgaacg gccagctgca agtgctgctg   1620
cgctttagca aggcggtgga cggtaacccg aatggtacca ataccgtcac ggatcaattt   1680
agcaaaaact acgcaacgac cggtggtaat ttcgattacg tcaaggttaa tggtaaccaa   1740
attgagtttt ctggctggca cgcgacgaat cagagcaatg ataagaacag ccaatggatt   1800
atcgtcttgg ttaacggtaa agaggtcaaa cgccagctgg tcaatgacac gaaagacggc   1860
gcagccggct tcaatcgtaa tgatgtgtat aaagtgaacc cagcgatcga aaatagcatt   1920
atgtctggct tccagggcat tatcacgttg ccggttacgg tgaaagacga aaacgtgcag   1980
ctggtgcacc gcttctccaa tgacgcaaaa acgggtgagg gcaattatgt cgatttctgg   2040
agcgaggtga tgtctgtgaa ggactctttc caaaagggta atggtccgct gaaccagttt   2100
ggcctgcaaa ccatcaacgg ccaacaatac tatattgacc cgacgaccgg ccagccgcgt   2160
aagaatttcc tgctgcaaaa cggcaacgat tggatttact tcgacaaaga cactggcgca   2220
ggcaccaacg cgctgaaatt gcagtttgat aagggcacga ttagcgctga cgaacaatac   2280
cgtcgcggca acgaggcgta ctcctacgat gataagagca ttgaaaatgt caacggttac   2340
ttgacggcgg acacgtggta ccgcccgaag cagatcctga aggatggcac cacttggacc   2400
gattccaaag aaaccgatat gcgtccgatc ttgatggtct ggtggccaaa cacggtgact   2460
caggcgtact atctgaacta catgaaacaa tatggcaatc tgctgccggc gagcctgccg   2520
agctttagca ccgacgccga tagcgcggag ttgaatcatt attccgagct ggtccaacag   2580
aatatcgaga aacgtattag cgagactggt agcactgatt ggctgcgtac cctgatgcac   2640
gagttcgtga cgaagaatag catgtggaac aaagatagcg agaacgttga ctacggtggc   2700
ctgcaactgc aaggtggttt cctgaagtac gttaacagcg acctgacgaa gtacgcaaac   2760
tctgattggc gtctgatgaa ccgtaccgcg acgaacattg acggtaagaa ttacggtggt   2820
gccgagtttc tgctggcgaa tgacatcgac aactctaacc cggtggtgca ggccgaagaa   2880
ttgaattggc tgtattatct gatgaacttc ggtaccatca ccggtaacaa cccagaagct   2940
aacttcgacg gcatccgtgt cgacgcggtc gataatgtgg atgttgatct gctgagcatt   3000
gcccgtgact actttaatgc agcgtataac atggaacaaa gcgatgctag cgcgaataag   3060
cacatcaata ttctggaaga ttggggctgg gacgatccgg cgtacgtgaa caaaatcggc   3120
aatccacagt tgaccatgga tgaccgcctg cgtaatgcaa ttatggacac cctgagcggt   3180
gcgccggata agaaccaagc gctgaacaag ctgattactc agtctctggt gaatcgcgca   3240
aatgataata ctgaaaacgc ggtgatccct tcctacaact ttgtccgcgc tcatgacagc   3300
aatgcccagg accagatccg tcaagcgatc caggcggcaa ccggcaaacc ttatggcgag   3360
ttcaacttgg atgatgagaa aaagggtatg gaggcttaca tcaatgacca aaatagcacc   3420
aataagaaat ggaacctgta caacatgccg agcgcatata ccatcctgct gacgaataag   3480
gactcggtcc cgcgtgtcta ctatggcgac ttgtaccagg atggtggcca gtacatggaa   3540
cacaaaactc gttactttga caccatcacg aatctgctga aacccgcgt caagtatgtc    3600
gcaggcggcc agaccatgtc tgtggataag aatggcattt tgactaatgt ccgtttcggt   3660
aagggtgcga tgaacgcaac tgacacgggt accgatgaaa cccgcaccga aggtatcggc   3720
gttgttatca gcaacaatac gaatttgaaa ctgaatgacg gcgaaagcgt tgtgctgcac   3780
```

```
atgggcgctg cccataagaa tcagaagtat cgtgcagtga tcctgaccac ggaggacggt   3840

gtgaagaatt acaccaacga caccgatgcg ccggtcgcat acaccgacgc gaacggcgat   3900

ttgcatttca ccaatactaa cctggacggt cagcaatata ccgccgttcg tggctacgca   3960

aacccggacg ttacgggtta tctggccgtc tgggttcctg ctggtgccgc cgatgaccaa   4020

gacgcacgta ccgctccgag cgacgaggcc cacaccacga aaacggcgta tcgttccaat   4080

gcggcattgg actccaacgt catctacgaa ggcttttcga actttatcta ttggccgacg   4140

accgagagcg agcgcacgaa tgtccgcatc gcgcagaacg cggatctgtt caaatcgtgg   4200

ggtatcacca ccttcgagct ggcgccacag tacaatagca gcaaggacgg tacgtttctg   4260

gattcgatca ttgacaatgg ttacgcgttt accgatcgtt atgacctggg tatgtctacc   4320

ccgaacaagt acggtagcga tgaggatctg cgtaacgccc tgcaagcact gcacaaggcc   4380

ggtctgcaag ccatcgcaga ttgggttccg gaccaaatct acaatctgcc gggcaaagag   4440

gctgtcacgg ttactcgtag cgatgaccac ggcactacct gggaggttag cccgatcaag   4500

aatgtggtgt atatcactaa taccatcggt ggtggcgaat accagaaaaa gtatggtggt   4560

gaatttctgg acaccttgca aaaagaatat ccgcagctgt ttagccaagt ttacccggtg   4620

acccaaacga cgattgaccc tagcgttaag attaaagagt ggtccgcgaa gtacttcaat   4680

ggtactaata tcctgcatcg cggtgcgggt tacgtcctgc gtagcaatga tggtaagtat   4740

tacaacctgg gtactagcac ccagcagttc ctgccgagcc agctgagcgt tcaagataat   4800

gagggttacg gtttcgttaa agagggtaac aactatcact attatgacga gaacaaacaa   4860

atggttaagg acgcgtttat ccaggatagc gtcggcaatt ggtactattt tgataagaac   4920

ggcaatatgg ttgcaaacca aagcccggtt gaaatcagca gcaacggtgc gagcggcacc   4980

tacttgtttt tgaataatgg taccagcttc cgcagcggcc tggtcaaaac ggatgcaggc   5040

acctattact acgatggtga cggtcgcatg gttcgtaatc aaacggtttc tgacggtgcc   5100

atgacgtacg ttctggacga aaatggtaaa ctggtcagcg aatcttttga tagcagcgcg   5160

accgaggccc atccgctgaa accgggcgat ctgaacggtc aaaagtaa               5208
```

```
<210> SEQ ID NO 58
<211> LENGTH: 1735
<212> TYPE: PRT
<213> ORGANISM: Lactobacillus reuteri

<400> SEQUENCE: 58

Met Asp Gln Gln Val Gln Ser Ser Thr Thr Gln Glu Gln Thr Ser Thr
1               5                   10                  15

Val Asn Ala Asp Thr Thr Lys Thr Val Asn Leu Asp Thr Asn Thr Asp
            20                  25                  30

Gln Pro Ala Gln Thr Thr Asp Lys Asn Gln Val Ala Asn Asp Thr Thr
        35                  40                  45

Thr Asn Gln Ser Lys Thr Asp Ser Thr Ser Thr Thr Val Lys Asn Pro
    50                  55                  60

Thr Phe Ile Pro Val Ser Thr Leu Ser Ser Ser Asp Asn Glu Lys Gln
65                  70                  75                  80

Ser Gln Asn Tyr Asn Lys Pro Asp Asn Gly Asn Tyr Gly Asn Val Asp
                85                  90                  95

Ala Ala Tyr Phe Asn Asn Asn Gln Leu His Ile Ser Gly Trp His Ala
            100                 105                 110

Thr Asn Ala Ser Gln Gly Thr Asp Ser Arg Gln Val Ile Val Arg Asp
        115                 120                 125
```

```
Ile Thr Thr Lys Thr Glu Leu Gly Arg Thr Asn Val Thr Asn Asn Val
    130                 135                 140

Leu Arg Pro Asp Val Lys Asn Val His Asn Val Tyr Asn Ala Asp Asn
145                 150                 155                 160

Ser Gly Phe Asp Val Asn Ile Asn Ile Asp Phe Ser Lys Met Lys Asp
                165                 170                 175

Tyr Arg Asp Ser Ile Glu Ile Val Ser Arg Tyr Ser Gly Asn Gly Lys
            180                 185                 190

Ser Val Asp Trp Trp Ser Gln Pro Ile Thr Phe Asp Lys Asn Asn Tyr
        195                 200                 205

Ala Tyr Leu Asp Thr Phe Glu Val Lys Asn Gly Glu Leu His Ala Thr
    210                 215                 220

Gly Trp Asn Ala Thr Asn Lys Ala Ile Asn Tyr Asn His His Phe Val
225                 230                 235                 240

Ile Leu Phe Asp Arg Thr Asn Gly Lys Glu Val Thr Arg Gln Glu Val
                245                 250                 255

Arg Asp Gly Gln Ser Arg Pro Asp Val Ala Lys Val Tyr Pro Gln Val
            260                 265                 270

Val Gly Ala Asn Asn Ser Gly Phe Asp Val Thr Phe Asn Ile Gly Asp
        275                 280                 285

Leu Asp Tyr Thr His Gln Tyr Gln Ile Leu Ser Arg Tyr Ser Asn Ala
    290                 295                 300

Asp Asn Gly Glu Gly Asp Tyr Val Thr Tyr Trp Phe Ala Pro Gln Ser
305                 310                 315                 320

Ile Ala Pro Ala Asn Gln Ser Asn Gln Gly Tyr Leu Asp Ser Phe Asp
                325                 330                 335

Ile Ser Lys Asn Gly Glu Val Thr Val Thr Gly Trp Asn Ala Thr Asp
            340                 345                 350

Leu Ser Glu Leu Gln Thr Asn His Tyr Val Ile Leu Phe Asp Gln Thr
        355                 360                 365

Ala Gly Gln Gln Val Ala Ser Ala Lys Val Asp Leu Ile Ser Arg Pro
    370                 375                 380

Asp Val Ala Lys Ala Tyr Pro Thr Val Lys Thr Ala Glu Thr Ser Gly
385                 390                 395                 400

Phe Lys Val Thr Phe Lys Val Ser Asn Leu Gln Pro Gly His Gln Tyr
                405                 410                 415

Ser Val Val Ser Arg Phe Ser Ala Asp Glu Asn Gly Asn Gly Asn Asp
            420                 425                 430

Lys Arg His Thr Asp Tyr Trp Tyr Ser Pro Val Thr Leu Asn Gln Thr
        435                 440                 445

Ala Ser Asn Ile Asp Thr Ile Thr Met Thr Ser Asn Gly Leu His Ile
    450                 455                 460

Thr Gly Trp Met Ala Ser Asp Asn Ser Ile Asn Glu Ala Thr Pro Tyr
465                 470                 475                 480

Ala Ile Ile Leu Asn Asn Gly Arg Glu Val Thr Arg Gln Lys Leu Thr
                485                 490                 495

Leu Ile Ala Arg Pro Asp Val Ala Ala Val Tyr Pro Ser Leu Tyr Asn
            500                 505                 510

Ser Ala Val Ser Gly Phe Asp Thr Thr Ile Lys Leu Thr Asn Ala Gln
        515                 520                 525

Tyr Gln Ala Leu Asn Gly Gln Leu Gln Val Leu Leu Arg Phe Ser Lys
    530                 535                 540
```

```
Ala Val Asp Gly Asn Pro Asn Gly Thr Asn Thr Val Thr Asp Gln Phe
545                 550                 555                 560

Ser Lys Asn Tyr Ala Thr Thr Gly Gly Asn Phe Asp Tyr Val Lys Val
                565                 570                 575

Asn Gly Asn Gln Ile Glu Phe Ser Gly Trp His Ala Thr Asn Gln Ser
            580                 585                 590

Asn Asp Lys Asn Ser Gln Trp Ile Ile Val Leu Val Asn Gly Lys Glu
        595                 600                 605

Val Lys Arg Gln Leu Val Asn Asp Thr Lys Asp Gly Ala Ala Gly Phe
    610                 615                 620

Asn Arg Asn Asp Val Tyr Lys Val Asn Pro Ala Ile Glu Asn Ser Ile
625                 630                 635                 640

Met Ser Gly Phe Gln Gly Ile Ile Thr Leu Pro Val Thr Val Lys Asp
                645                 650                 655

Glu Asn Val Gln Leu Val His Arg Phe Ser Asn Asp Ala Lys Thr Gly
            660                 665                 670

Glu Gly Asn Tyr Val Asp Phe Trp Ser Glu Val Met Ser Val Lys Asp
        675                 680                 685

Ser Phe Gln Lys Gly Asn Gly Pro Leu Asn Gln Phe Gly Leu Gln Thr
    690                 695                 700

Ile Asn Gly Gln Gln Tyr Tyr Ile Asp Pro Thr Thr Gly Gln Pro Arg
705                 710                 715                 720

Lys Asn Phe Leu Leu Gln Asn Gly Asn Asp Trp Ile Tyr Phe Asp Lys
                725                 730                 735

Asp Thr Gly Ala Gly Thr Asn Ala Leu Lys Leu Gln Phe Asp Lys Gly
            740                 745                 750

Thr Ile Ser Ala Asp Glu Gln Tyr Arg Arg Gly Asn Glu Ala Tyr Ser
        755                 760                 765

Tyr Asp Asp Lys Ser Ile Glu Asn Val Asn Gly Tyr Leu Thr Ala Asp
    770                 775                 780

Thr Trp Tyr Arg Pro Lys Gln Ile Leu Lys Asp Gly Thr Thr Trp Thr
785                 790                 795                 800

Asp Ser Lys Glu Thr Asp Met Arg Pro Ile Leu Met Val Trp Trp Pro
                805                 810                 815

Asn Thr Val Thr Gln Ala Tyr Tyr Leu Asn Tyr Met Lys Gln Tyr Gly
            820                 825                 830

Asn Leu Leu Pro Ala Ser Leu Pro Ser Phe Ser Thr Asp Ala Asp Ser
        835                 840                 845

Ala Glu Leu Asn His Tyr Ser Glu Leu Val Gln Gln Asn Ile Glu Lys
    850                 855                 860

Arg Ile Ser Glu Thr Gly Ser Thr Asp Trp Leu Arg Thr Leu Met His
865                 870                 875                 880

Glu Phe Val Thr Lys Asn Ser Met Trp Asn Lys Asp Ser Glu Asn Val
                885                 890                 895

Asp Tyr Gly Gly Leu Gln Leu Gln Gly Gly Phe Leu Lys Tyr Val Asn
            900                 905                 910

Ser Asp Leu Thr Lys Tyr Ala Asn Ser Asp Trp Arg Leu Met Asn Arg
        915                 920                 925

Thr Ala Thr Asn Ile Asp Gly Lys Asn Tyr Gly Gly Ala Glu Phe Leu
    930                 935                 940

Leu Ala Asn Asp Ile Asp Asn Ser Asn Pro Val Val Gln Ala Glu Glu
945                 950                 955                 960

Leu Asn Trp Leu Tyr Tyr Leu Met Asn Phe Gly Thr Ile Thr Gly Asn
```

```
                965                 970                 975

Asn Pro Glu Ala Asn Phe Asp Gly Ile Arg Val Asp Ala Val Asp Asn
            980                 985                 990

Val Asp Val Asp Leu Leu Ser Ile  Ala Arg Asp Tyr Phe  Asn Ala Ala
        995                 1000                1005

Tyr Asn  Met Glu Gln Ser Asp  Ala Ser Ala Asn Lys  His Ile Asn
    1010                 1015                 1020

Ile Leu  Glu Asp Trp Gly Trp  Asp Asp Pro Ala Tyr  Val Asn Lys
    1025                 1030                 1035

Ile Gly  Asn Pro Gln Leu Thr  Met Asp Asp Arg Leu  Arg Asn Ala
    1040                 1045                 1050

Ile Met  Asp Thr Leu Ser Gly  Ala Pro Asp Lys Asn  Gln Ala Leu
    1055                 1060                 1065

Asn Lys  Leu Ile Thr Gln Ser  Leu Val Asn Arg Ala  Asn Asp Asn
    1070                 1075                 1080

Thr Glu  Asn Ala Val Ile Pro  Ser Tyr Asn Phe Val  Arg Ala His
    1085                 1090                 1095

Asp Ser  Asn Ala Gln Asp Gln  Ile Arg Gln Ala Ile  Gln Ala Ala
    1100                 1105                 1110

Thr Gly  Lys Pro Tyr Gly Glu  Phe Asn Leu Asp Asp  Glu Lys Lys
    1115                 1120                 1125

Gly Met  Glu Ala Tyr Ile Asn  Asp Gln Asn Ser Thr  Asn Lys Lys
    1130                 1135                 1140

Trp Asn  Leu Tyr Asn Met Pro  Ser Ala Tyr Thr Ile  Leu Leu Thr
    1145                 1150                 1155

Asn Lys  Asp Ser Val Pro Arg  Val Tyr Tyr Gly Asp  Leu Tyr Gln
    1160                 1165                 1170

Asp Gly  Gly Gln Tyr Met Glu  His Lys Thr Arg Tyr  Phe Asp Thr
    1175                 1180                 1185

Ile Thr  Asn Leu Leu Lys Thr  Arg Val Lys Tyr Val  Ala Gly Gly
    1190                 1195                 1200

Gln Thr  Met Ser Val Asp Lys  Asn Gly Ile Leu Thr  Asn Val Arg
    1205                 1210                 1215

Phe Gly  Lys Gly Ala Met Asn  Ala Thr Asp Thr Gly  Thr Asp Glu
    1220                 1225                 1230

Thr Arg  Thr Glu Gly Ile Gly  Val Val Ile Ser Asn  Asn Thr Asn
    1235                 1240                 1245

Leu Lys  Leu Asn Asp Gly Glu  Ser Val Val Leu His  Met Gly Ala
    1250                 1255                 1260

Ala His  Lys Asn Gln Lys Tyr  Arg Ala Val Ile Leu  Thr Thr Glu
    1265                 1270                 1275

Asp Gly  Val Lys Asn Tyr Thr  Asn Asp Thr Asp Ala  Pro Val Ala
    1280                 1285                 1290

Tyr Thr  Asp Ala Asn Gly Asp  Leu His Phe Thr Asn  Thr Asn Leu
    1295                 1300                 1305

Asp Gly  Gln Gln Tyr Thr Ala  Val Arg Gly Tyr Ala  Asn Pro Asp
    1310                 1315                 1320

Val Thr  Gly Tyr Leu Ala Val  Trp Val Pro Ala Gly  Ala Ala Asp
    1325                 1330                 1335

Asp Gln  Asp Ala Arg Thr Ala  Pro Ser Asp Glu Ala  His Thr Thr
    1340                 1345                 1350

Lys Thr  Ala Tyr Arg Ser Asn  Ala Ala Leu Asp Ser  Asn Val Ile
    1355                 1360                 1365
```

```
Tyr Glu  Gly Phe Ser Asn Phe  Ile Tyr Trp Pro Thr  Thr Glu Ser
    1370                 1375                 1380

Glu Arg  Thr Asn Val Arg Ile  Ala Gln Asn Ala Asp  Leu Phe Lys
    1385                 1390                 1395

Ser Trp  Gly Ile Thr Thr Phe  Glu Leu Ala Pro Gln  Tyr Asn Ser
    1400                 1405                 1410

Ser Lys  Asp Gly Thr Phe Leu  Asp Ser Ile Ile Asp  Asn Gly Tyr
    1415                 1420                 1425

Ala Phe  Thr Asp Arg Tyr Asp  Leu Gly Met Ser Thr  Pro Asn Lys
    1430                 1435                 1440

Tyr Gly  Ser Asp Glu Asp Leu  Arg Asn Ala Leu Gln  Ala Leu His
    1445                 1450                 1455

Lys Ala  Gly Leu Gln Ala Ile  Ala Asp Trp Val Pro  Asp Gln Ile
    1460                 1465                 1470

Tyr Asn  Leu Pro Gly Lys Glu  Ala Val Thr Val Thr  Arg Ser Asp
    1475                 1480                 1485

Asp His  Gly Thr Thr Trp Glu  Val Ser Pro Ile Lys  Asn Val Val
    1490                 1495                 1500

Tyr Ile  Thr Asn Thr Ile Gly  Gly Gly Glu Tyr Gln  Lys Lys Tyr
    1505                 1510                 1515

Gly Gly  Glu Phe Leu Asp Thr  Leu Gln Lys Glu Tyr  Pro Gln Leu
    1520                 1525                 1530

Phe Ser  Gln Val Tyr Pro Val  Thr Gln Thr Thr Ile  Asp Pro Ser
    1535                 1540                 1545

Val Lys  Ile Lys Glu Trp Ser  Ala Lys Tyr Phe Asn  Gly Thr Asn
    1550                 1555                 1560

Ile Leu  His Arg Gly Ala Gly  Tyr Val Leu Arg Ser  Asn Asp Gly
    1565                 1570                 1575

Lys Tyr  Tyr Asn Leu Gly Thr  Ser Thr Gln Gln Phe  Leu Pro Ser
    1580                 1585                 1590

Gln Leu  Ser Val Gln Asp Asn  Glu Gly Tyr Gly Phe  Val Lys Glu
    1595                 1600                 1605

Gly Asn  Asn Tyr His Tyr Tyr  Asp Glu Asn Lys Gln  Met Val Lys
    1610                 1615                 1620

Asp Ala  Phe Ile Gln Asp Ser  Val Gly Asn Trp Tyr  Tyr Phe Asp
    1625                 1630                 1635

Lys Asn  Gly Asn Met Val Ala  Asn Gln Ser Pro Val  Glu Ile Ser
    1640                 1645                 1650

Ser Asn  Gly Ala Ser Gly Thr  Tyr Leu Phe Leu Asn  Asn Gly Thr
    1655                 1660                 1665

Ser Phe  Arg Ser Gly Leu Val  Lys Thr Asp Ala Gly  Thr Tyr Tyr
    1670                 1675                 1680

Tyr Asp  Gly Asp Gly Arg Met  Val Arg Asn Gln Thr  Val Ser Asp
    1685                 1690                 1695

Gly Ala  Met Thr Tyr Val Leu  Asp Glu Asn Gly Lys  Leu Val Ser
    1700                 1705                 1710

Glu Ser  Phe Asp Ser Ser Ala  Thr Glu Ala His Pro  Leu Lys Pro
    1715                 1720                 1725

Gly Asp  Leu Asn Gly Gln Lys
    1730                 1735
```

<210> SEQ ID NO 59
<211> LENGTH: 1242

<212> TYPE: PRT
<213> ORGANISM: Unknown
<220> FEATURE:
<223> OTHER INFORMATION: unknown Streptococcus species

<400> SEQUENCE: 59

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
        195                 200                 205

Ala Leu Leu Tyr Asn Asn Ser Asn Arg Thr Ser Tyr Ala Asn Ser Asp
    210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
        275                 280                 285

Glu Asn Phe Asp Gly Val Arg Val Asp Ala Val Asp Asn Val Asn Ala
    290                 295                 300

Asp Leu Leu Gln Ile Ala Ser Asp Tyr Phe Lys Ala Lys Tyr Gly Val
305                 310                 315                 320

Glu Lys Ser Glu Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
            340                 345                 350

Leu Pro Met Asp Asp Pro Leu Arg Leu Ala Met Val Phe Ser Phe Leu
        355                 360                 365

Arg Pro Ile Gly Asn Arg Ser Gly Leu Glu Pro Leu Ile Thr Asn Ser
    370                 375                 380
```

```
Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
        435                 440                 445

Arg Ser Ala Asn Lys Arg Tyr Thr Gln Tyr Asn Ile Pro Ser Ala Tyr
    450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
                485                 490                 495

His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
        515                 520                 525

Gly Trp Asp Ala Ser Gly Val Leu Thr Ser Val Arg Tyr Gly Lys Gly
    530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
        595                 600                 605

Asp Ala Asn Gly Ile Val Lys Tyr Thr Asp Ala Asn Gly Tyr Leu Thr
    610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
        675                 680                 685

Phe Gln Asp Phe Val Gln Asp Pro Ser Gln Tyr Thr Asn Lys Lys Ile
    690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
        755                 760                 765

Lys Ser Leu His Ala Val Gly Ile Ser Ala Ile Ala Asp Trp Val Pro
    770                 775                 780

Asp Gln Ile Tyr Asn Leu Pro Gly Asp Glu Val Val Thr Ala Thr Arg
785                 790                 795                 800

Val Asn Asn Tyr Gly Glu Thr Lys Asp Gly Ala Ile Ile Asp His Ser
```

```
                805                 810                 815

Leu Tyr Val Ala Lys Thr Arg Thr Phe Gly Asn Asp Tyr Gln Gly Lys
            820                 825                 830

Tyr Gly Gly Ala Tyr Leu Asp Glu Leu Lys Arg Leu Tyr Pro Gln Phe
        835                 840                 845

Phe Asp Arg Val Gln Ile Ser Thr Gly Lys Arg Leu Thr Thr Asp Glu
    850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
            900                 905                 910

Gln Ser Thr Asn Asn Asn Asn Gln Asn Gly Asp Gly Ser Gly Arg Phe
        915                 920                 925

Glu Lys Ser Trp Gly Ser Val Tyr Tyr Arg Tyr Asn Asp Gly Gln Arg
    930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe  Tyr Tyr Asp Glu Asn  Gly Ile Met
        995                 1000                 1005

Ser Gln  Thr Gly Lys Pro Ser  Pro Lys Pro Glu Pro  Lys Pro Asp
    1010                 1015                 1020

Asn Asn  Thr Phe Ser Arg Asn  Gln Phe Ile Gln Ile  Gly Asn Asn
    1025                 1030                 1035

Val Trp  Ala Tyr Tyr Asp Gly  Asn Gly Lys Arg Val  Ile Gly Arg
    1040                 1045                 1050

Gln Asn  Ile Asn Gly Gln Glu  Leu Phe Phe Asp Asn  Asn Gly Val
    1055                 1060                 1065

Gln Val  Lys Gly Arg Thr Ala  Gln Val Asp Gly Val  Thr Arg Tyr
    1070                 1075                 1080

Phe Asp  Ala Asn Ser Gly Glu  Met Ala Arg Asn Arg  Phe Ala Glu
    1085                 1090                 1095

Val Glu  Pro Gly Val Trp Ala  Tyr Phe Asn Asn Asp  Gly Ala Ala
    1100                 1105                 1110

Val Thr  Gly Ser Gln Asn Ile  Asn Gly Gln Thr Leu  Tyr Phe Asp
    1115                 1120                 1125

Gln Asn  Gly His Gln Val Lys  Gly Ala Leu Val Thr  Val Asp Gly
    1130                 1135                 1140

Asn Leu  Arg Tyr Tyr Asp Ala  Asn Ser Gly Asp Leu  Tyr Arg Asn
    1145                 1150                 1155

Arg Phe  Gln Glu Val Asn Gly  Ser Trp Tyr Tyr Phe  Asp Gly Asn
    1160                 1165                 1170

Gly Asn  Ala Val Lys Gly Met  Val Asn Ile Asn Gly  Gln Asn Leu
    1175                 1180                 1185

Leu Phe  Asp Asn Asp Gly Lys  Gln Val Lys Gly His  Leu Val Arg
    1190                 1195                 1200

Val Asn  Gly Val Ile Arg Tyr  Tyr Asp Pro Asn Ser  Gly Glu Met
    1205                 1210                 1215
```

```
Ala Val  Asn Arg Trp Val Glu  Ile Ser Ser Gly Trp  Trp Val Tyr
    1220                 1225                 1230

Phe Asp  Gly Glu Gly Arg Gly  Gln Ile
    1235                 1240


<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
```

-continued

```
            340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
        435                 440                 445

Tyr Leu Met Asn Trp Gly Ser Ile Val Met Gly Asp Lys Asp Ala Asn
    450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
        515                 520                 525

Met Glu Asn Lys Gln Arg Leu Ala Leu Leu Phe Ser Leu Ala Lys Pro
    530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
    610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
    690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765
```

```
Thr Ser Gly Gln Val Thr Leu Val Ala Asn Asn Pro Lys Leu Asn Leu
    770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
    850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
            980                 985                 990

Gly Ile Gln Ala Ile Ala Asp Trp  Val Pro Asp Gln Ile  Tyr Gln Leu
        995                 1000                1005

Pro Gly  Lys Glu Val Val Thr  Ala Thr Arg Thr Asp  Gly Ala Gly
    1010                 1015                1020

Arg Lys  Ile Ala Asp Ala Ile  Ile Asp His Ser Leu  Tyr Val Ala
    1025                 1030                1035

Asn Ser  Lys Ser Ser Gly Lys  Asp Tyr Gln Ala Lys  Tyr Gly Gly
    1040                 1045                1050

Glu Phe  Leu Ala Glu Leu Lys  Ala Lys Tyr Pro Glu  Met Phe Lys
    1055                 1060                1065

Val Asn  Met Ile Ser Thr Gly  Lys Pro Ile Asp Asp  Ser Val Lys
    1070                 1075                1080

Leu Lys  Gln Trp Lys Ala Glu  Tyr Phe Asn Gly Thr  Asn Val Leu
    1085                 1090                1095

Glu Arg  Gly Val Gly Tyr Val  Leu Ser Asp Glu Ala  Thr Gly Lys
    1100                 1105                1110

Tyr Phe  Thr Val Thr Lys Glu  Gly Asn Phe Ile Pro  Leu Gln Leu
    1115                 1120                1125

Thr Gly  Lys Glu Lys Val Ile  Thr Gly Phe Ser Ser  Asp Gly Lys
    1130                 1135                1140

Gly Ile  Thr Tyr Phe Gly Thr  Ser Gly Thr Gln Ala  Lys Ser Ala
    1145                 1150                1155

Phe Val  Thr Phe Asn Gly Asn  Thr Tyr Tyr Phe Asp  Ala Arg Gly
    1160                 1165                1170
```

```
His Met  Val Thr Asn Ser Glu  Tyr Ser Pro Asn Gly  Lys Asp Val
    1175                 1180                 1185

Tyr Arg  Phe Leu Pro Asn Gly  Ile Met Leu Ser Asn  Ala Phe Tyr
    1190                 1195                 1200

Ile Asp  Ala Asn Gly Asn Thr  Tyr Leu Tyr Asn Ser  Lys Gly Gln
    1205                 1210                 1215

Met Tyr  Lys Gly Gly Tyr Thr  Lys Phe Asp Val Ser  Glu Thr Asp
    1220                 1225                 1230

Lys Asp  Gly Lys Glu Ser Lys  Val Val Lys Phe Arg  Tyr Phe Thr
    1235                 1240                 1245

Asn Glu  Gly Val Met Ala Lys  Gly Val Thr Val Ile  Asp Gly Phe
    1250                 1255                 1260

Thr Gln  Tyr Phe Gly Glu Asp  Gly Phe Gln Ala Lys  Asp Lys Leu
    1265                 1270                 1275

Val Thr  Phe Lys Gly Lys Thr  Tyr Tyr Phe Asp Ala  His Thr Gly
    1280                 1285                 1290

Asn Gly  Ile Lys Asp Thr Trp  Arg Asn Ile Asn Gly  Lys Trp Tyr
    1295                 1300                 1305

Tyr Phe  Asp Ala Asn Gly Val  Ala Ala Thr Gly Ala  Gln Val Ile
    1310                 1315                 1320

Asn Gly  Gln Lys Leu Tyr Phe  Asn Glu Asp Gly Ser  Gln Val Lys
    1325                 1330                 1335

Gly Gly  Val Val Lys Asn Ala  Asp Gly Thr Tyr Ser  Lys Tyr Lys
    1340                 1345                 1350

Glu Gly  Phe Gly Glu Leu Val  Thr Asn Glu Phe Phe  Thr Thr Asp
    1355                 1360                 1365

Gly Asn  Val Trp Tyr Tyr Ala  Gly Ala Asn Gly Lys  Thr Val Thr
    1370                 1375                 1380

Gly Ala  Gln Val Ile Asn Gly  Gln His Leu Tyr Phe  Asn Ala Asp
    1385                 1390                 1395

Gly Ser  Gln Val Lys Gly Gly  Val Val Lys Asn Ala  Asp Gly Thr
    1400                 1405                 1410

Tyr Ser  Lys Tyr Asn Ala Ser  Thr Gly Glu Arg Leu  Thr Asn Glu
    1415                 1420                 1425

Phe Phe  Thr Thr Gly Asp Asn  Asn Trp Tyr Tyr Ile  Gly Ala Asn
    1430                 1435                 1440

Gly Lys  Ser Val Thr Gly Glu  Val Lys Ile Gly Asp  Asp Thr Tyr
    1445                 1450                 1455

Phe Phe  Ala Lys Asp Gly Lys  Gln Val Lys Gly Gln  Thr Val Ser
    1460                 1465                 1470

Ala Gly  Asn Gly Arg Ile Ser  Tyr Tyr Tyr Gly Asp  Ser Gly Lys
    1475                 1480                 1485

Arg Ala  Val Ser Thr Trp Ile  Glu Ile Gln Pro Gly  Val Tyr Val
    1490                 1495                 1500

Tyr Phe  Asp Lys Asn Gly Leu  Ala Tyr Pro Pro Arg  Val Leu Asn
    1505                 1510                 1515
```

<210> SEQ ID NO 61
<211> LENGTH: 1528
<212> TYPE: PRT
<213> ORGANISM: Streptococcus salivarius

<400> SEQUENCE: 61

```
Met Thr Asn Lys Ile Thr Gly Lys Ile Ile Met Glu Asn Lys Val His
1               5                   10                  15
```

```
Tyr Lys Leu His Lys Val Lys Lys Gln Trp Val Thr Ile Ala Val Ala
            20                  25                  30

Ser Ala Ala Leu Ala Thr Val Val Gly Gly Leu Ser Ala Thr Thr Ser
        35                  40                  45

Ser Val Ser Ala Asp Glu Thr Gln Asp Lys Ile Val Thr Gln Pro Asn
    50                  55                  60

Leu Asp Thr Thr Ala Asp Leu Val Thr Ser Thr Glu Ala Thr Lys Glu
65                  70                  75                  80

Val Asp Lys Arg Thr Asn Thr Lys Glu Ala Asp Val Leu Thr Pro Ala
                85                  90                  95

Lys Glu Thr Asn Ala Val Glu Thr Ala Thr Thr Thr Asn Thr Gln Ala
            100                 105                 110

Thr Ala Glu Ala Ala Thr Thr Ala Thr Thr Ser Asp Val Ala Val Ala
        115                 120                 125

Ala Val Pro Asn Lys Glu Ala Val Val Thr Thr Asp Ala Pro Ala Val
    130                 135                 140

Thr Thr Glu Lys Ala Glu Glu Gln Pro Ala Thr Val Lys Ala Glu Val
145                 150                 155                 160

Val Asn Thr Glu Val Lys Ala Pro Gln Ala Ala Leu Lys Asp Ser Glu
                165                 170                 175

Val Glu Ala Ala Leu Ser Leu Lys Asn Ile Lys Tyr Thr Asp Gly Lys
            180                 185                 190

Tyr Tyr Tyr Val Asn Glu Asp Gly Ser His Lys Glu Asn Phe Ala Ile
        195                 200                 205

Thr Val Asn Gly Gln Leu Leu Tyr Phe Gly Lys Asp Gly Ala Leu Thr
    210                 215                 220

Ser Ser Ser Thr His Ser Phe Thr Pro Gly Thr Thr Asn Ile Val Asp
225                 230                 235                 240

Gly Phe Ser Ile Asn Asn Arg Ala Tyr Asp Ser Ser Glu Ala Ser Phe
                245                 250                 255

Glu Leu Ile Asn Gly Tyr Leu Thr Ala Asp Ser Trp Tyr Arg Pro Val
            260                 265                 270

Ser Ile Ile Lys Asp Gly Val Thr Trp Gln Ala Ser Thr Ala Glu Asp
        275                 280                 285

Phe Arg Pro Leu Leu Met Ala Trp Trp Pro Asn Val Asp Thr Gln Val
    290                 295                 300

Asn Tyr Leu Asn Tyr Met Ser Lys Val Phe Asn Leu Glu Ala Lys Tyr
305                 310                 315                 320

Thr Ser Thr Asp Lys Gln Ala Asp Leu Asn Arg Ala Ala Lys Asp Ile
                325                 330                 335

Gln Val Lys Ile Glu Gln Lys Ile Gln Ala Glu Lys Ser Thr Gln Trp
            340                 345                 350

Leu Arg Glu Thr Ile Ser Ala Phe Val Lys Thr Gln Pro Gln Trp Asn
        355                 360                 365

Lys Glu Thr Glu Asn Tyr Ser Lys Gly Gly Gly Glu Asp His Leu Gln
    370                 375                 380

Gly Gly Ala Leu Leu Tyr Val Asn Asp Ser Arg Thr Pro Trp Ala Asn
385                 390                 395                 400

Ser Asn Tyr Arg Leu Leu Asn Arg Thr Ala Thr Asn Gln Thr Gly Thr
                405                 410                 415

Ile Asn Lys Ser Val Leu Asp Glu Gln Ser Asp Pro Asn His Met Gly
            420                 425                 430
```

```
Gly Phe Asp Phe Leu Leu Ala Asn Asp Val Asp Leu Ser Asn Pro Val
        435                 440                 445

Val Gln Ala Glu Gln Leu Asn Gln Ile His Tyr Leu Met Asn Trp Gly
    450                 455                 460

Ser Ile Val Met Gly Asp Lys Asp Ala Asn Phe Asp Gly Ile Arg Val
465                 470                 475                 480

Asp Ala Val Asp Asn Val Asn Ala Asp Met Leu Gln Leu Tyr Thr Asn
                485                 490                 495

Tyr Phe Arg Glu Tyr Tyr Gly Val Asn Lys Ser Glu Ala Gln Ala Leu
            500                 505                 510

Ala His Ile Ser Val Leu Glu Ala Trp Ser Leu Asn Asp Asn His Tyr
        515                 520                 525

Asn Asp Lys Thr Asp Gly Ala Ala Leu Ala Met Glu Asn Lys Gln Arg
    530                 535                 540

Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
        595                 600                 605

Gly Asp Ala Ser Gly Asn Tyr Val Phe Ile Arg Ala His Asp Asn Asn
    610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
            660                 665                 670

Asn Ile Pro Ala Ala Tyr Ala Val Met Leu Gln Asn Met Glu Thr Ile
        675                 680                 685

Thr Arg Val Tyr Tyr Gly Asp Leu Tyr Thr Asp Asp Gly His Tyr Met
    690                 695                 700

Glu Thr Lys Ser Pro Tyr His Asp Thr Ile Val Asn Leu Met Lys Asn
705                 710                 715                 720

Arg Ile Lys Tyr Val Ser Gly Gly Gln Ala Gln Arg Ser Tyr Trp Leu
                725                 730                 735

Pro Thr Asp Gly Lys Met Asp Asn Ser Asp Val Glu Leu Tyr Arg Thr
            740                 745                 750

Ser Glu Val Tyr Thr Ser Val Arg Tyr Gly Lys Asp Ile Met Thr Ala
        755                 760                 765

Asp Asp Thr Glu Gly Ser Lys Tyr Ser Arg Thr Ser Gly Gln Val Thr
    770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
                805                 810                 815

Ile Val Gly Thr Ala Asp Gly Ile Lys Asn Phe Thr Ser Asp Ala Glu
            820                 825                 830

Ala Ile Ala Ala Gly Tyr Val Lys Glu Thr Asp Ser Asn Gly Val Leu
        835                 840                 845

Thr Phe Gly Ala Asn Asp Ile Lys Gly Tyr Glu Thr Phe Asp Met Ser
```

```
    850                 855                 860

Gly Phe Val Ala Val Trp Val Pro Val Gly Ala Ser Asp Asp Gln Asp
865                 870                 875                 880

Ile Arg Val Ala Pro Ser Thr Glu Ala Lys Lys Glu Gly Glu Leu Thr
                885                 890                 895

Leu Lys Ala Thr Glu Ala Tyr Asp Ser Gln Leu Ile Tyr Glu Gly Phe
            900                 905                 910

Ser Asn Phe Gln Thr Ile Pro Asp Gly Ser Asp Pro Ser Val Tyr Thr
        915                 920                 925

Asn Arg Lys Ile Ala Glu Asn Val Asp Leu Phe Lys Ser Trp Gly Val
    930                 935                 940

Thr Ser Phe Glu Met Ala Pro Gln Phe Val Ser Ala Asp Asp Gly Thr
945                 950                 955                 960

Phe Leu Asp Ser Val Ile Gln Asn Gly Tyr Ala Phe Ala Asp Arg Tyr
                965                 970                 975

Asp Leu Ala Met Ser Lys Asn Asn Lys Tyr Gly Ser Lys Glu Asp Leu
            980                 985                 990

Arg Asp Ala Leu Lys Ala Leu His  Lys Ala Gly Ile Gln  Ala Ile Ala
        995                 1000                1005

Asp Trp  Val Pro Asp Gln Ile  Tyr Gln Leu Pro Gly  Lys Glu Val
    1010                1015                1020

Val Thr  Ala Thr Arg Thr Asp  Gly Ala Gly Arg Lys  Ile Ala Asp
    1025                1030                1035

Ala Ile  Ile Asp His Ser Leu  Tyr Val Ala Asn Ser  Lys Ser Ser
    1040                1045                1050

Gly Arg  Asp Tyr Gln Ala Gln  Tyr Gly Gly Glu Phe  Leu Ala Glu
    1055                1060                1065

Leu Lys  Ala Lys Tyr Pro Lys  Met Phe Thr Glu Asn  Met Ile Ser
    1070                1075                1080

Thr Gly  Lys Pro Ile Asp Asp  Ser Val Lys Leu Lys  Gln Trp Lys
    1085                1090                1095

Ala Lys  Tyr Phe Asn Gly Thr  Asn Val Leu Asp Arg  Gly Val Gly
    1100                1105                1110

Tyr Val  Leu Ser Asp Glu Ala  Thr Gly Lys Tyr Phe  Thr Val Thr
    1115                1120                1125

Lys Glu  Gly Asn Phe Ile Pro  Leu Gln Leu Thr Gly  Asn Glu Lys
    1130                1135                1140

Ala Val  Thr Gly Phe Ser Asn  Asp Gly Lys Gly Ile  Thr Tyr Phe
    1145                1150                1155

Gly Thr  Ser Gly Asn Gln Ala  Lys Ser Ala Phe Val  Thr Phe Asn
    1160                1165                1170

Gly Asn  Thr Tyr Tyr Phe Asp  Ala Arg Gly His Met  Val Thr Asn
    1175                1180                1185

Gly Glu  Tyr Ser Pro Asn Gly  Lys Asp Val Tyr Arg  Phe Leu Pro
    1190                1195                1200

Asn Gly  Ile Met Leu Ser Asn  Ala Phe Tyr Val Asp  Ala Asn Gly
    1205                1210                1215

Asn Thr  Tyr Leu Tyr Asn Tyr  Lys Gly Gln Met Tyr  Lys Gly Gly
    1220                1225                1230

Tyr Thr  Lys Phe Asp Val Thr  Glu Thr Asp Lys Asp  Gly Asn Glu
    1235                1240                1245

Ser Lys  Val Val Lys Phe Arg  Tyr Phe Thr Asn Glu  Gly Val Met
    1250                1255                1260
```

```
Ala Lys Gly Leu Thr Val Ile Asp Gly Ser Thr Gln Tyr Phe Gly
    1265                1270                1275

Glu Asp Gly Phe Gln Thr Lys Asp Lys Leu Ala Thr Tyr Lys Gly
    1280                1285                1290

Lys Thr Tyr Tyr Phe Glu Ala His Thr Gly Asn Ala Ile Lys Asn
    1295                1300                1305

Thr Trp Arg Asn Ile Asp Gly Lys Trp Tyr His Phe Asp Glu Asn
    1310                1315                1320

Gly Val Ala Ala Thr Gly Ala Gln Val Ile Asn Gly Gln Lys Leu
    1325                1330                1335

Tyr Phe Asn Glu Asp Gly Ser Gln Val Lys Gly Gly Val Val Lys
    1340                1345                1350

Asn Ala Asp Gly Thr Tyr Ser Lys Tyr Lys Glu Gly Ser Gly Glu
    1355                1360                1365

Leu Val Thr Asn Glu Phe Phe Thr Thr Asp Gly Asn Val Trp Tyr
    1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
    1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
    1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
    1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
    1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
    1520                1525
```

<210> SEQ ID NO 62
<211> LENGTH: 1518
<212> TYPE: PRT
<213> ORGANISM: Streptococcus salivarius

<400> SEQUENCE: 62

```
Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
```

```
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
        435                 440                 445

Tyr Leu Met Asn Trp Gly Ser Ile Val Met Gly Asp Lys Asp Ala Asn
    450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
            500                 505                 510
```

```
Leu Asn Asp Asn His Tyr Asn Asp Lys Thr Asp Gly Ala Ala Leu Ala
        515                 520                 525

Met Glu Asn Lys Gln Arg Leu Ala Leu Leu Phe Ser Leu Ala Lys Pro
    530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
    610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
    690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Thr Leu
    770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
    850                 855                 860

Ala Ser Asp Asp Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925
```

```
Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
            980                 985                 990

Gly Ile Gln Ala Ile Ala Asp Trp  Val Pro Asp Gln Ile  Tyr Gln Leu
        995                 1000                1005

Pro Gly  Lys Glu Val Val Thr  Ala Thr Arg Thr Asp  Gly Ala Gly
    1010                1015                1020

Arg Lys  Ile Ala Asp Ala Ile  Ile Asp His Ser Leu  Tyr Val Ala
    1025                1030                1035

Asn Thr  Lys Ser Ser Gly Lys  Asp Tyr Gln Ala Lys  Tyr Gly Gly
    1040                1045                1050

Glu Phe  Leu Ala Glu Leu Lys  Ala Lys Tyr Pro Glu  Met Phe Lys
    1055                1060                1065

Val Asn  Met Ile Ser Thr Gly  Lys Pro Ile Asp Asp  Ser Val Lys
    1070                1075                1080

Leu Lys  Gln Trp Lys Ala Glu  Tyr Phe Asn Gly Thr  Asn Val Leu
    1085                1090                1095

Glu Arg  Gly Val Gly Tyr Val  Leu Ser Asp Glu Ala  Thr Gly Lys
    1100                1105                1110

Tyr Phe  Thr Val Thr Lys Asp  Gly Asn Phe Ile Pro  Leu Gln Leu
    1115                1120                1125

Thr Gly  Asn Glu Lys Val Val  Thr Gly Phe Ser Asn  Asp Gly Lys
    1130                1135                1140

Gly Ile  Thr Tyr Phe Gly Thr  Ser Gly Thr Gln Ala  Lys Ser Ala
    1145                1150                1155

Phe Val  Thr Phe Asn Gly Asn  Thr Tyr Tyr Phe Asp  Ala Arg Gly
    1160                1165                1170

His Met  Val Thr Asn Gly Glu  Tyr Ser Pro Asn Gly  Lys Asp Val
    1175                1180                1185

Tyr Arg  Phe Leu Pro Asn Gly  Ile Met Leu Ser Asn  Ala Phe Tyr
    1190                1195                1200

Val Asp  Ala Asn Gly Asn Thr  Tyr Leu Tyr Asn Ser  Lys Gly Gln
    1205                1210                1215

Met Tyr  Lys Gly Gly Tyr Thr  Lys Phe Asp Val Thr  Glu Thr Asp
    1220                1225                1230

Lys Asp  Gly Lys Glu Ser Lys  Val Val Lys Phe Arg  Tyr Phe Thr
    1235                1240                1245

Asn Glu  Gly Val Met Ala Lys  Gly Val Thr Val Ile  Asp Gly Phe
    1250                1255                1260

Thr Gln  Tyr Phe Gly Glu Asp  Gly Phe Gln Ala Lys  Asp Lys Leu
    1265                1270                1275

Val Thr  Phe Lys Gly Lys Thr  Tyr Tyr Phe Asp Ala  His Thr Gly
    1280                1285                1290

Asn Ala  Ile Lys Asp Thr Trp  Arg Asn Ile Asn Gly  Lys Trp Tyr
    1295                1300                1305

His Phe  Asp Ala Asn Gly Val  Ala Ala Thr Gly Ala  Gln Val Ile
    1310                1315                1320

Asn Gly  Gln Lys Leu Tyr Phe  Asn Glu Asp Gly Ser  Gln Val Lys
```

```
    1325                1330                1335

Gly Gly  Val Val Lys Asn Ala  Asp Gly Thr Tyr Ser  Lys Tyr Lys
    1340                1345                1350

Glu Gly  Ser Gly Glu Leu Val  Thr Asn Glu Phe Phe  Thr Thr Asp
    1355                1360                1365

Gly Asn  Val Trp Tyr Tyr Ala  Gly Ala Asn Gly Lys  Thr Val Thr
    1370                1375                1380

Gly Ala  Gln Val Ile Asn Gly  Gln His Leu Tyr Phe  Asn Ala Asp
    1385                1390                1395

Gly Ser  Gln Val Lys Gly Gly  Val Val Lys Asn Ala  Asp Gly Thr
    1400                1405                1410

Tyr Ser  Lys Tyr Asp Ala Ser  Thr Gly Glu Arg Leu  Thr Asn Glu
    1415                1420                1425

Phe Phe  Thr Thr Gly Asp Asn  Asn Trp Tyr Tyr Ile  Gly Ala Asn
    1430                1435                1440

Gly Lys  Ser Val Thr Gly Glu  Val Lys Ile Gly Asp  Asp Thr Tyr
    1445                1450                1455

Phe Phe  Ala Lys Asp Gly Lys  Gln Val Lys Gly Gln  Thr Val Ser
    1460                1465                1470

Ala Gly  Asn Gly Arg Ile Ser  Tyr Tyr Tyr Gly Asp  Ser Gly Lys
    1475                1480                1485

Arg Ala  Val Ser Thr Trp Ile  Glu Ile Gln Pro Gly  Val Tyr Val
    1490                1495                1500

Tyr Phe  Asp Lys Asn Gly Ile  Ala Tyr Pro Pro Arg  Val Leu Asn
    1505                1510                1515


<210> SEQ ID NO 63
<211> LENGTH: 1431
<212> TYPE: PRT
<213> ORGANISM: Streptococcus salivarius

<400> SEQUENCE: 63

Met Thr Lys Glu Thr Asn Thr Val Asp Ala Ala Thr Thr Thr Asn Thr
1               5                   10                  15

Gln Ala Ala Ala Asp Ala Ala Thr Lys Thr Ala Asp Ala Ala Val Thr
            20                  25                  30

Ala Leu Pro Asn Lys Glu Ala Val Val Thr Thr Asp Ala Pro Ala Val
        35                  40                  45

Thr Thr Glu Lys Ala Ala Glu Gln Pro Ala Thr Val Lys Ser Glu Val
    50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
            100                 105                 110

Thr Val Asn Gly Gln Leu Leu Tyr Phe Gly Lys Asp Gly Ala Leu Thr
        115                 120                 125

Ser Ser Ser Thr Tyr Ser Phe Thr Gln Gly Thr Thr Asn Ile Val Asp
    130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175
```

```
Ser Ile Ile Lys Asp Gly Val Thr Trp Gln Ala Ser Thr Lys Glu Asp
            180                 185                 190

Phe Arg Pro Leu Leu Met Ala Trp Trp Pro Asn Val Asp Thr Gln Val
        195                 200                 205

Asn Tyr Leu Asn Tyr Met Ser Lys Val Phe Asn Leu Asp Ala Lys Tyr
    210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Glu Lys Ser Thr Gln Trp
                245                 250                 255

Leu Arg Glu Ala Ile Ser Ala Phe Val Lys Thr Gln Pro Gln Trp Asn
            260                 265                 270

Lys Glu Thr Glu Asn Phe Ser Lys Gly Gly Gly Glu Asp His Leu Gln
        275                 280                 285

Gly Gly Ala Leu Leu Tyr Val Asn Asp Pro Arg Thr Pro Trp Ala Asn
    290                 295                 300

Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
                325                 330                 335

Gly Phe Asp Phe Leu Leu Ala Asn Asp Val Asp Thr Ser Asn Pro Val
            340                 345                 350

Val Gln Ala Glu Gln Leu Asn Gln Ile His Tyr Leu Met Asn Trp Gly
        355                 360                 365

Ser Ile Val Met Gly Asp Lys Asp Ala Asn Phe Asp Gly Ile Arg Val
    370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
                405                 410                 415

Ala His Ile Ser Val Leu Glu Ala Trp Ser Leu Asn Asp Asn His Tyr
            420                 425                 430

Asn Asp Lys Thr Asp Gly Ala Ala Leu Ala Met Glu Asn Lys Gln Arg
        435                 440                 445

Leu Ala Leu Leu Phe Ser Leu Ala Lys Pro Ile Lys Glu Arg Thr Pro
    450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
                485                 490                 495

Asp Gly Thr Val Lys Gln Ser Thr Ile Gly Lys Tyr Asn Glu Lys Tyr
            500                 505                 510

Gly Asp Ala Ser Gly Asn Tyr Val Phe Ile Arg Ala His Asp Asn Asn
        515                 520                 525

Val Gln Asp Ile Ile Ala Glu Ile Ile Lys Lys Glu Ile Asn Pro Lys
    530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
                565                 570                 575

Asn Ile Pro Ala Ala Tyr Ala Val Met Leu Gln Asn Met Glu Thr Ile
            580                 585                 590

Thr Arg Val Tyr Tyr Gly Asp Leu Tyr Thr Asp Asp Gly His Tyr Met
```

-continued

```
        595                 600                 605

Glu Thr Lys Ser Pro Tyr Tyr Asp Thr Ile Val Asn Leu Met Lys Asn
    610                 615                 620

Arg Ile Lys Tyr Val Ser Gly Gly Gln Ala Gln Arg Ser Tyr Trp Leu
625                 630                 635                 640

Pro Thr Asp Gly Lys Met Asp Lys Ser Asp Val Glu Leu Tyr Arg Thr
                645                 650                 655

Asn Glu Val Tyr Thr Ser Val Arg Tyr Gly Lys Asp Ile Met Thr Ala
            660                 665                 670

Asp Asp Thr Gln Gly Ser Lys Tyr Ser Arg Thr Ser Gly Gln Val Thr
        675                 680                 685

Leu Val Val Asn Asn Pro Lys Leu Ser Leu Asp Lys Ser Ala Lys Leu
    690                 695                 700

Asp Val Glu Met Gly Lys Ile His Ala Asn Gln Lys Tyr Arg Ala Leu
705                 710                 715                 720

Ile Val Gly Thr Pro Asn Gly Ile Lys Asn Phe Thr Ser Asp Ala Glu
                725                 730                 735

Ala Ile Ala Ala Gly Tyr Val Lys Glu Thr Asp Gly Asn Gly Val Leu
            740                 745                 750

Thr Phe Gly Ala Asn Asp Ile Lys Gly Tyr Glu Thr Phe Asp Met Ser
        755                 760                 765

Gly Phe Val Ala Val Trp Val Pro Val Gly Ala Ser Asp Asp Gln Asp
    770                 775                 780

Ile Arg Val Ala Ala Ser Thr Ala Ala Lys Lys Glu Gly Glu Leu Thr
785                 790                 795                 800

Leu Lys Ala Thr Glu Ala Tyr Asp Ser Gln Leu Ile Tyr Glu Gly Phe
                805                 810                 815

Ser Asn Phe Gln Thr Ile Pro Asp Gly Ser Asp Pro Ser Val Tyr Thr
            820                 825                 830

Asn Arg Lys Ile Ala Glu Asn Val Asp Leu Phe Lys Ser Trp Gly Val
        835                 840                 845

Thr Ser Phe Glu Met Ala Pro Gln Phe Val Ser Ala Asp Asp Gly Thr
    850                 855                 860

Phe Leu Asp Ser Val Ile Gln Asn Gly Tyr Ala Phe Ala Asp Arg Tyr
865                 870                 875                 880

Asp Leu Ala Met Ser Lys Asn Asn Lys Tyr Gly Ser Lys Glu Asp Leu
                885                 890                 895

Arg Asn Ala Leu Lys Ala Leu His Lys Ala Gly Ile Gln Ala Ile Ala
            900                 905                 910

Asp Trp Val Pro Asp Gln Ile Tyr Gln Leu Pro Gly Lys Glu Val Val
        915                 920                 925

Thr Ala Thr Arg Thr Asp Gly Ala Gly Arg Lys Ile Ser Asp Ala Ile
    930                 935                 940

Ile Asp His Ser Leu Tyr Val Ala Asn Ser Lys Ser Ser Gly Lys Asp
945                 950                 955                 960

Tyr Gln Ala Lys Tyr Gly Gly Glu Phe Leu Ala Glu Leu Lys Ala Lys
                965                 970                 975

Tyr Pro Glu Met Phe Lys Val Asn Met Ile Ser Thr Gly Lys Pro Ile
            980                 985                 990

Asp Asp Ser Val Lys Leu Lys Gln  Trp Lys Ala Glu Tyr  Phe Asn Gly
        995                 1000                1005

Thr Asn  Val Leu Asp Arg Gly  Val Gly Tyr Val Leu  Ser Asp Glu
    1010                1015                1020
```

```
Ala Thr Gly Lys Tyr Phe Thr Val Thr Lys Glu Gly Asn Phe Ile
    1025                1030                1035

Pro Leu Gln Leu Lys Gly Asn Glu Lys Val Ile Thr Gly Phe Ser
    1040                1045                1050

Ser Asp Gly Lys Gly Ile Thr Tyr Phe Gly Thr Ser Gly Asn Gln
    1055                1060                1065

Ala Lys Ser Ala Phe Val Thr Phe Asn Gly Asn Thr Tyr Tyr Phe
    1070                1075                1080

Asp Ala Arg Gly His Met Val Thr Asn Gly Glu Tyr Ser Pro Asn
    1085                1090                1095

Gly Lys Asp Val Tyr Arg Phe Leu Pro Asn Gly Ile Met Leu Ser
    1100                1105                1110

Asn Ala Phe Tyr Val Asp Gly Asn Gly Asn Thr Tyr Leu Tyr Asn
    1115                1120                1125

Ser Lys Gly Gln Met Tyr Lys Gly Gly Tyr Ser Lys Phe Asp Val
    1130                1135                1140

Thr Glu Thr Lys Asp Gly Lys Glu Ser Lys Val Val Lys Phe Arg
    1145                1150                1155

Tyr Phe Thr Asn Glu Gly Val Met Ala Lys Gly Val Thr Val Val
    1160                1165                1170

Asp Gly Phe Thr Gln Tyr Phe Asn Glu Asp Gly Ile Gln Ser Lys
    1175                1180                1185

Asp Glu Leu Val Thr Tyr Asn Gly Lys Thr Tyr Tyr Phe Glu Ala
    1190                1195                1200

His Thr Gly Asn Ala Ile Lys Asn Thr Trp Arg Asn Ile Lys Gly
    1205                1210                1215

Lys Trp Tyr His Phe Asp Ala Asn Gly Val Ala Ala Thr Gly Ala
    1220                1225                1230

Gln Val Ile Asn Gly Gln His Leu Tyr Phe Asn Glu Asp Gly Ser
    1235                1240                1245

Gln Val Lys Gly Gly Val Val Lys Asn Ala Asp Gly Thr Phe Ser
    1250                1255                1260

Lys Tyr Lys Asp Gly Ser Gly Asp Leu Val Val Asn Glu Phe Phe
    1265                1270                1275

Thr Thr Gly Asp Asn Val Trp Tyr Tyr Ala Gly Ala Asn Gly Lys
    1280                1285                1290

Thr Val Thr Gly Ala Gln Val Ile Asn Gly Gln His Leu Phe Phe
    1295                1300                1305

Lys Glu Asp Gly Ser Gln Val Lys Gly Asp Phe Val Lys Asn Ser
    1310                1315                1320

Asp Gly Thr Tyr Ser Lys Tyr Asp Ala Ala Ser Gly Glu Arg Leu
    1325                1330                1335

Thr Asn Glu Phe Phe Thr Thr Gly Asp Asn His Trp Tyr Tyr Ile
    1340                1345                1350

Gly Ala Asn Gly Lys Thr Val Thr Gly Glu Val Lys Ile Gly Asp
    1355                1360                1365

Asp Thr Tyr Phe Phe Ala Lys Asp Gly Lys Gln Leu Lys Gly Gln
    1370                1375                1380

Ile Val Thr Thr Arg Ser Gly Arg Ile Ser Tyr Tyr Phe Gly Asp
    1385                1390                1395

Ser Gly Lys Lys Ala Ile Ser Thr Trp Val Glu Ile Gln Pro Gly
    1400                1405                1410
```

```
Val Phe  Val Phe Phe Asp Lys  Asn Gly Leu Ala Tyr  Pro Pro Glu
    1415                 1420                 1425

Asn Met  Asn
1430


<210> SEQ ID NO 64
<211> LENGTH: 1532
<212> TYPE: PRT
<213> ORGANISM: Unknown
<220> FEATURE:
<223> OTHER INFORMATION: unknown Streptococcus species

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
            20                  25                  30

Leu Ser Ala Thr Thr Ser Ser Val Ser Ala Asp Glu Thr Gln Asp Lys
        35                  40                  45

Thr Val Thr Gln Pro Asn Ser Asp Thr Thr Ala Asp Leu Val Thr Ser
    50                  55                  60

Thr Glu Ala Thr Lys Glu Val Asp Lys Arg Thr Asn Thr Lys Glu Ala
65                  70                  75                  80

Asp Val Leu Thr Pro Ala Lys Glu Thr Asn Thr Val Glu Thr Ala Ala
                85                  90                  95

Thr Thr Asn Thr Gln Ala Thr Ala Glu Ala Ala Lys Thr Ala Thr Thr
            100                 105                 110

Thr Asn Thr Gln Ala Thr Ala Glu Val Ala Lys Thr Ala Thr Thr Ala
        115                 120                 125

Asp Val Ala Val Ala Ala Val Pro Asn Lys Glu Ala Val Val Thr Thr
    130                 135                 140

Asp Ala Pro Ala Val Thr Thr Glu Lys Ala Glu Glu Gln Pro Ala Thr
145                 150                 155                 160

Val Lys Ala Glu Val Val Asn Thr Glu Val Lys Ala Pro Glu Ala Ala
                165                 170                 175

Leu Lys Asp Ser Glu Val Glu Ala Ala Leu Ser Leu Lys Asn Ile Lys
            180                 185                 190

Asn Ile Asp Gly Lys Tyr Tyr Tyr Val Asn Glu Asp Gly Ser His Lys
        195                 200                 205

Glu Asn Phe Ala Ile Thr Val Asn Gly Gln Leu Leu Tyr Phe Gly Lys
    210                 215                 220

Asp Gly Ala Leu Thr Ser Ser Ser Thr Tyr Ser Phe Thr Gln Gly Thr
225                 230                 235                 240

Thr Asn Ile Val Asp Gly Phe Ser Ile Asn Asn Arg Ala Tyr Asp Ser
                245                 250                 255

Ser Glu Ala Ser Phe Glu Leu Ile Asp Gly Tyr Leu Thr Ala Asp Ser
            260                 265                 270

Trp Tyr Arg Pro Ala Ser Ile Ile Lys Asp Gly Val Thr Trp Gln Ala
        275                 280                 285

Ser Thr Ala Glu Asp Phe Arg Pro Leu Leu Met Ala Trp Trp Pro Asn
    290                 295                 300

Val Asp Thr Gln Val Asn Tyr Leu Asn Tyr Met Ser Lys Val Phe Asn
305                 310                 315                 320

Leu Asp Ala Lys Tyr Ser Ser Thr Asp Lys Gln Glu Thr Leu Lys Val
                325                 330                 335
```

```
Ala Ala Lys Asp Ile Gln Ile Lys Ile Glu Gln Lys Ile Gln Ala Glu
            340                 345                 350

Lys Ser Thr Gln Trp Leu Arg Glu Thr Ile Ser Ala Phe Val Lys Thr
        355                 360                 365

Gln Pro Gln Trp Asn Lys Glu Thr Glu Asn Tyr Ser Lys Gly Gly Gly
    370                 375                 380

Glu Asp His Leu Gln Gly Gly Ala Leu Leu Tyr Val Asn Asp Ser Arg
385                 390                 395                 400

Thr Pro Trp Ala Asn Ser Asn Tyr Arg Leu Leu Asn Arg Thr Ala Thr
                405                 410                 415

Asn Gln Thr Gly Thr Ile Asp Lys Ser Ile Leu Asp Glu Gln Ser Asp
            420                 425                 430

Pro Asn His Met Gly Gly Phe Asp Phe Leu Leu Ala Asn Asp Val Asp
        435                 440                 445

Leu Ser Asn Pro Val Val Gln Ala Glu Gln Leu Asn Gln Ile His Tyr
    450                 455                 460

Leu Met Asn Trp Gly Ser Ile Val Met Gly Asp Lys Asp Ala Asn Phe
465                 470                 475                 480

Asp Gly Ile Arg Val Asp Ala Val Asp Asn Val Asp Ala Asp Met Leu
                485                 490                 495

Gln Leu Tyr Thr Asn Tyr Phe Arg Glu Tyr Tyr Gly Val Asn Lys Ser
            500                 505                 510

Glu Ala Asn Ala Leu Ala His Ile Ser Val Leu Glu Ala Trp Ser Leu
        515                 520                 525

Asn Asp Asn His Tyr Asn Asp Lys Thr Asp Val Ala Ala Leu Ala Met
    530                 535                 540

Glu Asn Lys Gln Arg Leu Ala Leu Leu Phe Ser Leu Ala Lys Pro Ile
545                 550                 555                 560

Lys Glu Arg Thr Pro Ala Val Ser Pro Leu Tyr Asn Asn Thr Phe Asn
                565                 570                 575

Thr Thr Gln Arg Asp Glu Lys Thr Asp Trp Ile Asn Lys Asp Gly Ser
            580                 585                 590

Lys Ala Tyr Asn Glu Asp Gly Thr Val Lys Lys Ser Thr Ile Gly Lys
        595                 600                 605

Tyr Asn Glu Lys Tyr Gly Asp Ala Ser Gly Asn Tyr Val Phe Ile Arg
    610                 615                 620

Ala His Asp Asn Asn Val Gln Asp Ile Ile Ala Glu Ile Ile Lys Lys
625                 630                 635                 640

Glu Ile Asn Glu Lys Ser Asp Gly Phe Thr Ile Thr Asp Ser Glu Met
                645                 650                 655

Lys Arg Ala Phe Glu Ile Tyr Asn Lys Asp Met Leu Ser Asn Asp Lys
            660                 665                 670

Lys Tyr Thr Leu Asn Asn Ile Pro Ala Ala Tyr Ala Val Met Leu Gln
        675                 680                 685

Asn Met Glu Thr Ile Thr Arg Val Tyr Tyr Gly Asp Leu Tyr Thr Asp
    690                 695                 700

Asp Gly Asn Tyr Met Glu Ala Lys Ser Pro Tyr Tyr Asp Thr Ile Val
705                 710                 715                 720

Asn Leu Met Lys Ser Arg Ile Lys Tyr Val Ser Gly Gly Gln Ala Gln
                725                 730                 735

Arg Ser Tyr Trp Leu Pro Thr Asp Gly Lys Met Asp Lys Ser Asp Val
            740                 745                 750

Glu Leu Tyr Arg Thr Asn Glu Val Tyr Thr Ser Val Arg Tyr Gly Lys
```

```
        755                 760                 765

Asp Ile Met Thr Ala Asp Asp Thr Gln Gly Ser Lys Tyr Ser Arg Thr
    770                 775                 780

Ser Gly Gln Val Thr Leu Val Val Asn Asn Pro Lys Leu Thr Leu Asp
785                 790                 795                 800

Gln Ser Ala Lys Leu Asn Val Val Met Gly Lys Ile His Ala Asn Gln
                805                 810                 815

Lys Tyr Arg Ala Leu Ile Val Gly Thr Pro Asn Gly Ile Lys Asn Phe
            820                 825                 830

Thr Ser Asp Ala Glu Ala Ile Ala Ala Gly Tyr Val Lys Glu Thr Asp
        835                 840                 845

Gly Asn Gly Val Leu Thr Phe Gly Ala Asn Asp Ile Lys Gly Tyr Glu
    850                 855                 860

Thr Phe Asp Met Ser Gly Phe Val Ala Val Trp Val Pro Val Gly Ala
865                 870                 875                 880

Ser Asp Asp Gln Asp Ile Arg Val Ala Ala Ser Thr Ala Ala Lys Lys
                885                 890                 895

Glu Gly Glu Leu Thr Leu Lys Ala Thr Glu Ala Tyr Asp Ser Gln Leu
            900                 905                 910

Ile Tyr Glu Gly Phe Ser Asn Phe Gln Thr Ile Pro Asp Gly Ser Asp
        915                 920                 925

Pro Ser Val Tyr Thr Asn Arg Lys Ile Ala Glu Asn Val Asp Leu Phe
    930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
                965                 970                 975

Phe Ala Asp Arg Tyr Asp Leu Ala Met Ser Lys Asn Asn Lys Tyr Gly
            980                 985                 990

Ser Lys Glu Asp Leu Arg Asn Ala  Leu Lys Ala Leu His  Lys Ala Gly
        995                 1000                1005

Ile Gln  Ala Ile Ala Asp Trp  Val Pro Asp Gln Ile  Tyr Gln Leu
    1010                1015                1020

Pro Gly  Lys Glu Val Val Thr  Ala Thr Arg Thr Asp  Gly Ala Gly
    1025                1030                1035

Arg Lys  Ile Ser Asp Ala Ile  Ile Asp His Ser Leu  Tyr Val Ala
    1040                1045                1050

Asn Ser  Lys Ser Ser Gly Lys  Asp Tyr Gln Ala Lys  Tyr Gly Gly
    1055                1060                1065

Glu Phe  Leu Ala Glu Leu Lys  Ala Lys Tyr Pro Glu  Met Phe Lys
    1070                1075                1080

Val Asn  Met Ile Ser Thr Gly  Lys Pro Ile Asp Asp  Ser Val Lys
    1085                1090                1095

Leu Lys  Gln Trp Lys Ala Glu  Tyr Phe Asn Gly Thr  Asn Val Leu
    1100                1105                1110

Asp Arg  Gly Val Gly Tyr Val  Leu Ser Asp Glu Ala  Thr Gly Lys
    1115                1120                1125

Tyr Phe  Thr Val Thr Lys Glu  Gly Asn Phe Ile Pro  Leu Gln Leu
    1130                1135                1140

Lys Gly  Asn Lys Lys Val Ile  Thr Gly Phe Ser Ser  Asp Gly Lys
    1145                1150                1155

Gly Ile  Thr Tyr Phe Gly Thr  Ser Gly Asn Gln Ala  Lys Ser Ala
    1160                1165                1170
```

```
Phe Val  Thr Phe Asn Gly Asn  Thr Tyr Tyr Phe Asp  Ala Arg Gly
    1175                 1180                 1185

His Met  Val Thr Asn Gly Glu  Tyr Ser Pro Asn Gly  Lys Asp Val
    1190                 1195                 1200

Tyr Arg  Phe Leu Pro Asn Gly  Ile Met Leu Ser Asn  Ala Phe Tyr
    1205                 1210                 1215

Val Asp  Gly Asn Gly Asn Thr  Tyr Leu Tyr Asn Ser  Lys Gly Gln
    1220                 1225                 1230

Met Tyr  Lys Gly Gly Tyr Ser  Lys Phe Asp Val Thr  Glu Thr Lys
    1235                 1240                 1245

Asp Gly  Lys Glu Ser Lys Val  Val Lys Phe Arg Tyr  Phe Thr Asn
    1250                 1255                 1260

Glu Gly  Val Met Ala Lys Gly  Val Thr Val Val Asp  Gly Phe Thr
    1265                 1270                 1275

Gln Tyr  Phe Asn Glu Asp Gly  Ile Gln Ser Lys Asp  Glu Leu Val
    1280                 1285                 1290

Thr Tyr  Asn Gly Lys Thr Tyr  Tyr Phe Glu Ala His  Thr Gly Asn
    1295                 1300                 1305

Ala Ile  Lys Asn Thr Trp Arg  Asn Ile Lys Gly Lys  Trp Tyr His
    1310                 1315                 1320

Phe Asp  Ala Asn Gly Val Ala  Ala Thr Gly Ala Gln  Val Ile Asn
    1325                 1330                 1335

Gly Gln  His Leu Tyr Phe Asn  Glu Asp Gly Ser Gln  Val Lys Gly
    1340                 1345                 1350

Ser Ile  Val Lys Asn Ala Asp  Gly Thr Phe Ser Lys  Tyr Lys Asp
    1355                 1360                 1365

Ser Ser  Gly Asp Leu Val Val  Asn Glu Phe Phe Thr  Thr Gly Asp
    1370                 1375                 1380

Asn Val  Trp Tyr Tyr Ala Gly  Ala Asn Gly Lys Thr  Val Thr Gly
    1385                 1390                 1395

Ala Gln  Val Ile Asn Gly Gln  His Leu Phe Phe Lys  Glu Asp Gly
    1400                 1405                 1410

Ser Gln  Val Lys Gly Asp Phe  Val Lys Asn Ser Asp  Gly Thr Tyr
    1415                 1420                 1425

Ser Lys  Tyr Asp Ala Ala Ser  Gly Glu Arg Leu Thr  Asn Glu Phe
    1430                 1435                 1440

Phe Thr  Thr Gly Asp Asn His  Trp Tyr Tyr Ile Gly  Ala Asn Gly
    1445                 1450                 1455

Lys Thr  Val Thr Gly Glu Val  Lys Ile Gly Asp Asp  Thr Tyr Phe
    1460                 1465                 1470

Phe Ala  Lys Asp Gly Lys Gln  Leu Lys Gly Gln Ile  Val Thr Thr
    1475                 1480                 1485

Arg Ser  Gly Arg Ile Ser Tyr  Tyr Phe Gly Asp Ser  Gly Lys Lys
    1490                 1495                 1500

Ala Ile  Ser Thr Trp Val Glu  Ile Gln Pro Gly Val  Phe Val Phe
    1505                 1510                 1515

Phe Asp  Lys Asn Gly Leu Ala  Tyr Pro Pro Glu Asn  Met Asn
    1520                 1525                 1530
```